US011613561B2

(12) United States Patent
Chahal et al.

(10) Patent No.: US 11,613,561 B2
(45) Date of Patent: Mar. 28, 2023

(54) ARTIFICIAL ALPHAVIRUS-DERIVED RNA REPLICON EXPRESSION SYSTEMS

(71) Applicant: TIBA BIOTECH, Cambridge, MA (US)

(72) Inventors: Jasdave S Chahal, Woburn, MA (US); Justine S McPartlan, Somerville, MA (US)

(73) Assignee: TIBA BIOTECH, LLC, Cambridge, MA (US)

( * ) Notice: Subject to any disclaimer, the term of this patent is extended or adjusted under 35 U.S.C. 154(b) by 0 days.

(21) Appl. No.: 17/698,300

(22) Filed: Mar. 18, 2022

(65) Prior Publication Data

US 2022/0298210 A1 Sep. 22, 2022

Related U.S. Application Data

(60) Provisional application No. 63/163,475, filed on Mar. 19, 2021.

(51) Int. Cl.
*C07K 14/005* (2006.01)
*C12N 7/00* (2006.01)
(Continued)

(52) U.S. Cl.
CPC .......... *C07K 14/005* (2013.01); *A61K 38/162* (2013.01); *A61K 38/1793* (2013.01); *A61K 38/4873* (2013.01); *A61K 39/12* (2013.01); *A61K 45/06* (2013.01); *A61P 35/00* (2018.01); *C07K 14/7156* (2013.01); *C12N 7/00* (2013.01); *C12N 9/506* (2013.01); *C12N 15/86* (2013.01); *C12Y 304/22028* (2013.01); *A61K 2039/5256* (2013.01); *A61K 2039/53* (2013.01); *A61K 2039/552* (2013.01); *A61K 2039/585* (2013.01); *A61K 2039/6075* (2013.01); *C07K 2319/00* (2013.01); *C12N 2770/36121* (2013.01); *C12N 2770/36122* (2013.01);
(Continued)

(58) Field of Classification Search
None
See application file for complete search history.

(56) References Cited

U.S. PATENT DOCUMENTS 3,536,809 A 10/1970 Applezweig
3,598,123 A 8/1971 Zaffaroni
(Continued)

FOREIGN PATENT DOCUMENTS

WO 2014170493 A2 10/2014
WO 2021 207020 A2 10/2021

OTHER PUBLICATIONS

Kinney et al. (Virology. 1986; 152: 400-413).*
(Continued)

*Primary Examiner* — Shanon A. Foley
(74) *Attorney, Agent, or Firm* — Volpe Koenig

(57) ABSTRACT

Synthetic alphavirus-derived replicon expression systems comprising nucleic acid sequences encoding at least one modified nonstructural protein, and synthetic nucleic acid sequences encoding at least one heterologous protein are described. Methods of producing at least one heterologous protein in a cell, or of inducing an immune response in a subject by administering and/or expressing the synthetic alphavirus-derived replicon expression systems are provided.

17 Claims, 39 Drawing Sheets

Specification includes a Sequence Listing.

(51) Int. Cl.
*C12N 9/50* (2006.01)
*C07K 14/715* (2006.01)
*C12N 15/86* (2006.01)
*A61P 35/00* (2006.01)
*A61K 39/12* (2006.01)
*A61K 38/16* (2006.01)
*A61K 38/17* (2006.01)
*A61K 38/48* (2006.01)
*A61K 45/06* (2006.01)
*A61K 39/00* (2006.01)

(52) U.S. Cl.
CPC .............. *C12N 2770/36133* (2013.01); *C12N 2770/36134* (2013.01); *C12N 2770/36143* (2013.01)

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 6,365,185 B1 | 4/2002 | Ritschel et al. | |
| 2003/0170871 A1* | 9/2003 | Dubensky, Jr. | C12N 15/86 435/235.1 |
| 2007/0166820 A1 | 7/2007 | Smith et al. | |
| 2014/0079734 A1 | 3/2014 | Frolov et al. | |
| 2017/0191065 A1 | 7/2017 | Paldi et al. | |
| 2020/0010849 A1 | 1/2020 | Blair et al. | |
| 2020/0197500 A1 | 6/2020 | Blair et al. | |
| 2020/0299725 A1 | 9/2020 | Beissert et al. | |
| 2021/0330600 A1 | 10/2021 | Talukder et al. | |
| 2021/0338789 A1 | 11/2021 | Khan et al. | |
| 2022/0298210 A1* | 9/2022 | Chahal | A61K 38/1793 |

OTHER PUBLICATIONS

Kinney et al. (Journal of General Virology. 1992; 73: 3301-3305).*

Sequence alignment of GenEmbl database accession No. EEVNSPEPA Kinney—1986 with: nt 500-7600 of instant SEQ ID No. 17.*

Sequence alignment of GenEmbl database accession No. EEVNSPEPA Kinney—1986 with: nt 500-7600 of instant SEQ ID No. 20.*

Sequence alignment of GenEmbl database accession No. EEVNSPEPA Kinney—1986 with: nt 500-7600 of instant SEQ ID No. 21.*

Sequence alignment of GenEmbl database accession No. EEVNSPEPA Kinney—1986 with: nt 500-7600 of instant SEQ ID No. 22.*

Sequence alignment of GenEmbl database accession No. EEVNSPEPA Kinney—1986 with: nt 500-7600 of instant SEQ ID No. 23.*

Sequence alignment of GenEmbl database accession No. EEVNSPEPA Kinney—1986 with: nt 500-7600 of instant SEQ ID No. 24.*

Sequence alignment of GenEmbl database accession No. EEVNSPEPA Kinney—1986 with: nt 500-7600 of instant SEQ ID No. 25.*

Sequence alignment of GenEmbl database accession No. EEVNSPEPA Kinney—1986 with: nt 500-7600 of instant SEQ ID No. 26.*

Kinney et al. (Virology. 1989; 170: 19-30).*

Snijder et al. (Journal of Biological Chemistry. 1996; 271 (9): 4864-4871).*

Heyes et al., 2005, Cationic lipid saturation influences intracellular delivery of encapsulated nucleic acid, J Controlled Release 107:276-87.

Kinney et al., 1986, Nucleotide sequence of the 26 S mRNAof the virulent Trinidad donkey strain of Venezuelan equine encephalitis virus and deduced sequence of the encoded structural proteins, Virology 152 (2), 400-413.

Smith, and Waterman, 1981, Identification of Common Molecular Subsequences, J Mol Biol 147, pp. 195-197.

Tomar et al. 2006, Catalytic core of alphavirus nonstructural protein nsP4 pissesses terminal adenyltransferase activity, J Virol. 80(20): 9962-9969.

International Search Report and Written Opinion issued for International Patent Application PCT/US2022/020881 dated Aug. 16, 2022.

* cited by examiner

FIG. 5
Construct 8
11,173 bp
XmnI (307)
(10,849) XmnI
T7 transcript start
CODON OPTIMIZED
AmpR
AmpR promoter
poly(A)100
3' UTR
GENE OF INTEREST
Subgenomic RNA 5'UTR

FIG. 9
Construct 5
11,173 bp
CODON OPTIMIZED
T7 transcript start
AmpR promoter
AmpR
ori
3' UTR
GENE OF INTEREST
Subgenomic RNA 5'UTR
SalI (3467)

FIG. 13
Construct 1
11,173 bp
NS
NS
NS
NS
T7 transcript start
AmpR promoter
AmpR
ori
poly(A)108
3' UTR
GENE OF INTEREST
Subgenomic RNA 5'UTR
CODON OPTIMIZED
10,000
8000

ARTIFICIAL ALPHAVIRUS-DERIVED RNA REPLICON EXPRESSION SYSTEMS

CROSS REFERENCE TO RELATED APPLICATION

This application claims the benefit of U.S. provisional application No. 63/163,475, filed Mar. 19, 2021, which is incorporated by reference as if fully set forth.

The sequence listing electronically filed with this application titled "Sequence Listing," which was created on Mar. 18, 2022 and had a size of 413,759 bytes is incorporated by reference herein as if fully set forth.

FIELD OF INVENTION

The present disclosure relates to self-replicating RNA molecules derived from the genomes of alphaviruses, and methods to improve their safety and gene expression capacity by mutation and otherwise editing the primary nucleotide sequence. The disclosure further relates to methods of producing and using such engineered RNA molecules for the treatment of and prophylaxis against disease in humans or animals.

BACKGROUND

Self-replicating RNAs, or "replicon" RNAs, have been used as a vector for transgene expression in vitro and in vivo. Viruses of the genus alphavirus are used as the template for the design of replicon RNAs, since the layout of their genomes is consistent across species, and is amenable to molecular biology manipulations. Alphavirus-based replicons derived from many different species of alphavirus (e.g., Venezuelan equine encephalitis virus, Sindbis virus, Semliki Forest virus) have been used as vectors for transgene expression both in vitro and in vivo. These vectors rely on the activity of nonstructural viral proteins encoded therein to mediate expression of an exogenous protein encoded in the place of the structural gene open reading frame (ORF) that is translated from subgenomic (SG) mRNAs synthesized late in the replicative life cycle.

Replicons are potent inducers of innate immune responses, making them useful for vaccine and other immune-modulatory applications. Alphaviral replicon RNAs are frequently based on common virus species such as Venezuelan equine encephalitis virus (VEEV), which is naturally occurring and endemic in much of the world. The risk of recombination with wild-type viruses is greater when the sequence of a replicon vector is identical to the wild-type genome. The primary sequence of RNA viruses is sensitive to alterations due to the conservation of secondary structures and non-protein-coding functions necessary for genome replication, translation, and packaging into virions.

It is difficult to tune the immune response to replicon RNAs, as the initial interferon responses are initiated in the early phase of the virus life cycle, when only the nonstructural polyprotein (nsP) is expressed at effective intracellular concentrations. Modifications to incorporate additional regulatory gene products into replicons must currently be performed by insertion into the SG ORF, leading to expression only in late phase of the viral replicative cycle and disrupting any other transgene sequence encoded in that ORF. RNA replicons would be far more useful if transgenes could be expressed in cis from, and in addition to, the nsP ORF, ensuring their expression early in the replicative life cycle when critical biological processes, such as the triggering of pattern-recognition receptors (PRRs) or post-translational processing of proteins, can be deliberately modulated by delivery of exogenous transgenes encoded therein. Furthermore, RNA replicons would be safer for field use if the coding sequence of the nsP region contained less sequence identity with naturally occurring virus genomes.

SUMMARY

In an aspect, the invention relates to a synthetic alphavirus-derived self-replicating, or replicon nucleic acid (RNA) molecule. The synthetic alphavirus-derived replicon nucleic acid molecule comprises a first nucleic acid encoding alphavirus nonstructural proteins nsP1, nsP2, nsP3, and nsP4, and comprising at least one silent mutation introduced at any position within a region from nt 503 to nt 658, nt 658 to nt 1620, nt 1620 to nt 2560, nt 2560 to nt 3954, nt 3954 to nt 4120, nt 6381 to nt 7083, and nt 6966 to nt 7526 in the sequence of the alphavirus genome as set forth in SEQ ID NO: 17. The synthetic alphavirus-derived replicon nucleic acid molecule also comprises a second nucleic acid comprising a subgenomic promoter (SGP) and a modified subgenomic open reading frame (SG ORF).

In an aspect, the invention relates to an alphavirus-derived RNA replicon expression system comprising any one of the synthetic alphavirus-derived replicon nucleic acid molecules. In the molecules, the C-terminus of the nonstructural protein 4 (nsP4) is fused to a heterologous protein via a non-cleavable, self-cleavable, or proteolytically cleavable peptide linker sequence. The synthetic alphavirus-derived replicon nucleic acid molecule also encodes a functional SGP sequence downstream from (i.e., 3' of) the nsP4-fused protein to drive expression of a modified SG ORF. In an aspect, at least one silent mutation in the nsP4 coding sequence is present that renders SGP-homologous sequences contained therein non-functional and non-identical to the functional SGP encoded downstream of the nsP4-fusion protein ORF.

In an aspect, the invention relates to an alphavirus-derived RNA replicon expression system. The alphavirus-derived RNA replicon expression system comprises any one of the synthetic alphavirus-derived replicon nucleic acid molecules described herein encapsulated or formulated for delivery into an organism's cells in the form of a virus, virus-like particle, liposome, or a lipid, polymeric, or dendrimer-based nanoparticle.

In an aspect the invention relates to a vaccine. The vaccine comprises any one of the synthetic alphavirus-derived replicon nucleic acid molecules described herein.

In an aspect the invention relates to a therapeutic drug or medicine. The therapeutic drug or medicine comprises any one of the synthetic alphavirus-derived replicon nucleic acid molecules described herein.

In an aspect, the invention relates to a method of producing at least one heterologous protein in a cell. The method comprises expressing any one of the synthetic alphavirus-derived replicon nucleic acid molecules described herein in a cell.

In an aspect, the invention relates to a method of preventing, inhibiting, or treating the symptoms of a disease or condition in a subject comprising administering to the subject a therapeutically effective amount of any one of the synthetic alphavirus-derived replicon nucleic acid molecules described herein.

BRIEF DESCRIPTION OF THE DRAWINGS

The following detailed description of preferred embodiments of the present invention will be better understood when read in conjunction with the appended drawings. For the purpose of illustrating the invention, particular embodiments are shown in the drawings. It is understood, however, that the invention is not limited to the precise arrangements and instrumentalities shown. In the drawings:

FIG. 17A is a bar graph showing the results of the SEAP expression tests on C01, C02, C03, C04, C05, C06, C07, and C08 replicon RNAs in comparison to wild-type (WT, noncodon-adapted replicon RNA similarly encoding SEAP), performed by sampling the conditioned supernatant of BHK cells transfected for the indicated time 4 hours (left bars), 16 hours (middle bars) and 24 hours (right bars).

FIGS. 17B and 17C are bar graphs showing the results of the SEAP expression tests by sampling the conditioned supernatant of BHK cells transfected for 16 hours with the indicated replicon RNA (FIG. 17B-C09, and FIG. 17C-C10) and quantifying SEAP expression by measuring absorbance at 650 nm in a colorimetric assay. It was observed that codon-adapted constructs expressed more strongly than the wild-type (WT) control.

FIG. 17D is a column scatter plot showing the results of SEAP expression as quantified by luminescent assay (RLU) for constructs C03, C05, and C06 compared to control wild-type RNA replicon (VEEVrep-SEAP; WT) and untreated (Untransf.) mice. In the treatment, four mice per group were injected with 1 μg of the indicated RNA and serum was collected the next day. Serum SEAP concentration was measured by luminescent assay in relative luminescence units (RLU). Bars: mean RLU of the group with error bars=S.D.

FIG. 20A shows results of fluorescence microscopy, demonstrating a plurality of GFP-positive cells when transfection is performed with nsP4 (GFP)-modified VEEV replicon RNA (VEEVrep-nsP4[GFP]-SEAP), and the absence of GFP expression in untransfected control cells.

FIG. 20B is a photograph of the immunoblots of transfected BHK cell lysates with a GFP-specific monoclonal antibody, with GAPDH detection serving as loading control that shows confirmation of GFP expression by two independently isolated clones of VEEVrep-nsP4 [GFP]-SEAP.

FIG. 20C is the bar graph that shows the function of the SG ORF encoding SEAP as tested by sampling the conditioned supernatant of the transfected BHK cells and quantifying SEAP expression by colorimetric assay.

FIG. 21A are photographs showing results of fluorescence microscopy, demonstrating a plurality of GFP-positive cells when transfection is performed with codon-adapted, nsP4 (GFP)-modified VEEV-SEAP replicon RNA (C13) (top panel, right), and the absence of GFP expression in untransfected control cells (bottom panel, right) compared to bright field (BF) microscopy (left panels).

FIG. 21B are charts showing the results of luminescent assay (RLU) to quantify the concentration of SEAP in serum collected from mice injected with wild type (WT) VEEV-SEAP replicon RNA, or with nsP4 (GFP)-modified (Modified) VEEV replicon RNA carrying optimized codons in nonstructural regions of the unstructured polyprotein gene compared to serum collected from uninjected control mice. The serum was collected on Day 1, Day 3, and Day 5 following the injections.

FIG. 22A is a schematic drawing showing a construct with modification of the nsP4 coding sequence of an alphaviral replicon to encode the 3Cpro protease required for picornavirus P1 structural polyprotein (O1 Manisa P1 polyprotein), referred to as VEEVrep-nsP4[3C]-P1. The sequence of the 5'UTR, nsP1-4,3Cpro, and SGP region of this RNA is set forth in SEQ ID NO: 32. The amino acid sequence of the P1 polyprotein encoded in the SG ORF is set forth in SEQ ID NO: 40.

FIG. 22B is a photograph of the immunoblot performed on lysates of BHK cells transfected with the following RNAs: lane 1, VEEVrep-nsP4[3C]-P1; lane 2, replicon RNA similar to that in lane 1 but carrying an insert mutation that introduces a premature stop codon and ablates expression of the 3Cpro polypeptide as a negative control (VEEVrep-nsP4[3Cmut]-P1); lane 3, VEEVrep-P1 (similar to VEEVrep-nsP4[3C]-P1 but lacking nsP4-fused 3Cpro); lane 4, VEEVrep-P1 transfected in combination with $1/40^{th}$ the mass of mRNA encoding 3Cpro as a positive control. Referring to this figure, the successful proteolytic processing of the ~100 kDa P1 polyprotein to the immunogenic ~35 kDa VP0 capsid fragment was mediated to completion only by VEEVrep-nsP4[3C]-P1. An intermediate incompletely cleaved product representing intact VP4+VP2+VP3 can be seen running at an apparent molecular weight of ~55 kDa. A VP2-specific antibody was used to probe the blot. M, molecular weight markers; C, untreated negative control cells.

FIG. 23A is a schematic drawing of construct VEEVrep-nsP4[STING]-SEAP, a replicon RNA that includes modification of the nsP4 coding sequence to encode a human STING protein, mutated to be constitutively active for IFN-stimulating activity, and the reporter gene, SEAP, encoded in the SG ORF. The sequence of the 5'UTR, nsP1-4, STING, and SGP region of this RNA is set forth in SEQ ID NO: 34.

FIG. 23B is a photograph of immunoblot performed on HEK-Lucia™ Null cells transfected with the following RNAs: lane 1, VEEVrep-SEAP; lane 2, VEEVrep-nsP4 [STING]-SEAP; lane 3, no transfection control.

FIG. 23C is a bar graph showing expression of the SEAP reporter gene (as measured by absorbance at 650 nm in a colorimetric assay) encoded in the SG ORF in VEEVrep-SEAP and VEEVrep-nsP4[STING]-SEAP replicon RNAs compared to control (untransfected cells).

FIG. 23D is a bar graph showing surrogate measurement of IFN signaling activity induced by VEEVrep-SEAP SEAP and VEEVrep-nsP4[STING]-SEAP replicon RNAs compared to control (untransfected cells).

FIG. 24A are photographs showing GFP expression in B16 melanoma cells cultured in 12-well dishes after transfection with 1 μg of VEEVrep-nsP4[GFP]-SEAP replicon RNA approximately 1 day post-transfection compared to untransfected control cells.

FIG. 24B is a bar graph showing SEAP expression in B16 melanoma cells cultured in 12-well dishes after transfection with 1 μg of the indicated replicon RNAs: VEEVrep-nsP4[STING]-SEAP, VEEVrep-nsP4[GFP]-SEAP, and VEEVrep-SEAP compared to untransfected control cells.

FIG. 24C is a bar graph showing measurement of IFN-beta secretion (measured by sandwich ELISA on culture supernatant) by B16 melanoma cells ~1 day after transfection with 1 μg of the indicated replicon RNAs: VEEVrep-nsP4[STING]-SEAP and VEEVrep-SEAP compared to untransfected control cells.

FIG. 24D are photographs of light microscopy examination of B16 cells 1 day after transfection with 2 μg of VEEVrep-nsP4[GFP]-SEAP or VEEVrep-nsP4[STING]-SEAP, compared to healthy untransfected control cells (left-most panel).

FIG. 25A is a bar graph showing SEAP expression in TC-1 cancer cells cultured in 12-well dishes 2 days after transfection with 2 μg of the indicated replicon RNA: VEEVrep-nsP4[GFP]-SEAP, VEEVrep-nsP4[STING]-SEAP compared to untransfected control cells. In this experiment, SEAP expression was quantified by colorimetric assay on culture medium, showing successful expression of the SEAP gene encoded in the SG ORF.

FIG. 25B is a bar graph showing measurement of IFN-beta secretion (measured by sandwich ELISA on culture supernatant) by TC-1 cancer cells 1 day after transfection with 2 μg of the indicated replicon RNA: VEEVrep-nsP4[GFP]-SEAP, or VEEVrep-nsP4[STING]-SEAP compared to untransfected control cells.

FIG. 25C are photographs showing GFP expression in TC-1 cancer cell agglomerates after transfection with 1 μg of VEEVrep-nsP4[GFP]-SEAP approximately 3 days post-transfection. Referring to this figure, extensive GFP expression was observed throughout the multicellular structure driven by coding of the fluorescent protein at the nsP4 C-terminal end of the construct (top panel, right) compared to no GFP expression in untreated control cells (bottom panel, right).

FIG. 25D are photographs showing results of light microscopy examination of TC-1 cancer cells 1 day after transfection with 4 μg of the indicated replicon RNA VEEVrep-nsP4[STING]-SEAP compared to untreated control cells. Referring to this figure, it was observed that untreated cells (Control) had proliferated to fill the dish; growth inhibition and cell death was observed after transfection with VEEVrep-nsP4[STING]-SEAP.

FIG. 26A is a schematic drawing of a DNA plasmid encoding the replicon sequence template of construct 12 (VEEVrepHK-SEAP). Referring to this figure, the DNA plasmid is similar to that shown in FIG. 5, except that only codons in genomic nucleotide positions 705-3406 (gray box) were altered to reduce homology to the wild-type virus, without regard to the possible presence of any secondary structure elements.

FIG. 26B is a schematic drawing of a DNA plasmid encoding the replicon sequence template of construct 13 (VEEVrepHK(ΔU)-SEAP). Referring to this figure, the DNA plasmid is similar to that shown in FIG. 58, except that only codons in genomic nucleotide positions 658-3359 (gray box) were altered to reduce homology to the wild-type virus, without regard to the possible presence of any secondary structure elements, and codons avoiding uracil bases were selected preferentially.

FIG. 26C is a schematic drawing of a DNA plasmid encoding the replicon sequence template of construct 14 (VEEVrepES-SEAP). Referring to this figure, the DNA plasmid is similar to that shown in FIG. 5, except that only codons in genomic nucleotide positions 4120-6965 (gray box) were altered to reduce homology to the wild-type virus, without regard to the possible presence of any secondary structure elements.

FIG. 26D is a schematic drawing of a DNA plasmid encoding the replicon sequence template of construct 15 (VEEVrepES(ΔU)-SEAP). Referring to this figure, the DNA plasmid is similar to that shown in FIG. 5, except that only codons in genomic nucleotide positions 4120-6965 (gray box) were altered to reduce homology to the wild-type virus, without regard to the possible presence of any secondary structure elements, and codons avoiding uracil bases were selected preferentially.

FIG. 26E is a bar graph showing SEAP expression in BHK cells cultured in 12-well dishes 16 hours after transfection with 1 μg of VEEVrep-SEAP, VEEVrepHK-SEAP, or VEEVrepHK(ΔU)-SEAP RNA compared to untransfected control cells. In this experiment, SEAP expression was quantified by colorimetric assay on culture medium, showing successful expression of the SEAP gene encoded in the SG ORF.

FIG. 26F is a bar graph showing SEAP expression in BHK cells cultured in 12-well dishes 16 hours after transfection with 1 μg of VEEVrep-SEAP, VEEVrepES-SEAP, or VEEVrepES(ΔU)-SEAP RNA compared to untransfected control.

FIG. 26G is a bar graph showing serum SEAP expression measured in vivo (by chemiluminescent assay) after injection of 2 μg of LNP-formulated VEEVrep-SEAP, VEEVrepHK-SEAP, or VEEVrepHK(ΔU)-SEAP compared to control (serum from untreated mice).

FIG. 27A is bar graph showing SEAP expression in normal HFF cells cultured in 12-well dishes 1 days after transfection with 2 or 4 μg of the indicated replicon RNA, VEEVrep-nsP4[STING]-SEAP, VEEVrep-SEAP compared to untransfected control cells. In this experiment, SEAP expression was quantified by colorimetric assay on culture medium, showing successful expression of the SEAP gene encoded in the SG ORF.

FIG. 27B are photographs of GFP expression in trypsin-dissociated normal human HFF cells after transfection with 4 μg of VEEVrep-nsP4[GFP]-SEAP approximately 4 days post-transfection, showing no efficient gene expression from the nsP4 C-terminal encoded GFP protein in these healthy, non-cancerous cells.

FIG. 27C is a bar graph showing measurement of IFN-beta activity from transfected HFFs. Conditioned medium from HFFs in 12-well dishes was collected 1 day after transfection with the indicated RNAs, VEEVrep-nsP4[STING]-SEAP, VEEVrep-nsP4[GFP]-SEAP, VEEVrep-SEAP compared to control untransfected HFF cells, and no-medium control, and doses and applied to HEK-Lucia NULL cells to measure the response to type I IFNs in the medium. In this experiment, the next day, the IFN-responsive reporter gene Lucia was assayed in the supernatant by chemiluminescent assay.

FIG. 27D are photographs of light microscopy examination of HFF cells 4 days after transfection with 4 μg of the indicated replicon RNAs, VEEVrep-nsP4[GFP]-SEAP and VEEVrep-nsP4[STING]-SEAP compared to untransfected control.

DETAILED DESCRIPTION OF THE PREFERRED EMBODIMENTS

Figure 1:
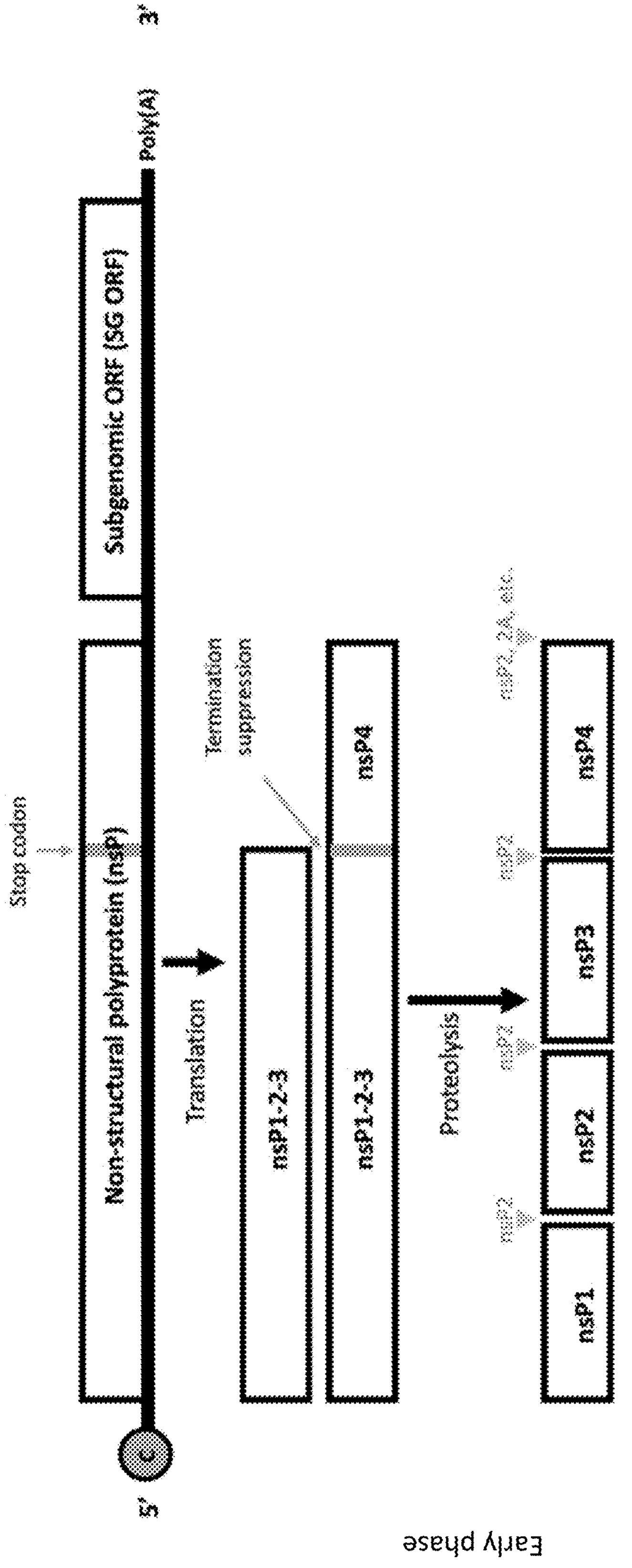
FIG. 1 is a schematic drawing illustrating the gene expression and post-translational processing steps of a wild-type alphavirus genome non-structural polyprotein (nsP1-nsP2-nsP3-nsP4).

The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

Alphavirus

As used herein, "alphavirus" refers to enveloped single-stranded positive sense RNA viruses of the family Togaviridae. The genus alphavirus contains approximately 30 members, which can infect humans as well as other animals. Alphavirus particles typically have a 70 nm diameter, tend to be spherical or slightly pleomorphic, and have a 40 nm isometric nucleocapsid.

The alphavirus genome is an approximately 12 000 nt long ssRNA molecule encoding two open reading frames (ORFs), the non-structural (ns) and structural (also referred to herein as subgenomic, or SG, ORF). The ns ORF begins close to the 5' end of the genome and represents the first two-thirds of the total genome length. It encodes the non-structural proteins (nsPs), i.e., nsP1, nsP2, nsP3, and nsP4, which are produced as a single polyprotein precursor, which is cleaved into the mature proteins through proteolytic processing. The nsPs are expressed by typical cap-dependent translation in the cell cytoplasm. After the infection, the alphavirus genomic RNA is translated to yield nsP polyprotein, which is cleaved into four proteins, nsP1, nsP2, nsP3, and nsP4 (FIG. 1), that act together to catalyze genome replication and transcription/translation of the second alphavirus ORF. nsP1 can be about 60 kDa in size and may have methyltransferase activity and be involved in the viral capping reaction. nsP2 has a size of about 90 kDa and may have helicase and protease activity while nsP3 is about 60 kDa and contains three domains: a macrodomain, a central (or alphavirus unique) domain, and a hypervariable domain (HVD). nsP4 is about 70 kDa in size and contains the core RNA-dependent RNA polymerase (RdRp) catalytic domain.

The structural SG ORF takes up approximately the one-third of the genome length, and in nature this ORF encodes the virion structural proteins: the core nucleocapsid protein C, and the envelope proteins P62 and E1 that associate as a heterodimer. The viral membrane-anchored surface glycoproteins are responsible for receptor recognition and entry into target cells through membrane fusion.

Translation of this SG ORF does not take place until the nsP products have mediated RNA-dependent RNA transcription of the genome to produce a complimentary negative-sense strand (−RNA) template. Starting from the 3' end of −RNA templates, the nsP products complete full-length transcription to recreate the original genome sequence, thus completing the cycle of genome copying. The onset of genome replication represents the transition from the 'early' phase of the virus replicative life cycle to the 'late' phase. As genome replication takes place via the creation of dsRNA intermediates, which constitute a pathogen-associated molecular pattern (PAMP), a strong innate immune response is triggered by intracellular pattern recognition receptors (PRRs). From −RNA templates, the nsP products also mediate transcription from an internal RNA-dependent RNA polymerase promoter ('sub-genomic promoter', or SGP) that maps to the genetic region immediately upstream of the second ORF (when read from the perspective of the original sense-strand RNA genome) to produce a smaller, or 'sub-genomic' (SG) mRNA that encodes only the second ORF. Transcription of the SG mRNA is more favored than transcription of the full-length genome, leading to a high copy number of the SG mRNA in infected cells and thus a high level of production of the structural genes encoded therein.

As used herein, RNA replicons refer to nucleic acid molecules derived in sequence from the genus alphavirus (family Togaviridae) genome that are capable of self-copying when introduced to the appropriate intracellular environment. Because they self-copy, RNA replicons may substantially amplify the production of an encoded protein, leading to sustained translation of a desired protein in vivo. The terms "replicon RNA" and "RNA replicon" are used herein interchangeably to refer to these RNA molecules.

In an embodiment, the RNA replicon may be an RNA replicon derived from an alphavirus species. The alphavirus specie may include but not be limited to Eastern equine encephalitis virus (EEEV), Venezuelan equine encephalitis virus (VEEV), Everglades virus (EVEV), Mucambo virus (MUCV), Semliki forest virus (SFV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), and Buggy Creek virus.

In an embodiment, RNA replicons may be replicons derived from the genomes of RNA viruses produced by natural selection.

In an embodiment, RNA replicons disclosed herein may be engineered, synthetic, or recombinant RNA replicons. The RNA replicons may be synthesized or modified in vitro. The modification may include, but not be limited to, the following procedures: performing chemical or enzymatic techniques, e.g., by using chemical nucleic acid synthesis, enzymes for the replication, polymerization, exonucleolytic digestion, endonucleolytic digestion, ligation, reverse transcription, transcription, base modification, e.g., methylation), or recombination of nucleic acid molecules. The RNA replicons may be engineered by using a rational design approach that selectively maintains critical sequence elements, additional functions and reduced homology to dangerous, circulating viruses. The RNA replicons may combine nucleotide sequences that are not combined in nature.

The RNA replicons may be manipulated using molecular cloning techniques such that it has one or more sequence changes or rearrangements with respect to the naturally occurring nucleotide sequence.

RNA replicons based on alphaviruses may be used as vectors for gene expression in vitro and in vivo. The structural genes of alphaviruses are encoded in a single subgenomic (SG) open reading frame (ORF) that may be replaced with a desired recombinant protein. The nonstructural (nsP) coding sequence in a separate, preceding ORF carries the necessary biochemical functionality to mediate replicon RNA replication within the cell, and translation of the SG ORF. When the nsP coding sequence is nearly identical in sequence to circulating alphaviruses, it generates the possibility of recombination in the field with pathogenic virus genomes and thus presents a safety risk. To prevent recombination with sequences of the pathogenic viruses, the nsP sequences may also be modified. Modification of the nsP is challenging as altering the primary amino acid sequence may affect biochemical function, and altering the primary nucleotide sequence may disrupt critical secondary structures required for translation and transcription of the replicon.

A Synthetic Alphavirus-Derived Replicon Nucleic Acid Molecule

In an embodiment, a synthetic alphavirus-derived replicon nucleic acid molecule is provided. The synthetic alphavirus-derived replicon nucleic acid molecule may comprise a first nucleic acid encoding alphavirus nonstructural proteins nsP1, nsP2, nsP3, and nsP4. The first nucleic acid may comprise a sequence ranging from the beginning of a 5' untranslated region (UTR) to the end of the subgenomic promoter (SGP). The first nucleic acid may comprise at least one silent mutation introduced at any position within a region from nt 503 to nt 658, nt 658 to nt 1620, nt 1620 to nt 2560, nt 2560 to nt 3954, nt 3954 to nt 4120, nt 6381 to nt 7083, and nt 6966 to nt 7526 in the sequence of the alphavirus genome as set forth in SEQ ID NO: 17. The synthetic alphavirus-derived replicon nucleic acid molecule may also comprise a second nucleic acid sequence comprising a modified subgenomic (SG) open reading frame (ORF). The modified SG ORF may comprise a sequence encoding a first heterologous protein. The first nucleic acid sequence may comprise a second heterologous protein encoded as a fusion to the C-terminal end of nsP4. The nsP4 coding sequence may contain at least one silent mutation introduced at any position within a region from nt 6966 to nt 7526.

As used herein, the term "heterologous protein" refers to any protein that is not present naturally in an organism.

As used herein, the term "silent mutation" refers to a change in the sequence of nucleotide bases that does not alter the amino acid sequence of an encoded protein. For instance, a silent mutation may be a point mutation that changes a first codon to a second codon that encodes for the same amino acid. A silent mutation may include changes in one or more than one nucleotide.

As used herein, the term "codon optimization" refers to a process used to improve gene expression and increase the translational efficiency of a gene of interest by accommodating codon bias of the host organism.

As used herein, the term "codon adaptation" refers to a process used to alter codons by silent mutation, such that the changes are selected so as not to affect secondary structure motifs as determined by bioinformatic analysis of RNA folding.

In an embodiment, the first nucleic acid may comprise at least one silent mutation introduced at any position within a region from nt 503 to nt 658 of the alphavirus genome. As used herein, all genome positions given refer to the Trinidad donkey strain of Venezuelan equine encephalitis virus, complete genome reference sequence L01442 in the NCBI GenBank database. (SEQ ID NO: 17; Kinney, R. M., Johnson, B. J., Brown, V. L. and Trent, D. W. 1986, Nucleotide sequence of the 26 S mRNA of the virulent Trinidad donkey strain of Venezuelan equine encephalitis virus and deduced sequence of the encoded structural proteins, Virology 152 (2), 400-413, which is incorporated herein by reference as if fully set forth).

The first nucleic acid that carries this silent mutation may comprise a polynucleotide encoding nsP1, and comprising a sequence with at least 70, 72, 75, 80, 85, 90, 91, 92, 93, 94, 95, 96, 97, 98, 99, or 100% identity to the reference sequence set forth in SEQ ID NO: 21.

In an embodiment, the first nucleic acid may comprise a sequence with at least one silent mutation introduced at any position within a region nt 658 to nt 1620 of the sequence of the sequence of the alphavirus genome as set forth in SEQ ID NO: 17. The first nucleic acid that carries this silent mutation may comprise a polynucleotide encoding nsP1, and comprising a sequence with at least 70, 72, 75, 80, 85, 90, 91, 92, 93, 94, 95, 96, 97, 98, 99, or 100% identity to the reference sequence set forth in SEQ ID NO: 25.

In an embodiment, the first nucleic acid may comprise a sequence with at least one silent mutation introduced at any position within a region nt 1620 to nt 2560 of the sequence of the alphavirus genome (SEQ ID NO: 17). The first nucleic acid including the silent mutation may comprise a polynucleotide encoding a junction of nsP1 and nsP2, and comprising a sequence with at least 70, 72, 75, 80, 85, 90, 91, 92, 93, 94, 95, 96, 97, 98, 99, or 100% identity to the reference sequence set forth in SEQ ID NO: 24.

In an embodiment, the first nucleic acid may comprise a sequence with at least one silent mutation introduced at any position within a region nt 3694 to nt 3954 of the sequence of the alphavirus genome (SEQ ID NO: 17). The first nucleic acid including the silent mutation may comprise a polynucleotide encoding a junction of nsP1 and nsP2, and comprising a sequence with at least 70, 72, 75, 80, 85, 90, 91, 92, 93, 94, 95, 96, 97, 98, 99, or 100% identity to the reference sequence set forth in SEQ ID NO: 22.

In an embodiment, the first nucleic acid may comprise a sequence with at least one silent mutation introduced at any position within a region from nt 2560 to nt 3954 of the sequence of the alphavirus genome (SEQ ID NO: 17). The nucleic acid including the silent mutation may comprise a polynucleotide encoding a junction of nsP1 and nsP2, and comprising a sequence with at least 70, 72, 75, 80, 85, 90, 91, 92, 93, 94, 95, 96, 97, 98, 99, or 100% identity to the reference sequence set forth in SEQ ID NO: 26.

In an embodiment, the first nucleic acid may comprise a sequence with at least one silent mutation is introduced at any position within a region from nt 3954 to nt 4120 of the sequence of the alphavirus genome (SEQ ID NO: 17). The first nucleic acid including the silent mutation may comprises a polynucleotide encoding a junction of nsP2 and nsP3, and comprising a sequence with at least 70, 72, 75, 80, 85, 90, 91, 92, 93, 94, 95, 96, 97, 98, 99, or 100% identity to the reference sequence set forth in SEQ ID NO: 23.

In an embodiment, the first nucleic acid may comprise a sequence with at least one silent mutation introduced at any position within a region from nt 6381 to nt 7083 of the sequence of the alphavirus genome (SEQ ID NO: 17). The first nucleic acid including the silent mutation may comprise a polynucleotide encoding nsP4 and comprising a sequence with at least 70, 72, 75, 80, 85, 90, 91, 92, 93, 94, 95, 96, 97, 98, 99, or 100% identity to the reference sequence set forth in SEQ ID NO: 20.

In an embodiment, the first nucleic acid sequence may comprise a sequence at least one silent mutation introduced at any position within a region from nt 6966 to nt 7526 of the sequence of the alphavirus genome (SEQ ID NO: 17). The first nucleic acid including the silent mutation may comprise a polynucleotide encoding the C-terminal region of nsP4 and comprising a sequence with at least 70, 72, 75, 80, 85, 90, 91, 92, 93, 94, 95, 96, 97, 98, 99, or 100% identity to the reference sequence set forth in SEQ ID NO: 18 or 19.

In an embodiment, the first nucleic acid may comprise a sequence with the silent mutation in more than one region of the genome. The nucleic acid may comprise more than one silent mutation introduced at any position within a region from nt 658 to nt 1620 and within a region of nt 2560 to nt 3954 of the sequence of alphavirus genome (SEQ ID NO: 17). The first nucleic acid including the silent mutation may comprise a polynucleotide encoding nsP1, and comprising a sequence with at least 70, 72, 75, 80, 85, 90, 91, 92, 93, 94, 95, 96, 97, 98, 99, or 100% identity to the reference sequence set forth in SEQ ID NO: 25, and a polynucleotide encoding nsP2, and comprising a sequence with at least 70, 72, 75, 80, 85, 90, 91, 92, 93, 94, 95, 96, 97, 98, 99, or 100% identity to the reference sequence set forth in SEQ ID NO: 26.

In an embodiment, the first nucleic acid may comprise a sequence with more than one silent mutation introduced at any position within a region from nt 3694 to nt 3954 and a region within nt 6381 to nt 7083 of the sequence of the alphavirus genome (SEQ ID NO: 17). The first nucleic acid including these silent mutations may comprise a polynucleotide encoding nsP2, and comprising a sequence with at least 70, 72, 75, 80, 85, 90, 91, 92, 93, 94, 95, 96, 97, 98, 99, or 100% identity to the reference sequence set forth in SEQ ID NO: 22, and a polynucleotide encoding nsP4, and comprising a sequence with at least 70, 72, 75, 80, 85, 90, 91, 92, 93, 94, 95, 96, 97, 98, 99, or 100% identity to the reference sequence set forth in SEQ ID NO: 20.

In an embodiment, the first nucleic acid may comprise a sequence with more than one silent mutation introduced at any position within a region from nt 503 to nt 658, within a region from nt 658 to nt 1620, within a region from nt 1620 to nt 2560, within a region from nt 2560 to nt 3954, within a region from nt 3954 to nt 4120 and within a region from nt 6381 to nt 7083 of the sequence of the alphavirus genome (SEQ ID NO: 17). The first nucleic acid including these silent mutations may comprise a polynucleotide encoding nsP1, and comprising a sequence with at least 70, 72, 75, 80, 85, 90, 91, 92, 93, 94, 95, 96, 97, 98, 99, or 100% identity to the reference sequence set forth in SEQ ID NO: 21; a polynucleotide encoding nsP1, and comprising a sequence with at least 70, 72, 75, 80, 85, 90, 91, 92, 93, 94, 95, 96, 97, 98, 99, or 100% identity to the reference sequence set forth in SEQ ID NO: 25 a polynucleotide encoding a junction of nsP1 and nsP2, and comprising a sequence with at least 70, 72, 75, 80, 85, 90, 91, 92, 93, 94, 95, 96, 97, 98, 99, or 100% identity to the reference sequence set forth in SEQ ID NO: 24 a polynucleotide encoding nsP2, and comprising a sequence with at least 70, 72, 75, 80, 85, 90, 91, 92, 93, 94, 95, 96, 97, 98, 99, or 100% identity to the reference sequence set forth in SEQ ID NO: 26; a polynucleotide encoding a junction of nsP2 and nsP3, and comprising a sequence with at least 70, 72, 75, 80, 85, 90, 91, 92, 93, 94, 95, 96, 97, 98, 99, or 100% identity to the reference sequence set forth in SEQ ID NO: 23; and a polynucleotide encoding nsP4, and comprising a sequence with at least 70, 72, 75, 80, 85, 90, 91, 92, 93, 94, 95, 96, 97, 98, 99, or 100% identity to the reference sequence set forth in SEQ ID NO: 20. The first nucleic acid including these silent mutations may comprise a polynucleotide encoding the nonstructural protein comprises a sequence with at least 70, 72, 75, 80, 85, 90, 91, 92, 93, 94, 95, 96, 97, 98, 99, or 100% identity to the reference sequence as set forth in SEQ ID NO: 30.

Determining percent identity of two amino acid sequences or two nucleic acid sequences may include aligning and comparing the amino acid residues or nucleotides at corresponding positions in the two sequences. If all positions in two sequences are occupied by identical amino acid residues or nucleotides then the sequences are said to be 100% identical. Percent identity is measured by the Smith Waterman algorithm (Smith T F, Waterman M S 1981 "Identification of Common Molecular Subsequences," J Mol Biol 147: 195-197, which is incorporated herein by reference as if fully set forth).

In an embodiment, the first nucleic acid may comprise a sequence of the nsP region of one of the alphaviruses listed in TABLE 1, wherein more than one silent mutation in the nsP1 coding sequence is created at a position later than amino acid position 85 such that 10-30% of the nucleotides differ from the wild-type nsP1 coding sequence.

TABLE 1

Alphaviruses and their corresponding nsP regions that can be modified as described herein by silent mutation to reduce homology to their cognate wild-type genome

| Antigenic Complex | Species | Sub Type | Reference sequence (NCBI GenBank) | nsP protein reference sequence | nsPamino acid positions | | | |
|---|---|---|---|---|---|---|---|---|
| | | | | | nsP1 | nsP2 | nsP3 | nsP4 |
| Barmah Forest virus complex | Barmah Forest virus | | NC_001786 | P87515 | 1-533 | 534-1331 | 1332-1801 | 1802-2411 |
| Eastern equine encephalitis complex | Eastern equine encephalitis virus | | NC_003899 | NP_632021 | 1-532 | 533-1326 | 1327-1878 | 1880-2493 |
| Middelburg virus complex | Middelburg virus | | NC_024887 | YP_009058892 | 1-537 | 538-1336 | 1327-1794 | 1795-2411 |

TABLE 1-continued

Alphaviruses and their corresponding nsP regions that can be modified as described herein by silent mutation to reduce homology to their cognate wild-type genome

| Antigenic Complex | Species | Sub Type | Reference sequence (NCBI GenBank) | nsP protein reference sequence | nsPamino acid positions nsP1 | nsP2 | nsP3 | nsP4 |
|---|---|---|---|---|---|---|---|---|
| Ndumu virus complex | Ndumu virus | | NC_016959 | YP_008888544 | 1-538 | 539-1332 | 1333-1822 | "1823-2433 |
| Semliki Forest virus complex | Bebaru virus | | NC_016962 | YP_008901140 | 1-535 | 536-1334 | 1335-1845 | 1846-2456 |
| | Chikungunya virus | | NC_004162 | Q8JUX6 | 1-535 | 536-1333 | 1334-1863 | 1864-2474 |
| | Getah virus | | NC_006558 | YP_164438 | 1-534 | 535-1332 | 1333-1856 | 1857-2467 |
| | Mayaro virus | | NC_003417 | NP_579968 | 1-538 | 539-1334 | 1335-1819 | 1820-2437 |
| | | Sub type: Una virus | NC_043403 | YP_009665988 | 1-560 | 561-1359 | 1360-1916 | N/A |
| | O'nyong'ny ong virus | | NC_001512 | NP_041254 | 1-535 | 536-1333 | 1334-1903 | 1904-2514 |
| | | Sub type: Igbo-Ora virus | MF409176 | O90370 | 1-535 | 536-1333 | 1334-1902 | 1903-2513 |
| | Ross River virus | | NC_001544 | NP_062879 | 1-533 | 534-1331 | 1332-1869 | 1870-2480 |
| | | Sub type: Sagiyama virus | MW410934 | Q9JGLO | 1-534 | 535-1332 | 1333-1856 | 1857-2467 |
| Venezuelan equine encephalitis complex | Cabassou virus | | NC_038670 | YP_009507794 | 1-535 | 536-1329 | 1330-1844 | 1845-2451 |
| | Everglades virus | | NC_038671 | YP_009507796 | 1-535 | 536-1329 | 1330-1871 | 1872-2478 |
| | Mossodas Pedras virus | | NC_038857 | YP_009508088 | 1-535 | 536-1329 | 1330-1899 | 1900-2505 |
| | Mucambo virus | | NC_038672 | YP_009507798 | 1-535 | 536-1329 | 1330-1848 | 1849-2455 |
| | Pixuna virus | | NC_038673 | YP_009507800 | 1-535 | 536-1329 | 1330-1870 | 1871-2477 |
| | Rio Negro virus | | NC_038674 | YP_009507802 | 1-535 | 536-1329 | 1330-1874 | 1875-2480 |
| | Venezuelan equine encephalitis virus | | NC_001449 | NP_040822 | 1-535 | 536-1329 | 1330-1886 | 1887-2492 |
| Western equine encephalitis (WEE) complex | Aura virus | | NC_003900 | NP_632023 | 1-539 | 540-1345 | 1346-1889 | 1890-2499 |
| | Sindbis virus | | NC_001547 | P03317 | 1-540 | 541-1347 | 1348-1903 | 1904-2513 |
| | Ockelbo virus | | M69205 | AAA96972 | 1-540 | 541-1347 | 1348-1905 | 1906-2515 |
| | Whataroa virus | | NC_016961 | YP_008888546 | 1-540 | 541-1347 | 1348-1861 | 1862-2471 |
| Recom binant species within the WEE complex | Fort Morgan virus | | NC_013528 | YP_003324587 | 1-533 | 534-1327 | 1328-1849 | 1850-2457 |
| | Highlands J virus | | NC_012561 | YP002802299 | 1-533 | 534-1327 | 1328-1842 | 1843-2450 |
| | Western equine encephalitis virus | | NC_003908 | NP_640330 | 1-533 | 534-1327 | 1328-1859 | 1860-2467 |
| Unclassified | Eilat virus | | NC_018615 | YP_008901141 | 1-543 | 544-1352 | 1353-1998 | 1999-2415 |
| | Mwinilunga alpha-virus | | LC361437 | BBC45634 | 1-543 | 545-1352 | 1354-1975 | 1976-2438 |
| | Sleeping disease virus | | NC_003433 | NP_598184 | 1-563 | 564-1420 | 1421-1984 | 1985-2593 |

TABLE 1-continued

Alphaviruses and their corresponding nsP regions that can be modified as described herein by silent mutation to reduce homology to their cognate wild-type genome

| Antigenic Complex | Species | Sub Type | Reference sequence (NCBI GenBank) | nsP protein reference sequence | nsPamino acid positions nsP1 | nsP2 | nsP3 | nsP4 |
|---|---|---|---|---|---|---|---|---|
| | Salmon pancreatic disease virus | | NC_003930 | NP_647496 | 1-562 | 563-1421 | 1422-1992 | 1993-2601 |
| | Southern elephant seal virus | | NC_016960 | YP_008888545 | 1-548 | 549-1343 | 1344-1832 | 1833-2442 |
| | Tonate virus | | NC_038675 | YP_009507804 | 1-535 | 536-1329 | 1330-1894 | 1895-2501 |
| | Caaingua virus | | MK353339 | QBM15857 | 1-535 | 536-1361 | 1362-2028 | 2029-2636 |
| | Harbor porpoise alpha-virus | | N/A | QJE50387 | 1-538 | 539-1360 | 1361-1879 | 1880-2489 |

In an embodiment, the first nucleic acid may comprise a sequence of the nsP region of one of the alphaviruses listed in TABLE 1, wherein more than one silent mutation in the nsP2 coding sequence is created such that 10-30% of the nucleotides differ from the wild-type nsP2 coding sequence.

In an embodiment, the first nucleic acid may comprise a sequence of the nsP region of one of the alphaviruses listed in TABLE 1, wherein more than one silent mutation in the nsP3 coding sequence is created such that 10-30% of the nucleotides differ from the wild-type nsP3 coding sequence.

In an embodiment, the first nucleic acid may comprise a sequence of the nsP region of one of the alphaviruses listed in TABLE 1, wherein more than one silent mutation in the nsP4 coding sequence is created at a position preceding the last 30 amino acids of the nsP, such that 10-30% of the nucleotides differ from the wild-type nsP4 coding sequence.

In an embodiment, the first nucleic acid may comprise a sequence of the nsP region of one of the alphaviruses listed in TABLE 1, wherein more than one silent mutation in the nsP4 coding sequence is created at a position within the last 30 amino acids of the nsP, such that 10-30% of the nucleotides differ from the wild-type nsP4 coding sequence and reduce homology to the endogenous SGP.

In an embodiment, the alphavirus-derived replicon nucleic acid molecule based on one of the species in TABLE 1 may comprise a second nucleic acid comprising a polynucleotide that encodes a first heterologous protein. The first heterologous protein may be a protein that replaces an alphavirus structural protein encoded by the alphavirus subgenomic (SG) ORF.

In an embodiment, the alphavirus-derived replicon nucleic acid molecule may comprise a polynucleotide that encodes a second heterologous protein. The second heterologous protein may be a protein inserted into an altered nsP1, nsP2, nsP3, or nsP4 protein.

In an embodiment, the altered nsP protein may be an altered nsP4 protein. The altered nsP4 may comprise a second heterologous protein fused to its C-terminal region. The polynucleotide sequence that encodes the heterologous C-terminal region may comprise at its 3' end a sequence encoding an alphaviral subgenomic promoter. The sequence may be inserted downstream (i.e. 3' of) the nsP4 coding sequence region and may be translatable into a protein. Alternatively, this inserted sequence may not be translated into a protein. An untranslated sequence inserted in this region may be a short hairpin RNA (shRNA).

In an embodiment, the altered nsP4 may comprise a GFP protein as the second heterologous protein. The altered nsP4 may comprise an amino acid sequence with at least 70, 72, 75, 80, 85, 90, 91, 92, 93, 94, 95, 96, 97, 98, 99, or 100% identity to the reference sequence as set forth in SEQ ID NO: 12 or 41. The altered nsP4 may be encoded by a polynucleotide sequence set forth in SEQ ID NO: 31. The altered nsP4 may comprise an amino acid sequence with at least 70, 72, 75, 80, 85, 90, 91, 92, 93, 94, 95, 96, 97, 98, 99, or 100% identity to the reference sequence as set forth in SEQ ID NO: 15.

The first heterologous protein (in the SG ORF) or the second heterologous protein (in the nsP ORF) may be any antigenic protein isolated or derived from a viral pathogen. The viral pathogen may be selected from the family of Adenoviridae, Papovaviridae, Parvoviridae, Herpesviridae, Poxviridae, Anelloviridae, Pleolipoviridae, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, Hepeviridae, Retroviridae, Caulimoviridae, or Hepadnaviridae. For example, the viral pathogen may be adenovirus, rhinovirus, rotavirus, West Nile virus, Zika virus, herpes, filovirus, or coronavirus (CoV). The coronavirus may be one of MERS CoV, SARS-CoV, and SARS-CoV-2.

As used herein, the term "antigenic protein" refers to a protein comprising one or more antigenic determinants that triggers an immune response. The immune response may involve either antibody production, or the activation of specific immunologically active cells, or both. The antigenic protein may be a structural component of a pathogen, or a cancer cell. The antigenic protein may be synthesized, produced recombinantly in a host, or may be derived from a biological sample, including but not limited to a tissue sample, cell, or a biological fluid.

The antigenic protein may be but is not limited to a parasite antigenic protein, bacterial antigenic protein, tumor antigenic protein, environmental antigenic protein, therapeutic antigenic protein, or an allergen. The antigenic protein may be a protein comprising one or more antigenic determinants of the viral pathogen described herein.

In an embodiment, the first heterologous protein or the second heterologous protein may be an enzyme. The enzyme may be of mammalian origin and regulate cell metabolism or cell signaling. The enzyme may be a cellular or viral protease. The viral protease may be a picornavirus 3C protease (3Cpro). As used herein, the terms "3 $C^{pro}$", "3C protease", "3Cpro" or "3CP" refer to a cysteine protease found in a picornavirus species, which typically contains a conserved Cysteine-Histidine-Aspartic Acid/Glutamic Acid catalytic triad or a Cysteine-Histidine dyad within its active site. The catalytic triad or dyad typically forms a charge-relay network that polarizes and activates the nucleophile (typically, cysteine) attacking the substrate to form a covalent intermediate, which is then hydrolyzed to regenerate free enzyme. $3C^{pro}$ conducts maturation cleavage in the structural and non-structural regions of the polyprotein and to have significant substrate preference in Glutamine-Glycine/Serine/Alanine/Valine/Histidine/Arginine and Glutamic Acid-Serine/Glycine/Arginine/Methionine. The 3Cpro protease may derive from the foot-and-mouth disease virus (FMDV).

FMDV 3C proteases are cysteine proteases having a molecular weight of about 23.1-kDa and which contain 213 amino acids. The cysteine-histidine-aspartic acid catalytic triad at the active site of the FMDV 3C protease is formed by the residues 1146, D84 and C163.

In an embodiment, the altered nsP4 may comprise the second heterologous protein that is a 3Cprotease. The altered nsP4 may comprise an amino acid sequence with at least least 70, 72, 75, 80, 85, 90, 91, 92, 93, 94, 95, 96, 97, 98, 99, or 100% identity to the reference sequence as set forth in SEQ ID NO: 40. The altered nsP4 comprising a 3Cprotease may be encoded by a polynucleotide sequence with at least 70, 72, 75, 80, 85, 90, 91, 92, 93, 94, 95, 96, 97, 98, 99, or 100% identity to the reference sequence set forth in SEQ ID NO: 32.

In an embodiment, the synthetic alphavirus-derived replicon nucleic acid molecule my further comprise the first heterologous protein that is an FMDV P1 precursor polypeptide or other polypeptide of interest. The FMDV P1 may derive from FMDV serovar O1 Manisa, and is referred to herein as O1 Manisa P1 polyprotein. The O1 Manisa P1 polyprotein may be encoded by a polynucleotide with at least 70, 72, 75, 80, 85, 90, 91, 92, 93, 94, 95, 96, 97, 98, 99, or 100% identity to the reference sequence set forth in SEQ ID NO: 33.

In an embodiment, the first heterologous protein may be FMDV P1 precursor polypeptide (O1 Manisa P1 polyprotein), and the second heterologous protein may be a 3C protease.

The first or second heterologous proteins may be a virus-derived or mammalian cell-derived regulator of cellular metabolic, immune, or signaling function. The expression of this heterologous protein may affect the cellular anti-viral innate immune response such that it enhances replication of alphaviral replicon RNA molecules.

In an embodiment, the second heterologous protein may be pattern recognition receptor (PRR) protein. The PRR protein may be a STING (stimulator of interferon genes) protein. The STING protein may be a wild type STING protein. The altered nsP4 comprising the STING protein may comprise an amino acid sequence with at least 70, 72, 75, 80, 85, 90, 91, 92, 93, 94, 95, 96, 97, 98, 99, or 100% identity to the reference sequence as set forth in SEQ ID NO: 42. The altered nsP4 comprising the STING protein may be encoded by a polynucleotide sequence with at least 70, 72, 75, 80, 85, 90, 91, 92, 93, 94, 95, 96, 97, 98, 99, or 100% identity to the reference sequence set forth in SEQ ID NO: 34. The first heterologous protein may comprise an antigenic protein protein and the second heterologous protein may comprise a STING protein.

The first heterologous protein or the second heterologous protein may be any immunogenic polypeptide suitable for protecting a subject against a disease. The disease may be cancer, or disease caused by a microbial, bacterial, protozoal, parasitic, or viral pathogen.

The first heterologous protein may be the same protein as the second heterologous protein.

In an embodiment, a synthetic alphavirus-derived replicon nucleic acid molecule may comprise a translation interrupter sequence, such as a 2A sequence. A translation interrupter sequence permits interruption of protein translation and effective cleavage at a site not necessarily recognized by a protease such as a site in an altered nsP4 protein. The 2A sequence may be inserted in the nucleic acid sequence encoding the altered nsP4 prior to the sequence encoding a second heterologous protein. Insertion of the 2A sequence may result in interruption of translation by 2A and production of a polypeptide not having an N-terminal Met residue. The 2A sequence may be an amino acid sequence of a 2A derived from, but not limited to, a Thosea asigna virus (SEQ ID NO: 43), porcine teschovirus-1 (SEQ ID NO: 44), foot-and-mouth disease virus (SEQ ID NO: 45), equine rhinitis A virus (SEQ ID NO: 46), or other Picornaviridae or Permutotetraviridae viruses.

In an embodiment, a synthetic alphavirus-derived replicon nucleic acid molecule may comprise a subgenomic (SGP) promoter that directs expression of sequences encoding the first heterologous protein and/or second heterologous protein. The subgenomic promoter may be 26S subgenomic promoter derived from a species of alphavirus (see TABLE 1). The sequences encoding heterologous proteins may also may be under the control of an internal ribosome entry site (IRES).

A synthetic alphavirus-derived replicon nucleic acid molecule described herein may comprise one or more modified nucleotides. The modified nucleotides may be 5-methyluridine, 5-methylcytidine, pseudouridine, or N6-methyladenosine.

A synthetic alphavirus-derived replicon nucleic acid molecule may have a 3' poly-A tail.

In an embodiment, the RNA sequence of the synthetic alphavirus-derived replicon nucleic acid molecule may be codon optimized to improve translation efficiency. The RNA molecule may be modified by any method known in the art to enhance stability and/or translation. The RNA molecule may be modified by adding a polyA tail, for example, of at least 30 adenosine residues. The RNA molecule may be modified by capping the 5-end with a modified ribonucleotide, for example, 7-methylguanosine cap, which may be incorporated during RNA synthesis or enzymatically engineered after RNA transcription.

In an embodiment, a nucleic acid comprising a DNA sequence encoding a synthetic alphavirus-derived replicon nucleic acid molecule is provided. The nucleic acid may be, for example, a DNA plasmid or a fragment of a linearized DNA plasmid. The nucleic acid may further comprise a promoter, such as a T7 promoter, operably linked to the 5'-end of the DNA sequence. The nucleic acid may be used for the production of an RNA replicon of the application using a method known in the art in view of the present disclosure. For example, a synthetic alphavirus-derived replicon nucleic acid molecule may be obtained by in vivo or in vitro transcription of the nucleic acid.

In an embodiment, the DNA sequence may be a DNA plasmid. The DNA plasmid may comprise a polynucleotide encoding nsP1 and comprising a sequence with at least 70, 72, 75, 80, 85, 90, 91, 92, 93, 94, 95, 96, 97, 98, 99, or 100% identity to the reference sequence set forth in SEQ ID NO: 2.

The DNA plasmid may comprise a polynucleotide encoding nsP1, and comprising a sequence with at least 70, 72, 75, 80, 85, 90, 91, 92, 93, 94, 95, 96, 97, 98, 99, or 100% identity to the reference sequence set forth in SEQ ID NO: 6.

The DNA plasmid may comprise a polynucleotide encoding a junction of nsP1 and nsP2, and comprising a sequence with at least 70, 72, 75, 80, 85, 90, 91, 92, 93, 94, 95, 96, 97, 98, 99, or 100% identity to the reference sequence set forth in SEQ ID NO: 5.

The DNA plasmid may comprise a polynucleotide encoding a junction of nsP1 and nsP2, and comprising a sequence with at least 70, 72, 75, 80, 85, 90, 91, 92, 93, 94, 95, 96, 97, 98, 99, or 100% identity to the reference sequence set forth in SEQ ID NO: 3.

The DNA plasmid may comprise a polynucleotide encoding a junction of nsP1 and nsP2, and comprising a sequence with at least 70, 72, 75, 80, 85, 90, 91, 92, 93, 94, 95, 96, 97, 98, 99, or 100% identity to the reference sequence set forth in SEQ ID NO: 7.

The DNA plasmid may comprise a polynucleotide encoding a junction of nsP2 and nsP3, and comprising a sequence with at least 70, 72, 75, 80, 85, 90, 91, 92, 93, 94, 95, 96, 97, 98, 99, or 100% identity to the reference sequence set forth in SEQ ID NO: 4.

The DNA plasmid may comprise a polynucleotide encoding nsP4 and comprising a sequence with at least 70, 72, 75, 80, 85, 90, 91, 92, 93, 94, 95, 96, 97, 98, 99, or 100% identity to the reference sequence set forth in SEQ ID NO: 1.

The DNA plasmid may comprise a polynucleotide encoding nsP1, and comprising a sequence with at least 70, 72, 75, 80, 85, 90, 91, 92, 93, 94, 95, 96, 97, 98, 99, or 100% identity to the reference sequence set forth in SEQ ID NO: 6, and a polynucleotide encoding nsP2, and comprising a sequence with at least 70, 72, 75, 80, 85, 90, 91, 92, 93, 94, 95, 96, 97, 98, 99, or 100% identity to the reference sequence set forth in SEQ ID NO: 7.

The DNA plasmid may comprise a polynucleotide encoding nsP2, and comprising a sequence with at least 70, 72, 75, 80, 85, 90, 91, 92, 93, 94, 95, 96, 97, 98, 99, or 100% identity to the reference sequence set forth in SEQ ID NO: 3, and a polynucleotide encoding nsP4, and comprising a sequence with at least 70, 72, 75, 80, 85, 90, 91, 92, 93, 94, 95, 96, 97, 98, 99, or 100% identity to the reference sequence set forth in SEQ ID NO: 1.

The DNA plasmid may comprise a polynucleotide encoding nsP1, and comprising a sequence with at least 70, 72, 75, 80, 85, 90, 91, 92, 93, 94, 95, 96, 97, 98, 99, or 100% identity to the reference sequence set forth in SEQ ID NO: 2; a polynucleotide encoding nsP1, and comprising a sequence with at least 70, 72, 75, 80, 85, 90, 91, 92, 93, 94, 95, 96, 97, 98, 99, or 100% identity to the reference sequence set forth in SEQ ID NO: 6, a polynucleotide encoding a junction of nsP1 and nsP2, and comprising a sequence with at least 70, 72, 75, 80, 85, 90, 91, 92, 93, 94, 95, 96, 97, 98, 99, or 100% identity to the reference sequence set forth in SEQ ID NO: 5 a polynucleotide encoding nsP2, and comprising a sequence with at least 70, 72, 75, 80, 85, 90, 91, 92, 93, 94, 95, 96, 97, 98, 99, or 100% identity to the reference sequence set forth in SEQ ID NO: 7; a polynucleotide encoding a junction of nsP2 and nsP3, and comprising a sequence with at least 70, 72, 75, 80, 85, 90, 91, 92, 93, 94, 95, 96, 97, 98, 99, or 100% identity to the reference sequence set forth in SEQ ID NO: 4; and a polynucleotide encoding nsP4, and comprising a sequence with at least 70, 72, 75, 80, 85, 90, 91, 92, 93, 94, 95, 96, 97, 98, 99, or 100% identity to the reference sequence set forth in SEQ ID NO: 1. The first nucleic acid including these silent mutations may comprise a polynucleotide encoding the nonstructural protein comprises a sequence with at least 70, 72, 75, 80, 85, 90, 91, 92, 93, 94, 95, 96, 97, 98, 99, or 100% identity to the reference sequence as set forth in SEQ ID NO: 11.

In an embodiment, the nucleic acid comprising a DNA sequence encoding the alphavirus-derived replicon nucleic acid molecule may comprise a second nucleic acid comprising a polynucleotide that encodes a first heterologous protein. The first heterologous protein may be a protein that replaces an alphavirus structural protein encoded by the alphavirus SG ORF.

In an embodiment, the nucleic acid may comprise a polynucleotide that encodes a second heterologous protein. The second heterologous protein may be a protein inserted into an altered nsP1, nsP2, nsP3, or nsP4 protein.

In an embodiment, the altered nsP protein may be an altered nsP4 protein. The altered nsP4 may comprise a second heterologous protein. The polynucleotide encoding the altered nsP4 may comprise a polynucleotide sequence encoding a first C-terminal region and a polynucleotide sequence encoding a second C-terminal region. The polynucleotide sequence that encodes the second C-terminal region may comprise a sequence encoding an alphaviral subgenomic promoter. The sequence encoding a subgenomic promoter may have at least 70, 72, 75, 80, 85, 90, 91, 92, 93, 94, 95, 96, 97, 98, 99, or 100% identity to the sequence set forth in SEQ ID NO: 14.

In an embodiment, the altered nsP4 may comprise a GFP protein as the second heterologous protein. The altered nsP4 may comprise an amino acid sequence with at least 70, 72, 75, 80, 85, 90, 91, 92, 93, 94, 95, 96, 97, 98, 99, or 100% identity to the reference sequence as set forth in SEQ ID NO: 12. The altered nsP4 may be encoded by a polynucleotide sequence set forth in SEQ ID NO: 13. The altered nsP4 may comprise an amino acid sequence with at least 70, 72, 75, 80, 85, 90, 91, 92, 93, 94, 95, 96, 97, 98, 99, or 100% identity to the reference sequence as set forth in SEQ ID NO: 15. The altered nsP4 may be encoded by a polynucleotide sequence set forth in SEQ ID NO: 16.

An Alphavirus-Derived RNA Replicon Expression System

In an embodiment, an alphavirus-derived RNA replicon expression system is provided. The alphavirus-derived RNA replicon expression system may comprise any one of the synthetic alphavirus-derived replicon nucleic acid molecules described herein and a host cell or cells.

The host cells may be, but not limited to, hamster ovary (CHO) cells, tumor cell lines, BHK cells, human cell lines, for example, HEK293 cells, PER.C6 cells. The host cells may be yeast, fungi, insect cells, animal or plant cells. Untransformed primary normal cells from humans or any mammalian species may be used, such as fibroblasts, stem cells, or cells of lymphoid or myeloid lineage.

In an embodiment, the production of a first heterologous protein and/or second heterologous protein in a host cell comprises the introduction of the synthetic alphavirus-derived replicon nucleic acid molecule comprising a nucleic acid sequence encoding a first heterologous protein and/or the second heterologous protein to be expressed the host cell, culturing the host cell under conditions suitable for expression of the nucleic acid molecules and allowing expression of the first heterologous protein and/or second heterologous protein in the host cell.

For expression in the host cell, a synthetic alphavirus-derived replicon nucleic acid molecule comprising a nucleic acid sequence encoding a first heterologous protein and/or the second heterologous protein may be included in an expression cassette that comprises regulatory sequences required for or promoting expression of the nucleic acid sequences. The regulatory sequences may include promoter, enhancer, promoter, and/or polyadenylation signal, and the like. The various promoters known in the art may be used for expressing nucleic acids disclosed herein in host cells. The promoters may be constitutive or inducible promoters. The promoters may be derived from prokaryotic or eukaryotic organisms, or may be designed artificially. The host cells may be cultured in suitable culture media commercially available for culturing cells for expressing the first heterologous protein and/or the second heterologous protein.

An embodiment provides a host cell that contains a synthetic alphavirus-derived replicon nucleic acid molecule comprising a nucleic acid sequence encoding a 3C protease. The host cell may also comprise one or more polynucleotide constructs encoding an FMDV P1 precursor polypeptide or other polypeptide of interest.

Method of Producing at Least One Heterologous Protein

In an embodiment, a method of producing at least one heterologous protein in a cell is provided. The method may comprise expressing any one of the synthetic alphavirus-derived replicon nucleic acid molecules described herein in the cell.

The successful editing of the nsP gene region of alphavirus replicons to reduce homology to wild-type virus, and incorporate novel biological function into the early phase of self-amplification of such artificial replicons that precedes translation of subgenomically encoded transgenes is herein described. This may be accomplished by identifying key stretches of nucleotides in the nsP region that can be safely edited without disrupting conserved structural elements, and appending additional sequences to the natural terminus of the nsP. This disclosure demonstrates how such modifications can be performed without impairing the self-amplifying functionality of the replicon. Therefore, the disclosure provides a method to generate safer replicons equipped with additional functionality to modify cellular and immunological parameters of the host cell.

In an embodiment, the method may comprise culturing the host cell using a suitable medium, and expressing a 3C protease in the host cell. The method may also comprise expressing and/or processing FMVD P1 precursor polypeptide (or other polypeptides of interest) into FMDV viral proteins. The method may comprise culturing the host cell and recovering viral proteins VP0, VP1, VP2, VP3, or VP4, or other cleavage products of the 3C protease.

In an embodiment, the method may comprise culturing the host cell and expressing contains a synthetic alphavirus-derived replicon nucleic acid molecule comprising a nucleic acid sequence encoding O1 Manisa P1 polyprotein as the first heterologous protein and a 3C protease as the second heterologous protein.

In an embodiment, the method may comprise culturing a synthetic alphavirus-derived replicon nucleic acid molecule containing a translation interrupter sequence, such as a 2A sequence. A translation interrupter sequence permits interruption of protein translation and effective cleavage at a site not necessarily recognized by a 3C protease such as a site in the altered nsP4 protein. The 2A sequence may be inserted in the nucleic acid sequence encoding the altered nsP4 prior to the sequence encoding a second heterologous protein. Insertion of the 2A sequence may result in interruption of translation by 2A and production of a polypeptide not having an N-terminal Met residue.

Compositions

In an embodiment, the synthetic alphavirus-derived replicon nucleic acid molecule or heterologous proteins described herein may be administered in a composition.

In an embodiment, the composition may be a treatment for autoimmune or allergic diseases. The treatment may comprise any one of alphavirus-derived replicon nucleic acid molecules comprising heterologous proteins described herein that express factors that inhibit or otherwise reduce the adaptive immune response against a desired target antigen.

In an embodiment, the composition may comprise the synthetic alphavirus-derived replicon nucleic acid molecule for expressing a target-specific antigen The target-specific antigen may be a tumor antigen. Cancer-specific antigen may be derived from either one of: total mRNA isolated from (a) target cell(s), one or more specific target mRNA molecules, protein lysates of (a) target cell(s), specific proteins from (a) target cell(s), or a synthetic target-specific peptide or protein and synthetic mRNA or DNA encoding a target-specific antigen or its derived peptides. Non-limiting examples are the following cancer or tumor-specific antigens: WT1, MUC1, LMP2, HPV E6 E7, EGFRvIII, HER-2/neu, Idiotype, MAGE A3, p53 (non-mutant), NY-ESO-1, PSMA, GD2, CEA, MelanA/MART1, Ras-mutant, gp100, p53 mutant, Proteinase3 (PR1), Bcr-abl, Tyrosinase, Survivin, PSA, hTERT, Sarcoma translocation breakpoints, EphA2, PAP, ML-IAP, AFP, EpCAM, ERG (TMPRSS2 ETS fusion gene), NA17, PAX3, ALK, Androgen receptor, Cyclin B1, Polysialic Acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-beta, MAD-CT-2, Fos-related antigen 1.

In an embodiment, the composition may be a treatment for cancer. The treatment may comprise any one of alphavirus-derived replicon nucleic acid molecules comprising heterologous proteins described herein that express factors that inhibit or otherwise reduce growth or proliferation of tumor cells in the body of a human or animal.

In an embodiment, the composition may comprise a 3C protease. Such composition may be used to induce or detect immune responses against the 3C protease, such as humoral or cellular immune responses directed against the 3C protease. The composition may further comprise precursor polypeptides, e.g., FMDV P1 precursor, that contain sites recognized by the modified FMDV 3C protease. The composition may be in a form useful for processing precursor polypeptides in vitro.

In an embodiment, the composition may be a vaccine. The vaccine may comprise any one of alphavirus-derived replicon nucleic acid molecules comprising antigenic proteins described herein. The term "vaccine" refers to an agent or composition containing an active component effective to induce a certain degree of immunity in a subject against a certain pathogen or disease, which will result in at least a decrease of the severity, duration, other manifestation, or elimination of symptoms associated with infection by the pathogen or the disease.

In an embodiment, the synthetic alphavirus-derived replicon nucleic acid molecules disclosed in any one of the embodiments herein may be encapsulated in a carrier system for in vivo administration. The carrier may be, but is not limited to, an anionic liposome, a cationic liposome, or a dendrimer. The term "anionic liposomes" refers to liposomes that include lipids comprising an anionic group. Anionic liposomes may be formed by anionic phospholipids. The term "cationic liposomes" refers to liposomes that are made in whole or part from positively charged lipids, or more specifically a lipid that comprises both a cationic group and a lipophilic portion. The positively charged moieties of cationic lipids used in cationic liposomes provide advantageous structural features. For instance, the lipophilic portion of the cationic lipid is hydrophobic and thus may direct itself away from the aqueous interior of the liposome and associate with other nonpolar and hydrophobic species, or conversely, the cationic moiety may associate with polar molecules and species with which it can complex in the aqueous interior of the cationic liposome. The positively charged liposomes may interact with the negatively charged nucleic acid molecules to form a stable complex.

Liposomes may include zwitterionic lipids. As used herein the term "zwitterionic" refers to a molecule that contains both positive and negative charges, but have a net neutral charge.

Liposomes may be formed from a single lipid or from a mixture of lipids. The hydrophilic portion of a lipid can be PEGylated, i.e., modified by covalent attachment of a polyethylene glycol to increase stability and prevent non-specific adsorption of the liposomes (Heyes et al. (2005) J Controlled Release 107:276-87, which is incorporated herein by reference as if fully set forth).

The term dendrimer" refers to a highly branched macromolecule with a spherical shape. The surface of the dendrimer molecule may be modified in many ways, and many of the properties of the resulting construct may be determined by its surface. The dendrimers may be modified to have a positive surface charge, i.e., to be cationic dendrimers. The cationic dendrimers may form temporary association with the nucleic acids. Upon reaching its destination the dendrimer-nucleic acid complex may be then taken into the cell via endocytosis.

An exemplary size for a single dendrimer-nucleic acid complex, also referred to herein as modified dendrimer nanoparticles (MDNPs), may be in the range of 30 nm to 1,000 nm in the longest dimension. MDNPs may have an average size from 30 nm to 450 nm, inclusive, from 50 nm to 300 nm, inclusive, or more from 60 nm to 250 nm, inclusive. MDNPS may be alkyl-modified dendrimer nanoparticles. Nanoparticle size may be influenced by the length of the alkyl chain that substitutes the core dendrimer. Methods of making and formulating modified dendrimer nanoparticles are described in WO2021 207020, published Oct. 14, 2021; US 20210330600, published Oct. 28, 2021; and US 20210338789, published Nov. 4, 2021; all of which are incorporated herein by reference as if fully set forth.

In an embodiment, the composition may further comprise one or more adjuvants. The term "adjuvant" refers to one or more substances that cause stimulation of the immune system. An adjuvant may be used to enhance an immune response to the heterologous proteins used for immunizing a subject against a disease. The one or more adjuvants may include aluminum, e.g., as aluminum hydroxide and/or aluminum phosphate; oil-emulsion compositions or oil-in-water compositions, for example, squalene-water emulsions, such as MF59; saponin formulations, for example, QS21 and Immunostimulating Complexes (ISCOMS); bacterial or microbial derivatives, for example, monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, nucleic acids and other TLR agonists, for example poly(I:C); and the like; eukaryotic proteins, e.g., antibodies or fragments thereof, and ligands to receptors, which stimulate immune response upon interaction with recipient cells.

In an embodiment, the composition described herein may be utilized without adjuvants.

In an embodiment, the composition may be administered in a pharmaceutically acceptable carrier or excipient. As used herein, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zincstearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (S) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyllaurate; (13) agar; (14) buffering agents, such as magnesium hydroxide and aluminum hydroxide; (15) alginic acid; (16) pyrogen-free water; (17) isotonic saline; (IS) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants may also be present in the formulation. The terms such as "excipient", "carrier", "pharmaceutically acceptable carrier" or the likes are used interchangeably herein. The pharmaceutically acceptable carriers and excipients are known in the art (Remington's Pharmaceutical Sciences, 18th edition, A. R. Gennaro, Ed., Mack Publishing Company, 1990; Pharmaceutical Formulation Development of Peptides and Proteins, S. Frokjaer and L. Hovgaard, Eds., Taylor & Francis, 2000; Handbook of Pharmaceutical Excipients, 3rd edition, A. Kibbe, Ed., Pharmaceutical Press, 2000). The the synthetic alphavirus-derived replicon nucleic acid molecule described herein may be formulated and administered as a sterile and/or lyophilized solution. Sterile solutions may be prepared by sterile filtration or by any other known methods. The solutions may be then lyophilized or filled into pharmaceutical dosage containers. The pH of the solution generally may be in the range of pH 3.0 to 9.5, e.g., pH 5.0 to 7.5. In an embodiment, a stabilizing agent may be added, such as albumin or additional sugars (e.g., sucrose). In an embodiment, detergent may be added. In an embodiment, the nucleic acid mixtures comprising any of the replicon RNAs described herein may be formulated into an injectable preparation.

An embodiment provides the use of a preparation of replicon RNA generated by the method disclosed herein in the manufacture of a vaccine capable of eliciting an immune response against cancer in a patient in need thereof.

In an embodiment, a method of inducing an immune response in a subject is provided. The method may comprise administering to the subject a therapeutically effective amount of a vaccine comprising any one of the synthetic alphavirus-derived replicon nucleic acid molecules described herein.

In an embodiment, a method for preventing and/or treating a subject against a disease or condition is provided. The method may comprise utilizing any one of compositions and vaccines described herein. The method may comprise administering to a subject in need thereof a therapeutically effective amount of a composition or vaccine comprising the synthetic alphavirus-derived replicon nucleic acid molecule described herein as described above.

Administration of the compositions or vaccines described herein may be performed using known routes of administration. The compositions or vaccines may be administered by using parenteral administration, such as intradermal, intramuscular, subcutaneous, transcutaneous, or mucosal administration, e.g., intranasal, oral, and the like. In one embodiment a composition is administered by intramuscular injection. As used herein, the term "administer" refers to the placement of a composition into a subject by a method or route which results in at least partial localization of the composition at a desired site such that desired effect is produced. A compound or composition described herein may be administered by any appropriate route known in the art including, but not limited to, oral or parenteral routes, including intravenous, intramuscular, subcutaneous, transdermal, airway (aerosol), pulmonary, nasal, rectal, or topical (including buccal and sublingual) administration.

Exemplary modes of administration include, but are not limited to, injection, infusion, instillation, inhalation, or ingestion. "Injection" include, without limitation, intravenous, intramuscular, intraarterial, intrathecal, intraventricular, intracapsular, intraorbital, intracardiac, intradermal, intraperitoneal, trans tracheal, subcutaneous, subcuticular, intraarticular, sub capsular, subarachnoid, intraspinal, intracerebro spinal, and intrastemal injection and infusion. In an embodiment, the compositions may be administered by intravenous infusion or injection.

Vaccines described herein may be administered by any known routes in order to induce an immune response to the antigen(s) in the vaccine.

In an embodiment, methods of administration or delivery may not limited to the above described methods, and any means for intracellular delivery may be used.

A therapeutically effective amount refers to an amount of a protein, or nucleic acid molecule, which is effective for preventing, ameliorating and/or treating a disease or condition resulting from infection by a pathogen. Prevention encompasses inhibiting or reducing the spread of pathogen or inhibiting or reducing the onset, development, or progression of one or more of the symptoms associated with infection by pathogen. Amelioration, as used in herein, refer to the reduction of visible or perceptible disease symptoms, viremia, or any other measurable manifestation of the infection induced by pathogen.

In connection with treating cancer, the "therapeutically effective amount" is that amount effective for preventing further development of a cancer or transformed growth, and even to effect regression of the cancer or solid tumor.

Determination of a therapeutically effective amount is generally well within the capability of those skilled in the art. Generally, a therapeutically effective amount can vary with the subject's history, age, condition, sex, as well as the severity and type of the medical condition in the subject, and administration of other agents alleviate the disease or disorder to be treated.

Toxicity and therapeutic efficacy may be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred. As used herein, the term ED denotes effective dose and is used in connection with animal models. The term EC denotes effective concentration and is used in connection with in vitro models.

The data obtained from the cell culture assays and animal studies may be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose may be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage may be monitored by a suitable bioassay.

The dosage may be determined by a physician and adjusted, as necessary, to suit observed effects of the treatment. Generally, the compositions may be administered so that the active agent is given at a dose from 1 μg/kg to 150 mg/kg, 1 μg/kg to 100 mg/kg, 1 μg/kg to 50 mg/kg, 1 μg/kg to 20 mg/kg, 1 μg/kg to 10 mg/kg, 1 μg/kg to 1 mg/kg, 100 μg/kg to 100 mg/kg, 100 μg/kg to 50 mg/kg, 100 μg/kg to 20 mg/kg, 100 μg/kg to 10 mg/kg, 100 μg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In an embodiment, the compositions may be administered at a dosage so that the active agent has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule may vary from once a week to daily depending on a number of clinical factors, such as the subject's sensitivity to the polypeptides. The desired dose may be administered every day or every third, fourth, fifth, or sixth day. The desired dose may be administered at one time or divided into subdoses, e.g., 2-4 subdoses and administered over a period of time, e.g., at appropriate intervals through the day or other appropriate schedule. Such sub-doses may be administered as unit dosage forms. In an embodiment, administration may be chronic, e.g., one or more doses daily over a period of weeks or months. Examples of dosing schedules may include administration daily, twice daily, three times daily or four or more times daily over a period of 1 week, 2 weeks, 3 weeks, 4 weeks, 1 month, 2 months, 3 months, 4 months, 5 months, or 6 months or more.

In an embodiment, a method of preparing a vaccine or a therapeutic composition against a disease or condition is provided. The method may comprise providing a vaccine or therapeutic composition described herein and formulating it into a pharmaceutically acceptable composition. The vaccine composition may comprise an effective amount of the heterologous immunogenic protein and/or a nucleic acid molecule encoding the protein, which results in an immune response against the disease.

In an embodiment, the disease may be caused by a viral pathogen. The pathogen may be a viral pathogen. The viral pathogen may be adenovirus, rhinovirus, rotavirus, West Nile virus, Zika virus, herpes, or coronavirus (CoV). The coronavirus may be one of MERS CoV, SARS-CoV and SARS-CoV-2 viruses.

In an embodiment, the disease may be a foot-and-mouth disease (FMD). FMD is an acute and highly contagious viral disease of domestic and wild cloven-hooved animals, including domestic and wild bovides and swines. Exemplary susceptible animals include cattle, water buffalo, sheep, goats, pigs, antelope, deer, and bison, hedgehogs and elephants; llamas and alpacas. In laboratory experiments, mice, rats, and chickens have been successfully infected by artificial means, but they are not believed to contract the disease under natural conditions. Humans are very rarely infected. Symptoms of FMD comprise high fever for approximately two to six days, followed by blisters inside the mouth and on the feet that may rupture and cause lameness. FMD has severe implications for animal farming, since it is highly infectious and can be spread by infected animals through aerosols, through contact with contaminated farming equipment, vehicles, clothing, or feed, and by domestic and wild predators. In particular symptoms in cattle and swine caused by a FMDV infection. Economic losses from FMD outbreaks are among the highest of all livestock diseases. The causative agent, foot-and-mouth disease virus (FMDV), is a member of the family Picornaviridae, and thus, the viral pathogen may be picornavirus. As used herein, the term "picornavirus" refers to a non-enveloped virus representing a family of small, cytoplasmic, plus-strand RNA (7.0-8.5 kb) viruses with an icosahedral capsid. It is a large viral family that includes multiple genera containing important human and animal pathogens such as the enteroviruses (human poliovirus), hepatoviruses (hepatitis A virus), and the aphthoviruses with FMDV as the prototypic member. FMDV exists as seven distinct serotypes (Euroasiatic serotypes A, O, C, and Asia1 and South African Territories [SAT] serotypes SAT1, SAT2, and SAT3) and multiple sub-types reflecting significant genetic variability. Genera within this family include Aphthovirus, Aquamavirus, Avihepatovirus, Cardiovirus, Cosavirus, Dicipivirus, Enterovirus, Erbovirus, Hepatovirus, Kobuvirus Megrivirus, Parechovirus. Piscevirus, Salivirus, Sapelovirus, Senecavirus, Teschovirus and Tremovirus. The viral genome of a picornavirus generally contains one open reading frame that encodes a single polyprotein comprising a structural protein region, P1, and non-structural protein regions, P2 and P3. The release of mature and functional proteins from the polyprotein is primarily mediated by viral proteinases including 3C protease.

Providing Vaccine Compositions and Immunization Regime

The "vaccine" described herein may be provided as a pharmaceutical composition. The composition may include a pharmaceutically acceptable diluent, carrier or excipient. The composition may comprise further active ingredients. The administration may be provided at a single dose or in a prime-boost setting. The prime-boost setting may involve "priming" and "boosting" immunization regimes, in which the immune response induced by a prime vaccine may be boosted by a boost vaccine. For example, following priming (at least once) with any one of polynucleotides encoding a first heterologous protein, a boost vaccine comprising an effective amount of a second heterologous antigenic protein, or a subunit thereof, may be administered to boost the immune response in the primed host.

Compositions described herein may be administered to a subject, e.g., a human subject. The total dose of the heterologous immunogenic proteins in a composition for a single administration may, for instance, be about 0.01 μg to about 10 mg, e.g., 1 μg-1 mg, e.g., 10 μg-100 μg. Determining the recommended dose may be carried out by experimentation and is routine for those skilled in the art.

The terms "subject" and "individual" are used interchangeably herein, and mean a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In an embodiment, the subject may be a mammal, e.g., a primate, e.g., a human. The terms, "patient" and "subject" are used interchangeably herein. The terms, "patient" and "subject" are used interchangeably herein. Preferably, the subject is a mammal. The mammal may be a human, non-human primate, mouse, rat, dog, cat, horse, or cow, but are not limited to these examples.

The following list includes particular embodiments of the present invention. But the list is not limiting and does not exclude alternate embodiments, or embodiments otherwise described herein. Percent identity described in the following embodiments list refers to the identity of the recited sequence along the entire length of the reference sequence.

Methods for Treating Cancer

An embodiment provides a method for treating cancer. The method may comprise administering a therapeutically effective amount of a composition comprising any one of the immunogenic proteins described herein to a subject in need thereof. The immunogenic proteins may comprise a pattern recognition receptor or effector protein that stimulates an innate immune response. The immunogenic protein may be an extracellular signaling molecule such as a cytokine, membrane surface receptor, membrane channel, or integrin or other glycoprotein affecting immune cell recognition. The immunogenic proteins may comprise a STING protein. The stimulator of interferon genes (STING) plays a central role in innate immunity during infection and cancer. STING is endogenously activated by 2',3'-cyclic-GMP-AMP (cGAMP), a cyclic dinucleotide synthesized by cGAMP synthase (cGAS) in response to cytosolic DNA as a danger signal. Activation of STING mediates a multifaceted type I interferon (IFN-I) response that promotes the maturation and migration of dendritic cells, and primes cytotoxic T lymphocytes and nature killer cells for spontaneous immune responses.

In an embodiment, the method for treating cancer may comprise administering a therapeutically effective amount of any one of the immunogenic proteins described herein to a subject in need thereof.

In an embodiment, the method may further comprise analyzing inhibition of tumor growth. The step of analyzing may include observing more than about 60%, 70%, 80% or about 90% inhibition of tumor growth in the subject.

A variety of known controlled- or extended-release dosage forms, formulations, and devices may be adapted for use with the immunogenic compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1, all of which are incorporated herein by reference as if fully set forth. These dosage forms may be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

As used herein, the term "cancer" refers to an uncontrolled growth of cells that may interfere with the normal functioning of the bodily organs and systems. The cancer may be either a primary cancer, or a metastatic cancer, or both. Cancers that migrate from their original location and seed vital organs can eventually lead to the death of the subject through the functional deterioration of the affected organs. Metastasis is a cancer cell or group of cancer cells, distinct from the primary tumor location resulting from the dissemination of cancer cells from the primary tumor to other parts of the body. At the time of diagnosis of the primary tumor mass, the subject may be monitored for the presence of in transit metastases, e.g., cancer cells in the process of dissemination.

As used herein, the term "cancer" also includes, but is not limited to, solid tumors and blood born tumors. The term cancer refers to disease of skin, tissues, organs, bone, cartilage, blood and vessels. The term "cancer" includes malignant epithelial tumors (from the lungs, stomach, duodenum, colon, rectum, mammary glands, uterus, prostate gland, urinary bladder, etc)

The term "cancer" further encompasses primary and metastatic cancers. Examples of cancers that can be treated with the method of the invention include, but are not limited to solid tumors; melanoma, brain cancer, including but not limited to gliomas, glioblastomas, glioblastoma multiforme (GBM), oligodendrogliomas, primitive neuroectodermal tumors, low, mid and high grade astrocytomas, ependymomas (e.g., myxopapillary ependymoma papillary ependymoma, subependymoma, anaplastic ependymoma), oligodendrogliomas, medulloblastomas, meningiomas, pituitary adenomas, neuroblastomas, and craniopharyngiomas; breast cancer, including but not limited to ductal carcinoma in situ, invasive (or infiltrating) ductal carcinoma, invasive (or infiltrating) lobular carcinoma, adenoid cystic (or adenocystic) carcinoma, low-grade adenosquamous carcinoma, medullary carcinoma, mucinous (or colloid) carcinoma papillary carcinoma, tubular carcinoma, inflammatory breast cancer, Paget disease of the nipple, phyllodes tumor, triple negative breast cancer, metastatic breast cancer; carcinoma, including that of the bladder, breast, colon, kidney, lung, ovary, pancreas, stomach, cervix, thyroid, and skin, including squamous cell carcinoma; other tumors includingseminoma, tetratocarcinoma; tumors of the central and peripheral nervous system; and other tumors including, but not limited to, xenoderma, pigmentosum, keratoactanthoma, thyroid follicular cancer, and teratocarcinoma.

The methods disclosed herein are useful for treating patients who have been previously treated for cancer, as well as those who have not previously been treated for cancer. Indeed, the methods and compositions described herein may be used in first-line and second-line cancer treatments.

As used herein, the term "precancerous condition" has its ordinary meaning, i.e., an unregulated growth without metastasis, and includes various forms of hyperplasia and benign hypertrophy. Accordingly, a "precancerous condition" is a disease, syndrome, or finding that, if left untreated, can lead to cancer. It is a generalized state associated with a significantly increased risk of cancer. Premalignant lesion is a morphologically altered tissue in which cancer is more likely to occur than its apparently normal counterpart. Examples of pre-malignant conditions include, but are not limited to, oral leukoplakia, actinic keratosis (solar keratosis), Barrett's esophagus, atrophic gastritis, benign hyperplasia of the prostate, precancerous polyps of the colon or rectum, gastric epithelial dysplasia, adenomatous dysplasia, hereditary nonpolyposis colon cancer syndrome (HNPCC), Barrett's esophagus, bladder dysplasia, precancerous cervical conditions, and cervical dysplasia.

In an embodiment, the cancer may be selected from the group consisting of: breast cancer; ovarian cancer; brain cancer; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer.

In an embodiment, the cancer may be breast cancer, including but not limited to ductal carcinoma in situ, invasive (or infiltrating) ductal carcinoma, invasive (or infiltrating) lobular carcinoma, adenoid cystic (or adenocystic) carcinoma, low-grade adenosquamous carcinoma, medullary carcinoma, mucinous (or colloid) carcinoma papillary carcinoma, tubular carcinoma, inflammatory breast cancer, Paget disease of the nipple, phyllodes tumor, triple negative breast cancer, metastatic breast cancer.

In an embodiment, the methods described herein may relate to treating a subject having or diagnosed as having cancer. Subjects having cancer may be identified by a physician using current methods of diagnosing cancer. Symptoms and/or complications of cancer which characterize these conditions and aid in diagnosis are well known in the art and may be, but are not limited to, growth of a tumor, impaired function of the organ or tissue harboring cancer cells, etc. Tests that may aid in a diagnosis of, e.g. cancer include, but are not limited to, tissue biopsies and histological examination. A family history of cancer, or exposure to risk factors for cancer (e.g. tobacco products, radiation, etc.) may also aid in determining if a subject is likely to have cancer or in making a diagnosis of cancer.

Further embodiments herein may be formed by supplementing an embodiment with one or more elements from any one or more other embodiments herein, and/or substituting one or more elements from one embodiment with one or more elements from one or more other embodiments

EXAMPLES

The following non-limiting examples are provided to illustrate particular embodiments. The embodiments throughout may be supplemented with one or more details from one or more examples below, and/or one or more elements from an embodiment may be substituted with one or more details from one or more examples below.

Example 1. Design of nsP4-Modified Replicon

FIG. 1 illustrates the gene expression steps of an alphavirus genome non-structural polyprotein (nsP; nsP1-nsP2-nsP3-nsP4). This drawing shows that expression of the non-structural polyprotein is a prerequisite for genome synthesis and subsequent expression of the subgenomic ORF (SG ORF), which in a natural virus encodes the Structural polyprotein. In the drawing, the nsP is shown to include an early stop codon present in wild-type VEEV, which leads to the termination of the translation of the nsP-1-2-3 polyprotein; the nsP4 is translated by low frequency translational read-through of the amber stop codon (UGA) at genome position 5682, incorporating an arginine, cysteine or tryptophan. Subsequent proteolysis of the polyprotein that results in separated nsP1, nsP2, nsP3 and nsP4 proteins.

The "early phase" of viral infection refers to the time post infection characterized predominantly by expression of the nsP polyprotein, before genome replication takes place. The "late phase" is defined by the gene expression pattern after genome replication has taken place and expression of the subgenomic polyprotein is the predominant viral gene product.

The successful editing of the nsP gene region of alphavirus replicons to reduce homology to wild-type virus, and incorporate novel biological function into the early phase of self-amplification of such artificial replicons that precedes translation of subgenomically encoded transgenes is reported herein. This is accomplished by identifying key stretches of nucleotides in the nsP region that can be safely edited without disrupting conserved structural elements, and appending additional sequences to the natural terminus of the nsP. This disclosure shows how such modifications can be performed without impairing the self-amplifying functionality of the replicon. Therefore, this disclosure provides a new method to generate safer replicons equipped with additional functionality to modify cellular and immunological parameters of the host cell.

Alphavirus replicons are currently used predominantly as vaccine vectors, wherein an antigen of interest is encoded in the subgenomic ORF such that it replaces the natural alphavirus structural proteins that would normally compose the virion particle. Currently, if auxiliary biological function is desired in the form of an additional polypeptide (for example, reporter genes, immunomodulatory, or other host-cell-function modulating factors), the auxiliary factor must be (i) encoded in the same subgenomic ORF as the first transgene by fusion of the coding sequences, (ii) encoded under control of a separate RNA transcriptional/translational promoter such as a duplicate subgenomic promoter (SGP) or internal ribosome entry site (IRES), or (iii) provided in trans separately from the replicon by mixing an additional nucleic acid or protein species with the replicon RNA product. Method (i) requires engineering of a functional polypeptide that is not always possible for certain antigens without altering its primary sequence. Method (ii) requires the addition of extensive extra nucleotide sequences to produce the SGP or IRES in addition to the desired auxiliary ORF. Both method (i) and the use of additional SGP as an approach in (ii) only permit expression of the auxiliary factor concurrently with the subgenomic ORF in the late phase of the viral replication cycle, making it unable to affect replicon function in the early phase. Method (iii) requires entirely additional biologic products to be manufactured, and co-delivery with the replicon RNA must be solved by some means. Currently, replicon nsP sequences essentially identical to circulating, endemic alphaviruses are used, which raises the risk of recombination in the case of co-infection of the host cell with another closely related alphavirus genome, such as a circulating pathogenic wild-type virus strain. Such recombination threatens to generate viable replicative virus, posing an environmental safety issue. Replicons with reduced homology to wild-type natural strains of virus would have the advantage of increased safety.

The challenge of (a) sequence homology to natural virus and (b) means of including auxiliary early phase biological function are solved by specifically editing the natural coding sequence of an alphavirus genome such that critical primary and secondary structure elements are deliberately left intact. By analyzing a region before editing to detect conserved primary and secondary sequence elements which are predicted to carry specific functionality (for example, as demonstrated in FIG. 6), the natural codons of the nsP coding region can be altered to yield silent mutations that yield the same protein product and do not impair functionality of the replicon. Extending this technique, the C terminus of the nsP polyprotein can be edited to allow for appendage of a new transgene x by fusion to the nsP coding sequence, again without functional impairment of the replicon. Duplication of the necessary non-coding elements of the nsP ORF's 3' region is performed to re-create the SGP and ensure SG ORF expression, and silent codon alterations are performed to the upstream duplicate to create the novel nsP-x fusion protein and eliminate spurious homology between duplicate sites that would inhibit propagation of DNA templates for such a construct in standard bacterial production strains.

Figure 2:
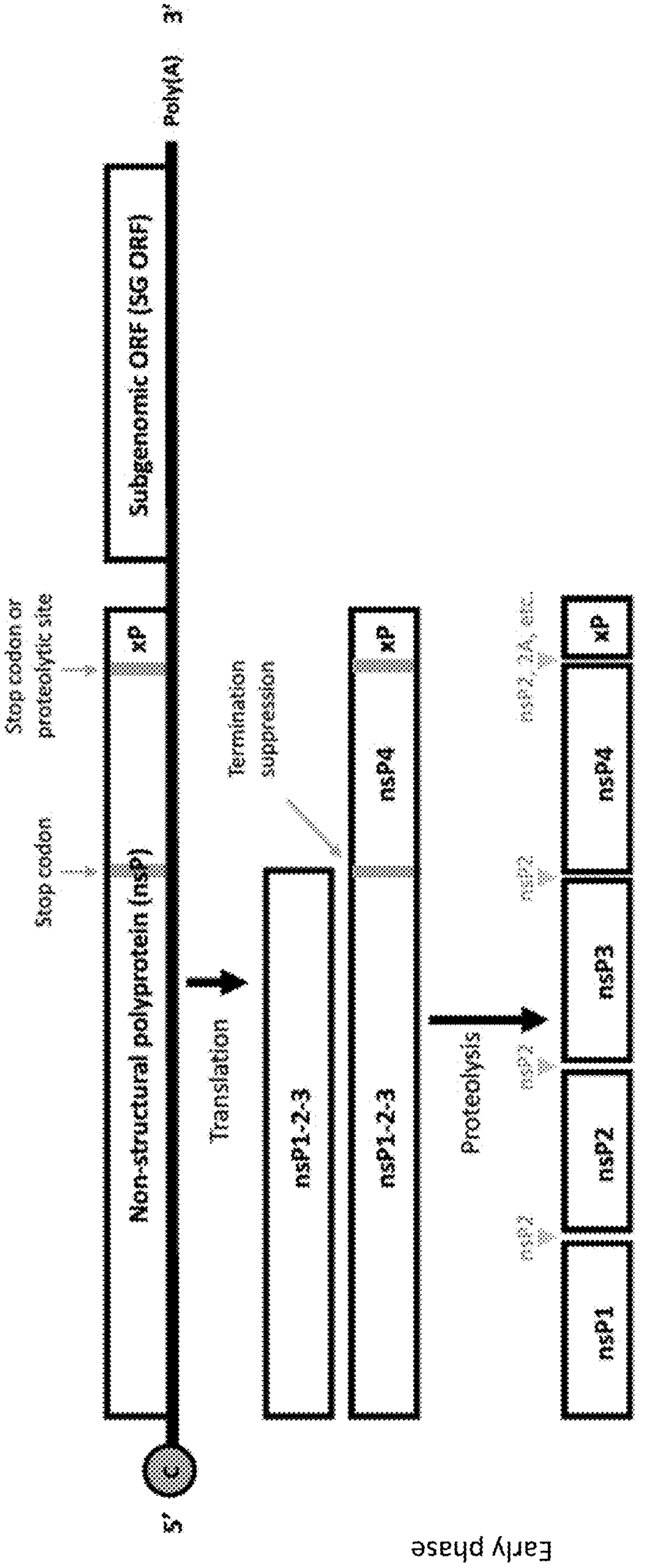
FIG. 2 is a schematic drawing illustrating the gene expression steps of an alphavirus genome non-structural polyprotein artificially modified to express an additional exogenous protein ("xP") by appendage in-frame with nsP4 (nsP1-nsP2-nsP3-nsP4-xP).

FIG. 2 illustrates the gene expression steps of an alphavirus genome non-structural polyprotein artificially modified to express an additional exogenous protein (generically, "xP") by appendage in-frame with nsP4 (nsP1-nsP2-nsP3-nsP4-xP). This figure shows that the exogenous protein xP is introduced within the gene encoding the nsP4 segment of the nsP polyprotein that results in translation and proteolysis of nsP4 and xP proteins together joined by a juncture The nsP4-xP juncture may comprise a non-cleavable, self-cleavable (e.g., 2A peptide), or proteolytically cleavable (e.g., nsP2 protease or furin recognition site) peptide linker sequence.

Figure 3:
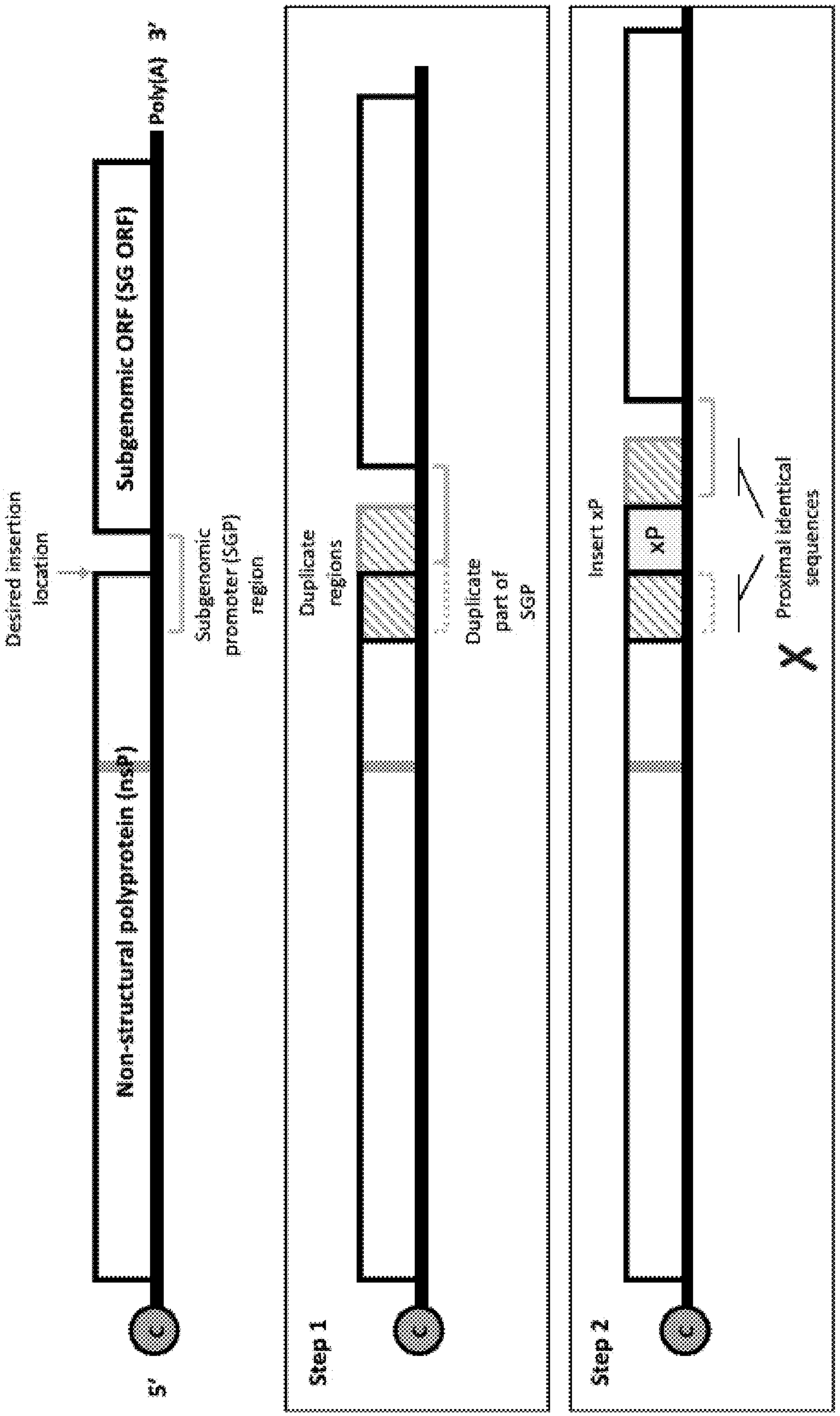
FIG. 3 is a schematic drawing illustrating the steps for cloning a modifiable nsP4 open reading frame (ORF) while maintaining an intact extended subgenomic promoter (SGP, duplicated region, striped boxes).

FIG. 3 is a schematic drawing that depicts the steps that can be undertaken to genetically modify an alphaviral replicon RNA sequence to generate a construct such as that described in FIG. 2. Referring to FIG. 3, the desired insertion location is within the subgenomic promoter (SGP) region, Step 1 involves duplication of the part of the SGP region. Step 2 involves insertion of the sequence encoding the xP protein in the duplicated region This method results in proximal identical sequences due to duplication of the SGP that render the construct genetically unstable. The solution to this problem is found in implementing silent codon alterations in the upstream duplicated element that eliminates the problematic homology.

Figure 4:
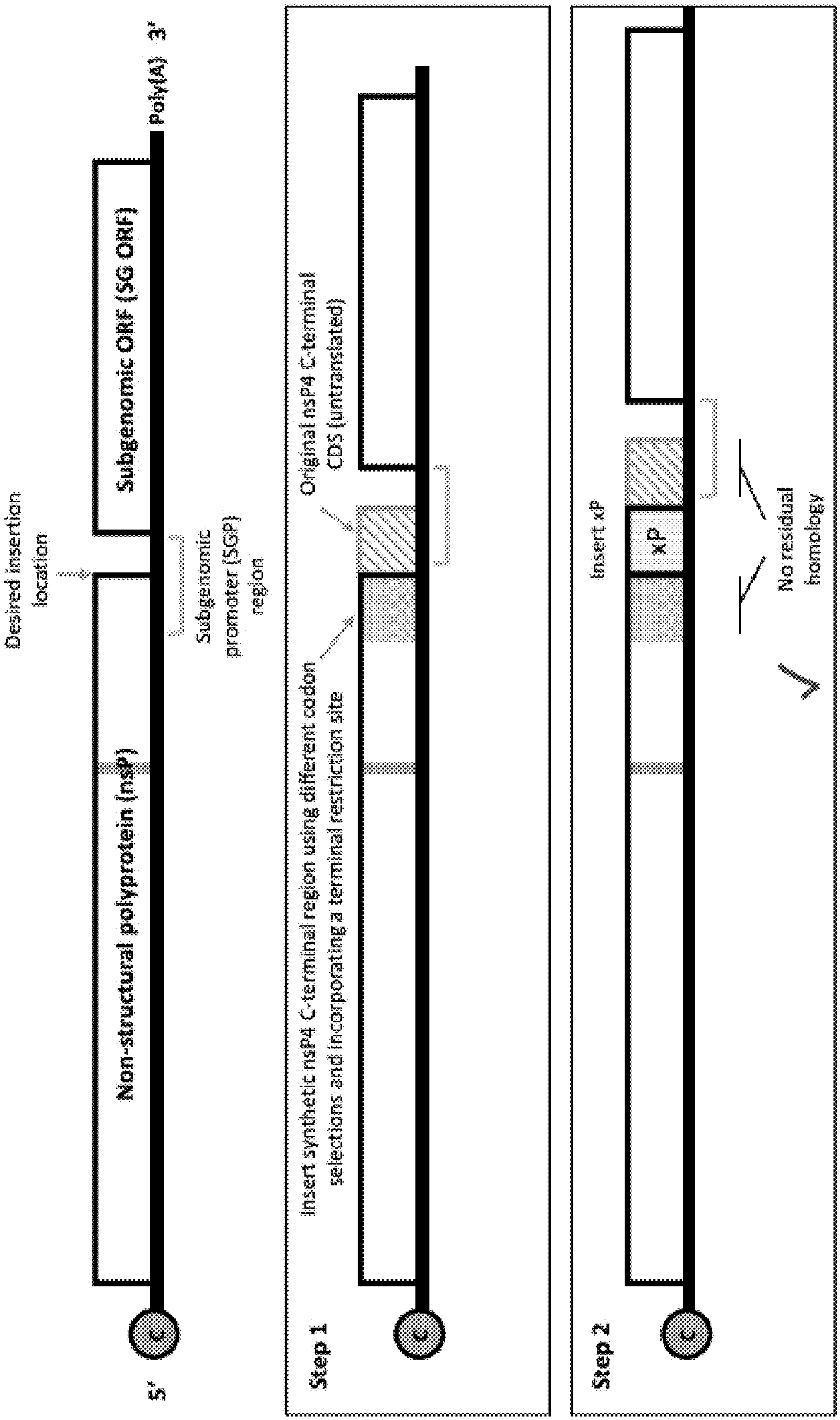
FIG. 4 is a schematic drawing illustrating optimal steps for cloning a modifiable nsP4 open reading frame (ORF) while maintaining an intact extended subgenomic promoter (SGP). In this figure, the gray boxes indicate the synthetic nsP4 C-terminal region, and the xP region, and the striped box indicates the original nsP4 C-terminal CDS (untranslated).

FIG. 4 illustrates optimal steps for cloning a modifiable nsP4 open reading frame (ORF) while maintaining an intact extended subgenomic promoter. Referring to FIG. 4, Step 1 involves insertion the synthetic nsP4 terminal region into the SGP region (gray box) using different codon optimized selections and incorporating a terminal restriction site. Step 2 involves insertion of the sequence encoding the xP protein between the synthetic nsP4 terminal region and the original nsP4 C-terminal coding sequence (untranslated coding sequence CDS, striped box). This method does not yield any proximal identical sequence stretches and produces a genetically stable construct. This approach eliminates problematic repetitive sequence elements and the DNA template can be easily propagated and manufactured in common bacterial strains. This modification of the nsP4 to append a transgene $\chi$ can be performed in combination with other silent mutations in the nsP region as described herein to create a further improved replicon RNA.

Figure 5:
FIG. 5 is a schematic drawing of a DNA plasmid encoding the replicon sequence template of construct 8 (C08). Transcription of the plasmid from the T7 promoter produces C08 replicon RNA. The 5' UTR, nsP1-4 ORF, and SGP of C08 is set forth in SEQ ID NO:27.

Example 2. VEEV Replicon RNA Modified with Homology-Reduced in the nsP1 within Nucleotide Positions 45-260 of the Genome To demonstrate the sensitivity of the alphavirus nsP to arbitrary nucleotide sequence alterations, a series of silent mutations were substituted across the beginning of the nsP1 protein corresponding to genomic nucleotide positions 45-260 as shown on FIG. 5. FIG. 5 is a schematic drawing of a DNA plasmid encoding the replicon sequence template of construct 8 (C08).

In this figure, the replicon sequence is derived from the Venezuelan equine encephalitis virus (VEEV) species of alphaviruses. The DNA encodes an ampicillin resistance gene (AmpR) to facilitate specific production in bacterial cell culture, an origin of replication (ori) to allow propagation in bacterial cells, and a DNA template of an engineered VEEV replicon (comprising the virus' genomic 5' UTR, nsPs, a subgenomic promoter and 5'UTR, a gene of interest in the subgenomic ORF, genomic 3'UTR, and a poly(A) tail) that can be transcribed into RNA by run-off transcription beginning at the T7 promoter. Codons in genomic nucleotide positions 45-260 (gray box) were altered to reduce homology to the wild-type virus. This 45-260 nt coding region contains the alphaviral conserved sequence element (CSE) required for RNA replication within cells. The CSE known to be required for replicon function has been disrupted at the secondary structure level by silent mutation (codon-adaptation) in this construct; it therefore serves as a negative control. In aggregate, the silent mutations reduced sequence identity of the nsP1 CDS to wild-type by 19.04%. Transcription of the plasmid from the T7 promoter produces C08 replicon RNA. The 5' UTR, nsP1-4 ORF, and SGP of C08 is set forth in SEQ ID NO: 27.

The C08 region includes the well-established alphaviral conserved sequence element (CSE), a 51nt span of nucleotides that fold into ordered stem-loops. This secondary structure motif is required for genome replication thus transgene expression from the subgenomic ORF. Transfection of BHK cells in vitro confirmed that this RNA (C08) was unable to mediate expression of a subgenomic ORF-encoded reporter gene, secreted embryonic alkaline phosphatase (shown on FIG. 17A).

Example 3. VEEV Replicon RNA Modified with Homology Reduced in the nsP1 within Nucleotide Positions 503-658 of the Genome In contrast to the construct C08 described in Example 1, a different nsP1 ORF modification was made in a region downstream of the CSE, where bioinformatic inspection of localized RNA folding based on thermodynamic parameters, as shown on FIG. 6, was used to select regions of unstructured nucleotides, and accordingly a series of silent mutations were substituted across the region to create the construct designated C02, as shown on FIG. 7.

Figure 6:
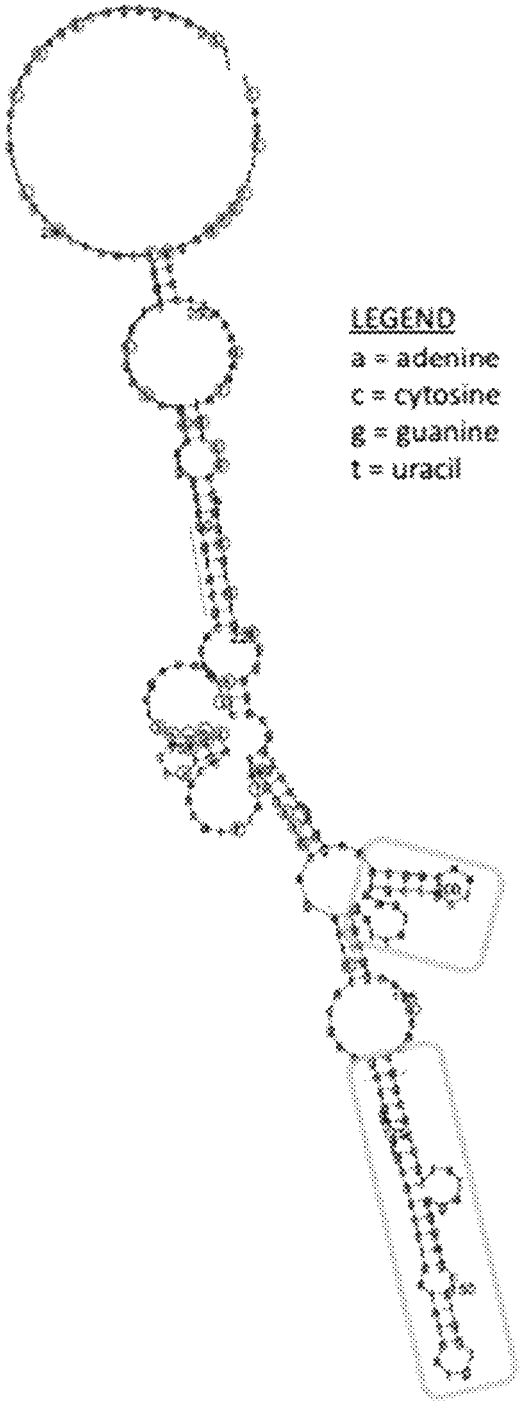
FIG. 6 is a schematic drawing that depicts an exemplary process used to select regions of an alphaviral genome that can be altered by applying silent mutations that reduce homology to the wild-type virus, without reducing replicative function of the replicon. In this figure, circled are the nucleobases that can be altered without disrupting secondary structure amino acid coding sequence. Altering of such nucleobases to produce silent mutations is termed the process of codon-adaptation.

FIG. 6 is a schematic drawing that depicts an exemplary process used to select regions of an alphaviral genome that can be altered by applying silent mutations that reduce homology to the wild-type virus, without reducing replicative function of the replicon. In this drawing, the RNA secondary structure of a region spanning the BsiWI-to-EcoNI restriction fragment of the wild-type VEEV genome (reference sequence L01442 in the NCBI GenBank database) is shown, as predicted by calculation of the minimum free energy of hybridization at 77° C. Boxed in the figure are polynucleotide stretches involved in local (i.e., within approximately a 100 nt window) hairpin structures which are left intact and unmutated to conserve overall secondary structure of the genome. Examples of nucleic acid positions that can be altered to create silent mutations while preserving the disordered nature of the local sequence are circled in the figure.

Figure 7:
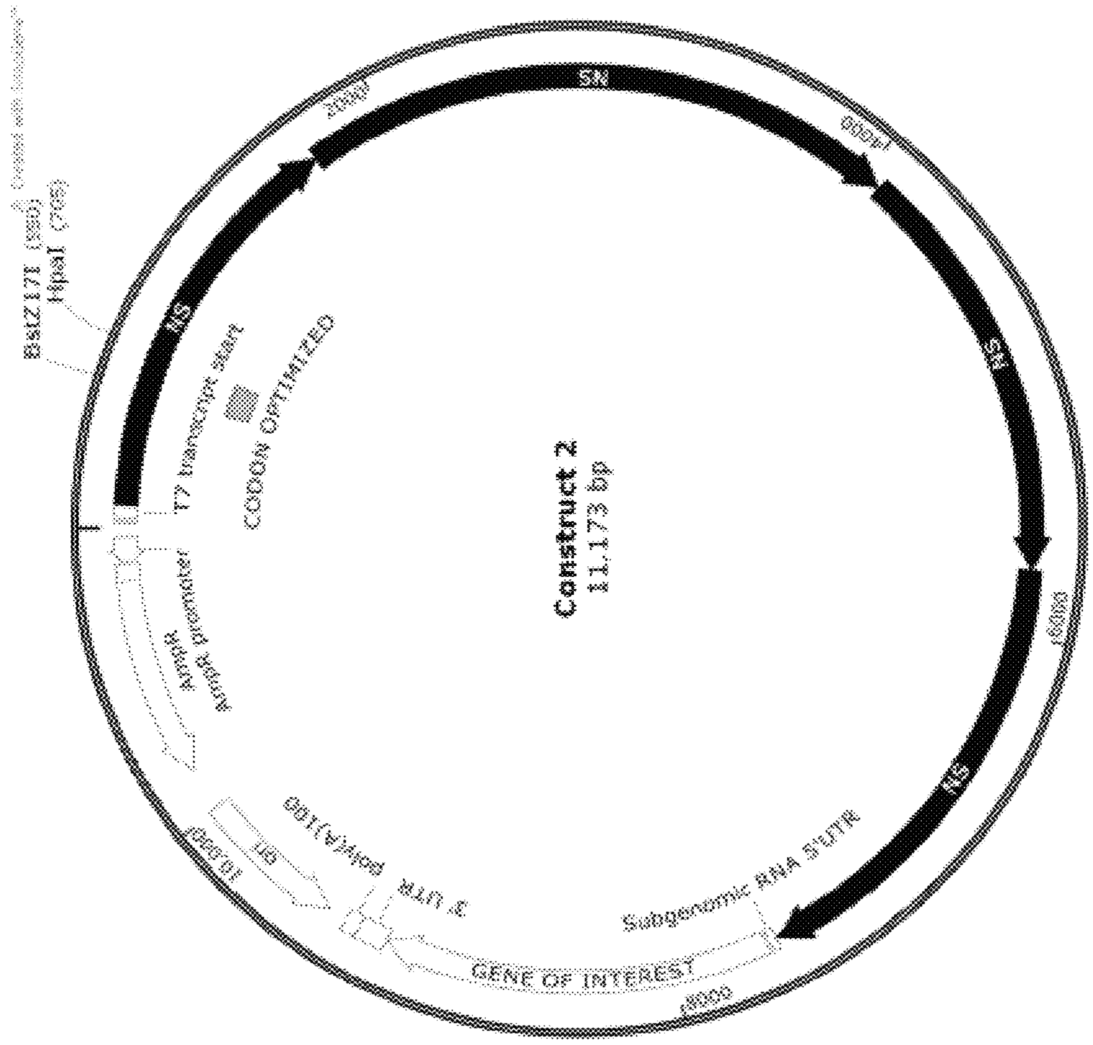
FIG. 7 is a schematic drawing of a DNA plasmid encoding the replicon sequence template of construct 2 (C02). In this figure, the DNA plasmid is similar to that shown in FIG. 5, except that only codons in genomic nucleotide positions 503-658 (gray box) were altered to reduce homology to the wild-type virus. Transcription of the plasmid from the T7 promoter produces C02 replicon RNA. The 5' UTR, nsP1-4 ORF, and SGP of C02 is set forth in SEQ ID NO: 21.

FIG. 7 is a schematic drawing of a DNA plasmid encoding the replicon sequence template of construct 2 (C02). In this figure, the DNA plasmid is similar to that shown in FIG. 5, except that only codons in genomic nucleotide positions 503-658 (gray box) were altered to reduce homology to the wild-type virus. In aggregate, the silent mutations reduced sequence identity of the nsP1 CDS to wild-type by 14.09%. Transcription of the plasmid from the T7 promoter produces C02 replicon RNA. The 5' UTR, nsP1-4 ORF, and SGP of C02 is set forth in SEQ ID NO: 21.

Figure 17A:
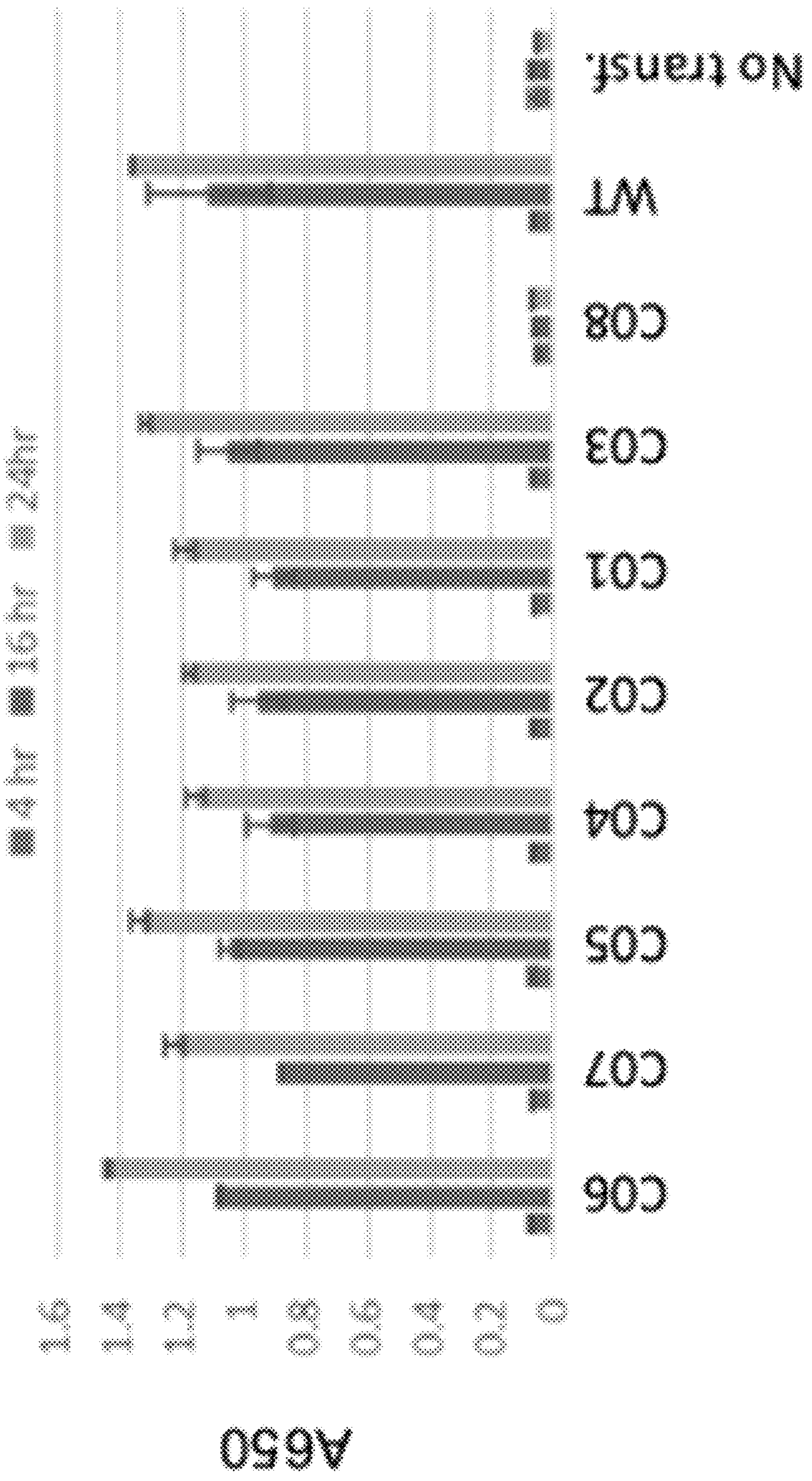
FIGS. 17A-17D illustrate the results of SEAP expression tests to demonstrate the function of the SG ORF encoding SEAP present in codon-adapted replicon RNAs and quantifying SEAP concentration by colorimetric assay.

It was observed that transfection of BHK cells in vitro confirmed that the RNA of CO2 construct was able to mediate expression of a subgenomic ORF-encoded reporter gene, secreted embryonic alkaline phosphatase (FIG. 17A).

Figure 8:
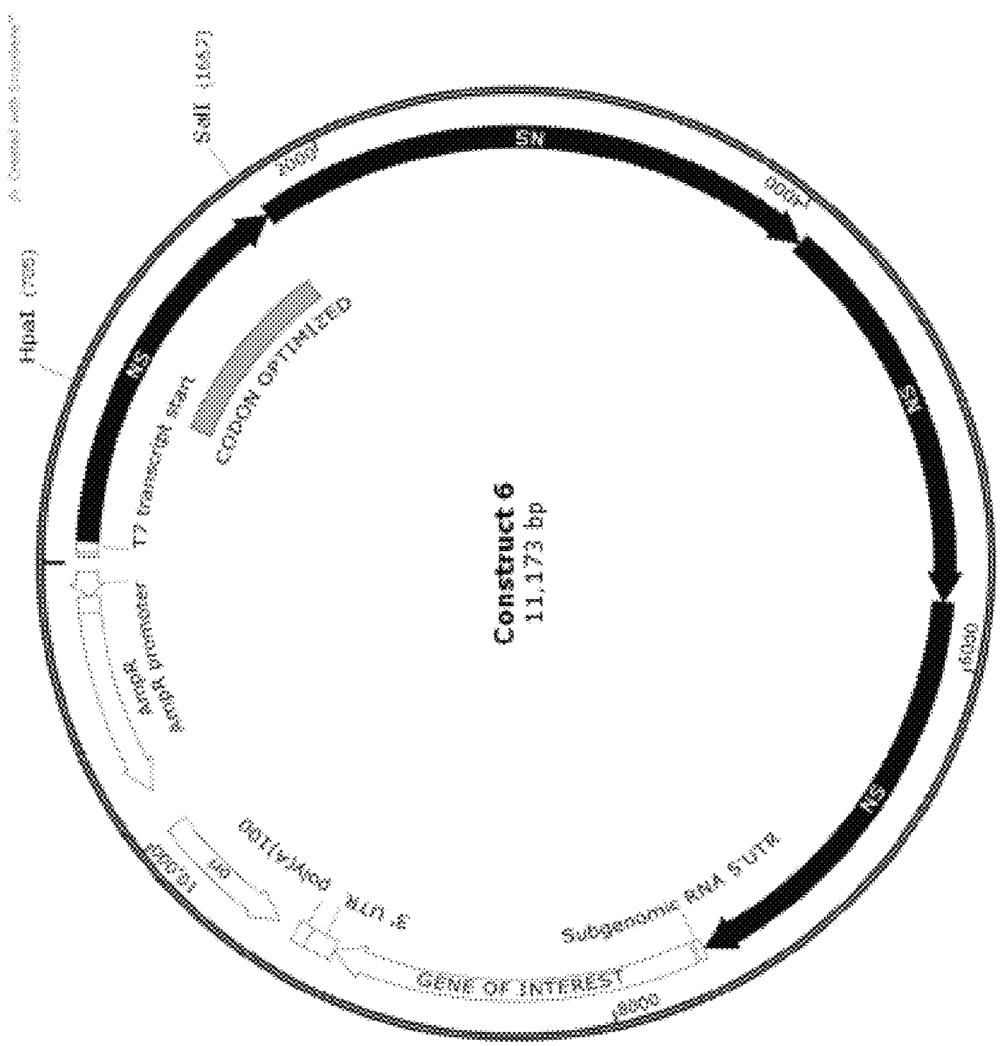
FIG. 8 is a schematic drawing of a DNA plasmid encoding the replicon sequence template of construct 6 (C06). In this figure, the DNA plasmid is similar to that shown in FIG. 5, except that only codons in genomic nucleotide positions 658-1620 (gray box) were altered to reduce homology to the wild-type virus. Transcription of the plasmid from the T7 promoter produces C06 replicon RNA. The 5' UTR, nsP1-4 ORF, and SGP of C06 is set forth in SEQ ID NO: 25.

Example 4. VEEV Replicon RNA Modified with Homology Reduced in the nsP1 within Nucleotide Positions 658-1620 of the Genome As was described in Example 2 for construct C02, bioinformatic inspection of localized RNA folding based on thermodynamic parameters was used to select regions of unstructured nucleotides, and accordingly a series of silent mutations were substituted across the region to create the construct designated C06. FIG. 8 is a schematic drawing of a DNA plasmid encoding the replicon sequence template of construct 6 (C06). In this figure, the DNA plasmid is similar to that shown in FIG. 5, except that only codons in genomic nucleotide positions 658-1620 (gray box) were altered to reduce homology to the wild-type virus. In aggregate, the silent mutations reduced sequence identity of the nsP1 CDS to wild-type by 8.96%. Transcription of the plasmid from the T7 promoter produces C06 replicon RNA. The 5' UTR, nsP1-4 ORF, and SGP of C06 is set forth in SEQ ID NO: 25.

It was observed that transfection of BHK cells in vitro confirmed that this RNA (construct C06) was able to mediate expression of a subgenomic ORF-encoded reporter gene, secreted embryonic alkaline phosphatase (FIG. 17A). Mice injected with this construct exhibited average SEAP serum expression on par with or greater than mice injected with wild-type VEEV-SEAP (FIG. 17D).

Figure 9:
FIG. 9 is a schematic drawing of a DNA plasmid encoding the replicon sequence template of construct 5 (C05). In this figure, the DNA plasmid is similar to that shown in FIG. 5, except that only codons in genomic nucleotide positions 1620-2560 (gray box) were altered to reduce homology to the wild-type virus. Transcription of the plasmid from the T7 promoter produces C05 replicon RNA. The 5' UTR, nsP1-4 ORF, and SGP of C05 is set forth in SEQ ID NO: 24.

Example 5. VEEV Replicon RNA Modified with Homology Reduced in the nsP1-nsP2 Junction Region within Nucleotide Positions 1620-2560 of the Genome As was described in Example 2 for construct C02, bioinformatic inspection of localized RNA folding based on thermodynamic parameters was used to select regions of unstructured nucleotides spanning across the nsP1 and nsP2 juncture, and accordingly a series of silent mutations were substituted across the region to create the construct designated C05. FIG. 9 is a schematic drawing of a DNA plasmid encoding the replicon sequence template of construct 5 (C05). In this figure, the DNA plasmid is similar to that shown in FIG. 5, except that only codons in genomic nucleotide positions 1620-2560 (gray box) were altered to reduce homology to the wild-type virus. In aggregate, the silent mutations reduced sequence identity of the nsP1 CDS to wild-type by 15.94%, and of the nsP2 CDS by 0.8%.

Transcription of the plasmid from the T7 promoter produces C05 replicon RNA. The 5' UTR, nsP1-4 ORF, and SGP of C05 is set forth in SEQ ID NO: 24.

Transfection of BHK cells in vitro confirmed that this RNA (C05) was able to mediate expression of a subgenomic ORF-encoded reporter gene, secreted embryonic alkaline phosphatase (FIG. 17A). Mice injected with this construct exhibited average SEAP serum expression on par with or greater than mice injected with wild-type VEEV-SEAP (FIG. 17D).

Figure 10:
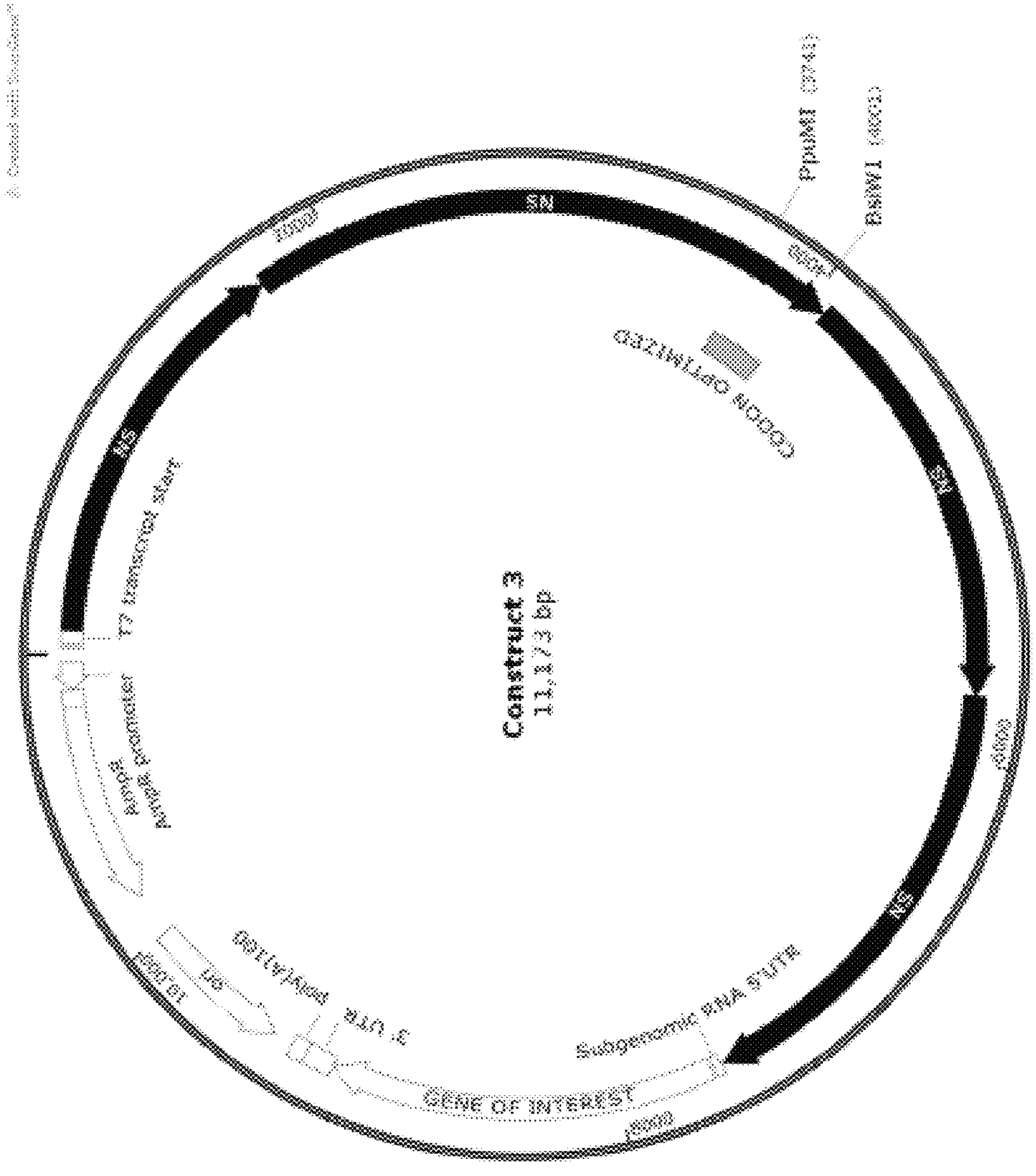
FIG. 10 is a schematic drawing of a DNA plasmid encoding the replicon sequence template of construct 3 (C03). In this figure, the DNA plasmid is similar to that shown in FIG. 5, except that only codons in genomic nucleotide positions 3694-3954 (gray box) were altered to reduce homology to the wild-type virus. Transcription of the plasmid from the T7 promoter produces C03 replicon RNA. The 5' UTR, nsP1-4 ORF, and SGP of C03 is set forth in SEQ ID NO: 22.

Example 6. VEEV Replicon RNA Modified with Homology Reduced in the nsP2 within Nucleotide Positions 3694-3954 of the Genome As was described in Example 2 for construct C02, bioinformatic inspection of localized RNA folding based on thermodynamic parameters was used to select regions of unstructured nucleotides within the nsP2 coding sequence, and accordingly a series of silent mutations were substituted across the region to create the construct designated C03. FIG. 10 is a schematic drawing of a DNA plasmid encoding the replicon sequence template of construct 3 (C03). In this figure, the DNA plasmid is similar to that shown in FIG. 5, except that only codons in genomic nucleotide positions 3694-3954 (gray box) were altered to reduce homology to the wild-type virus. In aggregate, the silent mutations reduced sequence identity of the nsP2 CDS to wild-type by 3.19%.

Transcription of the plasmid from the T7 promoter produces C03 replicon RNA. The 5' UTR, nsP1-4 ORF, and SGP of C03 is set forth in SEQ ID NO: 22.

Transfection of BHK cells in vitro confirmed that this RNA was able to mediate expression of a subgenomic ORF-encoded reporter gene, secreted embryonic alkaline phosphatase (FIG. 17A). It was observed that mice injected with construct C03 exhibited average SEAP serum expression on par with or greater than mice injected with wild-type VEEV-SEAP (FIG. 17D).

Figure 11:
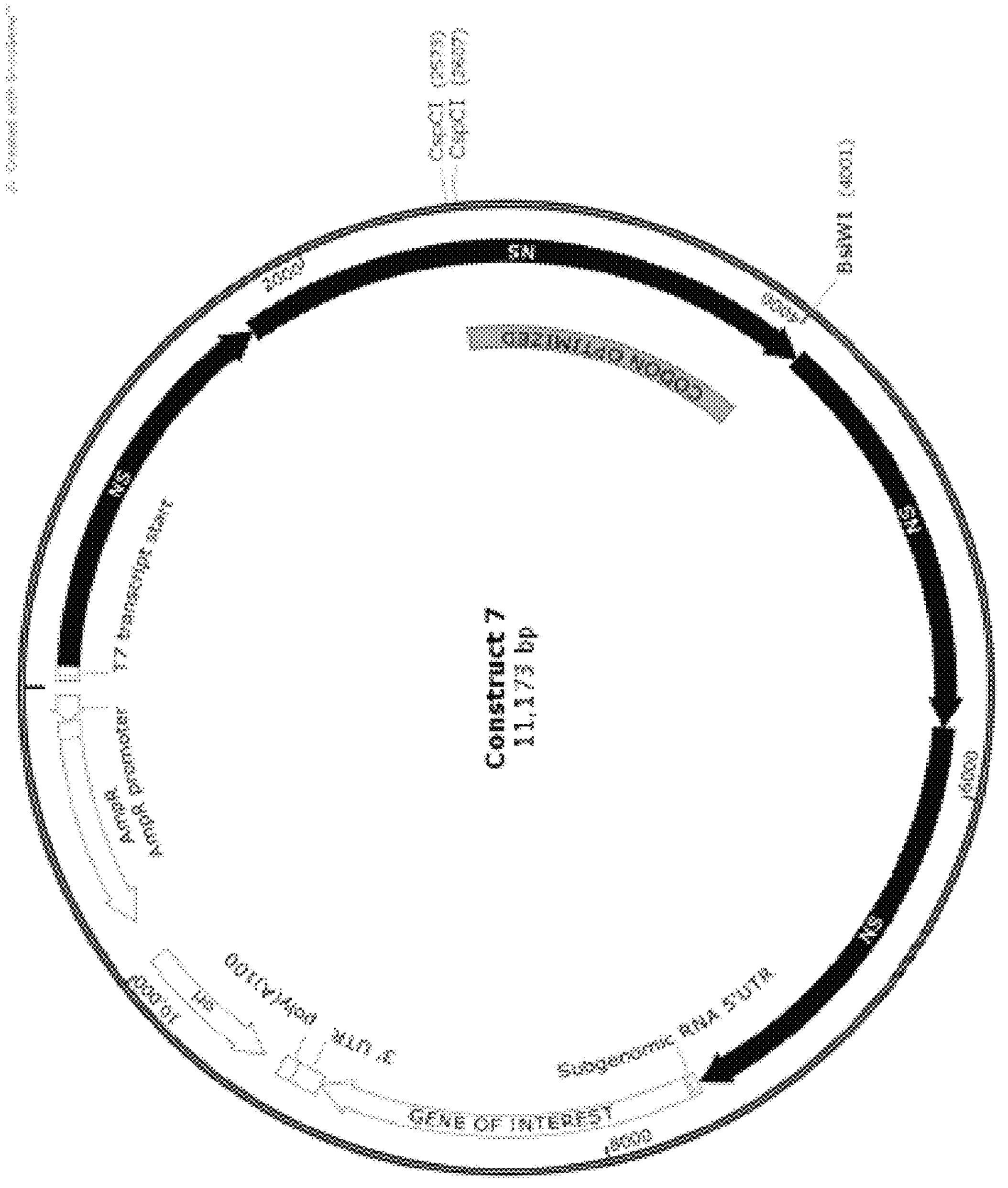
FIG. 11 is a schematic drawing of a DNA plasmid encoding the replicon sequence template of construct 7 (C07). In this figure, the DNA plasmid is similar to that shown in FIG. 5, except that only codons in genomic nucleotide positions 2560-3954 (gray box) were altered to reduce homology to the wild-type virus. Transcription of the plasmid from the T7 promoter produces C07 replicon RNA. The 5' UTR, nsP1-4 ORF, and SGP of C07 is set forth in SEQ ID NO: 26.

Example 7. VEEV Replicon RNA Modified with Homology Reduced in the nsP2 within Nucleotide Positions 2560-3954 of the Genome Given the success observed in Example 5, the homology-reduced region was extended further in the 5' direction. Bioinformatic inspection of localized RNA folding based on thermodynamic parameters across genomic nucleotide positions 2560-3954 was performed again and regions of unstructured nucleotides were accordingly substituted with silent mutations to create the construct designated C07. FIG. 11 is a schematic drawing of a DNA plasmid encoding the replicon sequence template of construct 7 (C07). In this figure, the DNA plasmid is similar to that shown in FIG. 5, except that only codons in genomic nucleotide positions 2560-3954 (gray box) were altered to reduce homology to the wild-type virus. In aggregate, the silent mutations reduced sequence identity of the nsP2 CDS to wild-type by 15.97%. Transcription of the plasmid from the T7 promoter produces C07 replicon RNA. The 5' UTR, nsP1-4 ORF, and SGP of C07 is set forth in SEQ ID NO: 26.

Transfection of BHK cells in vitro confirmed that this RNA (C07) was able to mediate expression of a subgenomic ORF-encoded reporter gene, secreted embryonic alkaline phosphatase (FIG. 17A).

Figure 12:
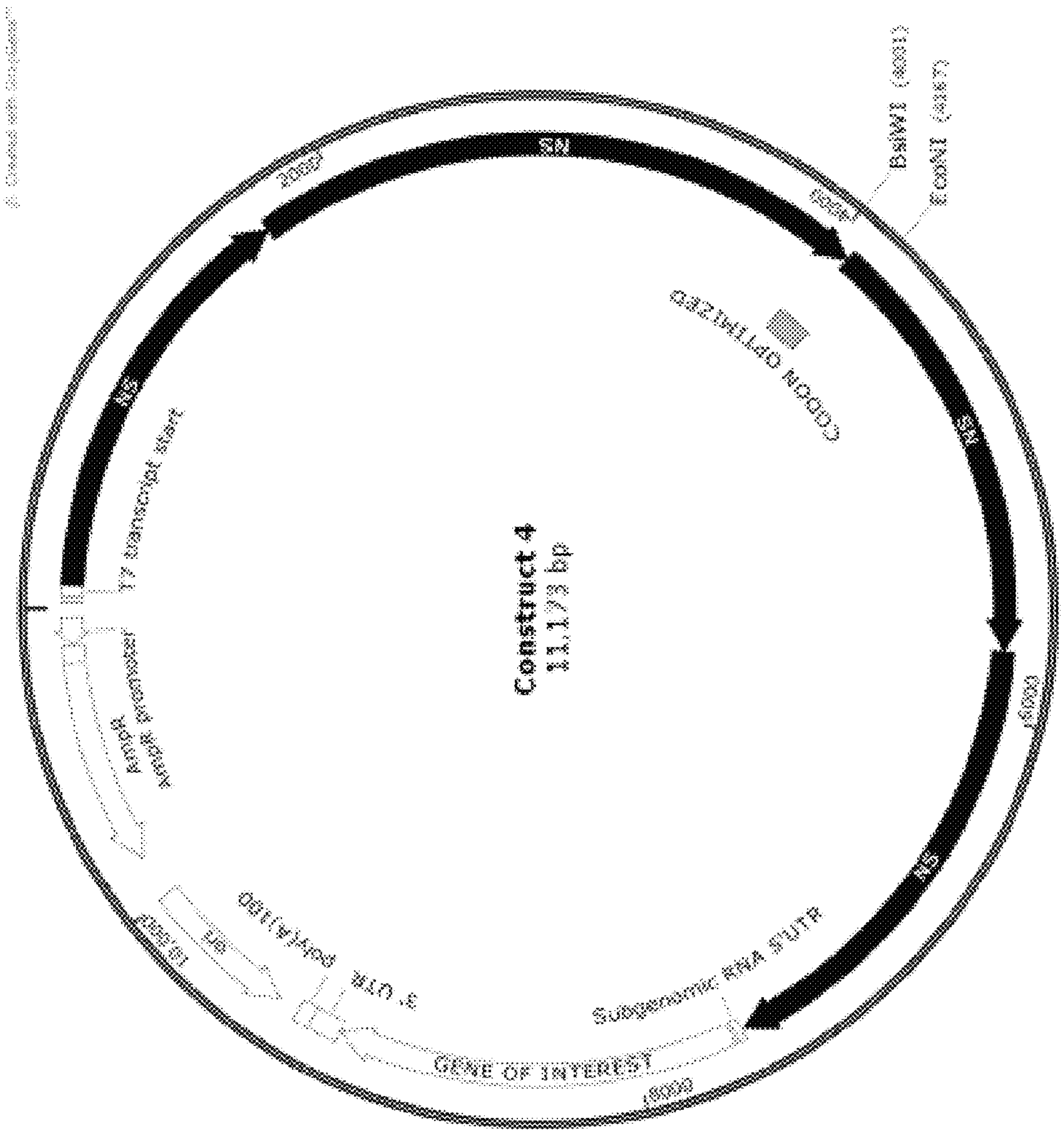
FIG. 12 is a schematic drawing of a DNA plasmid encoding the replicon sequence template of construct 4 (C04). In this figure, the DNA plasmid is similar to that shown in FIG. 5, except that only codons in genomic nucleotide positions 3954-4120 (gray box) were altered to reduce homology to the wild-type virus. Transcription of the plasmid from the T7 promoter produces C04 replicon RNA. The 5' UTR, nsP1-4 ORF, and SGP of C04 is set forth in SEQ ID NO: 23.

Example 8. VEEV Replicon RNA Modified with Homology Reduced in the nsP2-nsP3 Junction Region within Nucleotide Positions 3954-4120 of the Genome As was described in Example 2 for construct C02, bioinformatic inspection of localized RNA folding based on thermodynamic parameters was used to select regions of unstructured nucleotides spanning across the nsP2 and nsP3 juncture, and accordingly a series of silent mutations were substituted across the region to create the construct designated C04. FIG. 12 is a schematic drawing of a DNA plasmid encoding the replicon sequence template of construct 4 (C04). In this figure, the DNA plasmid is similar to that shown in FIG. 5, except that only codons in genomic nucleotide positions 3954-4120 (gray box) were altered to reduce homology to the wild-type virus. In aggregate, the silent mutations reduced sequence identity of the nsP2 CDS to wild-type by 4.61%, and of the nsP3 CDS by 0.12%.

Transcription of the plasmid from the T7 promoter produces C04 replicon RNA. The 5' UTR, nsP1-4 ORF, and SGP of C04 is set forth in SEQ ID NO: 23.

Transfection of BHK cells in vitro confirmed that this RNA was able to mediate expression of a subgenomic ORF-encoded reporter gene, secreted embryonic alkaline phosphatase (FIG. 17A).

Figure 13:
FIG. 13 is a schematic drawing of a DNA plasmid encoding the replicon sequence template of construct 1 (C01). In this figure, the DNA plasmid is similar to that shown in FIG. 5, except that only codons in genomic nucleotide positions 6381-7083 (gray box) were altered to reduce homology to the wild-type virus. Transcription of the plasmid from the T7 promoter produces C01 replicon RNA. The 5' UTR, nsP1-4 ORF, and SGP of C01 is set forth in SEQ ID NO: 20.

Example 9. VEEV Replicon RNA Modified with Homology Reduced in the nsP4 within Nucleotide Positions 6381-7083 of the Genome As was described in Example 2 for construct C02, bioinformatic inspection of localized RNA folding based on thermodynamic parameters was used to select regions of unstructured nucleotides within the nsP4 coding sequence, and accordingly a series of silent mutations were substituted across the region to create the construct designated C01. FIG. 13 is a schematic drawing of a DNA plasmid encoding the replicon sequence template of construct 1 (C01). In this figure, the DNA plasmid is similar to that shown in FIG. 5, except that only codons in genomic nucleotide positions 6381-7083 (gray box) were altered to reduce homology to the wild-type virus. In aggregate, the silent mutations reduced sequence identity of the nsP4 CDS to wild-type by 4.69%. Transcription of the plasmid from the T7 promoter produces C01 replicon RNA. The 5' UTR, nsP1-4 ORF, and SGP of C01 is set forth in SEQ ID NO: 20.

Transfection of BHK cells in vitro confirmed that this RNA (C01) was able to mediate expression of a subgenomic ORF-encoded reporter gene, secreted embryonic alkaline phosphatase (FIG. 17A).

Example 10. A Single VEEV Replicon RNA Modified with the nsP1 Homology Reductions of C06 and the nsP2 Homology Reductions of C07

Figure 14:
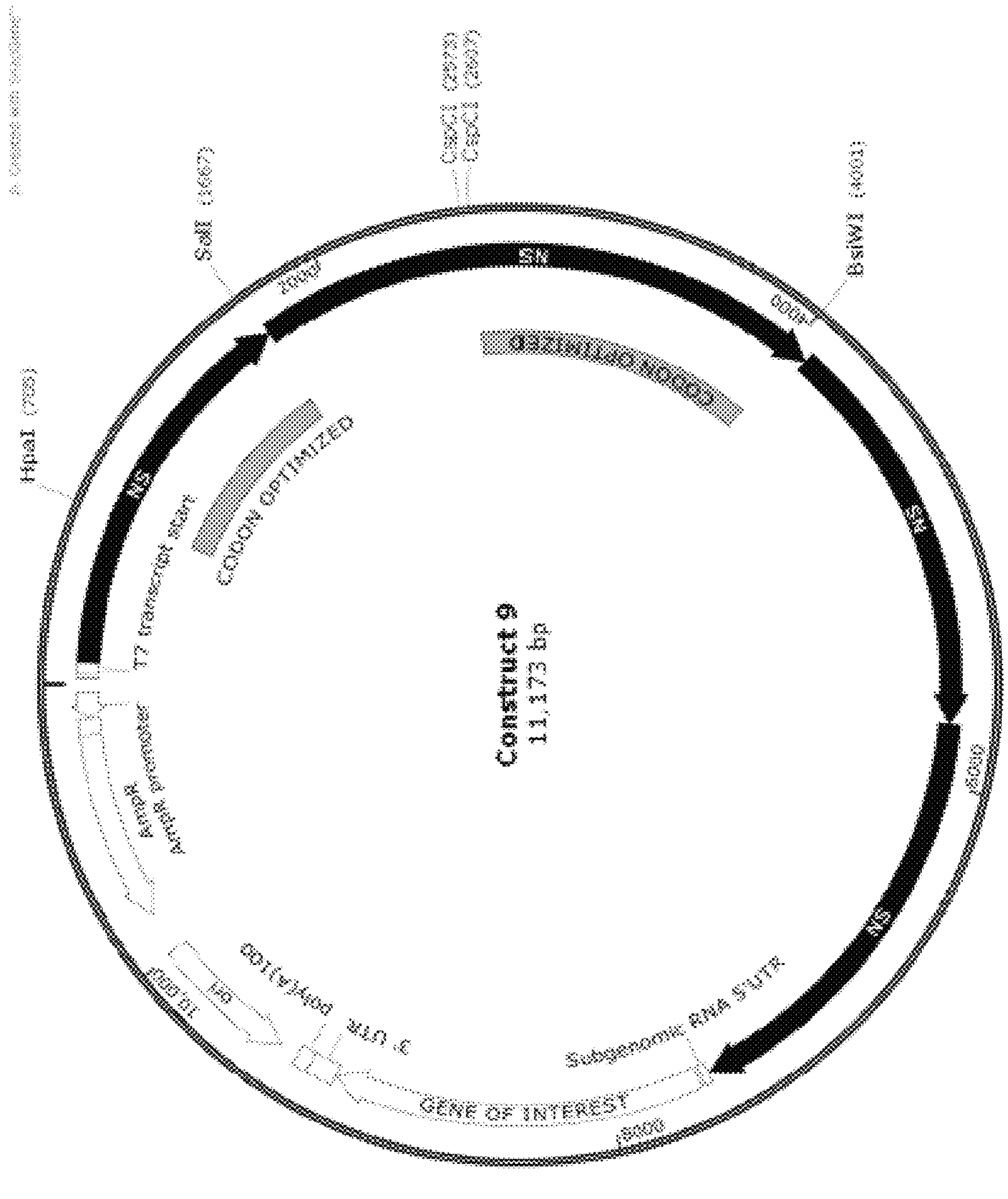
FIG. 14 is a schematic drawing of a DNA plasmid encoding the replicon sequence template of construct 9 (C09). In this figure, the DNA plasmid is similar to that shown in FIG. 5, except that only codons in genomic nucleotide positions 658-1620 and 2560-3954 (gray boxes) were altered to reduce homology to the wild-type virus. Transcription of the plasmid from the T7 promoter produces C09 replicon RNA. The 5' UTR, nsP1-4 ORF, and SGP of C09 is set forth in SEQ ID NO: 28.

Given the success observed in Examples 4 and 7, the homology-reduced regions were combined in a single clone to generate the construct designated C09. FIG. 14 is a schematic drawing of a DNA plasmid encoding the replicon sequence template of construct 9 (C09). In this figure, the DNA plasmid is similar to that shown in FIG. 5, except that only codons in genomic nucleotide positions 658-1620 and 2560-3954 (gray boxes) were altered to reduce homology to the wild-type virus. In aggregate, the silent mutations reduced sequence identity of the nsP1 CDS to wild-type by 8.96%, and of the nsP2 CDS by 15.97%. Transcription of the plasmid from the T7 promoter produces C09 replicon RNA. The 5' UTR, nsP1-4 ORF, and SGP of C09 is set forth in SEQ ID NO: 28.

Figure 17B:
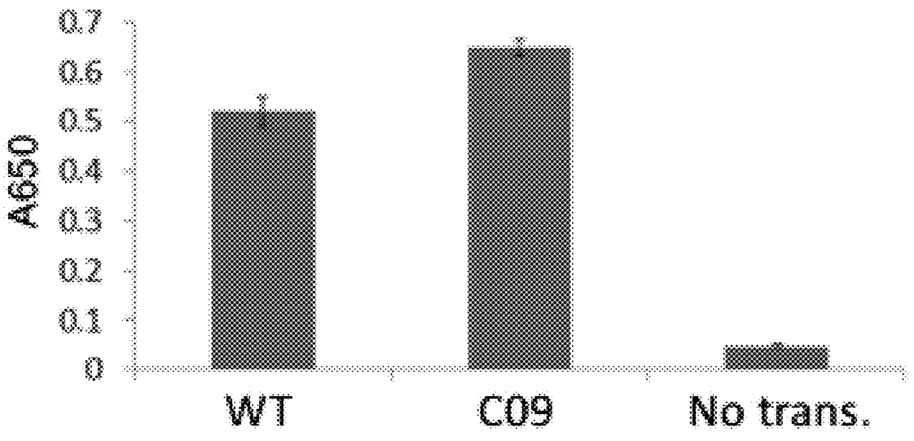

FIG. 17B is a bar graph that shows the results of the SEAP expression tests by sampling the conditioned supernatant of BHK cells transfected for 16 hours with the indicated replicon RNA and quantifying SEAP expression by measuring absorbance at 650 nm in a colorimetric assay.

Referring to FIG. 17B, transfection of BHK cells in vitro confirmed that this RNA (C09) was able to mediate expression of a subgenomic ORF-encoded reporter gene, secreted embryonic alkaline phosphatase.

Example 11. A Single VEEV Replicon RNA Modified with the nsP2 Homology Reductions of C03 and the nsP4 Homology Reductions of C01

Figure 15:
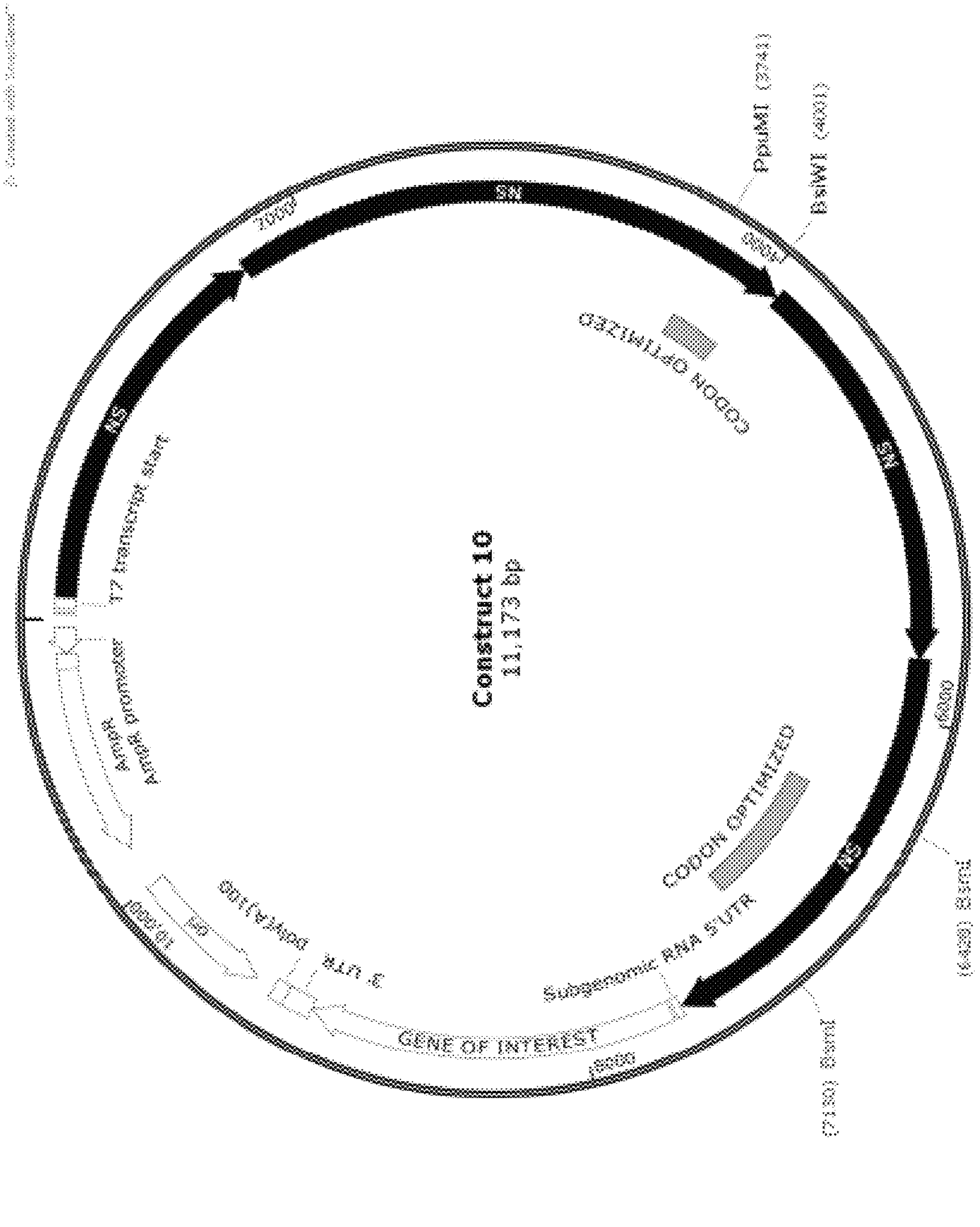
FIG. 15 is a schematic drawing of a DNA plasmid encoding the replicon sequence template of construct 10 (C10). In this figure, the DNA plasmid is similar to that shown in FIG. 5, except that only codons in genomic nucleotide positions 3694-3954 and 6381-7083 (gray boxes) were altered to reduce homology to the wild-type virus. Transcription of the plasmid from the T7 promoter produces C10 replicon RNA. The 5' UTR, nsP1-4 ORF, and SGP of C10 is set forth in SEQ ID NO 29.

Given the success observed in Examples 6 and 9, the homology-reduced regions were combined in a single clone to generate the construct designated C10. FIG. 15 is a schematic drawing of a DNA plasmid encoding the replicon sequence template of construct 10 (C10). In this figure, the DNA plasmid is similar to that shown in FIG. 5, except that only codons in genomic nucleotide positions 3694-3954 and 6381-7083 (gray boxes) were altered to reduce homology to the wild-type virus. In aggregate, the silent mutations reduced sequence identity of the nsP2 CDS to wild-type by 3.19%, and of the nsP4 CDS by 4.69%. Transcription of the plasmid from the T7 promoter produces C10 replicon RNA. The 5' UTR, nsP1-4 ORF, and SGP of C10 is set forth in SEQ ID NO 29.

Figure 17C:
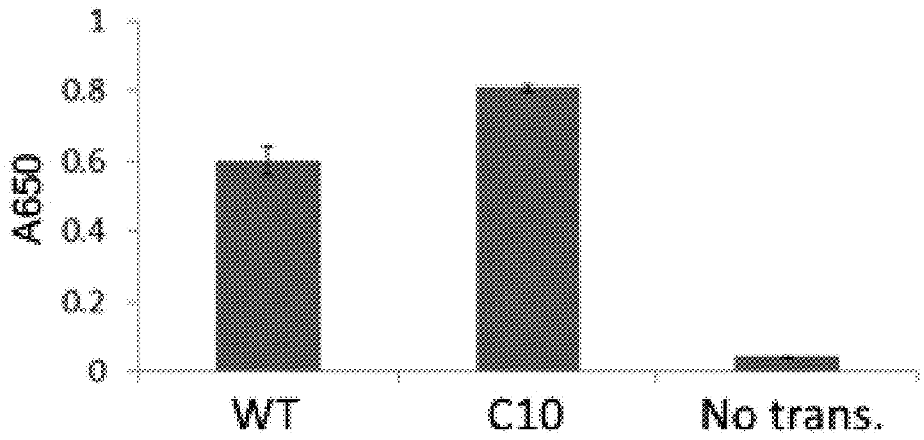
Figure 17D:
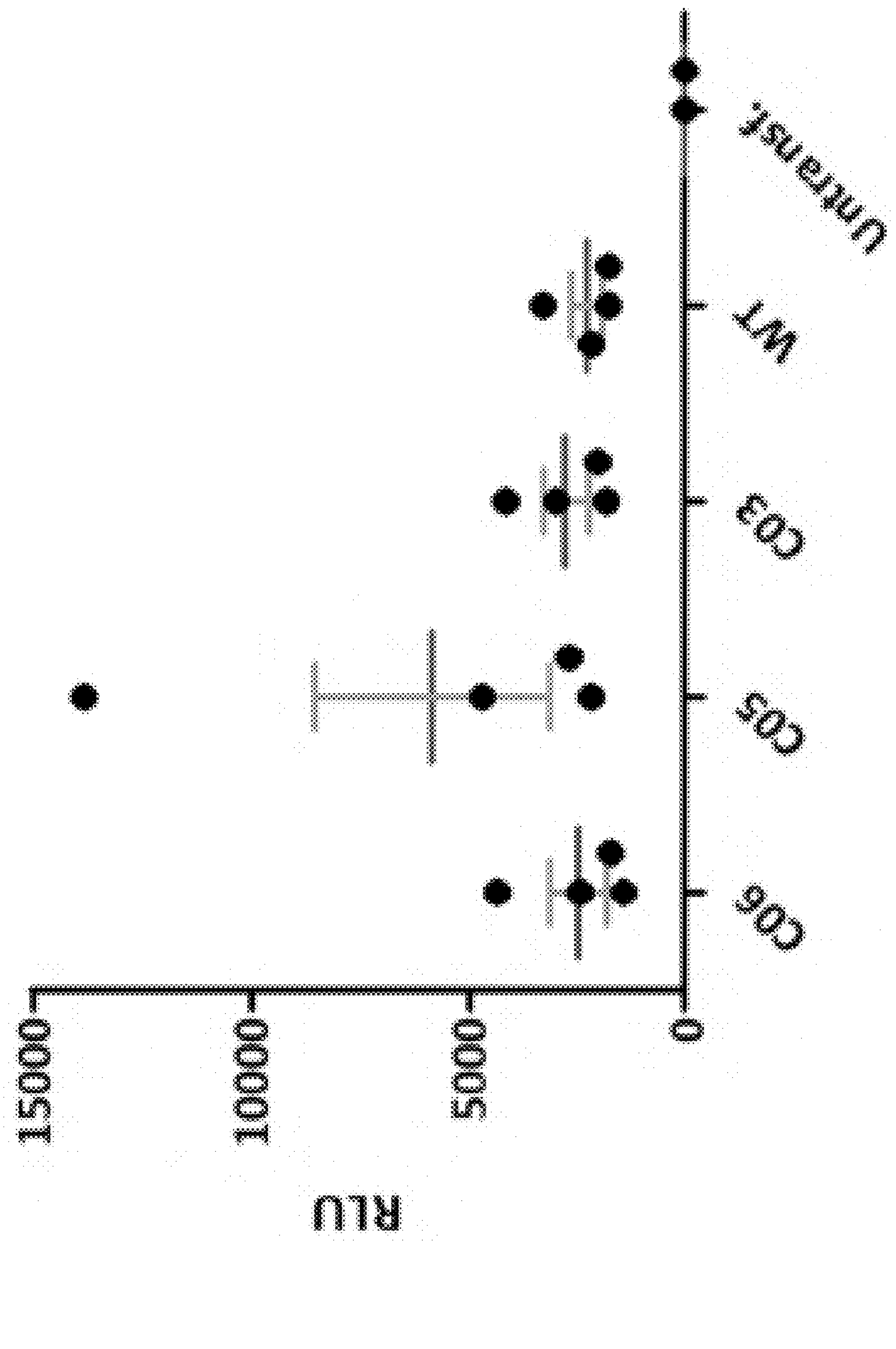

FIG. 17C is a bar graph that shows the results of the SEAP expression tests by sampling the conditioned supernatant of BHK cells transfected for 16 hours with the indicated replicon RNA and quantifying SEAP expression by measuring absorbance at 650 nm in a colorimetric assay.

Referring to FIG. 17C, transfection of BHK cells in vitro confirmed that this RNA (C10) was able to mediate expression of a subgenomic ORF-encoded reporter gene, secreted embryonic alkaline phosphatase.

Figure 16:
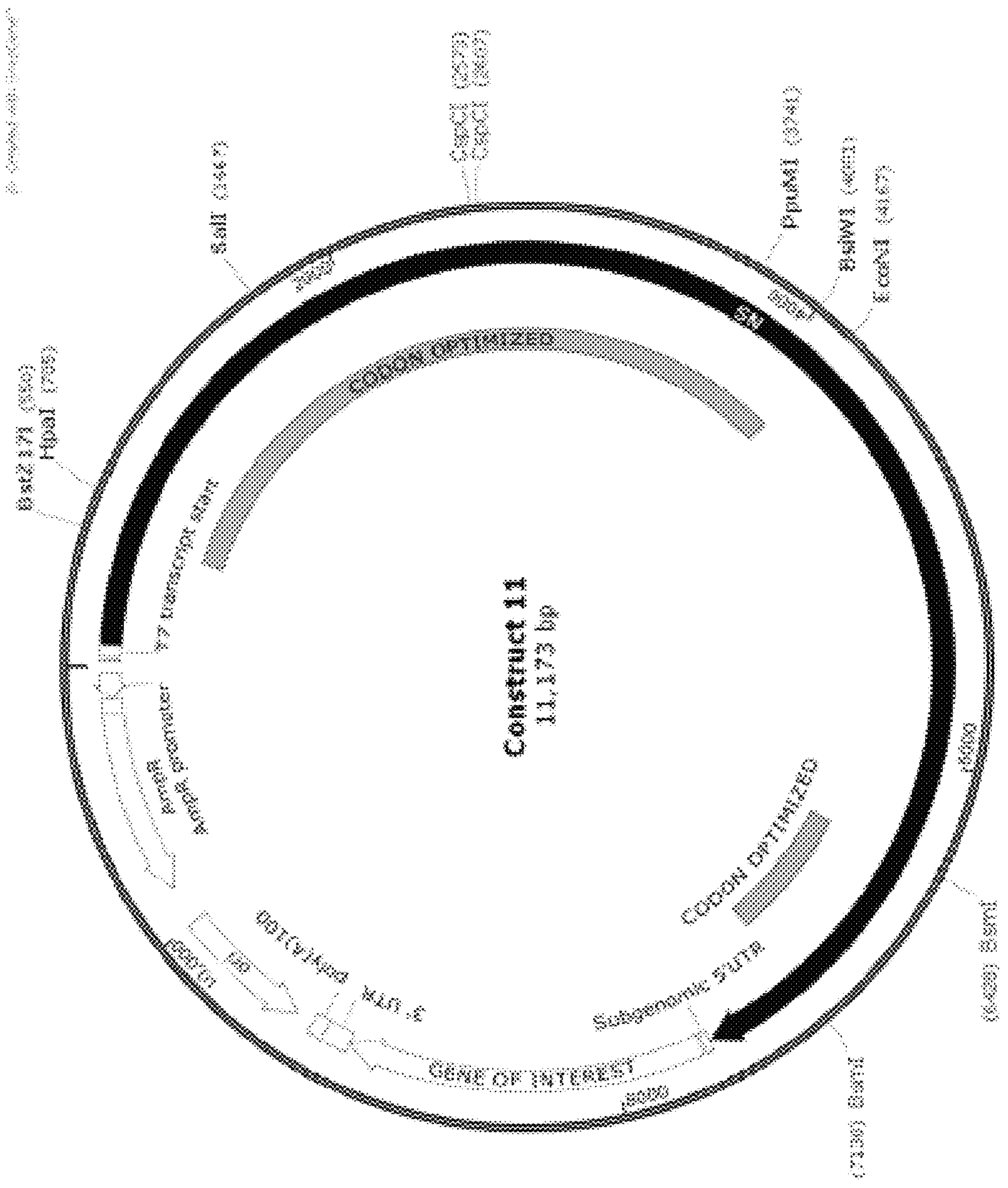
FIG. 16 is a schematic drawing of a DNA plasmid encoding the replicon sequence template of construct 11 (C11). In this figure, the DNA plasmid is similar to that shown in FIG. 5, except that only codons in genomic nucleotide positions 503-658, 658-1620, 1620-2560, 2560-3954, 3954-4120, and 6381-7083 (gray boxes) were altered to reduce homology to the wild-type virus. Transcription of the plasmid from the T7 promoter produces C11 replicon RNA. The 5' UTR, nsP1-4 ORF, and SGP of C11 is set forth in SEQ ID NO: 30.

Example 12. A Single VEEV Replicon RNA Modified with the Homology Reduction Represented in Regions Across all nsP Given the generalizable success of the approach described in previous Examples, the regions previously analyzed and homology-reduced to generate constructs C01, C02, C04, C05, C06, and C07 were re-analyzed in aggregate and silent mutations substituted across the determined non-structured nucleotide stretches to produce the construct designated C11. FIG. 16 is a schematic drawing of a DNA plasmid encoding the replicon sequence template of construct 11 (C11). In this figure, the DNA plasmid is similar to that shown in FIG. 5, except that only codons in genomic nucleotide positions 503-658, 658-1620, 1620-2560, 2560-3954, 3954-4120, and 6381-7083 (gray boxes) were altered to reduce homology to the wild-type virus. In this example, the applied silent mutations resulted in a total decrease in the homology of the nsP CDS by a degree equivalent to the sum of all previously mutated regions combined as compared to the wild-type virus. Transcription of the plasmid from the T7 promoter produces C11 replicon RNA. The 5' UTR, nsP1-4 ORF, and SGP of C11 is set forth in SEQ ID NO: 30.

FIGS. 17A-17D illustrate the results of SEAP expression tests to demonstrate the function of the subgenomic ORF encoding SEAP present in codon-adapted replicon RNAs. FIG. 17A is bar graph showing the results of the SEAP expression tests by sampling the conditioned supernatant of BHK cells transfected for the indicated time 4 hours (left bars), 16 hours (middle bars) and 24 hours (right bars) compared to control, wild type (WT) and untransfected (No transf.) cells. FIGS. 17B and 17C are bar graphs that show the results of the SEAP expression tests by sampling the conditioned supernatant of BHK cells transfected for 16 hours with the indicated replicon RNA (FIG. 17B-C09, and FIG. 17C-C10) and quantifying SEAP expression by measuring absorbance at 650 nm in a colorimetric assay. As demonstrated by this data, the modification of the nsP codons in regions identified by bioinformatic analysis does not negatively impact expression of a transgene encoded in the subgenomic ORF in vitro. FIG. 17D shows the results of SEAP expression in mice. In these experiments, four mice per group were administered by intramuscular injection with 1 μg of the indicated codon-adapted replicons. Serum was collected and the relative expression of SEAP was quantified by luminescent assay. Referring to FIG. 17D, mean RLU of each animal is shown, error bars, standard deviation of each group. Two uninjected mice (labeled "untransf") were used as negative controls to indicate background signal. As demonstrated by this data, the modification of the nsP codons in regions identified by bioinformatic analysis does not negatively impact expression of a transgene encoded in the subgenomic ORF in vivo.

Figure 18:
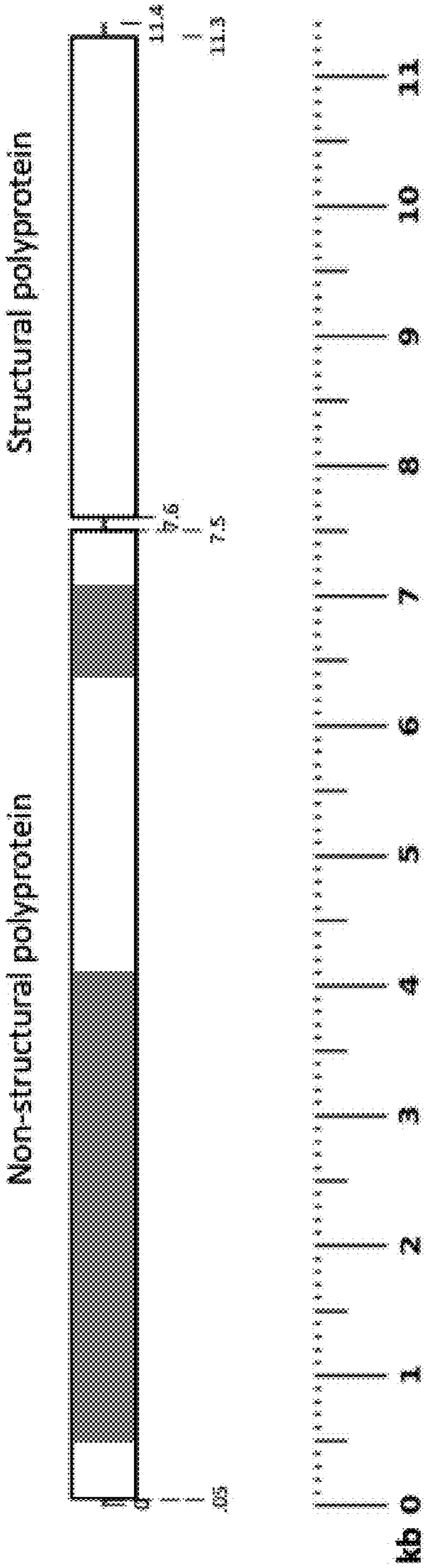
FIG. 18 is a scale diagram of the VEEV genome, where regions of the nonstructural polyprotein determined by RNA folding analysis and experiments described herein to be enriched in non-structured regions amenable to silent mutation are marked as gray boxes.

In aggregate, the extensive regions of nsP were revealed through this analysis to contain unstructured nucleotide stretches amenable to silent mutation that do not impact gene expression. FIG. 18 is a scale diagram of the VEEV genome, where regions of the nonstructural polyprotein determined by RNA folding analysis and experiments described herein to be enriched in non-structured regions amenable to silent mutation are marked as gray boxes. The embodiments herein disclose silent mutations across these regions such that the resulting sequence diverges from the naturally occurring VEEV type genome nsP coding region by up to 10% non-identity by Basic Local Alignment Search (BLAST).

Example 13. VEEV Replicon RNA with nsP4 C-Terminal Coding Region Duplicated to Introduce C-Terminal Fusion Site and Reinstate the Subgenomic Promoter (SGP)

Direct insertion of an arbitrary additional protein ("xP") by conventional cloning to fuse the nsP4 and xP ORFs disrupts primary nucleotide sequence elements that compose the SGP. Because the SGP is required to mediate transcription of the subgenomic RNA and thus late-phase translation of the subgenomic ORF, such an approach to fusing xP to the nsP4 C-terminus would destroy the replicon's capacity to mediate transgene expression from the subgenomic locus. FIG. 3 illustrates a process for circumventing this problem, by duplicating the SGP region, which includes the coding region of the nsP4 C-terminus. The upstream duplicate region can then be used as a target for in-frame insertion of xP by incorporation of nucleotides that generate a restriction site for conventional cloning. FIG. 3 illustrates an example of simple steps that can be followed to clone a modifiable nsP4 open reading frame (ORF) while maintaining an intact extended subgenomic promoter (SGP, striped box). This simplistic approach however leaves two regions of identical sequence that lead to genetic instability when propagating this DNA template sequence in bacterial strains necessary for manufacturing.

When this construct was cloned as DNA templates in practice, the identical sequences present representing the codons that encode the nsP4 C-terminal rendered standard bacterial strains (DH5-alpha) incapable of maintaining the repetitive sequence intact. All clones isolated from DNA templates constructed with the method outlined in FIG. 3 carried deletions eliminating the nsP4 C-terminal duplication.

Figure 19:
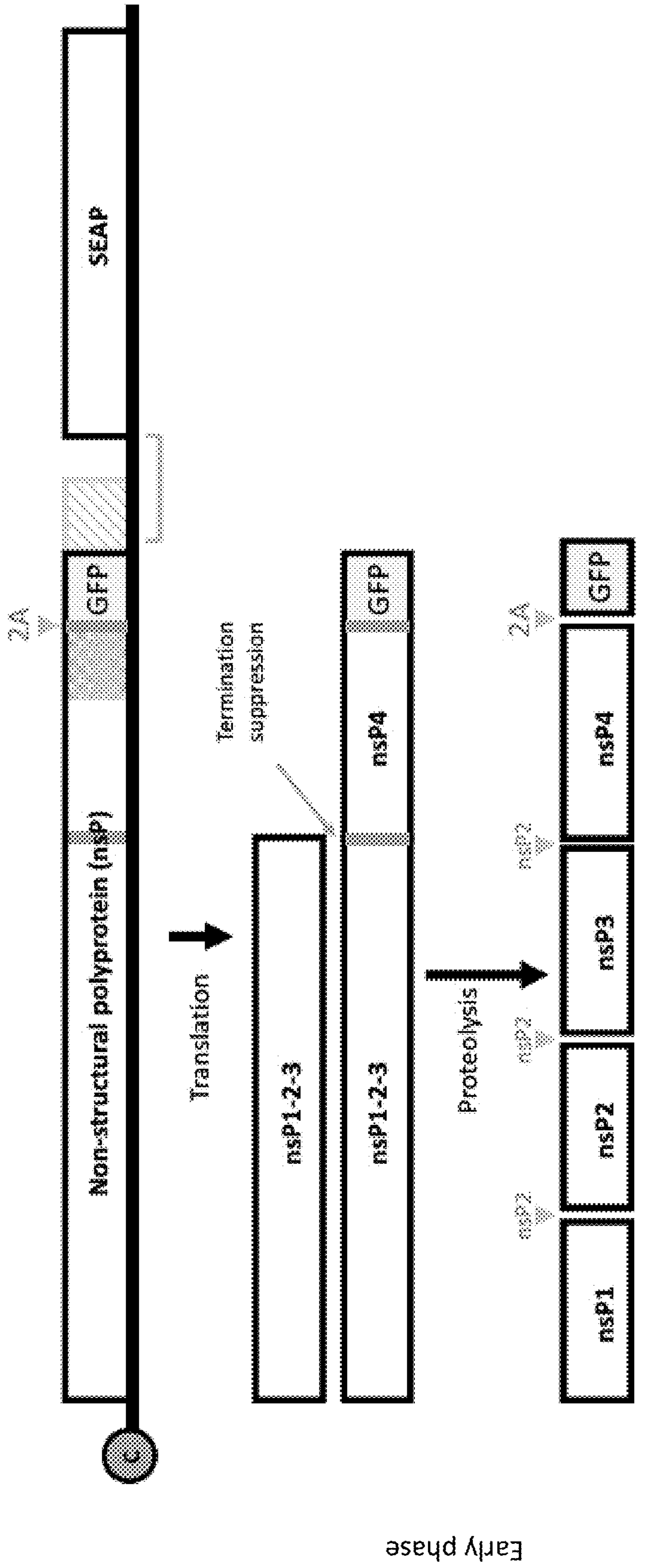
FIG. 19 is a schematic drawing illustrating an example of nsP4 replicon sequence as shown in FIG. 4 modified for experimentation, where the exogenous protein (xP) appended to the nsP4 protein is green fluorescent protein (GFP; gray box). In this figure, the structural polyprotein in the SG ORF is replaced with a reporter gene, SEAP. This replicon RNA is referred to as VEEVrep-nsP4[GFP]-SEAP, and the RNA sequence is as set forth in SEQ ID NO: 31.

Example 14. VEEV Replicon RNA with nsP4 C-Terminal Coding Region Duplicated and Homology-Reduced to Introduce C-Terminal Fusion Site, Thus Reinstating the Subgenomic Promoter (SGP), and Eliminating Repetitive Sequence Elements FIG. 4 illustrates an example of optimal steps that can be followed to clone a modifiable nsP4 open reading frame (ORF) while maintaining an intact extended subgenomic promoter (SGP, striped box). This approach eliminates problematic repetitive sequence elements and the DNA template can be easily propagated and manufactured in common bacterial strains FIG. 4 illustrates an optimal process for installing an xP fusion to the nsP4 C-terminus while maintaining an intact SGP region. The upstream duplicate sequence has its codons altered first to remove homology to the downstream duplicate, which maintains wild-type sequence to ensure an intact SGP proximal to the subgenomic ORF. The sequence of the downstream SGP, placed 3' of an arbitrary xP, is set forth as SEQ ID NO: 14. The upstream reduced-homology duplicate region region (exemplified in the sequence set forth as SEQ ID NO: 18) can then be fused by conventional molecular cloning to any xP inserted in-frame at the terminus of nsP4. An example of the final nsP4 coding RNA sequence is set forth in SEQ ID NO: 19. FIG. 19 is a schematic drawing illustrating an nsP4 replicon sequence modified for experimentation, where the exogenous protein (xP) appended to the nsP4 protein is green fluorescent protein (GFP). In this figure, the structural polyprotein in the SG ORF is replaced with a reporter gene, SEAP. In this figure, the nsP includes a gene encoding the GFP preceded by a self-cleaving 2A peptide as xP, and the subgenomic ORF includes the secreted embryonic alkaline phosphatase (SEAP) reporter gene. The nsP1-nsP2-nsP3-nsP4-2A fusion polyprotein amino acid sequence resulting from these alterations, to which a xP of interest (such as GFP) can be further fused, is set forth as SEQ ID NO: 12. An exemplary DNA sequence encoding this engineered nsP-2A ORF is set forth as SEQ ID NO: 13. The nsP1-nsP2-nsP3-nsP4-2A-GFP amino acid sequence is set forth in SEQ ID NO: 15, and an exemplary DNA sequence encoding this engineered nsP-2A-GFP ORF is set forth in SEQ ID NO: 16. The total nsP4-2A-GFP modified replicon RNA construct is designated C16. This replicon RNA is referred to as VEEVrep-nsP4[GFP]-SEAP, and the corresponding RNA sequence of the 5' UTR, nsP1-4-GFP fusion ORF, and SGP is as set forth in SEQ ID NO: 31.

Figure 20A:
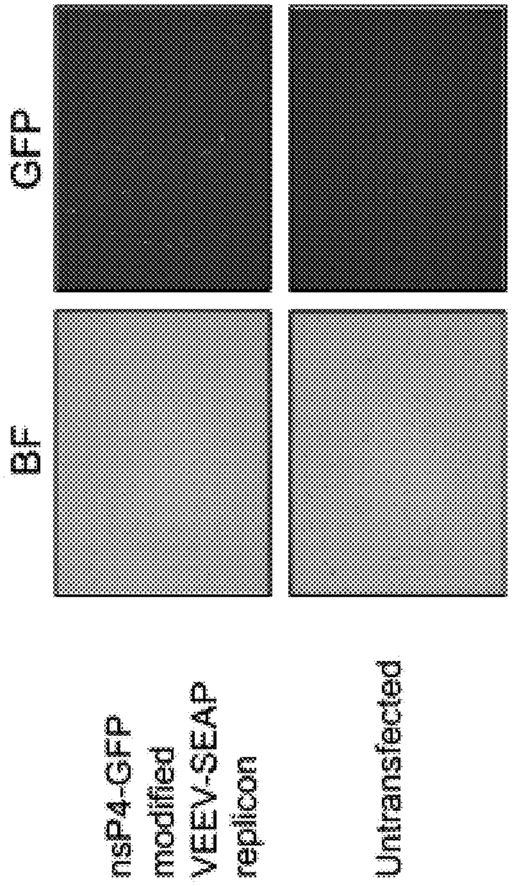
FIG. 20A-20C illustrate gene expression mediated by an engineered nsP4-modified VEEV replicon in cells in vitro. BHK were cells transfected with the experimental nsP4-modified replicon encoding GFP in the nonstructural protein ORF and SEAP in the SG ORF (VEEVrep-nsP4[GFP]-SEAP).
Figure 20C:
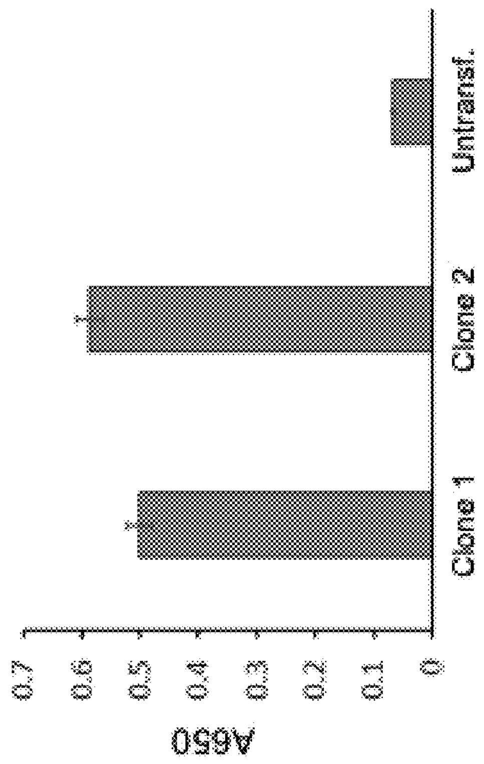
Figure 20B:
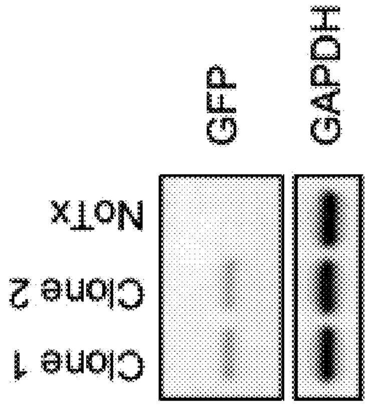

FIGS. 20A-20C illustrate gene expression mediated by an engineered nsP4-modified VEEV replicon in cells in vitro. BHK cells were transfected with the experimental nsP4-modified replicon encoding GFP in the nonstructural protein ORF and SEAP in the subgenomic ORF (VEEVrep-nsP4 [GFP]-SEAP). FIG. 20A shows results of fluorescence microscopy, demonstrating a plurality of GFP-positive cells when transfection is performed with nsP4 (GFP)-modified VEEV-SEAP replicon RNA (top right), and the absence of GFP expression in untransfected control cells (bottom right). FIG. 20B are the immunoblots of transfected BHK cell lysates with a GFP-specific monoclonal antibody (top bands), with GAPDH detection serving as loading control (lower bands) that shows confirmation of GFP expression by two independently isolated clones of nsP4 (GFP)-modified VEEV replicon RNA (Clone 1 and Clone 2) compared to the untransfected control (NoTx). FIG. 20C are the bar graphs that shows the function of the subgenomic ORF encoding SEAP as tested by sampling the conditioned supernatant of the transfected BHK cells and quantifying SEAP expression by colorimetric assay. Referring to this figure, both Clone 1 and Clone 2 shows high SEAP expression compared to untransfected (Untrasf.) control, from which only assay background absorbance was observed. Referring to FIGS. 20A-20C, this RNA, when transfected into BHK cells, drove both GFP expression (FIGS. 20A and 29B) and SEAP expression (FIG. 20C) simultaneously. This confirmed that both the nsP4 function mediating genome replicative transcription and SGP-mediated translation were maintained, while an additional accessory functional protein (GFP) was successfully produced from an early-phase translated locus independent of the subgenomic ORF.

Figure 21A:
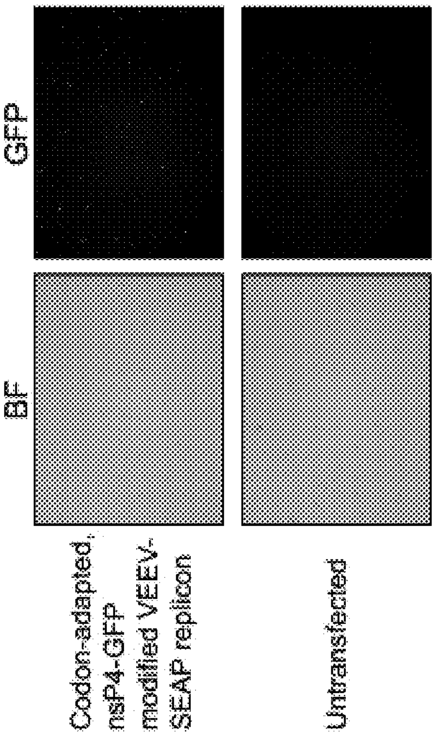
FIGS. 21A-21B illustrate gene expression mediated by an engineered nsP4-modified VEEV replicon. This replicon RNA combines codon-adaptation and nsP4 C-terminal modification as described in embodiments herein.
Figure 21B:
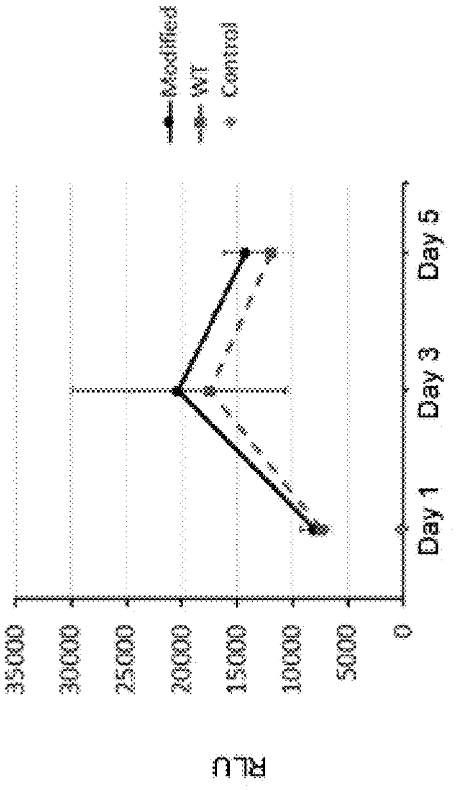

Example 15. A Single VEEV Replicon RNA Incorporating Both nsP4 C-Terminal xP Fusion and Homology-Reduced nsP Given the successes in Examples 9 and 12, a VEEV replicon was generated that combined the homology-reduced regions of C09 and the nsP4-2A-GFP modification of C16, to create the new construct designated C13. FIGS. 21A-21B illustrates gene expression mediated by this engineered nsP4-modified VEEV replicon. This replicon RNA combines codon-adaptation and nsP4 C-terminal modification as laid out in this filing.

FIG. 21A are photographs showing results of fluorescence microscopy, demonstrating a plurality of GFP-positive cells when transfection is performed with codon-adapted, nsP4 (GFP)-modified VEEV-SEAP replicon RNA (C13) (top panel, right), and the absence of GFP expression in Untransfected control cells (bottom panel, right).

FIG. 21B are charts showing the results of luminescent assay (RLU) to quantify the concentration of SEAP in serum collected from mice injected with wild type (WT) VEEVrep-SEAP replicon RNA, or with nsP4 (GFP)-modified (Modified) VEEV replicon RNA (similar to VEEVrep-nsP4[GFP]-SEAP) carrying optimized codons in unstructured regions of the nonstructural polyprotein gene compared to serum collected from uninjected control mice. The serum was collected on Day 1, Day 3, and Day 5 following the injections. In these experiments, mice (three per group) were administered by intramuscular injection a standard VEEV-SEAP replicon RNA or an equal dose of nsP4 (GFP)-modified VEEV replicon RNA carrying optimized codons in nonstructural regions of the nonstructural polyprotein gene. At the indicated times serum was collected and the concentration of SEAP was quantified by luminescent assay. Mean RLU of each group of mice is shown, error bars, standard deviation. Two uninjected mice were used as negative control to indicate background signal. As demonstrated by this data, the modification of the nsP4 gene by the method described here does not negatively impact expression of transgenes encoded in the subgenomic ORF in vivo.

Referring to FIG. 21A, it was observed that this RNA was capable of expressing GFP in cells transfected in vitro. Referring to FIG. 21B, it was also observed that injection of C13 in mice led to equivalent SEAP serum concentrations as the parental VEEV-SEAP replicon RNA, indicating that the reduced homology to wild-type virus, and combined additional transgene payload incorporated by fusion to nsP4, did not hinder gene expression efficacy in vivo.

Example 16. A Replicon RNA Encoding a Functional Enzyme Fused to the nsP4 C-Terminus and Separate Transgene in the SG ORF Following the design described in Example 14, an enzyme may be installed at the nsP4 C-terminus (i.e., xP may be a functional enzyme). As outlined above and depicted in SEQ ID NOS: 18 and SEQ ID NO: 14, the SGP can be maintained by duplication, placing the wild-type SGP sequence downstream of the xP fusion (in this Example, downstream of the enzyme) and the upstream duplicated sequence in the C-terminal coding region of nsP4 altered to maintain the correct amino acid sequence while reducing homology to the wild-type SGP. This ensures genetic stability of the construct and avoids homology-driven recombination that would otherwise result in deletion of the xP (as exemplified to occur in Example 13 if no codon-alterations are made).

Figure 22A:
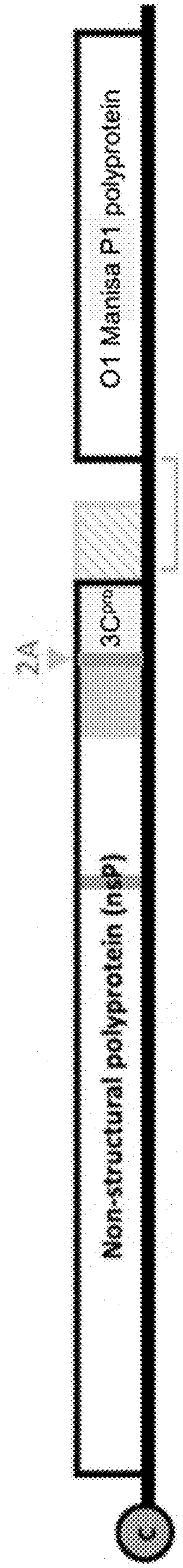
FIGS. 22A-22B illustrate gene expression from an alphaviral replicon RNA modified to encode the 3Cpro protease required for picornavirus P1 structural polyprotein (which is encoded in the SG ORF).
Figure 22B:
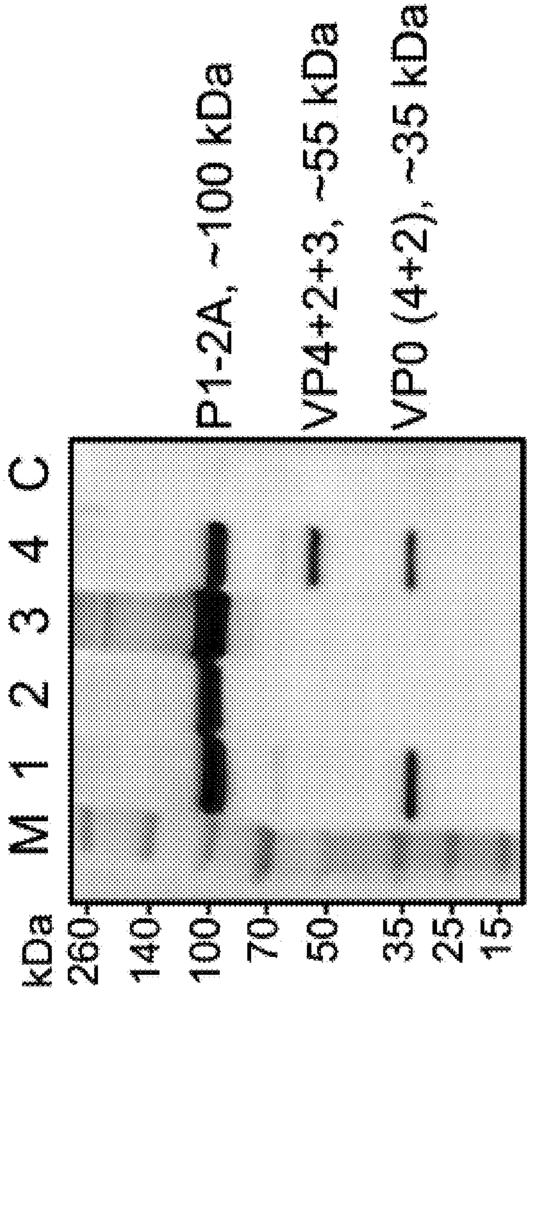

FIGS. 22A-22B illustrate gene expression from an alphaviral replicon RNA modified to encode the 3Cpro protease required for proteolytic processing of the picornavirus P1 structural polyprotein (which is encoded in the SG ORF).

FIG. 22A is a schematic drawing showing a construct with modification of the nsP4 coding sequence of an alphaviral replicon to encode the 3Cpro protease required for picornavirus P1 structural polyprotein (O1 Manisa P1 polyprotein), referred to as VEEVrep-nsP4[3C]-P1. The sequence of the 5'UTR, nsP1-4, 3Cpro, and SGP region of this RNA is set forth in SEQ ID NO: 32. The RNA sequence encoding the P1 structural polyprotein in the SG ORF is set forth in SEQ ID NO: 33. The amino acid sequence of the nsP4-2A-3Cpro fusion polyprotein encoded in the nsP ORF is set forth in SEQ ID NO: 40.

This figure illustrates the design of an exemplary VEEV replicon RNA where the C-terminus is fused via a 2A self-cleaving peptide to a viral protease using the approach described herein. The viral protease in this example is the 3Cpro of a picornavirus, Foot-and-mouth disease virus (FMDV), strain A12. The 3Cpro enzyme is an example of a good candidate for insertion into the NPS4 modified region of the replicon. 3Cpro is a highly processive enzyme, and, when delivered exogenously to cells, requires only a relatively low molecular copy number compared to its substrates. The 3Cpro activity is required for post-translational processing of the picornavirus capsid polyprotein (referred to as the P1 polyprotein). In addition to being fully functional at low expression levels, the low copy number for 3Cpro is ideal due to the inherent toxicity of the protease. When high levels of the 3Cpro are expressed in vitro, cell metabolism arrests and viability decreases. Attempts have been made to create FMDV vaccines in which a replicon RNA encoding the P1 polyprotein and an mRNA encoding the 3Cpro are co-formulated, with the goal of delivering both molecules to the same cell and allowing for processing of the P1 (trans-complementation). In this trans-complementing vaccine design, a ratio of P1-2A to 3Cpro of ~30-40:1 is required to minimize toxicity of the 3Cpro. While there are delivery platforms that allow for co-encapsulation and delivery of multiple RNA molecules to the same cell, it is unlikely that 100% of nanoparticles will contain at least one copy of the mRNA encoding the 3Cpro due to these ratio requirements. The trans-complementation approach therefore minimizes the potential efficacy of the vaccine product, as individual nanoparticles that do not have at least one copy of both RNA molecules will not be effective in generating processed capsid and thus fail to contribute to a humoral immune response.

Given that the 3Cpro enzyme is highly cytotoxic, and must be maintained at low steady-state concentrations to avoid terminally disrupting cellular processes through its proteolytic activity, it was encoded in the nsP4 C-terminal region to mediate expression as part of an FMDV vaccine construct. The P1 polyprotein comprises the VP0, VP2, and VP3 subunits, which must be cleaved by 3Cpro into separate polypeptide chains to allow assembly into capsid structures. To make a functional picornavirus vaccine, these capsid structures must assemble in order to be recognized by the immune system, and thus drive neutralizing antibody production. The VP0 fragment of the P1 polyprotein further comprises the VP4 and VP2 proteins which undergo cleavage by 3Cpro independent processes, and is not required for capsid assembly. To make a useful FMDV vaccine, the P1 polyprotein of FMDV strain O1 Manisa was encoded in the SG ORF of VEEV-based replicons. The replicon termed VEEVrep-nsP4[3C]-P1 provides 3Cpro activity in cis by encoding it at the nsP4 C-terminal as shown in FIG. 22A. An additional replicon, VEEVrep-nsP4[3C$^{mut}$]-P1, contains an insertion mutation that aborts translation of the 3Cpro sequence to serve as a parallel control. As an additional control, a replicon with a wild-type nsP4 and SGP region was produced that only encodes the P1 polyprotein in the SG ORF (VEEVrep-P1). These RNAs were synthesized by in vitro transcription and post-transcriptional capping. BHK cells in 12-well dishes were transfected with 1 μg per well of each P1-encoding replicon, and cell lysates prepared for analysis by immunoblot ~1 day later.

FIG. 22B is a photograph of the immunoblot performed on lysates of BHK cells transfected with the following RNAs: lane 1, VEEVrep-nsP4[3C]-P1; lane 2, replicon RNA similar to that in lane 1 but carrying an insert mutation that introduces a premature stop codon and ablates expression of the 3Cpro polypeptide as a negative control (VEEVrep-nsP4[3Cmut]-P1); lane 3, VEEVrep-P1 (similar to VEEVrep-nsP4[3C]-P1 but lacking nsP4-fused 3Cpro); lane 4, VEEVrep-P1 transfected in combination with 1/40$^{th}$ the mass of mRNA encoding 3Cpro as a positive control. Referring to this figure, the successful proteolytic processing of the ~100 kDa P1 polyprotein to the immunogenic ~35 kDa VP0 capsid fragment was mediated to completion only by VEEVrep-nsP4[3C]-P1 (lane 1). An intermediate incompletely cleaved product representing intact VP4+VP2+VP3 can be seen running at an apparent molecular weight of ~55 kDa (lane 4). A VP2-specific antibody was used to probe the blot. M, molecular weight markers; C, untreated negative control cells. This figure shows the result of immunoblot on the samples after probing with an FMDV VP2-specific monoclonal antibody. VEEVrep-nsP4[3Cmut]-P1 and VEEVrep-P1, which lack any 3Cpro activity, only produced full-length intact P1 polypeptide, seen as a ~100 kDa band. VEEVrep-nsP4[3C]-P1 successfully produced the desired fully processed VP0 fragment, indicating capsid processing took place as desired. Notably, processing was superior to the positive control (lane 4), wherein VEEVrep-P1 was transfected in combination with a separate 3Cpro encoded in trans in a conventional mRNA molecule at a 40:1 mass ratio (a ratio known to generate protective antibody titers in swine when administered as a vaccine). The superior processing efficiency is evident in the lack of processing intermediate fragment VP4+2+3. This demonstrates the utility of encoding a functional protein, in this particular example an enzyme, in the nsP4 C-terminal region using the methods explained in this disclosure to elicit a desired biochemical result.

Example 17. A Replicon RNA Encoding an Immunomodulatory Factor Fused to the nsP4 C-Terminus and Separate Transgene in the SG ORF It is useful to increase or decrease the immune response elicited by replicon RNA activity in a cell in order to produce a desired outcome. For example, it is possible to treat cancer by inducing strong innate immune responses in cancer cells.

FIGS. 23A-23D illustrate gene expression data from alphaviral replicon RNA modified to encode a human STING protein, mutated to be constitutively active for IFN-stimulating activity, and to encode the reporter gene, SEAP, in the SG ORF.

Figure 23A:
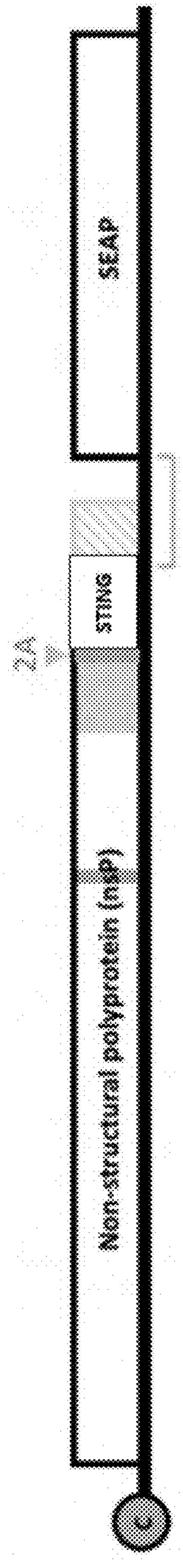
FIGS. 23A-23D illustrate gene expression data from alphaviral replicon RNA modified to encode a human STING protein, mutated to be constitutively active for IFN-stimulating activity, and to encode the reporter gene, SEAP, in the SG ORF.
Figure 23B:
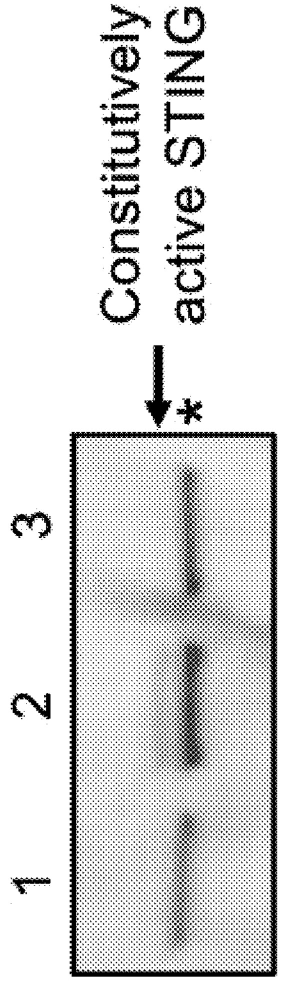

FIG. 23A is a schematic drawing of construct VEEVrep-nsP4[STING]-SEAP, a replicon RNA that includes modification of the nsP4 coding sequence of an alphaviral replicon to encode a human STING protein, mutated to be constitutively active for IFN-stimulating activity, and the reporter gene, SEAP, encoded in the SG ORF. The sequence of the 5'UTR, nsP1-4, STING, and SGP region of this RNA is set forth in SEQ ID NO: 34. The resulting translated amino acid sequence of the nsP4-2A-STING fusion polypeptide is set forth in SEQ ID NO: 42. This figure shows a replicon RNA construct where a potent immunomodulatory protein, STING (mutated to be constitutively active), is encoded by fusion to the nsP4 C-terminus. The SG ORF, in the case of cancer treatment, is where a tumor-associated antigen or additional immune regulatory factor may be encoded to drive specific cellular immunity against the desired cancer target. For illustration of the function of the STING-modified nsP4, in this example the SG ORF encodes a reporter gene, SEAP, that can be readily quantified from cultures of tumor cells. To demonstrate that the STING- and SEAP-coding replicon of this design, termed VEEVrep-nsP4 [STING]-SEAP, functions in human cells, HEK-Lucia™ Null cells transfected in 12 well dishes using commercial transfection reagents (TransIT-mRNA, Mirus) with 1 μg of VEEVrep-nsP4[STING]-SEAP or non-nsP4-modified VEEVrep-SEAP as a control. After ~1 day, supernatant culture medium was sampled and cells were lysed to analyze STING content by immunoblot. FIG. 23B is a photograph of immunoblot performed on HEK-Lucia™ Null cells transfected with the following RNAs: lane 1, VEEVrep-SEAP; lane 2, VEEVrep-nsP4[STING]-SEAP; lane 3, no transfection control. In this figure, a common background band is marked with an asterisk (*, possibly endogenous wild-type STING), and a human STING-specific antibody was used to probe the blot. It was observed that only VEEVrep-nsP4 [STING]-SEAP exhibited an additional band representing the constitutively active STING protein encoded in the nsP4 C-terminal region.

Figure 23D:
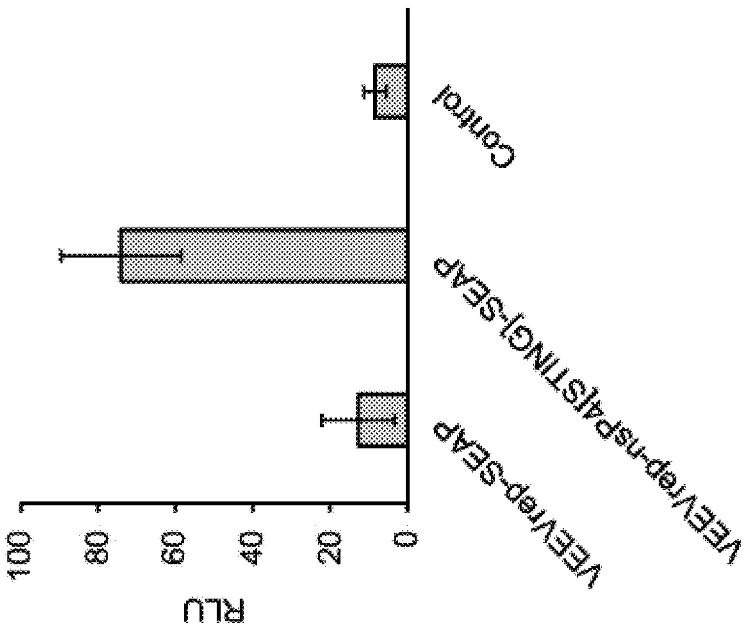
Figure 23C:
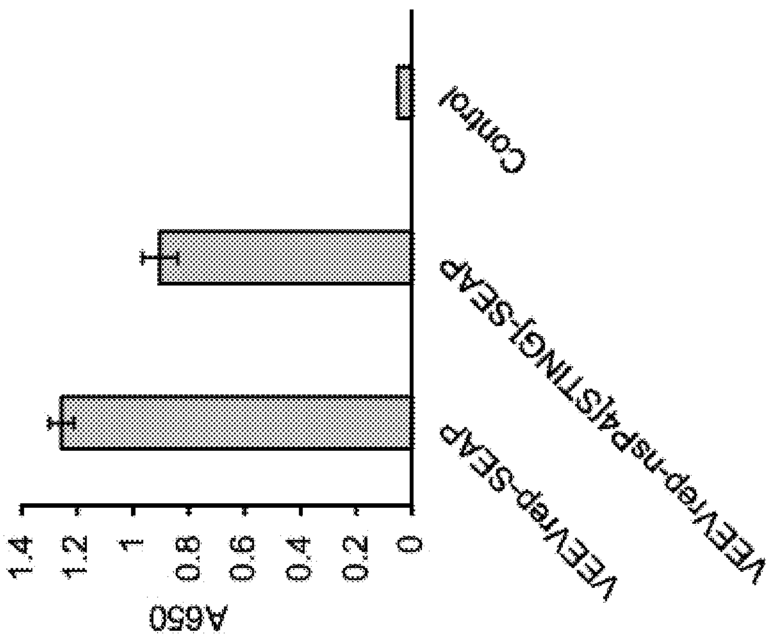

FIG. 23C is a bar graph showing expression of the SEAP reporter gene (as measured by absorbance at 650 nm in a colorimetric assay) encoded in the SG ORF in VEEVrep-SEAP and VEEVrep-nsP4[STING]-SEAP replicon RNAs compared to control (untransfected cells). It was observed that VEEVrep-nsP4[STING]-SEAP subgenomic promoter activity is retained and transgene expression is intact despite the novel nsP4 C-terminal modification with an immunomodulatory polypeptide. Referring to this figure, in a colorimetric assay to quantify SEAP in the culture supernatants, the gene was shown to be expressed by both constructs, proving that the VEEVrep-nsP4[STING]-SEAP construct successfully underwent replication and expression of transgene driven by the SGP. The lower SEAP expression is likely due to reduced viability of the HEK cells, induced by the strong innate immune response triggered by the STING protein. Type I IFN signaling activity can be measured from HEK-Lucia™ Null cells by the supernatant media concentration of secreted luciferase, which in these cells is encoded under the control of an IFN-inducible promoter comprising the IFN-stimulated genes (ISG) 54 promoter enhanced by a multimeric IFN-stimulated response elements (ISRE). FIG. 23D is a bar graph showing surrogate measurement of IFN signaling activity induced by VEEVrep-SEAP and VEEVrep-nsP4[STING]-SEAP replicon RNAs compared to control (untransfected cells). HEK-Lucia™ Null cells encode a secreted luciferase reporter gene under control of an IFN-inducible promoter comprising the IFN-stimulated genes (ISG) 54 promoter enhanced by a multimeric IFN-stimulated response elements (ISRE). It was observed that the VEEVrep-nsP4[STING]-SEAP RNA triggers potent IFN signaling whereas the unmodified VEEVrep-SEAP RNA does not.

Referring to FIG. 23D, in a luminescence-based assay for secreted luciferase, only VEEVrep-nsP4[STING]-SEAP showed IFN type I signal activation, demonstrating the active STING protein was functional and conferred the desired effect on the transfected human cells. STING represents an immunomodulatory protein with both immune stimulating and immune suppressing properties via IFN signaling cascades, depending on the tissue and cell type context of administration. Therefore, this approach of embedding STING or other immunomodulatory protein represents a method of either inducing or attenuating the adaptive immune response, making the engineered replicon useful in the treatment of not only infectious disease and cancer, but auto-immune diseases and allergies by triggering immune tolerance when desired.

Example 18. Treatment of Melanoma

Replicons engineered to express accessory factors from the nsP4 coding region using the methods described herein may be used to treat cancers such as melanoma. FIGS. 24A-24D illustrate gene expression and biological effects in B16 melanoma from alphaviral replicon RNA modified to encode GFP or a human STING protein (mutated to be constitutively active for IFN-stimulating activity) in the nsP ORF, and to encode the reporter gene, SEAP, in the SG ORF.

Figure 24B:
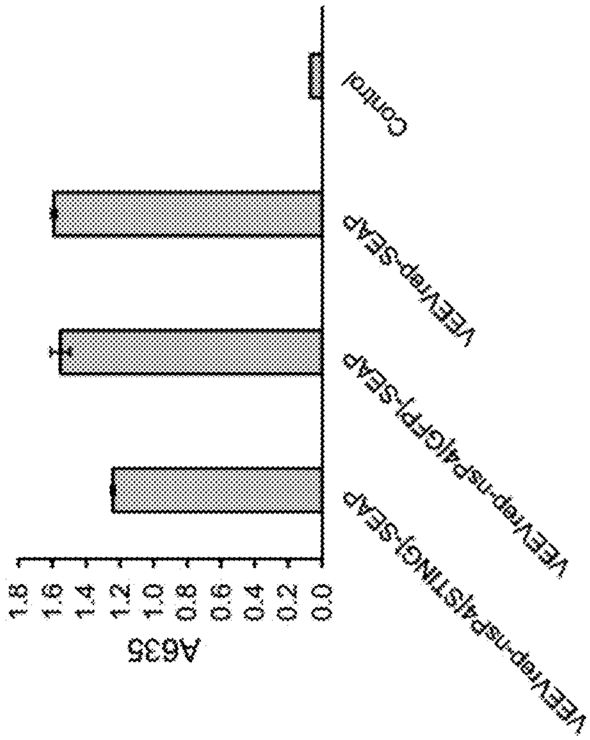
FIGS. 24A-24D illustrate gene expression in B16 melanoma from alphaviral replicon RNA modified to encode a human STING protein, mutated to be constitutively active for IFN-stimulating activity, and to encode the reporter gene, SEAP, in the SG ORF.
Figure 24A:
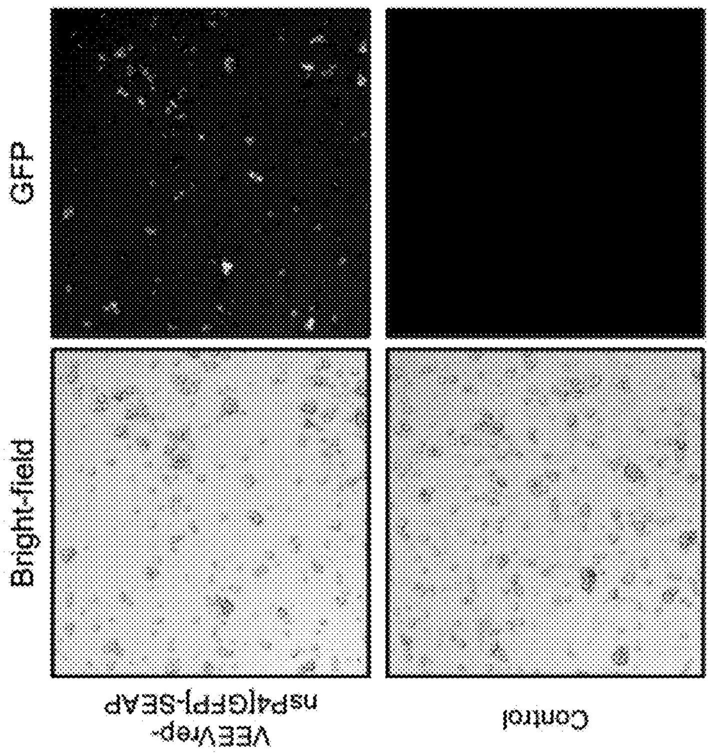

FIG. 24A are photographs showing GFP expression in B16 melanoma cells cultured in 12-well dishes after transfection with 1 μg of VEEVrep-nsP4[GFP]-SEAP approximately 1 day post-transfection compared to untransfected control cells. Extensive GFP expression driven by coding of the fluorescent protein at the nsP4 C-terminal end of constructs described herein was observed. FIG. 24A depicts successful GFP expression in B16 melanoma cells mediated by RNA VEEVrep-nsP4[GFP]-SEAP, which demonstrates the ability of nsP4-fusion proteins to express efficiently in tumor cell lineages.

FIG. 24B is a bar graph showing SEAP expression in B16 melanoma cells cultured in 12-well dishes after transfection with 1 μg of the indicated replicon RNAs: VEEVrep-nsP4[STING]-SEAP, VEEVrep-nsP4[GFP]-SEAP, and VEEVrep-SEAP compared to untransfected control cells. In the experiments, SEAP expression was quantified by colorimetric assay on culture medium 1 day post-transfection, showing successful expression of the SEAP gene encoded in the SG ORF. Referring to FIG. 24B, the reporter gene encoded in the SG ORF (SEAP) (representing the transgene location for an antigen or other cancer-treating genetic sequence) is efficiently expressed in the same cells regardless of the nature of the nsP4 fusion protein.

Figure 24C:
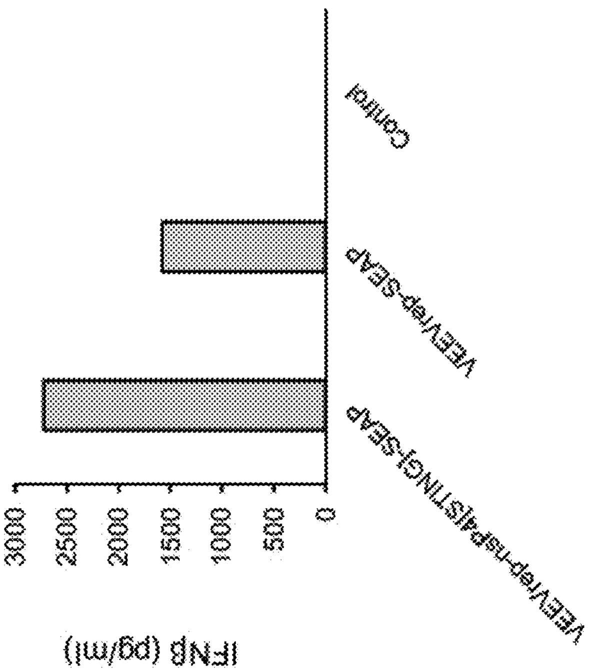

FIG. 24C is a bar graph showing measurement of IFN-beta secretion (measured by sandwich ELISA on culture supernatant) by B16 melanoma cells ~1 day after transfection with 1 μg of the indicated replicon RNAs: VEEVrep-nsP4[STING]-SEAP and VEEVrep-SEAP compared to untransfected control cells. Referring to this figure, it was observed that VEEVrep-nsP4[STING]-SEAP RNA successfully induced IFN-beta secretion in these cancer cells, at a level approximately 73% greater than VEEVrep-SEAP. This indicates that the STING protein expressed by fusion to nsP4 successfully induced an innate immune response in the cancer cells, which correlates with successful clearance of tumors in the clinical setting.

Figure 24D:
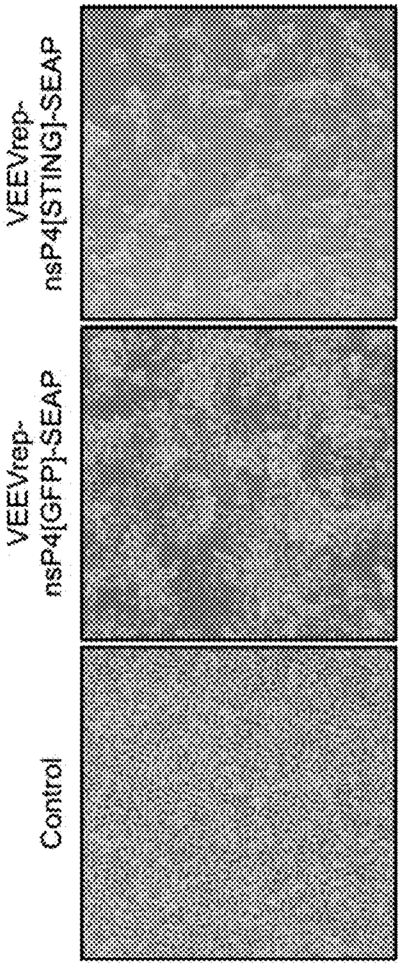

FIG. 24D are photographs of light microscopy examination of B16 cells 1 day after transfection with 2 μg of VEEVrep-nsP4[GFP]-SEAP or VEEVrep-nsP4[STING]-SEAP, compared to healthy untransfected control cells (Control; leftmost panel). Referring to this figure, untransfected control cells had proliferated to fill the dish; moderate failure to grow and cytopathology was observed after transfection with VEEVrep-nsP4[GFP]-SEAP; the greatest growth inhibition and cell death was observed after transfection with VEEVrep-nsP4[STING]-SEAP.

Referring to FIG. 24D, when examining B16 cells by brightfield microscopy 1 day after transfection, untreated cells (control) had proliferated to fill the dish as expected; in contrast, moderate failure to grow and cytopathology was observed upon transfection with VEEVrep-nsP4[GFP]-SEAP, and an even greater degree of growth inhibition and cell death was observed upon transfection with VEEVrep-nsP4[STING]-SEAP. In aggregate, the data shows that nsP4-modified replicons can replicate in melanoma cells, drive gene expression from both the nsP4 C-terminal encoded ORF and the SG ORF, activate higher innate immune responses when an immunomodulatory protein is fused to the nsP4, and inhibit melanoma cell growth and survival. In all the B16 melanoma cell experiments described in this Example, cells were grown in 12-well dishes in DMEM+10% inactivated fetal bovine serum (IFS). For analysis of gene expression (GFP, SEAP) or immune activation (IFN-beta), cells were transfected with 1 μg of the indicated RNA, and analyzed 1 day later. To measure cell proliferation and viability by microscopy, cells were transfected with 2 μg of RNA and images captured 1 day later.

Example 19. Treatment of HPV-Induced Epithelial Tumors

To demonstrate the universal applicability of replicons engineered as disclosed in this filing, function of the nsP4-modified replicon RNAs was demonstrated in an additional tumor cell type: TC-1 epithelial tumor cells, which exhibit malignant growth driven by HPV E6 and E7 oncogene transformation.

FIG. 25A-25D illustrate gene expression and biological effects in TC-1 cancer cells from alphaviral replicon RNA modified to encode GFP or a human STING protein (mutated to be constitutively active for IFN-stimulating activity) in the nsP ORF, and to encode the reporter gene, SEAP, in the SG ORF.

Figure 25B:
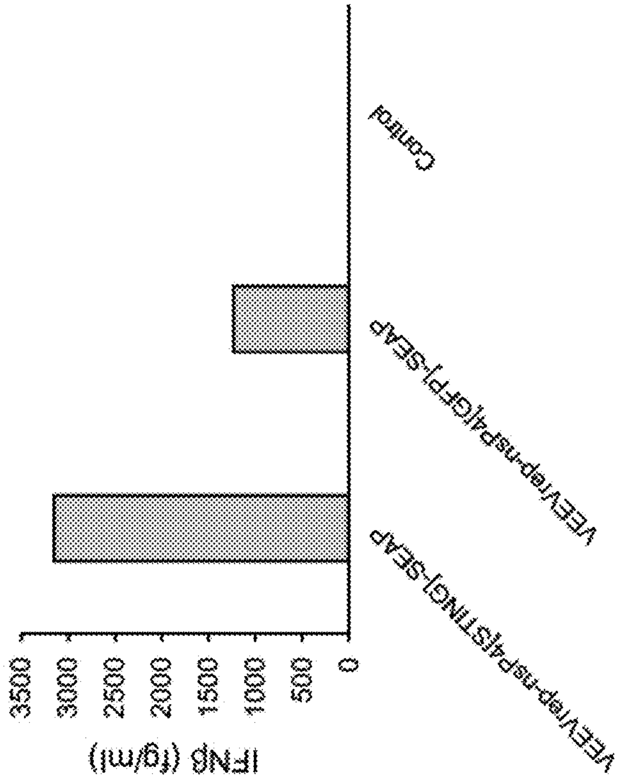
FIG. 25A-25D illustrate gene expression in in TC-1 cancer cells from alphaviral replicon RNA modified to encode a human STING protein, mutated to be constitutively active for IFN-stimulating activity, and to encode the reporter gene, SEAP, in the SG ORF.
Figure 25A:
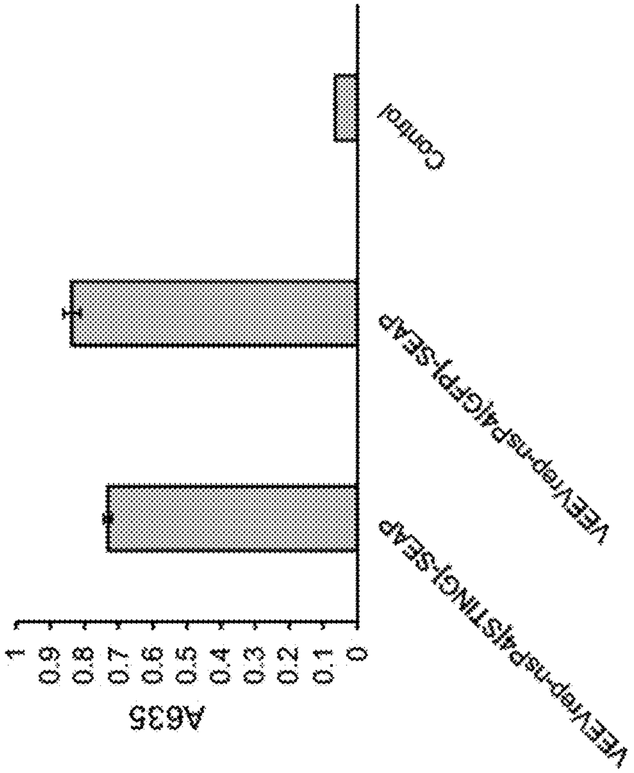

FIG. 25A is a bar graph showing SEAP expression in TC-1 cancer cells cultured in 12-well dishes 2 days after transfection with 2 μg of the indicated replicon RNA: VEEVrep-nsP4[GFP]-SEAP, VEEVrep-nsP4[STING]-SEAP compared to untransfected control cells. In this experiment, SEAP expression was quantified by colorimetric assay on culture medium, showing successful expression of the SEAP gene encoded in the SG ORF. Referring to FIG. 25A, as was seen in B16 melanoma (Example 18), SEAP expression confirmed activity of the SG ORF for both VEEVrep-nsP4[STING]-SEAP and VEEVrep-nsP4[GFP]-SEAP RNA in this unrelated cancer type.

FIG. 25B is a bar graph showing measurement of IFN-beta secretion (measured by sandwich ELISA on culture supernatant) by TC-1 cancer cells 1 day after transfection with 2 μg of the indicated replicon RNA: VEEVrep-nsP4[GFP]-SEAP, or VEEVrep-nsP4[STING]-SEAP compared to untransfected control cells. Referring to FIG. 25B, the nsP4-encoded constitutively active STING fusion protein induced greater IFN-beta secretion than non-STING containing replicon.

Figure 25D:
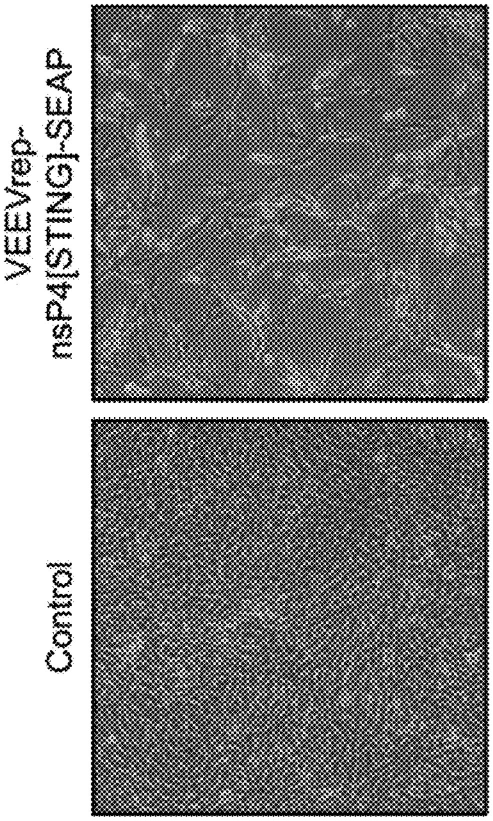
Figure 25C:
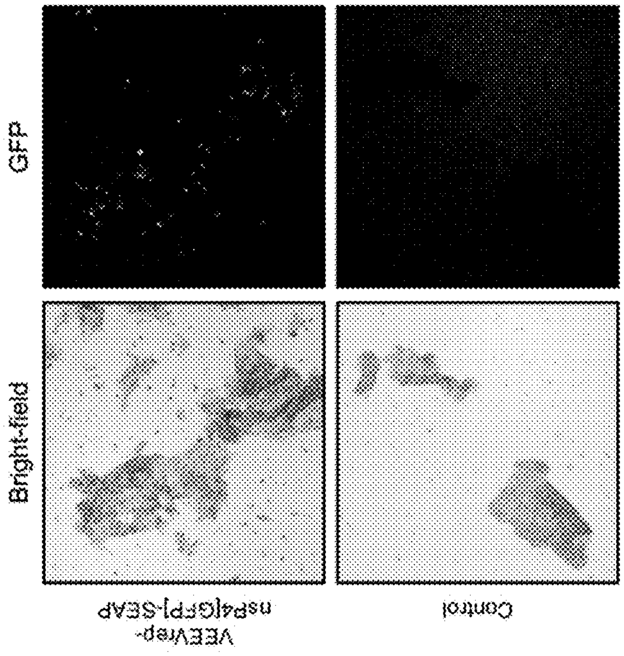

FIG. 25C are photographs showing GFP expression in TC-1 cancer cell agglomerates after transfection with 1 μg of VEEVrep-nsP4[GFP]-SEAP approximately 3 days post-transfection. Referring to this figure, extensive GFP expression was observed throughout the multicellular structure driven by coding of the fluorescent protein at the nsP4 C-terminal end of the construct (top panel, right) compared to no GFP expression in untreated control cells (bottom panel, right). Referring to FIG. 25C, in cellular agglomerates isolated from the TC-1 cultures, GFP expression by VEEVrep-nsP4[GFP]-SEAP was confirmed to be widespread throughout the structure.

FIG. 25D are photographs showing results of light microscopy examination of TC-1 cancer cells 1 day after transfection with 4 μg of the indicated replicon RNA VEEVrep-nsP4[STING]-SEAP compared to untransfected control cells. Referring to this figure, it was observed that untreated cells (Control) had proliferated to fill the dish; growth inhibition and cell death was observed after transfection with VEEVrep-nsP4[STING]-SEAP.

Referring to FIG. 25D, as was observed for B16 melanoma cells, proliferation and viability was severely inhibited by treatment with VEEVrep-nsP4[STING]-SEAP.

These data confirm that nsP4-modified replicons have broad applicability in the treatment of divergent cancer types. In all the TC-1 cancer cell experiments described in this Example, cells were grown in 12-well dishes in DMEM+10% IFS. For analysis of GFP expression by microscopy, cells were transfected with 1 μg of RNA, scraped to release agglomerates, and imaged 3 days later. To measure immune activation by IFN-beta ELISA, cells were transfected with 2 μg of the indicated RNA, and culture media analyzed 1 day later. To measure cell proliferation and viability by microscopy, cells were transfected with 4 μg of RNA and images captured 1 day later. SEAP expression was measured by colorimetric assay performed on culture medium 2 days after transfection with 2 μg of the indicated RNAs.

Figure 26A:
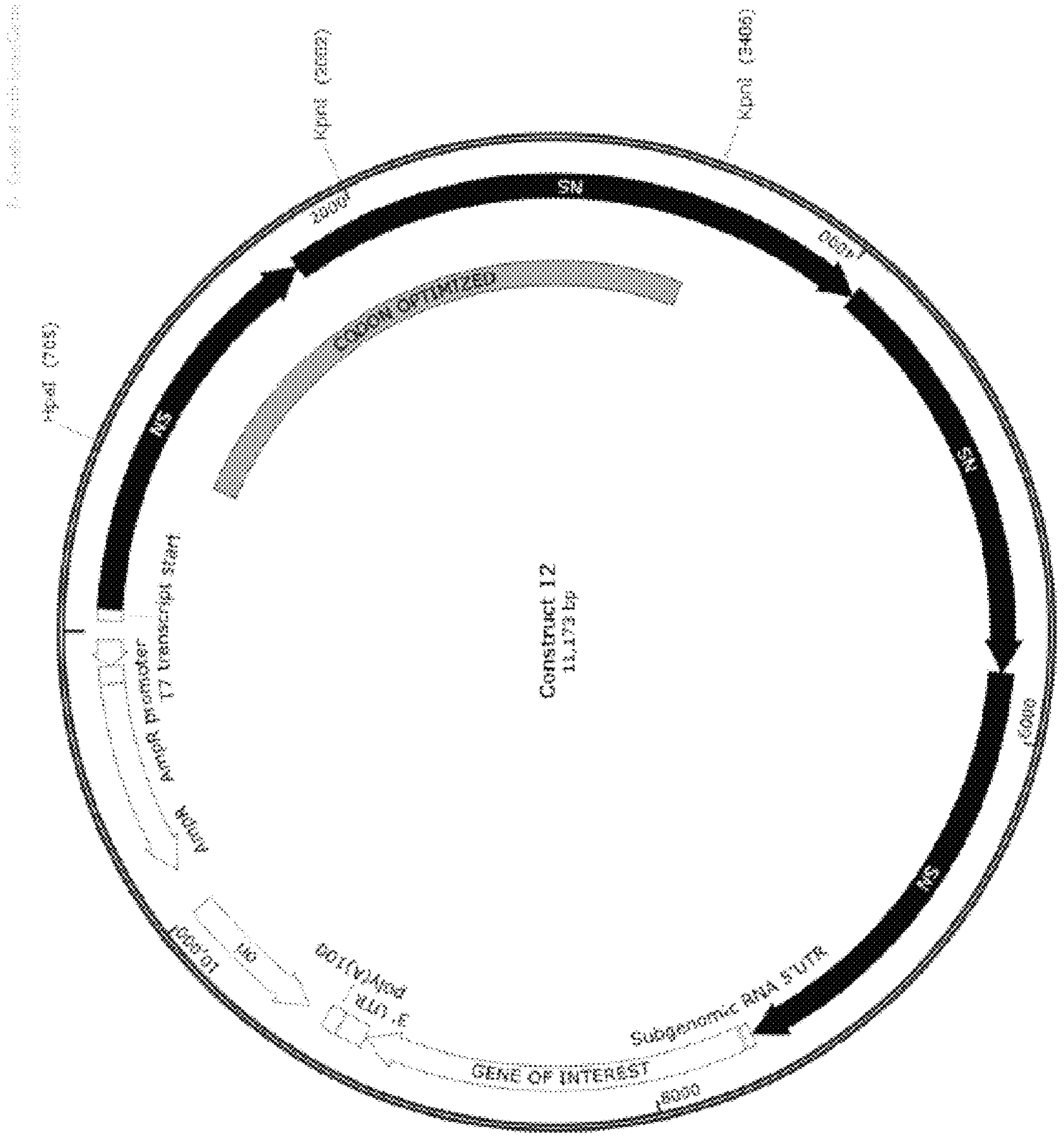
FIGS. 26A-26G show VEEV replicon RNAs modified with reduced homology to wild type RNAs and expression data from these constructs.

Example 20. VEEV Replicon RNAs Modified with Homology Reduced without Bioinformatic Inspection Four additional homology-reduced replicon RNAs were generated. FIGS. 26A-26G show VEEV replicon RNAs modified with reduced homology to wild type RNAs and expression data from these constructs. VEEVrepHK-SEAP was generated by applying a series of silent mutations across the nsP1 and nsP2 juncture between nucleotide positions 658 and 3359 (FIG. 26A); the nucleotide positions are in reference to the VEEV genome sequence SEQ ID NO: 17. FIG. 26A is a schematic drawing of construct 12 (C12; VEEVrepHK-SEAP). Referring to this figure, the DNA plasmid is similar to that shown in FIG. 5, except that only codons in genomic nucleotide positions 658-3359 (gray box) were altered to reduce homology to the wild-type virus, without regard to the possible presence of any secondary structure elements. The 5'UTR, nsP1-4 coding region, and SGP of RNA produced by transcription of C12 plasmid is set forth in SEQ ID NO: 35.

Figure 26B:
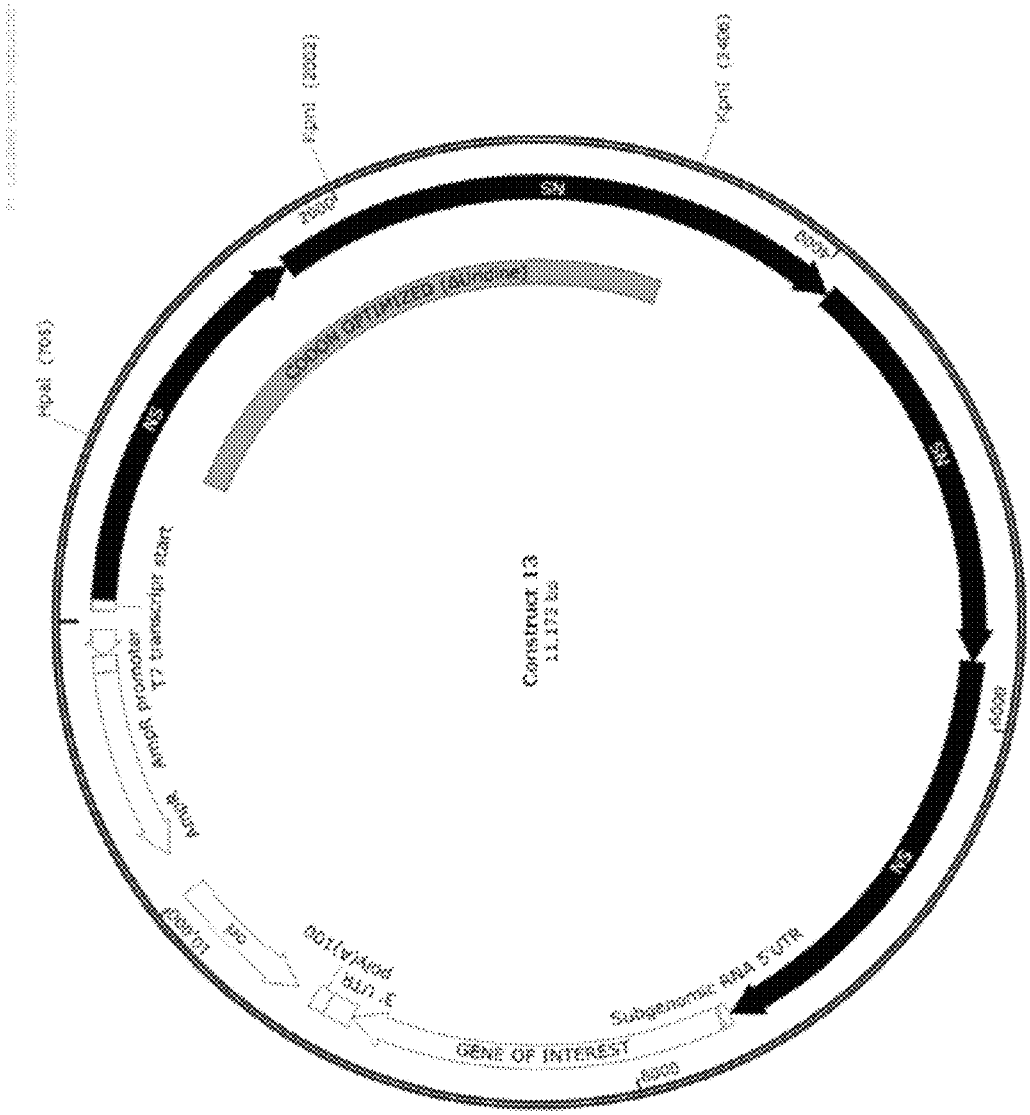

VEEVrepHK(ΔU)-SEAP was similarly mutated across the same region but by selecting only codons that omitted uridine bases where possible (FIG. 26B). FIG. 26B is a schematic drawing of construct 13 (C13; VEEVrepHK(ΔU)-SEAP). Referring to this figure, the DNA plasmid is similar to that shown in FIG. 5, except that only codons in genomic nucleotide positions 658-3359 (gray box) were altered to reduce homology to the wild-type virus, without regard to the possible presence of any secondary structure elements, and codons avoiding uracil bases were selected preferentially. The 5'UTR, nsP1-4 coding region, and SGP of RNA produced by transcription of C13 plasmid is set forth in SEQ ID NO: 36.

Figure 26C:
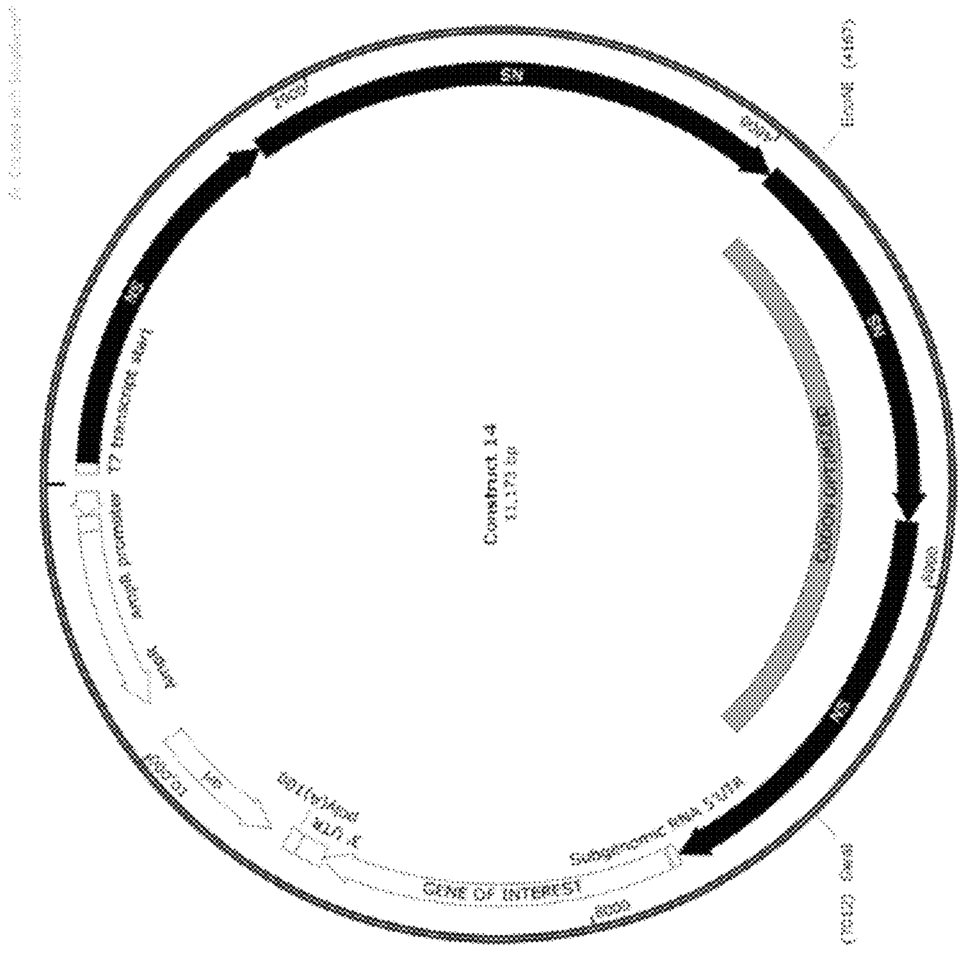

VEEVrepES-SEAP was generated by applying a series of silent mutations across the nsP3 and nsP4 juncture between nucleotide positions 4120 and 6965. FIG. 26C is a schematic drawing of construct 14 (C14; VEEVrepES-SEAP). Referring to this figure, the DNA plasmid is similar to that shown in FIG. 5, except that only codons in genomic nucleotide positions 4120-6965 (gray box) were altered to reduce homology to the wild-type virus, without regard to the possible presence of any secondary structure elements. The 5'UTR, nsP1-4 coding region, and SGP of RNA produced by transcription of C14 plasmid is set forth in SEQ ID NO: 37.

Figure 26D:
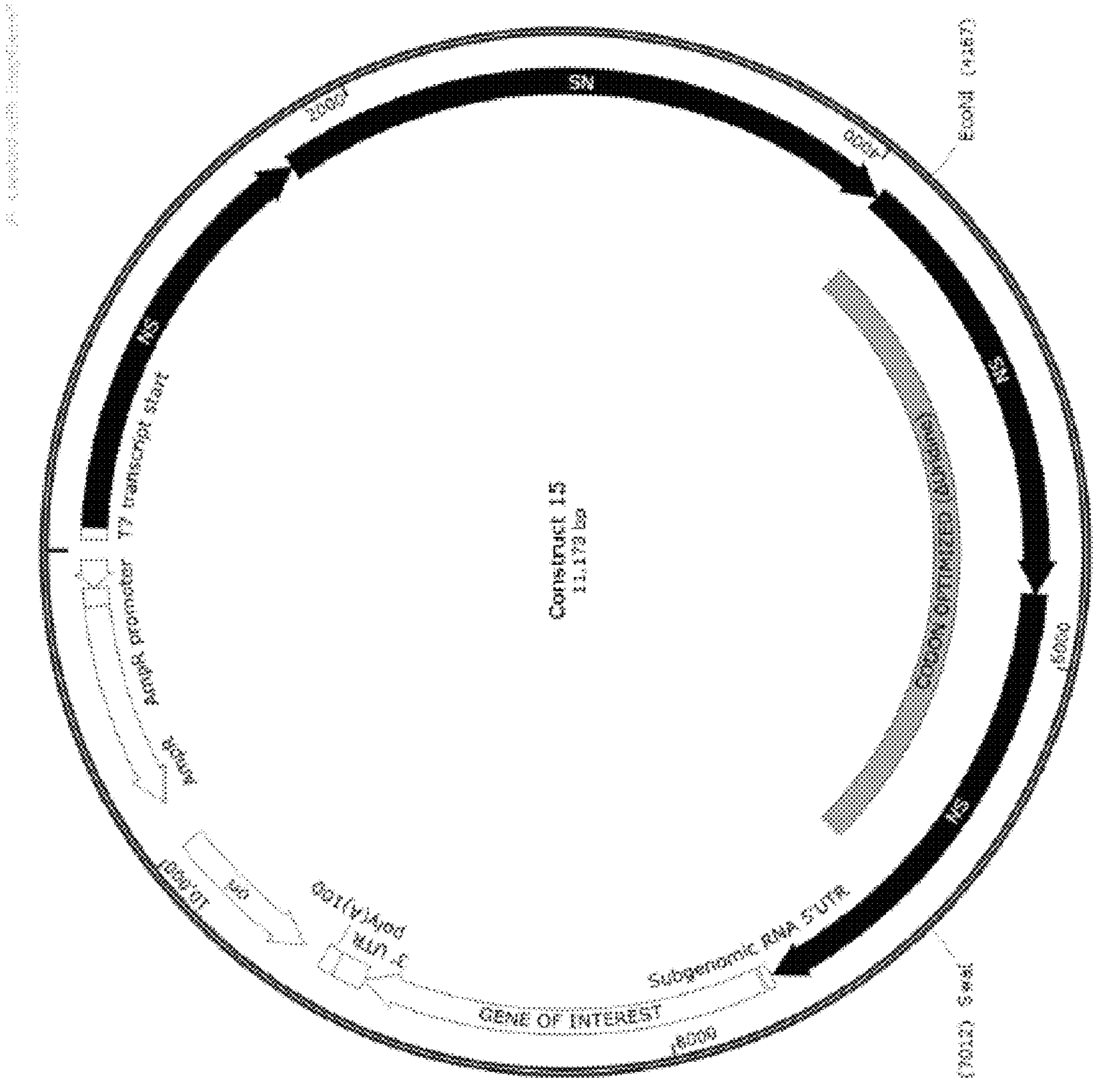

VEEVrepES(ΔU)-SEAP was similarly mutated across the same region but by selecting only codons that omitted uridine bases where possible (FIG. 26D). FIG. 26D is a schematic drawing of construct 15 (C15; VEEVrepES(ΔU)-SEAP). Referring to this figure, the DNA plasmid is similar to that shown in FIG. 5, except that only codons in genomic nucleotide positions 4120-6965 (gray box) were altered to reduce homology to the wild-type virus, without regard to the possible presence of any secondary structure elements, and codons avoiding uracil bases were selected preferentially. The 5'UTR, nsP1-4 coding region, and SGP of RNA produced by transcription of C15 plasmid is set forth in SEQ ID NO: 38.

These constructs were generated without consideration of the secondary structure elements present in the sequence, to evaluate performance of a typical non-bioinformatic approach to reducing homology to the wild-type virus.

Figure 26F:
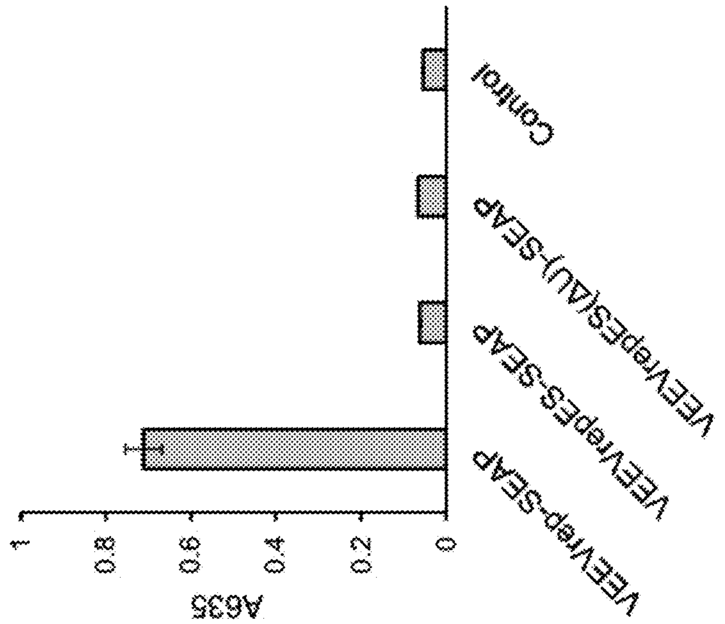
Figure 26E:
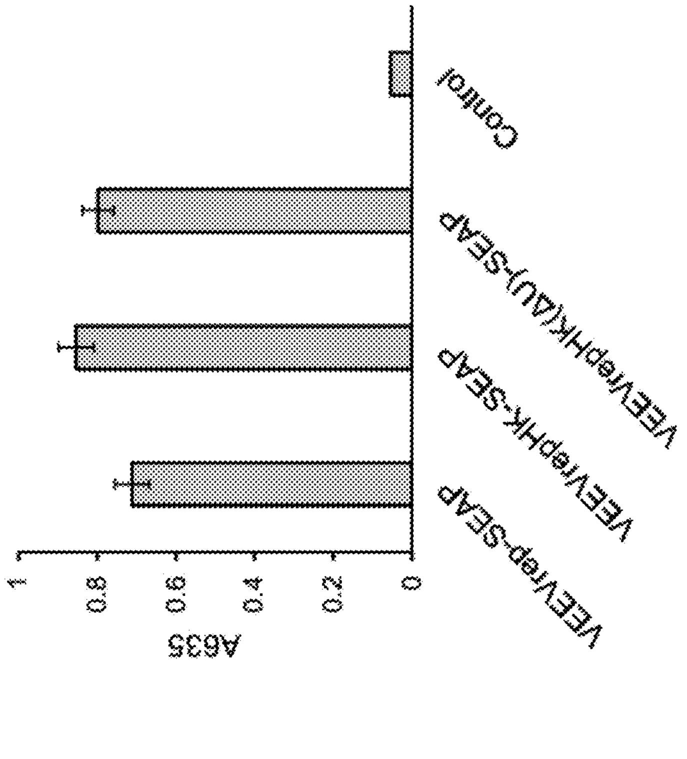

FIG. 26E is a bar graph showing SEAP expression in BHK cells cultured in 12-well dishes 16 hours after transfection with 1 μg of VEEVrep-SEAP, VEEVrepHK-SEAP, or VEEVrepHK(ΔU)-SEAP RNA compared to untransfected control cells. In this experiment, SEAP expression was quantified by colorimetric assay on culture medium, showing successful expression of the SEAP gene encoded in the SG ORF.

FIG. 26F is a bar graph showing SEAP expression in BHK cells cultured in 12-well dishes 16 hours after transfection with 1 μg of VEEVrep-SEAP, VEEVrepES-SEAP, or VEEVrepES(ΔU)-SEAP RNA compared to untransfected control. In this experiment, SEAP expression was quantified by colorimetric assay on culture medium, showing no expression of the SEAP gene encoded in the SG ORF for the VEEVrepES-SEAP or VEEVrepES(ΔU)-SEAP constructs.

Figure 26G:
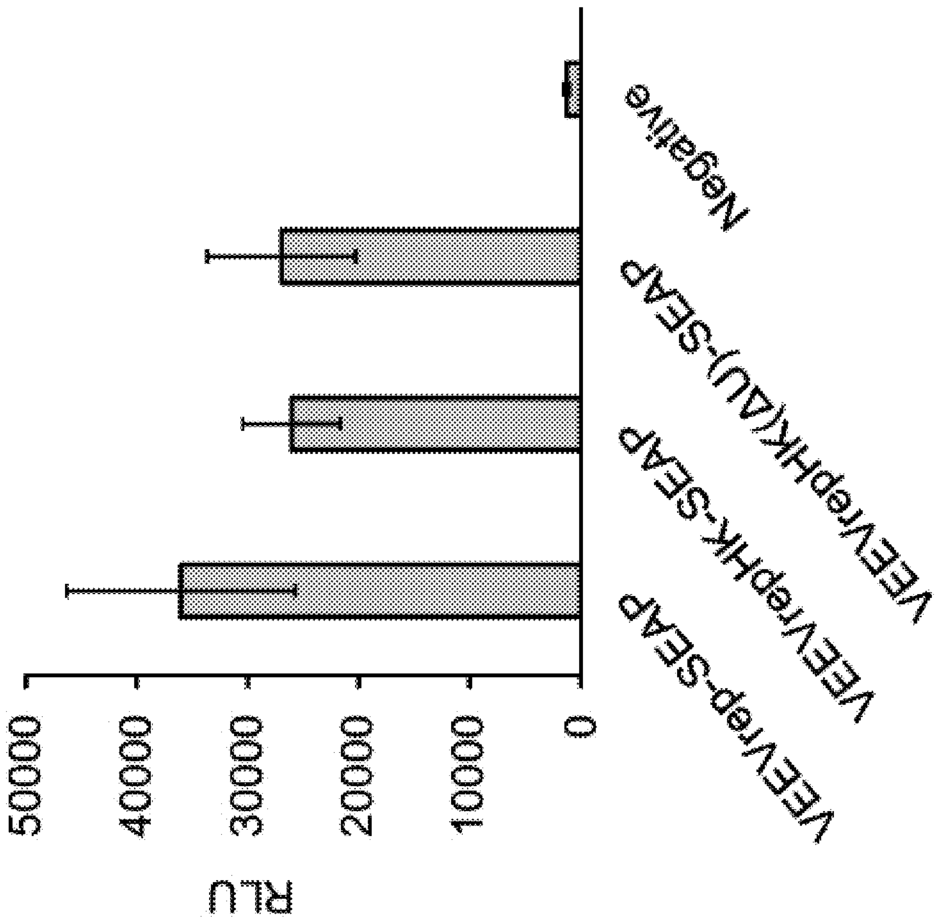

Transfection of BHK cells in vitro confirmed that VEEVrepHK-SEAP and VEEVrepHK(ΔU)-SEAP were able to mediate expression of a subgenomic ORF-encoded reporter gene, secreted embryonic alkaline phosphatase (FIG. 26E), but VEEVrepES-SEAP and VEEVrepES(ΔU)-SEAP were not (FIG. 26F). This showed that without inspection of the primary RNA sequence to identify secondary structure elements, functional replicon could not be reliably obtained through silent mutation of an arbitrary coding segment. VEEVrepHK-SEAP and VEEVrepHK (ΔU)-SEAP appeared to represent a serendipitous finding indicating that the naïve approach can spontaneously yield working replicon, however further characterization revealed that both these constructs lost SEAP-expression activity in vivo, as measured by serum SEAP concentrations in mice (n=5) 1 day after i.m. injection of 2 μg of LNP-formulated RNA by chemiluminescent assay. FIG. 26G is a bar graph showing serum SEAP expression measured in vivo (by chemiluminescent assay) after injection of 2 μg of LNP-formulated VEEVrep-SEAP, VEEVrepHK-SEAP, or VEEVrepHK(ΔU)-SEAP compared to control (serum from untreated mice). In this experiment, mice (five per group) were administered the indicated RNA by intramuscular (i.m.) injection and serum sampled the next day, and SEAP was quantified by chemiluminescent assay. Mean RLU of each group of mice were plotted; error bars, standard deviation. Serum from two untreated mice (n=2) was used as a negative control group.

While the performance in vivo was confirmed, the expression was sub-par, and highlights the superiority of the bioinformatic methods described in this disclosure that yielded equivalent or superior gene expression in vivo compared to wild-type replicons (see Example 15).

Example 21. Engineered Replicons are Safe and do not Harm Healthy Human Cells To demonstrate the safety of replicons engineered as disclosed in this filing, function of the nsP4-modified replicon RNAs was confirmed to be low in non-cancerous human cells. Human foreskin fibroblasts (HFFs) are a commonly studied normal cell type, representing healthy non-transformed cell biology while still serving as an efficient transfection and infection host for a plethora of nucleic acid and virus species. FIG. 27A-27D show VEEV replicon RNAs expression and effects in normal HFF cells. FIG. 27A is bar graph showing SEAP expression in normal HFF cells cultured in 12-well dishes 1 days after transfection with 2 or 4 μg of the indicated replicon RNA, VEEVrep-nsP4[STING]-SEAP, or VEEVrep-SEAP compared to untransfected control cells. In this experiment, SEAP expression was quantified by colorimetric assay on culture medium.

Referring to this figure, transfection of HFFs in 12-well dishes with 2 or 4 μg of non-engineered replicon encoding the SEAP reporter gene in the SG ORF (VEEVrep-SEAP) led to low levels of SEAP expression as measured by colorimetric assay performed on the culture medium 1 day post-transfection; in contrast, the replicon containing nsP4-encoded constitutively active STING fusion protein (VEEVrep-nsP4[STING]-SEAP) did not induce SEAP secretion, indicating that replication and transgene expression in healthy cells is suppressed for the engineered replicon.

Figure 27B:
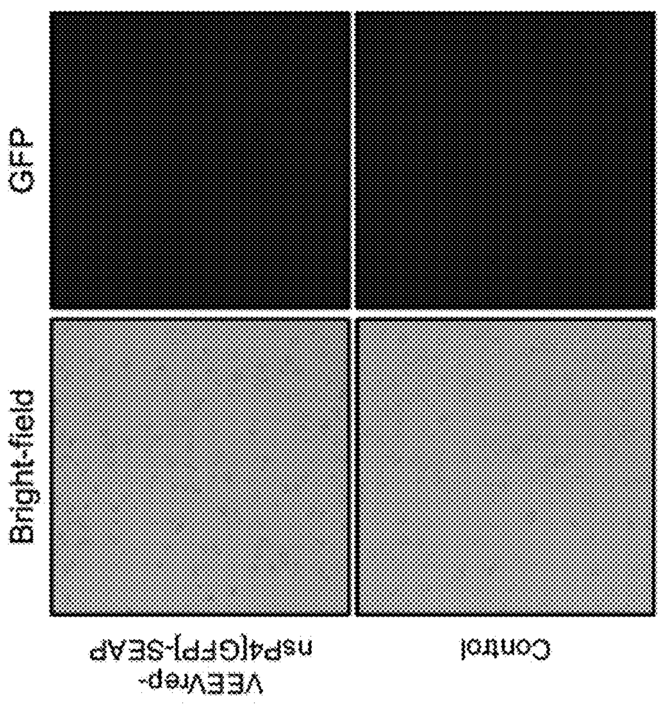
FIG. 27A-27D show VEEV replicon RNAs expression in normal HFF cells.
Figure 27A:
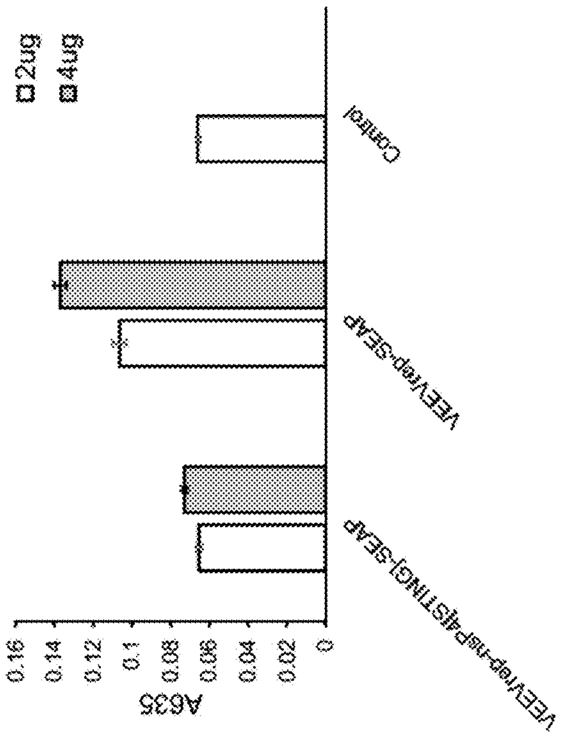

FIG. 27B are photographs of GFP expression in trypsin-dissociated normal human HFF cells after transfection with 4 μg of VEEVrep-nsP4[GFP]-SEAP approximately 4 days post-transfection, showing no efficient gene expression from the nsP4 C-terminal encoded GFP protein in these healthy, non-cancerous cells. Referring to this figure, no GFP expression was observed in HFF cells transfected with VEEVrep-nsP4[GFP]-SEAP, unlike in the cancer cell types tested above (see Examples 18 and 19).

Figure 27C:
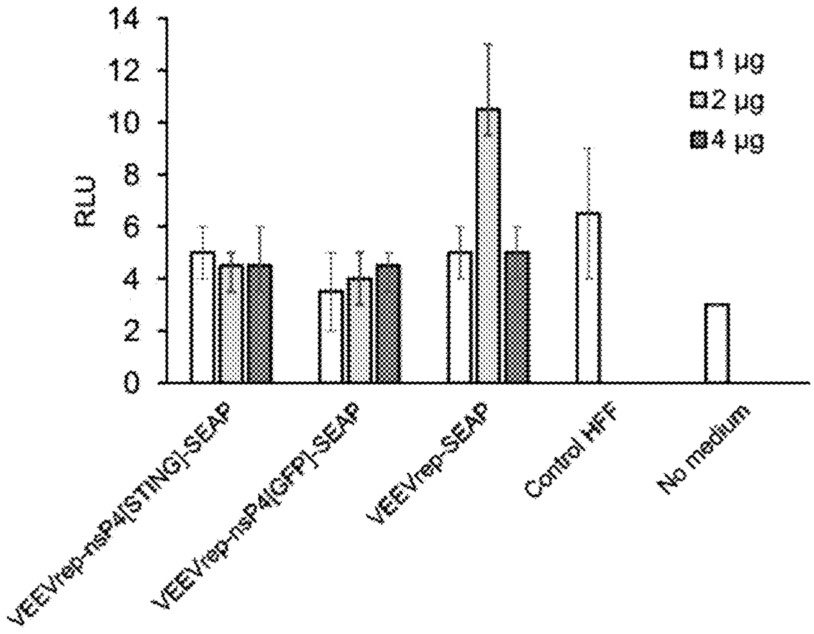

FIG. 27C is a bar graph showing measurement of IFN-beta activity from transfected HFFs. Conditioned medium from HFFs in 12-well dishes was collected 1 day after transfection with the indicated RNAs, VEEVrep-nsP4[STING]-SEAP, VEEVrep-nsP4[GFP]-SEAP, VEEVrep-SEAP at 1, 2 and 4 μg doses. Medium was collected from untransfected cells as a negative control (Control HFF). The collected medium was applied to HEK-Lucia Null cells to measure the response to type I IFNs in the medium. Untreated HEK-Lucia Null cells were included as an additional negative control (No medium control). In this experiment, the next day, the IFN-responsive reporter gene Lucia was assayed in the supernatant of the HEK-Lucia Null cells by chemiluminescent assay. The replicons engineered as described in this disclosure, VEEVrep-nsP4[GFP]-SEAP and VEEVrep-nsP4[STING]-SEAP, did not stimulate type I IFN innate immune responses in the healthy HFF cell type. Referring to FIG. 27C, based on the results of treatment of IFN-beta sensitive HEK-Lucia NULL cells with the conditioned HFF culture medium, the engineered replicons VEEVrep-nsP4[STING]-SEAP and VEEVrep-nsP4[GFP]-SEAP also did not drive a spike in type I IFN signaling in these normal cells.

Figure 27D:
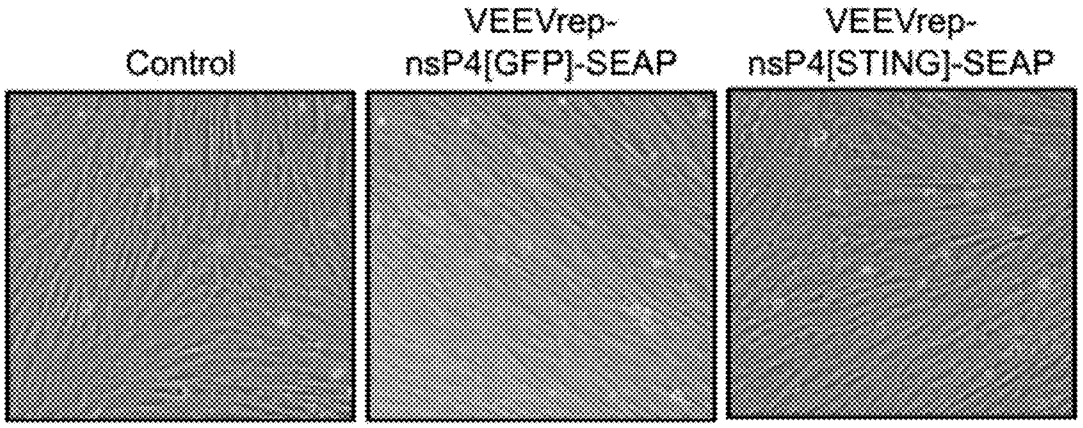

FIG. 27D are photographs of light microscopy examination of HFF cells 4 days after transfection with 4 μg of the indicated replicon RNAs, VEEVrep-nsP4[GFP]-SEAP and VEEVrep-nsP4[STING]-SEAP compared to untransfected control. It was observed that untreated cells (Control) had proliferated to fill the dish and display healthy fibrous morphology. The RNA transfected cells exhibited equal proliferation and healthy morphology. Referring to FIG. 27D, no detrimental effect on cell growth, morphology, or viability was observed. To measure cell proliferation and assess health by microscopy, cells were transfected with 2 or 4 μg of RNA and images captured 3 days later. Cells under all conditions had proliferated and remained intact with the expected fibrous morphology even when transfected with a high 4 μg dose of RNA (FIG. 27D), suggesting that these RNAs are safe to administer in the context of healthy cells and exhibit negligible off-target immunogenicity to non-cancerous bystander cells. This contrasts with their effect on cancer cells, where the nsP4-fused protein and SG ORF both expressed strongly and were able to hinder cancer cell growth and trigger innate immune responses (see Examples 18 and 19).

REFERENCES

US20140079734A1—A modification to alphavirus replicons duplicating a component from 5' end of the genome into the subgenomic region to affect replication WO2014170493A2—Different modifications to replicons, with mention of mutations in the 3' region of nsP4 to modulate the SGP J Virol. 2006 October; 80(20): 9962-9969—Describes functions of nsP4 and C-terminal tagging of the protein, suggesting that structure may be maintained by modifying this terminus.

What is claimed is:

1. A synthetic alphavirus-derived replicon nucleic acid molecule comprising: (i) a first nucleic acid encoding alphavirus nonstructural proteins nsP1, nsP2, nsP3, and nsP4, and comprising at least one silent mutation introduced within a region from nt 6381 to nt 7083, in the sequence of the alphavirus genome as set forth in SEQ ID NO: 17 and comprising a polynucleotide sequence with at least 90% identity to the reference sequence as set forth in SEQ ID NO: 18; and (ii) a second nucleic acid comprising a modified subgenomic open reading frame (ORF).

2. The synthetic alphavirus-derived replicon nucleic acid molecule of claim 1, wherein the modified subgenomic ORF comprises a sequence encoding a first heterologous protein.

3. The synthetic alphavirus-derived replicon nucleic acid molecule of claim 2, wherein the first nucleic acid comprises a polynucleotide encoding an altered nsP4 that comprises a second heterologous protein.

4. The synthetic alphavirus-derived replicon nucleic acid molecule of claim 1, wherein the first nucleic acid comprises a polynucleotide encoding nsP4 and comprising a sequence with at least 90% identity to the reference sequence set forth in SEQ ID NO: 19 or 20.

5. The synthetic alphavirus-derived replicon nucleic acid molecule of claim 1, wherein the first nucleic acid comprises a polynucleotide encoding the nonstructural polyprotein and comprising a polynucleotide sequence with at least 90% identity to the reference sequence as set forth in SEQ ID NO: 30.

6. The synthetic alphavirus-derived replicon nucleic acid molecule of claim 3, wherein the first heterologous protein or the second heterologous protein comprises an immunomodulatory protein.

7. The synthetic alphavirus-derived replicon nucleic acid molecule of claim 3, wherein the first heterologous protein or the second heterologous protein comprises an antigenic protein isolated or derived from a viral pathogen.

8. The synthetic alphavirus-derived replicon nucleic acid molecule of claim 7, wherein the viral pathogen is picornavirus.

9. The synthetic alphavirus-derived replicon nucleic acid molecule of claim 3, wherein the second heterologous protein comprises a 3Cprotease protein, and the altered nsP4 comprises an amino acid sequence with at least 90% identity to the reference sequence as set forth in SEQ ID NO: 40.

10. The synthetic alphavirus-derived replicon nucleic acid molecule of claim 9, wherein the altered nsP4 is encoded by a polynucleotide sequence with at least 90% identity to the reference sequence set forth in SEQ ID NO: 32.

11. The synthetic alphavirus-derived replicon nucleic acid molecule of claim 3, wherein the second nucleic acid comprises a polynucleotide encoding an O1 Manisa P1 protein and comprising a sequence with at least 90% identity to the reference sequence set forth in SEQ ID NO: 33.

12. The synthetic alphavirus-derived replicon nucleic acid molecule of claim 3, wherein the first heterologous protein comprises an O1 Manisa P1 protein and the second heterologous protein comprises a 3Cprotease.

13. The synthetic alphavirus-derived replicon nucleic acid molecule of claim 3, wherein the second nucleic acid comprises a polynucleotide encoding an antigenic protein.

14. The synthetic alphavirus-derived replicon nucleic acid molecule of claim 3, wherein the second heterologous protein comprises a STING protein, and the altered nsP4 comprises an amino acid sequence with at least 90% identity to the reference sequence as set forth in SEQ ID NO: 42.

15. The synthetic alphavirus-derived replicon nucleic acid molecule of claim 3, wherein the first heterologous protein comprises an antigenic protein and the second heterologous protein comprises a STING protein.

16. An alphavirus derived RNA replicon expression system comprising the synthetic alphavirus-derived replicon nucleic acid molecule of claim 1 and a host cell.

17. A pharmaceutically acceptable composition comprising an alphavirus-derived replicon of claim 1, and a pharmaceutically acceptable carrier or excipient.

* * * * *

SEQUENCE LISTING

<160> NUMBER OF SEQ ID NOS: 46

<210> SEQ ID NO 1
<211> LENGTH: 7482
<212> TYPE: DNA
<213> ORGANISM: Artificial Sequence
<220> FEATURE:
<223> OTHER INFORMATION: Synthetic construct, C01 nsP coding sequence DNA

<400> SEQUENCE: 1

```
atggagaaag ttcacgttga catcgaggaa gacagcccat tcctcagagc tttgcagcgg     60
agcttcccgc agtttgaggt agaagccaag caggtcactg ataatgacca tgctaatgcc    120
agagcgtttt cgcatctggc ttcaaaactg atcgaaacgg aggtggaccc atccgacacg    180
atccttgaca ttggaagtgc gcccgcccgc agaatgtatt ctaagcacaa gtatcattgt    240
atctgtccga tgagatgtgc ggaagatccg gacagattgt ataagtatgc aactaagctg    300
aagaaaaact gtaaggaaat aactgataag gaattggaca agaaaatgaa ggagctcgcc    360
gccgtcatga gcgaccctga cctggaaact gagactatgt gcctccacga cgacgagtcg    420
tgtcgctacg aagggcaagt cgctgtttac caggatgtat acgcggttga cggaccgaca    480
agtctctatc accaagccaa taagggagtt agagtcgcct actggatagg ctttgacacc    540
accccttta tgtttaagaa cttggctgga gcatatccat catactctac caactgggcc     600
gacgaaaccg tgttaacggc tcgtaacata ggcctatgca gctctgacgt tatggagcgg    660
tcacgtagag ggatgtccat tcttagaaag aagtatttga aaccatccaa caatgttcta    720
ttctctgttg gctcgaccat ctaccacgag aagagggact tactgaggag ctggcacctg    780
ccgtctgtat ttcacttacg tggcaagcaa aattacacat gtcggtgtga gactatagtt    840
agttgcgacg ggtacgtcgt taaaagaata gctatcagtc caggcctgta tgggaagcct    900
tcaggctatg ctgctacgat gcaccgcgag ggattcttgt gctgcaaagt gacagacaca    960
ttgaacgggg agagggtctc ttttcccgtg tgcacgtatg tgccagctac attgtgtgac   1020
caaatgactg gcatactggc aacagatgtc agtgcggacg acgcgcaaaa actgctggtt   1080
gggctcaacc agcgtatagt cgtcaacggt cgcacccaga gaaacaccaa taccatgaaa   1140
aattaccttt tgcccgtagt ggcccaggca tttgctaggt gggcaaagga atataaggaa   1200
gatcaagaag atgaaaggcc actaggacta cgagatagac agttagtcat ggggtgttgt   1260
tgggctttta gaaggcacaa gataacatct atttataagc gcccggatac ccaaaccatc   1320
atcaaagtga acagcgattt ccactcattc gtgctgccca ggataggcag taacacattg   1380
gagatcgggc tgagaacaag aatcaggaaa atgttagagg agcacaagga gccgtcacct   1440
ctcattaccg ccgaggacgt acaagaagct aagtgcgcag ccgatgaggc taaggaggtg   1500
cgtgaagccg aggagttgcg cgcagctcta ccacctttgg cagctgatgt tgaggagccc   1560
actctggaag ccgatgtcga cttgatgtta caagaggctg gggccggctc agtggagaca   1620
cctcgtggct tgataaaggt taccagctac gctggcgagg acaagatcgg ctcttacgct   1680
gtgctttctc cgcaggctgt actcaagagt gaaaaattat cttgcatcca ccctctcgct   1740
gaacaagtca tagtgataac acactctggc cgaaaagggc gttatgccgt ggaaccatac   1800
catggtaaag tagtggtgcc agagggacat gcaatacccg tccaggactt tcaagctctg   1860
agtgaaagtg ccaccattgt gtacaacgaa cgtgagttcg taaacaggta cctgcaccat   1920
attgccacac atggaggagc gctgaacact gatgaagaat attacaaaac tgtcaagccc   1980
```

-continued

```
agcgagcacg acggcgaata cctgtacgac atcgacagga aacagtgcgt caagaaagaa   2040
ctagtcactg ggctagggct cacaggcgag ctggtggatc ctcccttcca tgaattcgcc   2100
tacgagagtc tgagaacacg accagccgct ccttaccaag taccaaccat aggggtgtat   2160
ggcgtgccag gatcaggcaa gtctggcatc attaaaagcg cagtcaccaa aaaagatcta   2220
gtggtgagcg ccaagaaaga aaactgtgca gaaattataa gggacgtcaa gaaaatgaaa   2280
gggctggacg tcaatgccag aactgtggac tcagtgctct tgaatggatg caaacacccc   2340
gtagagaccc tgtatattga cgaagctttt gcttgtcatg caggtactct cagagcgctc   2400
atagccatta taagacctaa aaaggcagtg ctctgcgggg atcccaaaca gtgcggtttt   2460
tttaacatga tgtgcctgaa agtgcatttt aaccacgaga tttgcacaca agtcttccac   2520
aaaagcatct ctcgccgttg cactaaatct gtgacttcgg tcgtctcaac cttgttttac   2580
gacaaaaaaa tgagaacgac gaatccgaaa gagactaaga ttgtgattga cactaccggc   2640
agtaccaaac ctaagcagga cgatctcatt ctcacttgtt tcagagggtg ggtgaagcag   2700
ttgcaaatag attacaaagg caacgaaata atgacggcag ctgcctctca agggctgacc   2760
cgtaaaggtg tgtatgccgt tcggtacaag gtgaatgaaa atcctctgta cgcacccacc   2820
tcagaacatg tgaacgtcct actgacccgc acggaggacc gcatcgtgtg gaaaacacta   2880
gccggcgacc catggataaa aacactgact gccaagtacc ctgggaattt cactgccacg   2940
atagaggagt ggcaagcaga gcatgatgcc atcatgaggc acatcttgga gagaccggac   3000
cctaccgacg tcttccagaa taaggcaaac gtgtgttggg ccaaggcttt agtgccggtg   3060
ctgaagaccg ctggcataga catgaccact gaacaatgga acactgtgga ttattttgaa   3120
acggacaaag ctcactcagc agagatagta ttgaaccaac tatgcgtgag gttctttgga   3180
ctcgatctgg actccggtct attttctgca cccactgttc cgttatccat taggaataat   3240
cactgggata actccccgtc gcctaacatg tacgggctga ataaagaagt ggtccgtcag   3300
ctctctcgca ggtacccaca actgcctcgg gcagttgcca ctggaagagt ctatgacatg   3360
aacactggta cactgcgcaa ttatgatccg cgcataaacc tagtacctgt aaacagaaga   3420
ctgcctcatg ctttagtcct ccaccataat gaacacccac agagtgactt ttcttcattc   3480
gtcagcaaat tgaagggcag aactgtcctg gtggtcgggg aaaagttgtc cgtcccaggc   3540
aaaatggttg actggttgtc agaccggcct gaggctacct tcagagctcg gctggattta   3600
ggcatcccag gtgatgtgcc caaatatgac ataatatttg ttaatgtgag gaccccatat   3660
aaataccatc actatcagca gtgtgaagac catgccatta agcttagcat gttgaccaag   3720
aaagcttgtc tgcatctgaa tcccggcgga acctgtgtca gcataggtta tggttacgct   3780
gacagggcca gcgaaagcat cattggtgct atagcgcggc agttcaagtt ttcccgggta   3840
tgcaaaccga aatcctcact tgaagagacg gaagttctgt ttgtattcat tgggtacgat   3900
cgcaaggccc gtacgcacaa tccttacaag ctttcatcaa ccttgaccaa catttataca   3960
ggttccagac tccacgaagc cggatgtgca ccctcatatc atgtggtgcg aggggatatt   4020
gccacggcca ccgaaggagt gattataaat gctgctaaca gcaaaggaca acctggcgga   4080
ggggtgtgcg gagcgctgta taagaaattc ccggaaagct tcgatttaca gccgatcgaa   4140
gtaggaaaag cgcgactggt caaaggtgca gctaaacata tcattcatgc cgtaggacca   4200
aacttcaaca aagtttcgga ggttgaaggt gacaaacagt tggcagaggc ttatgagtcc   4260
atcgctaaga ttgtcaacga taacaattac aagtcagtag cgattccact gttgtccacc   4320
ggcatctttt ccgggaacaa agatcgacta acccaatcat tgaaccattt gctgacagct   4380
```

-continued

```
ttagacacca ctgatgcaga tgtagccata tactgcaggg acaagaaatg ggaaatgact   4440
ctcaaggaag cagtggctag gagagaagca gtggaggaga tatgcatatc cgacgactct   4500
tcagtgacag aacctgatgc agagctggtg agggtgcatc cgaagagttc tttggctgga   4560
aggaagggct acagcacaag cgatggcaaa actttctcat atttggaagg gaccaagttt   4620
caccaggcgg ccaaggatat agcagaaatt aatgccatgt ggcccgttgc aacggaggcc   4680
aatgagcagg tatgcatgta tatcctcgga gaaagcatga gcagtattag gtcgaaatgc   4740
cccgtcgaag agtcggaagc ctccacacca cctagcacgc tgccttgctt gtgcatccat   4800
gccatgactc cagaaagagt acagcgccta aaagcctcac gtccagaaca aattactgtg   4860
tgctcatcct ttccattgcc gaagtataga atcactggtg tgcagaagat ccaatgctcc   4920
cagcctatat tgttctcacc gaaagtgcct gcgtatattc atccaaggaa gtatctcgtg   4980
gaaacaccac cggtagacga gactccggag ccatcggcag agaaccaatc cacagagggg   5040
acacctgaac aaccaccact tataaccgag gatgagacca ggactagaac gcctgagccg   5100
atcatcatcg aagaggaaga agaggatagc ataagtttgc tgtcagatgg cccgacccac   5160
caggtgctgc aagtcgaggc agacattcac gggccgccct ctgtatctag ctcatcctgg   5220
tccattcctc atgcatccga ctttgatgtg gacagtttat ccatacttga caccctggag   5280
ggagctagcg tgaccagcgg ggcaacgtca gccgagacta actcttactt cgcaaagagt   5340
atggagtttc tggcgcgacc ggtgcctgcg cctcgaacag tattcaggaa ccctccacat   5400
cccgctccgc gcacaagaac accgtcactt gcacccagca gggcctgctc gagaaccagc   5460
ctagtttcca ccccgccagg cgtgaatagg gtgatcacta gagaggagct cgaggcgctt   5520
accccgtcac gcactcctag caggtcggtc tcgagaacca gcctggtctc caacccgcca   5580
ggcgtaaata gggtgattac aagagaggag tttgaggcgt tcgtagcaca acaacaatga   5640
cggtttgatg cgggtgcata catcttttcc tccgacaccg gtcaagggca tttacaacaa   5700
aaatcagtaa ggcaaacggt gctatccgaa gtggtgttgg agaggaccga attggagatt   5760
tcgtatgccc cgcgcctcga ccaagaaaaa gaagaattac tacgcaagaa attacagtta   5820
aatcccacac ctgctaacag aagcagatac cagtccagga aggtggagaa catgaaagcc   5880
ataacagcta gacgtattct gcaaggccta gggcattatt tgaaggcaga aggaaaagtg   5940
gagtgctacc gaaccctgca tcctgttcct ttgtattcat ctagtgtgaa ccgtgccttt   6000
tcaagcccca aggtcgcagt ggaagcctgt aacgccatgt tgaaagagaa ctttccgact   6060
gtggcttctt actgtattat tccagagtac gatgcctatt tggacatggt tgacggagct   6120
tcatgctgct tagacactgc cagtttttgc cctgcaaagc tgcgcagctt tccaaagaaa   6180
cactcctatt tggaacccac aatacgatcg gcagtgcctt cagcgatcca gaacacgctc   6240
cagaacgtcc tggcagctgc cacaaaaaga aattgcaatg tcacgcaaat gagagaattg   6300
cccgtattgg attcggcggc ctttaatgtg gaatgcttca agaagtacgc ctgcaacaac   6360
gagtactggg agacattcaa agagaacccc atccggctga ccgaggaaaa cgtggtcaac   6420
tacatcacca agctgaaggg ccccaaagcc gccgctctgt ttgccaagac acacaacctg   6480
aacatgctgc aggacatccc catggacaga ttcgtgatgg acctgaagcg ggacgtgaaa   6540
gtgacccctg gcaccaagca caccgaggaa cggcctaagg tgcaagtgat ccaggccgct   6600
gatcctctgg ccacagccta tctgtgtggc atccacagag aactcgtgcg gagactgaat   6660
gccgtgctgc ttccgaacat tcatacactg tttgatatgt cggctgaaga ctttgacgct   6720
```

-continued attatagccg agcacttcca gcctggggat tgtgttctgg aaactgacat cgcgtcgttt 6780
gataaaagtg aggacgacgc catggctctg accgcgctga tgattctgga agatctcgga 6840
gtggacgccg agctgctgac actgattgaa gccgcctttg gcgagatcag cagcatccat 6900
ctgcctacca agaccaagtt caagttcggc gccatgatga aatctggaat gttcctcaca 6960
ctgtttgtga acacagtcat taacattgta atcgcaagca gagtgttgag agaacggcta 7020
acaggcagcc cttgtgcagc attcattgga gatgacaata tcgtgaaagg agtcaaatcg 7080
gacaaattaa tggcagacag gtgcgccacc tggttgaata tggaagtcaa gattatagat 7140
gctgtggtgg gcgagaaagc gccttatttc tgtggagggt ttattttgtg tgactccgtg 7200
accggcacag cgtgccgtgt ggcagacccc ctaaaaaggc tgtttaagct tggcaaacct 7260
ctggcagcag acgatgaaca tgatgatgac aggagaaggg cattgcatga agagtcaaca 7320
cgctggaacc gagtgggtat tctttcagag ctgtgcaagg cagtagaatc aaggtatgaa 7380
accgtaggaa cttccatcat agttatggcc atgactactc tagctagcag tgttaaatca 7440
ttcagctacc tgagaggggc ccctataact ctctacggct aa 7482

<210> SEQ ID NO 2
<211> LENGTH: 7482
<212> TYPE: DNA
<213> ORGANISM: Artificial Sequence
<220> FEATURE:
<223> OTHER INFORMATION: Synthetic construct, C02 nsP coding sequence DNA

<400> SEQUENCE: 2
atggagaaag ttcacgttga catcgaggaa gacagcccat tcctcagagc tttgcagcgg 60
agcttcccgc agtttgaggt agaagccaag caggtcactg ataatgacca tgctaatgcc 120
agagcgtttt cgcatctggc ttcaaaactg atcgaaacgg aggtggaccc atccgacacg 180
atccttgaca ttggaagtgc gcccgcccgc agaatgtatt ctaagcacaa gtatcattgt 240
atctgtccga tgagatgtgc ggaagatccg gacagattgt ataagtatgc aactaagctg 300
aagaaaaact gtaaggaaat aactgataag gaattggaca agaaaatgaa ggagctcgcc 360
gccgtcatga gcgaccctga cctggaaact gagactatgt gcctccacga cgacgagtcg 420
tgtcgctacg aagggcaagt cgctgtttac caggatgtat atgccgtgga tggccctaca 480
agcctgtacc accaggccaa caagggcgtc agagtggcct actggatcgg cttcgacacc 540
acacctttca tgttcaagaa cctggctggc gcttacccca gctacagcac aaactgggcc 600
gacgaaaccg tgttaacggc tcgtaacata ggcctatgca gctctgacgt tatggagcgg 660
tcacgtagag ggatgtccat tcttagaaag aagtatttga aaccatccaa caatgttcta 720
ttctctgttg gctcgaccat ctaccacgag aagagggact tactgaggag ctggcacctg 780
ccgtctgtat ttcacttacg tggcaagcaa aattacacat gtcggtgtga gactatagtt 840
agttgcgacg ggtacgtcgt taaaagaata gctatcagtc caggcctgta tgggaagcct 900
tcaggctatg ctgctacgat gcaccgcgag ggattcttgt gctgcaaagt gacagacaca 960
ttgaacgggg agagggtctc ttttcccgtg tgcacgtatg tgccagctac attgtgtgac 1020
caaatgactg gcatactggc aacagatgtc agtgcggacg acgcgcaaaa actgctggtt 1080
gggctcaacc agcgtatagt cgtcaacggt cgcacccaga gaaacaccaa taccatgaaa 1140
aattaccttt tgcccgtagt ggcccaggca tttgctaggt gggcaaagga atataaggaa 1200
gatcaagaag atgaaaggcc actaggacta cgagatagac agttagtcat ggggtgttgt 1260

-continued

```
tgggctttta gaaggcacaa gataacatct atttataagc gcccggatac ccaaaccatc   1320
atcaaagtga acagcgattt ccactcattc gtgctgccca ggataggcag taacacattg   1380
gagatcgggc tgagaacaag aatcaggaaa atgttagagg agcacaagga gccgtcacct   1440
ctcattaccg ccgaggacgt acaagaagct aagtgcgcag ccgatgaggc taaggaggtg   1500
cgtgaagccg aggagttgcg cgcagctcta ccacctttgg cagctgatgt tgaggagccc   1560
actctggaag ccgatgtcga cttgatgtta caagaggctg gggccggctc agtggagaca   1620
cctcgtggct tgataaaggt taccagctac gctggcgagg acaagatcgg ctcttacgct   1680
gtgctttctc cgcaggctgt actcaagagt gaaaaattat cttgcatcca ccctctcgct   1740
gaacaagtca tagtgataac acactctggc cgaaaagggc gttatgccgt ggaaccatac   1800
catggtaaag tagtggtgcc agagggacat gcaatacccg tccaggactt tcaagctctg   1860
agtgaaagtg ccaccattgt gtacaacgaa cgtgagttcg taaacaggta cctgcaccat   1920
attgccacac atggaggagc gctgaacact gatgaagaat attacaaaac tgtcaagccc   1980
agcgagcacg acggcgaata cctgtacgac atcgacagga aacagtgcgt caagaaagaa   2040
ctagtcactg ggctagggct cacaggcgag ctggtggatc ctcccttcca tgaattcgcc   2100
tacgagagtc tgagaacacg accagccgct ccttaccaag taccaaccat aggggtgtat   2160
ggcgtgccag gatcaggcaa gtctggcatc attaaaagcg cagtcaccaa aaaagatcta   2220
gtggtgagcg ccaagaaaga aaactgtgca gaaattataa gggacgtcaa gaaaatgaaa   2280
gggctggacg tcaatgccag aactgtggac tcagtgctct tgaatggatg caaacacccc   2340
gtagagaccc tgtatattga cgaagctttt gcttgtcatg caggtactct cagagcgctc   2400
atagccatta taagacctaa aaaggcagtg ctctgcgggg atcccaaaca gtgcggtttt   2460
tttaacatga tgtgcctgaa agtgcatttt aaccacgaga tttgcacaca agtcttccac   2520
aaaagcatct ctcgccgttg cactaaatct gtgacttcgg tcgtctcaac cttgttttac   2580
gacaaaaaaa tgagaacgac gaatccgaaa gagactaaga ttgtgattga cactaccggc   2640
agtaccaaac ctaagcagga cgatctcatt ctcacttgtt tcagagggtg ggtgaagcag   2700
ttgcaaatag attacaaagg caacgaaata atgacggcag ctgcctctca agggctgacc   2760
cgtaaaggtg tgtatgccgt tcggtacaag gtgaatgaaa atcctctgta cgcacccacc   2820
tcagaacatg tgaacgtcct actgacccgc acggaggacc gcatcgtgtg gaaaacacta   2880
gccggcgacc catggataaa aacactgact gccaagtacc ctgggaattt cactgccacg   2940
atagaggagt ggcaagcaga gcatgatgcc atcatgaggc acatcttgga gagaccggac   3000
cctaccgacg tcttccagaa taaggcaaac gtgtgttggg ccaaggcttt agtgccggtg   3060
ctgaagaccg ctggcataga catgaccact gaacaatgga acactgtgga ttattttgaa   3120
acggacaaag ctcactcagc agagatagta ttgaaccaac tatgcgtgag gttctttgga   3180
ctcgatctgg actccggtct attttctgca cccactgttc cgttatccat taggaataat   3240
cactgggata actccccgtc gcctaacatg tacgggctga ataaagaagt ggtccgtcag   3300
ctctctcgca ggtacccaca actgcctcgg gcagttgcca ctggaagagt ctatgacatg   3360
aacactggta cactgcgcaa ttatgatccg cgcataaacc tagtacctgt aaacagaaga   3420
ctgcctcatg ctttagtcct ccaccataat gaacacccac agagtgactt ttcttcattc   3480
gtcagcaaat tgaagggcag aactgtcctg gtggtcgggg aaaagttgtc cgtcccaggc   3540
aaaatggttg actggttgtc agaccggcct gaggctacct tcagagctcg gctggattta   3600
ggcatcccag gtgatgtgcc caaatatgac ataatatttg ttaatgtgag gaccccatat   3660
```

-continued

```
aaataccatc actatcagca gtgtgaagac catgccatta agcttagcat gttgaccaag   3720
aaagcttgtc tgcatctgaa tcccggcgga acctgtgtca gcataggtta tggttacgct   3780
gacagggcca gcgaaagcat cattggtgct atagcgcggc agttcaagtt ttcccgggta   3840
tgcaaaccga aatcctcact tgaagagacg gaagttctgt ttgtattcat tgggtacgat   3900
cgcaaggccc gtacgcacaa tccttacaag ctttcatcaa ccttgaccaa catttataca   3960
ggttccagac tccacgaagc cggatgtgca ccctcatatc atgtggtgcg aggggatatt   4020
gccacggcca ccgaaggagt gattataaat gctgctaaca gcaaaggaca acctggcgga   4080
ggggtgtgcg gagcgctgta taagaaattc ccggaaagct tcgatttaca gccgatcgaa   4140
gtaggaaaag cgcgactggt caaaggtgca gctaaacata tcattcatgc cgtaggacca   4200
aacttcaaca aagtttcgga ggttgaaggt gacaaacagt tggcagaggc ttatgagtcc   4260
atcgctaaga ttgtcaacga taacaattac aagtcagtag cgattccact gttgtccacc   4320
ggcatctttt ccgggaacaa agatcgacta acccaatcat tgaaccattt gctgacagct   4380
ttagacacca ctgatgcaga tgtagccata tactgcaggg acaagaaatg ggaaatgact   4440
ctcaaggaag cagtggctag gagagaagca gtggaggaga tatgcatatc cgacgactct   4500
tcagtgacag aacctgatgc agagctggtg agggtgcatc cgaagagttc tttggctgga   4560
aggaagggct acagcacaag cgatggcaaa actttctcat atttggaagg gaccaagttt   4620
caccaggcgg ccaaggatat agcagaaatt aatgccatgt ggcccgttgc aacggaggcc   4680
aatgagcagg tatgcatgta tatcctcgga gaaagcatga gcagtattag gtcgaaatgc   4740
cccgtcgaag agtcggaagc ctccacacca cctagcacgc tgccttgctt gtgcatccat   4800
gccatgactc cagaaagagt acagcgccta aaagcctcac gtccagaaca aattactgtg   4860
tgctcatcct ttccattgcc gaagtataga atcactggtg tgcagaagat ccaatgctcc   4920
cagcctatat tgttctcacc gaaagtgcct gcgtatattc atccaaggaa gtatctcgtg   4980
gaaacaccac cggtagacga gactccggag ccatcggcag agaaccaatc cacagagggg   5040
acacctgaac aaccaccact tataaccgag gatgagacca ggactagaac gcctgagccg   5100
atcatcatcg aagaggaaga agaggatagc ataagtttgc tgtcagatgg cccgacccac   5160
caggtgctgc aagtcgaggc agacattcac gggccgccct ctgtatctag ctcatcctgg   5220
tccattcctc atgcatccga ctttgatgtg gacagtttat ccatacttga caccctggag   5280
ggagctagcg tgaccagcgg ggcaacgtca gccgagacta actcttactt cgcaaagagt   5340
atggagtttc tggcgcgacc ggtgcctgcg cctcgaacag tattcaggaa ccctccacat   5400
cccgctccgc gcacaagaac accgtcactt gcacccagca gggcctgctc gagaaccagc   5460
ctagtttcca ccccgccagg cgtgaatagg gtgatcacta gagaggagct cgaggcgctt   5520
accccgtcac gcactcctag caggtcggtc tcgagaacca gcctggtctc caacccgcca   5580
ggcgtaaata gggtgattac aagagaggag tttgaggcgt tcgtagcaca acaacaatga   5640
cggtttgatg cgggtgcata catcttttcc tccgacaccg gtcaagggca tttacaacaa   5700
aaatcagtaa ggcaaacggt gctatccgaa gtggtgttgg agaggaccga attggagatt   5760
tcgtatgccc cgcgcctcga ccaagaaaaa gaagaattac tacgcaagaa attacagtta   5820
aatcccacac ctgctaacag aagcagatac cagtccagga aggtggagaa catgaaagcc   5880
ataacagcta gacgtattct gcaaggccta gggcattatt tgaaggcaga aggaaaagtg   5940
gagtgctacc gaaccctgca tcctgttcct ttgtattcat ctagtgtgaa ccgtgccttt   6000
```

-continued

```
tcaagcccca aggtcgcagt ggaagcctgt aacgccatgt tgaaagagaa ctttccgact   6060

gtggcttctt actgtattat tccagagtac gatgcctatt tggacatggt tgacggagct   6120

tcatgctgct tagacactgc cagtttttgc cctgcaaagc tgcgcagctt tccaaagaaa   6180

cactcctatt tggaacccac aatacgatcg gcagtgcctt cagcgatcca gaacacgctc   6240

cagaacgtcc tggcagctgc cacaaaaaga aattgcaatg tcacgcaaat gagagaattg   6300

cccgtattgg attcggcggc ctttaatgtg gaatgcttca agaaatatgc gtgtaataat   6360

gaatattggg aaacgtttaa agaaaacccc atcaggctta ctgaagaaaa cgtggtaaat   6420

tacattacca aattaaaagg accaaaagct gctgctcttt ttgcgaagac acataatttg   6480

aatatgttgc aggacatacc aatggacagg tttgtaatgg acttaaagag agacgtgaaa   6540

gtgactccag gaacaaaaca tactgaagaa cggcccaagg tacaggtgat ccaggctgcc   6600

gatccgctag caacagcgta tctgtgcgga atccaccgag agctggttag gagattaaat   6660

gcggtcctgc ttccgaacat tcatacactg tttgatatgt cggctgaaga ctttgacgct   6720

attatagccg agcacttcca gcctggggat tgtgttctgg aaactgacat cgcgtcgttt   6780

gataaaagtg aggacgacgc catggctctg accgcgttaa tgattctgga agacttaggt   6840

gtggacgcag agctgttgac gctgattgag gcggctttcg gcgaaatttc atcaatacat   6900

ttgcccacta aaactaaatt taaattcgga gccatgatga aatctggaat gttcctcaca   6960

ctgtttgtga acacagtcat taacattgta atcgcaagca gagtgttgag agaacggcta   7020

accggatcac catgtgcagc attcattgga gatgacaata tcgtgaaagg agtcaaatcg   7080

gacaaattaa tggcagacag gtgcgccacc tggttgaata tggaagtcaa gattatagat   7140

gctgtggtgg gcgagaaagc gccttatttc tgtggagggt ttattttgtg tgactccgtg   7200

accggcacag cgtgccgtgt ggcagacccc ctaaaaaggc tgtttaagct tggcaaacct   7260

ctggcagcag acgatgaaca tgatgatgac aggagaaggg cattgcatga agagtcaaca   7320

cgctggaacc gagtgggtat tctttcagag ctgtgcaagg cagtagaatc aaggtatgaa   7380

accgtaggaa cttccatcat agttatggcc atgactactc tagctagcag tgttaaatca   7440

ttcagctacc tgagaggggc ccctataact ctctacggct aa                      7482
```

<210> SEQ ID NO 3
<211> LENGTH: 7482
<212> TYPE: DNA
<213> ORGANISM: Artificial Sequence
<220> FEATURE:
<223> OTHER INFORMATION: Synthetic construct, C03 nsP coding sequence
      DNA

<400> SEQUENCE: 3

```
atggagaaag ttcacgttga catcgaggaa gacagcccat tcctcagagc tttgcagcgg     60

agcttcccgc agtttgaggt agaagccaag caggtcactg ataatgacca tgctaatgcc    120

agagcgtttt cgcatctggc ttcaaaactg atcgaaacgg aggtggaccc atccgacacg    180

atccttgaca ttggaagtgc gcccgcccgc agaatgtatt ctaagcacaa gtatcattgt    240

atctgtccga tgagatgtgc ggaagatccg gacagattgt ataagtatgc aactaagctg    300

aagaaaaact gtaaggaaat aactgataag gaattggaca agaaaatgaa ggagctcgcc    360

gccgtcatga gcgaccctga cctggaaact gagactatgt gcctccacga cgacgagtcg    420

tgtcgctacg aagggcaagt cgctgtttac caggatgtat acgcggttga cggaccgaca    480

agtctctatc accaagccaa taagggagtt agagtcgcct actggatagg ctttgacacc    540
```

acccctttta tgtttaagaa cttggctgga gcatatccat catactctac caactgggcc 600
gacgaaaccg tgttaacggc tcgtaacata ggcctatgca gctctgacgt tatggagcgg 660
tcacgtagag ggatgtccat tcttagaaag aagtatttga aaccatccaa caatgttcta 720
ttctctgttg gctcgaccat ctaccacgag aagagggact tactgaggag ctggcacctg 780
ccgtctgtat ttcacttacg tggcaagcaa aattacacat gtcggtgtga gactatagtt 840
agttgcgacg ggtacgtcgt taaaagaata gctatcagtc caggcctgta tgggaagcct 900
tcaggctatg ctgctacgat gcaccgcgag ggattcttgt gctgcaaagt gacagacaca 960
ttgaacgggg agagggtctc ttttcccgtg tgcacgtatg tgccagctac attgtgtgac 1020
caaatgactg gcatactggc aacagatgtc agtgcggacg acgcgcaaaa actgctggtt 1080
gggctcaacc agcgtatagt cgtcaacggt cgcacccaga gaaacaccaa taccatgaaa 1140
aattaccttt tgcccgtagt ggcccaggca tttgctaggt gggcaaagga atataaggaa 1200
gatcaagaag atgaaaggcc actaggacta cgagatagac agttagtcat ggggtgttgt 1260
tgggctttta gaaggcacaa gataacatct atttataagc gcccggatac ccaaaccatc 1320
atcaaagtga acagcgattt ccactcattc gtgctgccca ggataggcag taacacattg 1380
gagatcgggc tgagaacaag aatcaggaaa atgttagagg agcacaagga gccgtcacct 1440
ctcattaccg ccgaggacgt acaagaagct aagtgcgcag ccgatgaggc taaggaggtg 1500
cgtgaagccg aggagttgcg cgcagctcta ccacctttgg cagctgatgt tgaggagccc 1560
actctggaag ccgatgtcga cttgatgtta caagaggctg gggccggctc agtggagaca 1620
cctcgtggct tgataaaggt taccagctac gctggcgagg acaagatcgg ctcttacgct 1680
gtgctttctc cgcaggctgt actcaagagt gaaaaattat cttgcatcca ccctctcgct 1740
gaacaagtca tagtgataac acactctggc cgaaaagggc gttatgccgt ggaaccatac 1800
catggtaaag tagtggtgcc agagggacat gcaatacccg tccaggactt tcaagctctg 1860
agtgaaagtg ccaccattgt gtacaacgaa cgtgagttcg taaacaggta cctgcaccat 1920
attgccacac atggaggagc gctgaacact gatgaagaat attacaaaac tgtcaagccc 1980
agcgagcacg acggcgaata cctgtacgac atcgacagga aacagtgcgt caagaaagaa 2040
ctagtcactg ggctagggct cacaggcgag ctggtggatc ctcccttcca tgaattcgcc 2100
tacgagagtc tgagaacacg accagccgct ccttaccaag taccaaccat aggggtgtat 2160
ggcgtgccag gatcaggcaa gtctggcatc attaaaagcg cagtcaccaa aaaagatcta 2220
gtggtgagcg ccaagaaaga aaactgtgca gaaattataa gggacgtcaa gaaaatgaaa 2280
gggctggacg tcaatgccag aactgtggac tcagtgctct tgaatggatg caaacacccc 2340
gtagagaccc tgtatattga cgaagctttt gcttgtcatg caggtactct cagagcgctc 2400
atagccatta taagacctaa aaaggcagtg ctctgcgggg atcccaaaca gtgcggtttt 2460
tttaacatga tgtgcctgaa agtgcatttt aaccacgaga tttgcacaca agtcttccac 2520
aaaagcatct ctcgccgttg cactaaatct gtgacttcgg tcgtctcaac cttgttttac 2580
gacaaaaaaa tgagaacgac gaatccgaaa gagactaaga ttgtgattga cactaccggc 2640
agtaccaaac ctaagcagga cgatctcatt ctcacttgtt tcagagggtg ggtgaagcag 2700
ttgcaaatag attacaaagg caacgaaata atgacggcag ctgcctctca agggctgacc 2760
cgtaaaggtg tgtatgccgt tcggtacaag gtgaatgaaa atcctctgta cgcacccacc 2820
tcagaacatg tgaacgtcct actgacccgc acggaggacc gcatcgtgtg gaaaacacta 2880
gccggcgacc catggataaa aacactgact gccaagtacc ctgggaattt cactgccacg 2940

-continued

```
atagaggagt ggcaagcaga gcatgatgcc atcatgaggc acatcttgga gagaccggac   3000
cctaccgacg tcttccagaa taaggcaaac gtgtgttggg ccaaggcttt agtgccggtg   3060
ctgaagaccg ctggcataga catgaccact gaacaatgga acactgtgga ttattttgaa   3120
acggacaaag ctcactcagc agagatagta ttgaaccaac tatgcgtgag gttctttgga   3180
ctcgatctgg actccggtct attttctgca cccactgttc cgttatccat taggaataat   3240
cactgggata actccccgtc gcctaacatg tacgggctga ataaagaagt ggtccgtcag   3300
ctctctcgca ggtacccaca actgcctcgg gcagttgcca ctggaagagt ctatgacatg   3360
aacactggta cactgcgcaa ttatgatccg cgcataaacc tagtacctgt aaacagaaga   3420
ctgcctcatg ctttagtcct ccaccataat gaacacccac agagtgactt ttcttcattc   3480
gtcagcaaat tgaagggcag aactgtcctg gtggtcgggg aaaagttgtc cgtcccaggc   3540
aaaatggttg actggttgtc agaccggcct gaggctacct tcagagctcg gctggattta   3600
ggcatcccag gtgatgtgcc caaatatgac ataatatttg ttaatgtgag gaccccctac   3660
aagtaccacc actaccagca gtgcgaggac cacgccatca agctgagcat gctgaccaag   3720
aaggcctgcc tgcatctgaa tcccggcgga acctgtgtca gcataggtta tggttacgct   3780
gacagggcca gcgaaagcat cattggtgct atagcgcggc agttcaagtt ttcccgggta   3840
tgcaaaccga aatcctcact tgaagagacg gaagttctgt ttgtattcat cggctacgac   3900
agaaaggccc gtacgcacaa tccttacaag ctttcatcaa ccttgaccaa catttataca   3960
ggttccagac tccacgaagc cggatgtgca ccctcatatc atgtggtgcg aggggatatt   4020
gccacggcca ccgaaggagt gattataaat gctgctaaca gcaaaggaca acctggcgga   4080
ggggtgtgcg gagcgctgta taagaaattc ccggaaagct tcgatttaca gccgatcgaa   4140
gtaggaaaag cgcgactggt caaaggtgca gctaaacata tcattcatgc cgtaggacca   4200
aacttcaaca aagtttcgga ggttgaaggt gacaaacagt tggcagaggc ttatgagtcc   4260
atcgctaaga ttgtcaacga taacaattac aagtcagtag cgattccact gttgtccacc   4320
ggcatctttt ccgggaacaa agatcgacta acccaatcat tgaaccattt gctgacagct   4380
ttagacacca ctgatgcaga tgtagccata tactgcaggg acaagaaatg ggaaatgact   4440
ctcaaggaag cagtggctag gagagaagca gtggaggaga tatgcatatc cgacgactct   4500
tcagtgacag aacctgatgc agagctggtg agggtgcatc cgaagagttc tttggctgga   4560
aggaagggct acagcacaag cgatggcaaa actttctcat atttggaagg gaccaagttt   4620
caccaggcgg ccaaggatat agcagaaatt aatgccatgt ggcccgttgc aacggaggcc   4680
aatgagcagg tatgcatgta tatcctcgga gaaagcatga gcagtattag gtcgaaatgc   4740
cccgtcgaag agtcggaagc ctccacacca cctagcacgc tgccttgctt gtgcatccat   4800
gccatgactc cagaaagagt acagcgccta aaagcctcac gtccagaaca aattactgtg   4860
tgctcatcct ttccattgcc gaagtataga atcactggtg tgcagaagat ccaatgctcc   4920
cagcctatat tgttctcacc gaaagtgcct gcgtatattc atccaaggaa gtatctcgtg   4980
gaaacaccac cggtagacga gactccggag ccatcggcag agaaccaatc cacagagggg   5040
acacctgaac aaccaccact tataaccgag gatgagacca ggactagaac gcctgagccg   5100
atcatcatcg aagaggaaga agaggatagc ataagtttgc tgtcagatgg cccgacccac   5160
caggtgctgc aagtcgaggc agacattcac gggccgccct ctgtatctag ctcatcctgg   5220
tccattcctc atgcatccga ctttgatgtg gacagtttat ccatacttga caccctggag   5280
```

-continued

```
ggagctagcg tgaccagcgg ggcaacgtca gccgagacta actcttactt cgcaaagagt   5340
atggagtttc tggcgcgacc ggtgcctgcg cctcgaacag tattcaggaa ccctccacat   5400
cccgctccgc gcacaagaac accgtcactt gcacccagca gggcctgctc gagaaccagc   5460
ctagtttcca ccccgccagg cgtgaatagg gtgatcacta gagaggagct cgaggcgctt   5520
accccgtcac gcactcctag caggtcggtc tcgagaacca gcctggtctc caacccgcca   5580
ggcgtaaata gggtgattac aagagaggag tttgaggcgt tcgtagcaca acaacaatga   5640
cggtttgatg cgggtgcata catctttttcc tccgacaccg gtcaagggca tttacaacaa   5700
aaatcagtaa ggcaaacggt gctatccgaa gtggtgttgg agaggaccga attggagatt   5760
tcgtatgccc cgcgcctcga ccaagaaaaa gaagaattac tacgcaagaa attacagtta   5820
aatcccacac ctgctaacag aagcagatac cagtccagga aggtggagaa catgaaagcc   5880
ataacagcta gacgtattct gcaaggccta gggcattatt tgaaggcaga aggaaaagtg   5940
gagtgctacc gaaccctgca tcctgttcct ttgtattcat ctagtgtgaa ccgtgccttt   6000
tcaagcccca aggtcgcagt ggaagcctgt aacgccatgt tgaaagagaa ctttccgact   6060
gtggcttctt actgtattat tccagagtac gatgcctatt tggacatggt tgacggagct   6120
tcatgctgct tagacactgc cagtttttgc cctgcaaagc tgcgcagctt tccaaagaaa   6180
cactcctatt tggaacccac aatacgatcg gcagtgcctt cagcgatcca gaacacgctc   6240
cagaacgtcc tggcagctgc cacaaaaaga aattgcaatg tcacgcaaat gagagaattg   6300
cccgtattgg attcggcggc ctttaatgtg gaatgcttca agaaatatgc gtgtaataat   6360
gaatattggg aaacgtttaa agaaaacccc atcaggctta ctgaagaaaa cgtggtaaat   6420
tacattacca aattaaaagg accaaaagct gctgctcttt ttgcgaagac acataatttg   6480
aatatgttgc aggacatacc aatggacagg tttgtaatgg acttaaagag agacgtgaaa   6540
gtgactccag gaacaaaaca tactgaagaa cggcccaagg tacaggtgat ccaggctgcc   6600
gatccgctag caacagcgta tctgtgcgga atccaccgag agctggttag gagattaaat   6660
gcggtcctgc ttccgaacat tcatacactg tttgatatgt cggctgaaga ctttgacgct   6720
attatagccg agcacttcca gcctggggat tgtgttctgg aaactgacat cgcgtcgttt   6780
gataaaagtg aggacgacgc catggctctg accgcgttaa tgattctgga agacttaggt   6840
gtggacgcag agctgttgac gctgattgag gcggctttcg gcgaaatttc atcaatacat   6900
ttgcccacta aaactaaatt taaattcgga gccatgatga aatctggaat gttcctcaca   6960
ctgtttgtga acacagtcat taacattgta atcgcaagca gagtgttgag agaacggcta   7020
accggatcac catgtgcagc attcattgga gatgacaata tcgtgaaagg agtcaaatcg   7080
gacaaattaa tggcagacag gtgcgccacc tggttgaata tggaagtcaa gattatagat   7140
gctgtggtgg gcgagaaagc gccttatttc tgtggagggt ttattttgtg tgactccgtg   7200
accggcacag cgtgccgtgt ggcagacccc ctaaaaaggc tgtttaagct tggcaaacct   7260
ctggcagcag acgatgaaca tgatgatgac aggagaaggg cattgcatga agagtcaaca   7320
cgctggaacc gagtgggtat tctttcagag ctgtgcaagg cagtagaatc aaggtatgaa   7380
accgtaggaa cttccatcat agttatggcc atgactactc tagctagcag tgttaaatca   7440
ttcagctacc tgagaggggc ccctataact ctctacggct aa                      7482
```

<210> SEQ ID NO 4
<211> LENGTH: 7482
<212> TYPE: DNA
<213> ORGANISM: Artificial Sequence -continued
<220> FEATURE:
<223> OTHER INFORMATION: Synthetic construct, C04 nsP coding sequence
      DNA

<400> SEQUENCE: 4

```
atggagaaag ttcacgttga catcgaggaa gacagcccat tcctcagagc tttgcagcgg     60
agcttcccgc agtttgaggt agaagccaag caggtcactg ataatgacca tgctaatgcc    120
agagcgtttt cgcatctggc ttcaaaactg atcgaaacgg aggtggaccc atccgacacg    180
atccttgaca ttggaagtgc gcccgcccgc agaatgtatt ctaagcacaa gtatcattgt    240
atctgtccga tgagatgtgc ggaagatccg gacagattgt ataagtatgc aactaagctg    300
aagaaaaact gtaaggaaat aactgataag gaattggaca agaaaatgaa ggagctcgcc    360
gccgtcatga gcgaccctga cctggaaact gagactatgt gcctccacga cgacgagtcg    420
tgtcgctacg aagggcaagt cgctgtttac caggatgtat acgcggttga cggaccgaca    480
agtctctatc accaagccaa taagggagtt agagtcgcct actggatagg ctttgacacc    540
accccttta tgtttaagaa cttggctgga gcatatccat catactctac caactgggcc    600
gacgaaaccg tgttaacggc tcgtaacata ggcctatgca gctctgacgt tatggagcgg    660
tcacgtagag ggatgtccat tcttagaaag aagtatttga aaccatccaa caatgttcta    720
ttctctgttg gctcgaccat ctaccacgag aagagggact tactgaggag ctggcacctg    780
ccgtctgtat ttcacttacg tggcaagcaa aattacacat gtcggtgtga gactatagtt    840
agttgcgacg ggtacgtcgt taaaagaata gctatcagtc caggcctgta tgggaagcct    900
tcaggctatg ctgctacgat gcaccgcgag ggattcttgt gctgcaaagt gacagacaca    960
ttgaacgggg agagggtctc ttttcccgtg tgcacgtatg tgccagctac attgtgtgac   1020
caaatgactg gcatactggc aacagatgtc agtgcggacg acgcgcaaaa actgctggtt   1080
gggctcaacc agcgtatagt cgtcaacggt cgcacccaga gaaacaccaa taccatgaaa   1140
aattaccttt tgcccgtagt ggcccaggca tttgctaggt gggcaaagga atataaggaa   1200
gatcaagaag atgaaaggcc actaggacta cgagatagac agttagtcat ggggtgttgt   1260
tgggctttta gaaggcacaa gataacatct atttataagc gcccggatac ccaaaccatc   1320
atcaaagtga acagcgattt ccactcattc gtgctgccca ggataggcag taacacattg   1380
gagatcgggc tgagaacaag aatcaggaaa atgttagagg agcacaagga gccgtcacct   1440
ctcattaccg ccgaggacgt acaagaagct aagtgcgcag ccgatgaggc taaggaggtg   1500
cgtgaagccg aggagttgcg cgcagctcta ccacctttgg cagctgatgt tgaggagccc   1560
actctggaag ccgatgtcga cttgatgtta caagaggctg gggccggctc agtggagaca   1620
cctcgtggct tgataaaggt taccagctac gctggcgagg acaagatcgg ctcttacgct   1680
gtgctttctc cgcaggctgt actcaagagt gaaaaattat cttgcatcca ccctctcgct   1740
gaacaagtca tagtgataac acactctggc cgaaaagggc gttatgccgt ggaaccatac   1800
catggtaaag tagtggtgcc agagggacat gcaatacccg tccaggactt tcaagctctg   1860
agtgaaagtg ccaccattgt gtacaacgaa cgtgagttcg taaacaggta cctgcaccat   1920
attgccacac atggaggagc gctgaacact gatgaagaat attacaaaac tgtcaagccc   1980
agcgagcacg acggcgaata cctgtacgac atcgacagga aacagtgcgt caagaaagaa   2040
ctagtcactg ggctagggct cacaggcgag ctggtggatc ctcccttcca tgaattcgcc   2100
tacgagagtc tgagaacacg accagccgct ccttaccaag taccaaccat aggggtgtat   2160
ggcgtgccag gatcaggcaa gtctggcatc attaaaagcg cagtcaccaa aaaagatcta   2220
```

```
gtggtgagcg ccaagaaaga aaactgtgca gaaattataa gggacgtcaa gaaaatgaaa   2280
gggctggacg tcaatgccag aactgtggac tcagtgctct tgaatggatg caaacacccc   2340
gtagagaccc tgtatattga cgaagctttt gcttgtcatg caggtactct cagagcgctc   2400
atagccatta taagacctaa aaaggcagtg ctctgcgggg atcccaaaca gtgcggtttt   2460
tttaacatga tgtgcctgaa agtgcatttt aaccacgaga tttgcacaca agtcttccac   2520
aaaagcatct ctcgccgttg cactaaatct gtgacttcgg tcgtctcaac cttgttttac   2580
gacaaaaaaa tgagaacgac gaatccgaaa gagactaaga ttgtgattga cactaccggc   2640
agtaccaaac ctaagcagga cgatctcatt ctcacttgtt tcagagggtg ggtgaagcag   2700
ttgcaaatag attacaaagg caacgaaata atgacggcag ctgcctctca agggctgacc   2760
cgtaaaggtg tgtatgccgt tcggtacaag gtgaatgaaa atcctctgta cgcacccacc   2820
tcagaacatg tgaacgtcct actgacccgc acggaggacc gcatcgtgtg gaaaacacta   2880
gccggcgacc catggataaa aacactgact gccaagtacc ctgggaattt cactgccacg   2940
atagaggagt ggcaagcaga gcatgatgcc atcatgaggc acatcttgga gagaccggac   3000
cctaccgacg tcttccagaa taaggcaaac gtgtgttggg ccaaggcttt agtgccggtg   3060
ctgaagaccg ctggcataga catgaccact gaacaatgga acactgtgga ttattttgaa   3120
acggacaaag ctcactcagc agagatagta ttgaaccaac tatgcgtgag gttctttgga   3180
ctcgatctgg actccggtct attttctgca cccactgttc cgttatccat taggaataat   3240
cactgggata actccccgtc gcctaacatg tacgggctga ataaagaagt ggtccgtcag   3300
ctctctcgca ggtacccaca actgcctcgg gcagttgcca ctggaagagt ctatgacatg   3360
aacactggta cactgcgcaa ttatgatccg cgcataaacc tagtacctgt aaacagaaga   3420
ctgcctcatg ctttagtcct ccaccataat gaacacccac agagtgactt ttcttcattc   3480
gtcagcaaat tgaagggcag aactgtcctg gtggtcgggg aaaagttgtc cgtcccaggc   3540
aaaatggttg actggttgtc agaccggcct gaggctacct tcagagctcg gctggattta   3600
ggcatcccag gtgatgtgcc caaatatgac ataatatttg ttaatgtgag gaccccatat   3660
aaataccatc actatcagca gtgtgaagac catgccatta agcttagcat gttgaccaag   3720
aaagcttgtc tgcatctgaa tcccggcgga acctgtgtca gcataggtta tggttacgct   3780
gacagggcca gcgaaagcat cattggtgct atagcgcggc agttcaagtt ttcccgggta   3840
tgcaaaccga aatcctcact tgaagagacg gaagttctgt ttgtattcat tgggtacgat   3900
cgcaaggccc gtacgcacaa cccctacaag ctgagcagca ccctgaccaa catctacacc   3960
ggcagcagac tgcacgaagc cggatgtgca ccctcatatc atgtggtgcg aggggatatt   4020
gccacagcca cagaaggagt gattataaat gctgctaaca gcaaaggaca acctggcgga   4080
ggggtgtgcg gagcgctgta taagaaattc ccggaaagct tcgatttaca gccgatcgaa   4140
gtaggaaaag cgcgactggt caaaggtgca gctaaacata tcattcatgc cgtaggacca   4200
aacttcaaca aagtttcgga ggttgaaggt gacaaacagt tggcagaggc ttatgagtcc   4260
atcgctaaga ttgtcaacga taacaattac aagtcagtag cgattccact gttgtccacc   4320
ggcatctttt ccgggaacaa agatcgacta acccaatcat tgaaccattt gctgacagct   4380
ttagacacca ctgatgcaga tgtagccata tactgcaggg acaagaaatg ggaaatgact   4440
ctcaaggaag cagtggctag gagagaagca gtggaggaga tatgcatatc cgacgactct   4500
tcagtgacag aacctgatgc agagctggtg agggtgcatc cgaagagttc tttggctgga   4560
```

-continued aggaagggct acagcacaag cgatggcaaa actttctcat atttggaagg gaccaagttt 4620
caccaggcgg ccaaggatat agcagaaatt aatgccatgt ggcccgttgc aacggaggcc 4680
aatgagcagg tatgcatgta tatcctcgga gaaagcatga gcagtattag gtcgaaatgc 4740
cccgtcgaag agtcggaagc ctccacacca cctagcacgc tgccttgctt gtgcatccat 4800
gccatgactc cagaaagagt acagcgccta aaagcctcac gtccagaaca aattactgtg 4860
tgctcatcct ttccattgcc gaagtataga atcactggtg tgcagaagat ccaatgctcc 4920
cagcctatat tgttctcacc gaaagtgcct gcgtatattc atccaaggaa gtatctcgtg 4980
gaaacaccac cggtagacga gactccggag ccatcggcag agaaccaatc cacagagggg 5040
acacctgaac aaccaccact tataaccgag gatgagacca ggactagaac gcctgagccg 5100
atcatcatcg aagaggaaga agaggatagc ataagtttgc tgtcagatgg cccgacccac 5160
caggtgctgc aagtcgaggc agacattcac gggccgccct ctgtatctag ctcatcctgg 5220
tccattcctc atgcatccga ctttgatgtg gacagtttat ccatacttga caccctggag 5280
ggagctagcg tgaccagcgg ggcaacgtca gccgagacta actcttactt cgcaaagagt 5340
atggagtttc tggcgcgacc ggtgcctgcg cctcgaacag tattcaggaa ccctccacat 5400
cccgctccgc gcacaagaac accgtcactt gcacccagca gggcctgctc gagaaccagc 5460
ctagtttcca ccccgccagg cgtgaatagg gtgatcacta gagaggagct cgaggcgctt 5520
accccgtcac gcactcctag caggtcggtc tcgagaacca gcctggtctc caacccgcca 5580
ggcgtaaata gggtgattac aagagaggag tttgaggcgt tcgtagcaca acaacaatga 5640
cggtttgatg cgggtgcata catcttttcc tccgacaccg gtcaagggca tttacaacaa 5700
aaatcagtaa ggcaaacggt gctatccgaa gtggtgttgg agaggaccga attggagatt 5760
tcgtatgccc cgcgcctcga ccaagaaaaa gaagaattac tacgcaagaa attacagtta 5820
aatcccacac ctgctaacag aagcagatac cagtccagga aggtggagaa catgaaagcc 5880
ataacagcta gacgtattct gcaaggccta gggcattatt tgaaggcaga aggaaaagtg 5940
gagtgctacc gaaccctgca tcctgttcct ttgtattcat ctagtgtgaa ccgtgccttt 6000
tcaagcccca aggtcgcagt ggaagcctgt aacgccatgt tgaaagagaa ctttccgact 6060
gtggcttctt actgtattat tccagagtac gatgcctatt tggacatggt tgacggagct 6120
tcatgctgct tagacactgc cagtttttgc cctgcaaagc tgcgcagctt tccaaagaaa 6180
cactcctatt tggaacccac aatacgatcg gcagtgcctt cagcgatcca gaacacgctc 6240
cagaacgtcc tggcagctgc cacaaaaaga aattgcaatg tcacgcaaat gagagaattg 6300
cccgtattgg attcggcggc ctttaatgtg gaatgcttca agaaatatgc gtgtaataat 6360
gaatattggg aaacgtttaa agaaaacccc atcaggctta ctgaagaaaa cgtggtaaat 6420
tacattacca aattaaaagg accaaaagct gctgctcttt ttgcgaagac acataatttg 6480
aatatgttgc aggacatacc aatggacagg tttgtaatgg acttaaagag agacgtgaaa 6540
gtgactccag gaacaaaaca tactgaagaa cggcccaagg tacaggtgat ccaggctgcc 6600
gatccgctag caacagcgta tctgtgcgga atccaccgag agctggttag gagattaaat 6660
gcggtcctgc ttccgaacat tcatacactg tttgatatgt cggctgaaga ctttgacgct 6720
attatagccg agcacttcca gcctggggat tgtgttctgg aaactgacat cgcgtcgttt 6780
gataaaagtg aggacgacgc catggctctg accgcgttaa tgattctgga agacttaggt 6840
gtggacgcag agctgttgac gctgattgag gcggctttcg gcgaaatttc atcaatacat 6900
ttgcccacta aaactaaatt taaattcgga gccatgatga aatctggaat gttcctcaca 6960
ctgtttgtga acacagtcat taacattgta atcgcaagca gagtgttgag agaacggcta 7020
accggatcac catgtgcagc attcattgga gatgacaata tcgtgaaagg agtcaaatcg 7080
gacaaattaa tggcagacag gtgcgccacc tggttgaata tggaagtcaa gattatagat 7140
gctgtggtgg gcgagaaagc gccttatttc tgtggagggt ttattttgtg tgactccgtg 7200
accggcacag cgtgccgtgt ggcagacccc ctaaaaaggc tgtttaagct tggcaaacct 7260
ctggcagcag acgatgaaca tgatgatgac aggagaaggg cattgcatga agagtcaaca 7320
cgctggaacc gagtgggtat tctttcagag ctgtgcaagg cagtagaatc aaggtatgaa 7380
accgtaggaa cttccatcat agttatggcc atgactactc tagctagcag tgttaaatca 7440
ttcagctacc tgagaggggc ccctataact ctctacggct aa 7482

<210> SEQ ID NO 5
<211> LENGTH: 7482
<212> TYPE: DNA
<213> ORGANISM: Artificial Sequence
<220> FEATURE:
<223> OTHER INFORMATION: Synthetic construct, C05 nsP coding sequence DNA

<400> SEQUENCE: 5
atggagaaag ttcacgttga catcgaggaa gacagcccat tcctcagagc tttgcagcgg 60
agcttcccgc agtttgaggt agaagccaag caggtcactg ataatgacca tgctaatgcc 120
agagcgtttt cgcatctggc ttcaaaactg atcgaaacgg aggtggaccc atccgacacg 180
atccttgaca ttggaagtgc gcccgcccgc agaatgtatt ctaagcacaa gtatcattgt 240
atctgtccga tgagatgtgc ggaagatccg gacagattgt ataagtatgc aactaagctg 300
aagaaaaact gtaaggaaat aactgataag gaattggaca agaaaatgaa ggagctcgcc 360
gccgtcatga gcgaccctga cctggaaact gagactatgt gcctccacga cgacgagtcg 420
tgtcgctacg aagggcaagt cgctgtttac caggatgtat acgcggttga cggaccgaca 480
agtctctatc accaagccaa taagggagtt agagtcgcct actggatagg ctttgacacc 540 accccttta tgtttaagaa cttggctgga gcatatccat catactctac caactgggcc 600
gacgaaaccg tgttaacggc tcgtaacata ggcctatgca gctctgacgt tatggagcgg 660
tcacgtagag ggatgtccat tcttagaaag aagtatttga aaccatccaa caatgttcta 720
ttctctgttg gctcgaccat ctaccacgag aagagggact tactgaggag ctggcacctg 780
ccgtctgtat ttcacttacg tggcaagcaa aattacacat gtcggtgtga gactatagtt 840
agttgcgacg ggtacgtcgt taaaagaata gctatcagtc caggcctgta tgggaagcct 900
tcaggctatg ctgctacgat gcaccgcgag ggattcttgt gctgcaaagt gacagacaca 960
ttgaacgggg agagggtctc ttttcccgtg tgcacgtatg tgccagctac attgtgtgac 1020
caaatgactg gcatactggc aacagatgtc agtgcggacg acgcgcaaaa actgctggtt 1080
gggctcaacc agcgtatagt cgtcaacggt cgcacccaga gaaacaccaa taccatgaaa 1140
aattaccttt tgcccgtagt ggcccaggca tttgctaggt gggcaaagga atataaggaa 1200
gatcaagaag atgaaaggcc actaggacta cgagatagac agttagtcat ggggtgttgt 1260
tgggctttta gaaggcacaa gataacatct atttataagc gcccggatac ccaaaccatc 1320
atcaaagtga acagcgattt ccactcattc gtgctgccca ggataggcag taacacattg 1380
gagatcgggc tgagaacaag aatcaggaaa atgttagagg agcacaagga gccgtcacct 1440
ctcattaccg ccgaggacgt acaagaagct aagtgcgcag ccgatgaggc taaggaggtg 1500

-continued

```
cgtgaagccg aggagttgcg cgcagctcta ccacctttgg cagctgatgt tgaggagccc   1560
actctggaag ccgatgtcga cttgatgtta caagaggctg gggccggctc agtggagaca   1620
cctcgtggct tgataaaggt taccagctac gctggcgagg acaagatcgg ctcttacgct   1680
gtgctttctc cgcaggctgt actcaagagc gagaagctga gctgcattca ccctctggcc   1740
gagcaagtga tcgtgatcac acacagcggc cggaagggca gatatgccgt ggaaccttat   1800
cacggcaagg tggtggtgcc tgagggacac gctattccag tgcaggactt tcaggccctg   1860
agcgagtctg ccaccatcgt gtacaacgag cgcgagttcg tgaacagata cctgcaccac   1920
attgccacac acggcggagc cctgaacacc gacgaagagt actacaagac cgtgaagccc   1980
agcgagcacg acggcgaata cctgtacgac atcgacagga aacagtgcgt caagaaagaa   2040
ctagtcactg ggctagggct cacaggcgag ctggtggatc ctcccttcca tgaattcgcc   2100
tacgagagtc tgagaacacg accagccgct ccttaccaag taccaaccat aggggtgtat   2160
ggcgtgccag gatcaggcaa gtctggcatc attaaaagcg cagtcaccaa aaaagatcta   2220
gtggtgagcg ccaagaaaga aaactgtgca gaaattataa gggacgtcaa gaaaatgaaa   2280
gggctggacg tcaatgccag aactgtggat agcgtgctgc tgaacggctg caagcacccc   2340
gtagagaccc tgtatattga cgaagctttt gcttgtcatg caggtactct cagagcgctc   2400
atagccatta taagacctaa aaaggcagtg ctctgcgggg atcctaagca gtgcggcttc   2460
ttcaacatga tgtgcctgaa ggtgcacttc aaccacgaga tctgcaccca ggtgttccac   2520
aaaagcatct ctcgccgttg cactaaatct gtgacttcgg tcgtctcaac cttgttttac   2580
gacaaaaaaa tgagaacgac gaatccgaaa gagactaaga ttgtgattga cactaccggc   2640
agtaccaaac ctaagcagga cgatctcatt ctcacttgtt tcagagggtg ggtgaagcag   2700
ttgcaaatag attacaaagg caacgaaata atgacggcag ctgcctctca agggctgacc   2760
cgtaaaggtg tgtatgccgt tcggtacaag gtgaatgaaa atcctctgta cgcacccacc   2820
tcagaacatg tgaacgtcct actgacccgc acggaggacc gcatcgtgtg gaaaacacta   2880
gccggcgacc catggataaa aacactgact gccaagtacc ctgggaattt cactgccacg   2940
atagaggagt ggcaagcaga gcatgatgcc atcatgaggc acatcttgga gagaccggac   3000
cctaccgacg tcttccagaa taaggcaaac gtgtgttggg ccaaggcttt agtgccggtg   3060
ctgaagaccg ctggcataga catgaccact gaacaatgga acactgtgga ttattttgaa   3120
acggacaaag ctcactcagc agagatagta ttgaaccaac tatgcgtgag gttctttgga   3180
ctcgatctgg actccggtct attttctgca cccactgttc cgttatccat taggaataat   3240
cactgggata actccccgtc gcctaacatg tacgggctga ataaagaagt ggtccgtcag   3300
ctctctcgca ggtacccaca actgcctcgg gcagttgcca ctggaagagt ctatgacatg   3360
aacactggta cactgcgcaa ttatgatccg cgcataaacc tagtacctgt aaacagaaga   3420
ctgcctcatg ctttagtcct ccaccataat gaacacccac agagtgactt ttcttcattc   3480
gtcagcaaat tgaagggcag aactgtcctg gtggtcgggg aaaagttgtc cgtcccaggc   3540
aaaatggttg actggttgtc agaccggcct gaggctacct tcagagctcg gctggattta   3600
ggcatcccag gtgatgtgcc caaatatgac ataatatttg ttaatgtgag gaccccatat   3660
aaataccatc actatcagca gtgtgaagac catgccatta agcttagcat gttgaccaag   3720
aaagcttgtc tgcatctgaa tcccggcgga acctgtgtca gcataggtta tggttacgct   3780
gacagggcca gcgaaagcat cattggtgct atagcgcggc agttcaagtt ttcccgggta   3840
```

-continued

```
tgcaaaccga aatcctcact tgaagagacg gaagttctgt ttgtattcat tgggtacgat   3900
cgcaaggccc gtacgcacaa tccttacaag ctttcatcaa ccttgaccaa catttataca   3960
ggttccagac tccacgaagc cggatgtgca ccctcatatc atgtggtgcg aggggatatt   4020
gccacggcca ccgaaggagt gattataaat gctgctaaca gcaaaggaca acctggcgga   4080
ggggtgtgcg gagcgctgta taagaaattc ccggaaagct tcgatttaca gccgatcgaa   4140
gtaggaaaag cgcgactggt caaaggtgca gctaaacata tcattcatgc cgtaggacca   4200
aacttcaaca aagtttcgga ggttgaaggt gacaaacagt tggcagaggc ttatgagtcc   4260
atcgctaaga ttgtcaacga taacaattac aagtcagtag cgattccact gttgtccacc   4320
ggcatctttt ccgggaacaa agatcgacta acccaatcat tgaaccattt gctgacagct   4380
ttagacacca ctgatgcaga tgtagccata tactgcaggg acaagaaatg ggaaatgact   4440
ctcaaggaag cagtggctag gagagaagca gtggaggaga tatgcatatc cgacgactct   4500
tcagtgacag aacctgatgc agagctggtg agggtgcatc cgaagagttc tttggctgga   4560
aggaagggct acagcacaag cgatggcaaa actttctcat atttggaagg gaccaagttt   4620
caccaggcgg ccaaggatat agcagaaatt aatgccatgt ggcccgttgc aacggaggcc   4680
aatgagcagg tatgcatgta tatcctcgga gaaagcatga gcagtattag gtcgaaatgc   4740
cccgtcgaag agtcggaagc ctccacacca cctagcacgc tgccttgctt gtgcatccat   4800
gccatgactc cagaaagagt acagcgccta aaagcctcac gtccagaaca aattactgtg   4860
tgctcatcct ttccattgcc gaagtataga atcactggtg tgcagaagat ccaatgctcc   4920
cagcctatat tgttctcacc gaaagtgcct gcgtatattc atccaaggaa gtatctcgtg   4980
gaaacaccac cggtagacga gactccggag ccatcggcag agaaccaatc cacagagggg   5040
acacctgaac aaccaccact tataaccgag gatgagacca ggactagaac gcctgagccg   5100
atcatcatcg aagaggaaga agaggatagc ataagtttgc tgtcagatgg cccgacccac   5160
caggtgctgc aagtcgaggc agacattcac gggccgccct ctgtatctag ctcatcctgg   5220
tccattcctc atgcatccga ctttgatgtg gacagtttat ccatacttga caccctggag   5280
ggagctagcg tgaccagcgg ggcaacgtca gccgagacta actcttactt cgcaaagagt   5340
atggagtttc tggcgcgacc ggtgcctgcg cctcgaacag tattcaggaa ccctccacat   5400
cccgctccgc gcacaagaac accgtcactt gcacccagca gggcctgctc gagaaccagc   5460
ctagtttcca ccccgccagg cgtgaatagg gtgatcacta gagaggagct cgaggcgctt   5520
accccgtcac gcactcctag caggtcggtc tcgagaacca gcctggtctc caacccgcca   5580
ggcgtaaata gggtgattac aagagaggag tttgaggcgt tcgtagcaca acaacaatga   5640
cggtttgatg cgggtgcata catcttttcc tccgacaccg gtcaagggca tttacaacaa   5700
aaatcagtaa ggcaaacggt gctatccgaa gtggtgttgg agaggaccga attggagatt   5760
tcgtatgccc cgcgcctcga ccaagaaaaa gaagaattac tacgcaagaa attacagtta   5820
aatcccacac ctgctaacag aagcagatac cagtccagga aggtggagaa catgaaagcc   5880
ataacagcta gacgtattct gcaaggccta gggcattatt tgaaggcaga aggaaaagtg   5940
gagtgctacc gaaccctgca tcctgttcct ttgtattcat ctagtgtgaa ccgtgccttt   6000
tcaagcccca aggtcgcagt ggaagcctgt aacgccatgt tgaaagagaa ctttccgact   6060
gtggcttctt actgtattat tccagagtac gatgcctatt tggacatggt tgacggagct   6120
tcatgctgct tagacactgc cagtttttgc cctgcaaagc tgcgcagctt tccaaagaaa   6180
cactcctatt tggaacccac aatacgatcg gcagtgcctt cagcgatcca gaacacgctc   6240
```

cagaacgtcc tggcagctgc cacaaaaaga aattgcaatg tcacgcaaat gagagaattg 6300
cccgtattgg attcggcggc ctttaatgtg gaatgcttca agaaatatgc gtgtaataat 6360
gaatattggg aaacgtttaa agaaaacccc atcaggctta ctgaagaaaa cgtggtaaat 6420
tacattacca aattaaaagg accaaaagct gctgctcttt ttgcgaagac acataatttg 6480
aatatgttgc aggacatacc aatggacagg tttgtaatgg acttaaagag agacgtgaaa 6540
gtgactccag gaacaaaaca tactgaagaa cggcccaagg tacaggtgat ccaggctgcc 6600
gatccgctag caacagcgta tctgtgcgga atccaccgag agctggttag gagattaaat 6660
gcggtcctgc ttccgaacat tcatacactg tttgatatgt cggctgaaga ctttgacgct 6720
attatagccg agcacttcca gcctggggat tgtgttctgg aaactgacat cgcgtcgttt 6780
gataaaagtg aggacgacgc catggctctg accgcgttaa tgattctgga agacttaggt 6840
gtggacgcag agctgttgac gctgattgag gcggctttcg gcgaaatttc atcaatacat 6900
ttgcccacta aaactaaatt taaattcgga gccatgatga aatctggaat gttcctcaca 6960
ctgtttgtga acacagtcat taacattgta atcgcaagca gagtgttgag agaacggcta 7020
accggatcac catgtgcagc attcattgga gatgacaata tcgtgaaagg agtcaaatcg 7080
gacaaattaa tggcagacag gtgcgccacc tggttgaata tggaagtcaa gattatagat 7140
gctgtggtgg gcgagaaagc gccttatttc tgtggagggt ttattttgtg tgactccgtg 7200
accggcacag cgtgccgtgt ggcagacccc ctaaaaaggc tgtttaagct tggcaaacct 7260
ctggcagcag acgatgaaca tgatgatgac aggagaaggg cattgcatga agagtcaaca 7320
cgctggaacc gagtgggtat tctttcagag ctgtgcaagg cagtagaatc aaggtatgaa 7380
accgtaggaa cttccatcat agttatggcc atgactactc tagctagcag tgttaaatca 7440
ttcagctacc tgagaggggc ccctataact ctctacggct aa 7482

<210> SEQ ID NO 6
<211> LENGTH: 7482
<212> TYPE: DNA
<213> ORGANISM: Artificial Sequence
<220> FEATURE:
<223> OTHER INFORMATION: Synthetic construct, C06 nsP coding sequence DNA

<400> SEQUENCE: 6
atggagaaag ttcacgttga catcgaggaa gacagcccat tcctcagagc tttgcagcgg 60
agcttcccgc agtttgaggt agaagccaag caggtcactg ataatgacca tgctaatgcc 120
agagcgtttt cgcatctggc ttcaaaactg atcgaaacgg aggtggaccc atccgacacg 180
atccttgaca ttggaagtgc gcccgcccgc agaatgtatt ctaagcacaa gtatcattgt 240
atctgtccga tgagatgtgc ggaagatccg gacagattgt ataagtatgc aactaagctg 300
aagaaaaact gtaaggaaat aactgataag gaattggaca agaaaatgaa ggagctcgcc 360
gccgtcatga gcgaccctga cctggaaact gagactatgt gcctccacga cgacgagtcg 420
tgtcgctacg aagggcaagt cgctgtttac caggatgtat acgcggttga cggaccgaca 480
agtctctatc accaagccaa taagggagtt agagtcgcct actggatagg ctttgacacc 540
acccctttta tgtttaagaa cttggctgga gcatatccat catactctac caactgggcc 600
gacgaaaccg tgttaacggc cagaaatatc ggcctgtgta gcagcgacgt gatggaaaga 660
tccagacggg gcatgagcat cctgcggaag aagtacctga agcctagcaa caacgtgctg 720
ttcagcgtgg gcagcaccat ctaccacgag aagagggacc tgctgcggag ctggcatctg 780

-continued

```
ccttccgtgt ttcacctgag aggcaagcag aactacacct gtagatgcga gacaatcgtg    840
tcctgcgacg gctacgtggt caagcggatc gccatttctc ctggcctgta cggcaagcct    900
tctggctatg ccgccaccat gcacagagaa ggctttctgt gttgcaaagt gaccgacaca    960
ctgaacggcg agcgggtgtc ctttcctgtg tgtacctatg tgcccgccac actgtgcgat   1020
cagatgacag gcattctggc caccgacgtg tcagccgacg atgcccagaa actgctcgtg   1080
ggcctgaacc agagaatcgt ggtcaacggc agaacccagc ggaacaccaa caccatgaag   1140
aactacctgc tgcctgtggt ggcccaggcc tttgccagat gggccaaaga gtacaaagag   1200
gatcaagagg acgagcggcc cctgggcctg agagatagac aactggtcat gggctgctgc   1260
tgggccttca gaaggcacaa gatcaccagc atctacaagc ggcccgacac acagaccatc   1320
atcaaagtga acagcgactt ccacagcttc gtgctgcctc ggatcggcag caacacactg   1380
gaaatcggcc tgcggacccg gatcagaaag atgctggaag aacacaaaga gccctctcca   1440
ctgatcaccg ccgaggatgt gcaagaggcc aaatgtgccg ccgacgaggc taaagaagtg   1500
cgcgaagccg aggaactgag agccgcactt cctcctctgg ccgccgatgt tgaagaaccc   1560
actctggaag ccgacgtcga cttgatgtta caagaggctg gggccggctc agtggagaca   1620
cctcgtggct tgataaaggt taccagctac gctggcgagg acaagatcgg ctcttacgct   1680
gtgctttctc cgcaggctgt actcaagagt gaaaaattat cttgcatcca ccctctcgct   1740
gaacaagtca tagtgataac acactctggc cgaaaagggc gttatgccgt ggaaccatac   1800
catggtaaag tagtggtgcc agagggacat gcaatacccg tccaggactt tcaagctctg   1860
agtgaaagtg ccaccattgt gtacaacgaa cgtgagttcg taaacaggta cctgcaccat   1920
attgccacac atggaggagc gctgaacact gatgaagaat attacaaaac tgtcaagccc   1980
agcgagcacg acggcgaata cctgtacgac atcgacagga aacagtgcgt caagaaagaa   2040
ctagtcactg ggctagggct cacaggcgag ctggtggatc ctcccttcca tgaattcgcc   2100
tacgagagtc tgagaacacg accagccgct ccttaccaag taccaaccat aggggtgtat   2160
ggcgtgccag gatcaggcaa gtctggcatc attaaaagcg cagtcaccaa aaaagatcta   2220
gtggtgagcg ccaagaaaga aaactgtgca gaaattataa gggacgtcaa gaaaatgaaa   2280
gggctggacg tcaatgccag aactgtggac tcagtgctct tgaatggatg caaacacccc   2340
gtagagaccc tgtatattga cgaagctttt gcttgtcatg caggtactct cagagcgctc   2400
atagccatta taagacctaa aaaggcagtg ctctgcgggg atcccaaaca gtgcggtttt   2460
tttaacatga tgtgcctgaa agtgcatttt aaccacgaga tttgcacaca agtcttccac   2520
aaaagcatct ctcgccgttg cactaaatct gtgacttcgg tcgtctcaac cttgttttac   2580
gacaaaaaaa tgagaacgac gaatccgaaa gagactaaga ttgtgattga cactaccggc   2640
agtaccaaac ctaagcagga cgatctcatt ctcacttgtt tcagagggtg ggtgaagcag   2700
ttgcaaatag attacaaagg caacgaaata atgacggcag ctgcctctca agggctgacc   2760
cgtaaaggtg tgtatgccgt tcggtacaag gtgaatgaaa atcctctgta cgcacccacc   2820
tcagaacatg tgaacgtcct actgacccgc acggaggacc gcatcgtgtg gaaaacacta   2880
gccggcgacc catggataaa aacactgact gccaagtacc ctgggaattt cactgccacg   2940
atagaggagt ggcaagcaga gcatgatgcc atcatgaggc acatcttgga gagaccggac   3000
cctaccgacg tcttccagaa taaggcaaac gtgtgttggg ccaaggcttt agtgccggtg   3060
ctgaagaccg ctggcataga catgaccact gaacaatgga acactgtgga ttattttgaa   3120
```

acggacaaag ctcactcagc agagatagta ttgaaccaac tatgcgtgag gttctttgga 3180
ctcgatctgg actccggtct attttctgca cccactgttc cgttatccat taggaataat 3240
cactgggata actccccgtc gcctaacatg tacgggctga ataaagaagt ggtccgtcag 3300
ctctctcgca ggtacccaca actgcctcgg gcagttgcca ctggaagagt ctatgacatg 3360
aacactggta cactgcgcaa ttatgatccg cgcataaacc tagtacctgt aaacagaaga 3420
ctgcctcatg ctttagtcct ccaccataat gaacacccac agagtgactt ttcttcattc 3480
gtcagcaaat tgaagggcag aactgtcctg gtggtcgggg aaaagttgtc cgtcccaggc 3540
aaaatggttg actggttgtc agaccggcct gaggctacct tcagagctcg gctggattta 3600
ggcatcccag gtgatgtgcc caaatatgac ataatatttg ttaatgtgag gaccccatat 3660
aaataccatc actatcagca gtgtgaagac catgccatta agcttagcat gttgaccaag 3720
aaagcttgtc tgcatctgaa tcccggcgga acctgtgtca gcataggtta tggttacgct 3780
gacagggcca gcgaaagcat cattggtgct atagcgcggc agttcaagtt ttcccgggta 3840
tgcaaaccga aatcctcact tgaagagacg gaagttctgt ttgtattcat tgggtacgat 3900
cgcaaggccc gtacgcacaa tccttacaag ctttcatcaa ccttgaccaa catttataca 3960
ggttccagac tccacgaagc cggatgtgca ccctcatatc atgtggtgcg aggggatatt 4020
gccacggcca ccgaaggagt gattataaat gctgctaaca gcaaaggaca acctggcgga 4080
ggggtgtgcg gagcgctgta taagaaattc ccggaaagct tcgatttaca gccgatcgaa 4140
gtaggaaaag cgcgactggt caaaggtgca gctaaacata tcattcatgc cgtaggacca 4200
aacttcaaca aagtttcgga ggttgaaggt gacaaacagt tggcagaggc ttatgagtcc 4260
atcgctaaga ttgtcaacga taacaattac aagtcagtag cgattccact gttgtccacc 4320
ggcatctttt ccgggaacaa agatcgacta acccaatcat tgaaccattt gctgacagct 4380
ttagacacca ctgatgcaga tgtagccata tactgcaggg acaagaaatg ggaaatgact 4440
ctcaaggaag cagtggctag gagagaagca gtggaggaga tatgcatatc cgacgactct 4500
tcagtgacag aacctgatgc agagctggtg agggtgcatc cgaagagttc tttggctgga 4560
aggaagggct acagcacaag cgatggcaaa actttctcat atttggaagg gaccaagttt 4620
caccaggcgg ccaaggatat agcagaaatt aatgccatgt ggcccgttgc aacggaggcc 4680
aatgagcagg tatgcatgta tatcctcgga gaaagcatga gcagtattag gtcgaaatgc 4740
cccgtcgaag agtcggaagc ctccacacca cctagcacgc tgccttgctt gtgcatccat 4800
gccatgactc cagaaagagt acagcgccta aaagcctcac gtccagaaca aattactgtg 4860
tgctcatcct ttccattgcc gaagtataga atcactggtg tgcagaagat ccaatgctcc 4920
cagcctatat tgttctcacc gaaagtgcct gcgtatattc atccaaggaa gtatctcgtg 4980
gaaacaccac cggtagacga gactccggag ccatcggcag agaaccaatc cacagagggg 5040
acacctgaac aaccaccact tataaccgag gatgagacca ggactagaac gcctgagccg 5100
atcatcatcg aagaggaaga agaggatagc ataagtttgc tgtcagatgg cccgacccac 5160
caggtgctgc aagtcgaggc agacattcac gggccgccct ctgtatctag ctcatcctgg 5220
tccattcctc atgcatccga ctttgatgtg gacagtttat ccatacttga caccctggag 5280
ggagctagcg tgaccagcgg ggcaacgtca gccgagacta actcttactt cgcaaagagt 5340
atggagtttc tggcgcgacc ggtgcctgcg cctcgaacag tattcaggaa ccctccacat 5400
cccgctccgc gcacaagaac accgtcactt gcacccagca gggcctgctc gagaaccagc 5460
ctagtttcca ccccgccagg cgtgaatagg gtgatcacta gagaggagct cgaggcgctt 5520

```
accccgtcac gcactcctag caggtcggtc tcgagaacca gcctggtctc caacccgcca   5580
ggcgtaaata gggtgattac aagagaggag tttgaggcgt tcgtagcaca acaacaatga   5640
cggtttgatg cgggtgcata catcttttcc tccgacaccg gtcaagggca tttacaacaa   5700
aaatcagtaa ggcaaacggt gctatccgaa gtggtgttgg agaggaccga attggagatt   5760
tcgtatgccc cgcgcctcga ccaagaaaaa gaagaattac tacgcaagaa attacagtta   5820
aatcccacac ctgctaacag aagcagatac cagtccagga aggtggagaa catgaaagcc   5880
ataacagcta gacgtattct gcaaggccta gggcattatt tgaaggcaga aggaaaagtg   5940
gagtgctacc gaaccctgca tcctgttcct ttgtattcat ctagtgtgaa ccgtgccttt   6000
tcaagcccca aggtcgcagt ggaagcctgt aacgccatgt tgaaagagaa ctttccgact   6060
gtggcttctt actgtattat tccagagtac gatgcctatt tggacatggt tgacggagct   6120
tcatgctgct tagacactgc cagtttttgc cctgcaaagc tgcgcagctt tccaaagaaa   6180
cactcctatt tggaacccac aatacgatcg gcagtgcctt cagcgatcca gaacacgctc   6240
cagaacgtcc tggcagctgc cacaaaaaga aattgcaatg tcacgcaaat gagagaattg   6300
cccgtattgg attcggcggc ctttaatgtg gaatgcttca agaaatatgc gtgtaataat   6360
gaatattggg aaacgtttaa agaaaacccc atcaggctta ctgaagaaaa cgtggtaaat   6420
tacattacca aattaaaagg accaaaagct gctgctcttt ttgcgaagac acataatttg   6480
aatatgttgc aggacatacc aatggacagg tttgtaatgg acttaaagag agacgtgaaa   6540
gtgactccag gaacaaaaca tactgaagaa cggcccaagg tacaggtgat ccaggctgcc   6600
gatccgctag caacagcgta tctgtgcgga atccaccgag agctggttag gagattaaat   6660
gcggtcctgc ttccgaacat tcatacactg tttgatatgt cggctgaaga ctttgacgct   6720
attatagccg agcacttcca gcctggggat tgtgttctgg aaactgacat cgcgtcgttt   6780
gataaaagtg aggacgacgc catggctctg accgcgttaa tgattctgga agacttaggt   6840
gtggacgcag agctgttgac gctgattgag gcggctttcg gcgaaatttc atcaatacat   6900
ttgcccacta aaactaaatt taaattcgga gccatgatga aatctggaat gttcctcaca   6960
ctgtttgtga acacagtcat taacattgta atcgcaagca gagtgttgag agaacggcta   7020
accggatcac catgtgcagc attcattgga gatgacaata tcgtgaaagg agtcaaatcg   7080
gacaaattaa tggcagacag gtgcgccacc tggttgaata tggaagtcaa gattatagat   7140
gctgtggtgg gcgagaaagc gccttatttc tgtggagggt ttattttgtg tgactccgtg   7200
accggcacag cgtgccgtgt ggcagacccc ctaaaaaggc tgtttaagct tggcaaacct   7260
ctggcagcag acgatgaaca tgatgatgac aggagaaggg cattgcatga agagtcaaca   7320
cgctggaacc gagtgggtat tctttcagag ctgtgcaagg cagtagaatc aaggtatgaa   7380
accgtaggaa cttccatcat agttatggcc atgactactc tagctagcag tgttaaatca   7440
ttcagctacc tgagaggggc ccctataact ctctacggct aa                      7482
```

```
<210> SEQ ID NO 7
<211> LENGTH: 7482
<212> TYPE: DNA
<213> ORGANISM: Artificial Sequence
<220> FEATURE:
<223> OTHER INFORMATION: Synthetic construct, C07 nsP coding sequence
      DNA

<400> SEQUENCE: 7

atggagaaag ttcacgttga catcgaggaa gacagcccat tcctcagagc tttgcagcgg     60
```

```
agcttcccgc agtttgaggt agaagccaag caggtcactg ataatgacca tgctaatgcc    120
agagcgtttt cgcatctggc ttcaaaactg atcgaaacgg aggtggaccc atccgacacg    180
atccttgaca ttggaagtgc gcccgcccgc agaatgtatt ctaagcacaa gtatcattgt    240
atctgtccga tgagatgtgc ggaagatccg gacagattgt ataagtatgc aactaagctg    300
aagaaaaact gtaaggaaat aactgataag gaattggaca agaaaatgaa ggagctcgcc    360
gccgtcatga gcgaccctga cctggaaact gagactatgt gcctccacga cgacgagtcg    420
tgtcgctacg aagggcaagt cgctgtttac caggatgtat acgcggttga cggaccgaca    480
agtctctatc accaagccaa taagggagtt agagtcgcct actggatagg ctttgacacc    540
accccttta tgtttaagaa cttggctgga gcatatccat catactctac caactgggcc    600
gacgaaaccg tgttaacggc tcgtaacata ggcctatgca gctctgacgt tatggagcgg    660
tcacgtagag ggatgtccat tcttagaaag aagtatttga aaccatccaa caatgttcta    720
ttctctgttg gctcgaccat ctaccacgag aagagggact tactgaggag ctggcacctg    780
ccgtctgtat ttcacttacg tggcaagcaa aattacacat gtcggtgtga gactatagtt    840
agttgcgacg ggtacgtcgt taaaagaata gctatcagtc caggcctgta tgggaagcct    900
tcaggctatg ctgctacgat gcaccgcgag ggattcttgt gctgcaaagt gacagacaca    960
ttgaacgggg agagggtctc ttttcccgtg tgcacgtatg tgccagctac attgtgtgac   1020
caaatgactg gcatactggc aacagatgtc agtgcggacg acgcgcaaaa actgctggtt   1080
gggctcaacc agcgtatagt cgtcaacggt cgcacccaga gaaacaccaa taccatgaaa   1140
aattaccttt tgcccgtagt ggcccaggca tttgctaggt gggcaaagga atataaggaa   1200
gatcaagaag atgaaaggcc actaggacta cgagatagac agttagtcat ggggtgttgt   1260
tgggctttta gaaggcacaa gataacatct atttataagc gcccggatac ccaaaccatc   1320
atcaaagtga acagcgattt ccactcattc gtgctgccca ggataggcag taacacattg   1380
gagatcgggc tgagaacaag aatcaggaaa atgttagagg agcacaagga gccgtcacct   1440
ctcattaccg ccgaggacgt acaagaagct aagtgcgcag ccgatgaggc taaggaggtg   1500
cgtgaagccg aggagttgcg cgcagctcta ccacctttgg cagctgatgt tgaggagccc   1560
actctggaag ccgatgtcga cttgatgtta caagaggctg gggccggctc agtggagaca   1620
cctcgtggct tgataaaggt taccagctac gctggcgagg acaagatcgg ctcttacgct   1680
gtgctttctc cgcaggctgt actcaagagt gaaaaattat cttgcatcca ccctctcgct   1740
gaacaagtca tagtgataac acactctggc cgaaaagggc gttatgccgt ggaaccatac   1800
catggtaaag tagtggtgcc agagggacat gcaatacccg tccaggactt tcaagctctg   1860
agtgaaagtg ccaccattgt gtacaacgaa cgtgagttcg taaacaggta cctgcaccat   1920
attgccacac atggaggagc gctgaacact gatgaagaat attacaaaac tgtcaagccc   1980
agcgagcacg acggcgaata cctgtacgac atcgacagga aacagtgcgt caagaaagaa   2040
ctagtcactg ggctagggct cacaggcgag ctggtggatc ctcccttcca tgaattcgcc   2100
tacgagagtc tgagaacacg accagccgct ccttaccaag taccaaccat aggggtgtat   2160
ggcgtgccag gatcaggcaa gtctggcatc attaaaagcg cagtcaccaa aaaagatcta   2220
gtggtgagcg ccaagaaaga aaactgtgca gaaattataa gggacgtcaa gaaaatgaaa   2280
gggctggacg tcaatgccag aactgtggac tcagtgctct tgaatggatg caaacacccc   2340
gtagagaccc tgtatattga cgaagctttt gcttgtcatg caggtactct cagagcgctc   2400
```

-continued

```
atagccatta taagacctaa aaaggcagtg ctctgcgggg atcccaaaca gtgcggtttt   2460
tttaacatga tgtgcctgaa agtgcatttt aaccacgaga tttgcacaca agtcttccac   2520
aagagcatca gcagacggtg caccaagagc gtgaccagcg tggtgtctac cctgttctac   2580
gacaagaaga tgcggacgac aaaccccaaa gagacaaaga tcgtcatcga caccaccggc   2640
agcaccaagc ctaagcagga cgatctgatc ctgacctgct tcagaggctg ggtcaagcag   2700
ctgcagatcg actacaaggg caacgagatc atgaccgccg ctgcctctca gggcctgaca   2760
agaaaaggcg tgtacgccgt gcggtacaaa gtgaacgaga accctctgta cgcccctacc   2820
agcgagcatg tgaatgtgct gctgacccgg accgaggacc ggatcgtttg gaaaacactg   2880
gccggcgatc cctggatcaa gaccctgaca gccaagtatc ccggcaactt caccgccacc   2940
atcgaggaat ggcaggccga gcacgatgcc atcatgcggc acatcctgga aagacccgat   3000
cctaccgacg tgttccagaa caaggccaac gtgtgctggg ccaaagctct ggtgcctgtg   3060
ctgaaaaccg ccggcatcga tatgaccacc gagcagtgga acaccgtgga ctacttcgag   3120
acagacaagg cccacagcgc cgagatcgtg ctgaatcagc tgtgcgtgcg gttcttcggc   3180
ctggatctgg atagcggcct gttctctgct cctaccgtgc ctctgagcat ccggaacaac   3240
cactgggaca acagcccctc tcctaatatg tacggcctga acaaagaagt cgtgcggcag   3300
ctgagcagaa gatacccaca gctgcctaga gccgtggcca caggcagagt gtacgacatg   3360
aataccggca cactgcggaa ctacgacccc agaatcaatc tggtgcccgt gaacagaagg   3420
ctgccccacg ctctggttct gcaccacaat gagcaccctc agagcgactt cagcagcttc   3480
gtgtccaagc tgaagggcag aaccgtgctg gttgtgggcg agaagctgtc tgtgcctggc   3540
aagatggtgg actggctgag cgatagaccc gaggccacct ttagagccag actggacctt   3600
ggaatccctg gcgacgtgcc caaatacgac atcatcttcg tgaacgtgcg gacgccctac   3660
aagtaccacc actaccagca gtgcgaggac cacgccatca agctgagcat gctgaccaag   3720
aaggcctgcc tgcacctgaa tcctggcggc acctgtgtgt ctatcggcta cggctatgcc   3780
gacagagcca gcgagtctat catcggcgcc attgccagac agttcaagtt cagcagagtg   3840
tgcaagccca agagcagcct ggaagagaca gaggtgctgt tcgtgttcat cggctatgac   3900
cggaaggccc gtacgcacaa tccttacaag ctttcatcaa ccttgaccaa catttataca   3960
ggttccagac tccacgaagc cggatgtgca ccctcatatc atgtggtgcg aggggatatt   4020
gccacggcca ccgaaggagt gattataaat gctgctaaca gcaaaggaca acctggcgga   4080
ggggtgtgcg gagcgctgta taagaaattc ccggaaagct tcgatttaca gccgatcgaa   4140
gtaggaaaag cgcgactggt caaaggtgca gctaaacata tcattcatgc cgtaggacca   4200
aacttcaaca aagtttcgga ggttgaaggt gacaaacagt tggcagaggc ttatgagtcc   4260
atcgctaaga ttgtcaacga taacaattac aagtcagtag cgattccact gttgtccacc   4320
ggcatctttt ccgggaacaa agatcgacta acccaatcat tgaaccattt gctgacagct   4380
ttagacacca ctgatgcaga tgtagccata tactgcaggg acaagaaatg ggaaatgact   4440
ctcaaggaag cagtggctag gagagaagca gtggaggaga tatgcatatc cgacgactct   4500
tcagtgacag aacctgatgc agagctggtg agggtgcatc cgaagagttc tttggctgga   4560
aggaagggct acagcacaag cgatggcaaa actttctcat atttggaagg gaccaagttt   4620
caccaggcgg ccaaggatat agcagaaatt aatgccatgt ggcccgttgc aacggaggcc   4680
aatgagcagg tatgcatgta tatcctcgga gaaagcatga gcagtattag gtcgaaatgc   4740
cccgtcgaag agtcggaagc ctccacacca cctagcacgc tgccttgctt gtgcatccat   4800
```

-continued

```
gccatgactc cagaaagagt acagcgccta aaagcctcac gtccagaaca aattactgtg   4860
tgctcatcct ttccattgcc gaagtataga atcactggtg tgcagaagat ccaatgctcc   4920
cagcctatat tgttctcacc gaaagtgcct gcgtatattc atccaaggaa gtatctcgtg   4980
gaaacaccac cggtagacga gactccggag ccatcggcag agaaccaatc cacagagggg   5040
acacctgaac aaccaccact tataaccgag gatgagacca ggactagaac gcctgagccg   5100
atcatcatcg aagaggaaga agaggatagc ataagtttgc tgtcagatgg cccgacccac   5160
caggtgctgc aagtcgaggc agacattcac gggccgccct ctgtatctag ctcatcctgg   5220
tccattcctc atgcatccga ctttgatgtg gacagtttat ccatacttga caccctggag   5280
ggagctagcg tgaccagcgg ggcaacgtca gccgagacta actcttactt cgcaaagagt   5340
atggagtttc tggcgcgacc ggtgcctgcg cctcgaacag tattcaggaa ccctccacat   5400
cccgctccgc gcacaagaac accgtcactt gcacccagca gggcctgctc gagaaccagc   5460
ctagtttcca ccccgccagg cgtgaatagg gtgatcacta gagaggagct cgaggcgctt   5520
accccgtcac gcactcctag caggtcggtc tcgagaacca gcctggtctc caacccgcca   5580
ggcgtaaata gggtgattac aagagaggag tttgaggcgt tcgtagcaca acaacaatga   5640
cggtttgatg cgggtgcata catcttttcc tccgacaccg gtcaagggca tttacaacaa   5700
aaatcagtaa ggcaaacggt gctatccgaa gtggtgttgg agaggaccga attggagatt   5760
tcgtatgccc cgcgcctcga ccaagaaaaa gaagaattac tacgcaagaa attacagtta   5820
aatcccacac ctgctaacag aagcagatac cagtccagga aggtggagaa catgaaagcc   5880
ataacagcta gacgtattct gcaaggccta gggcattatt tgaaggcaga aggaaaagtg   5940
gagtgctacc gaaccctgca tcctgttcct ttgtattcat ctagtgtgaa ccgtgccttt   6000
tcaagcccca aggtcgcagt ggaagcctgt aacgccatgt tgaaagagaa ctttccgact   6060
gtggcttctt actgtattat tccagagtac gatgcctatt tggacatggt tgacggagct   6120
tcatgctgct tagacactgc cagtttttgc cctgcaaagc tgcgcagctt tccaaagaaa   6180
cactcctatt tggaacccac aatacgatcg gcagtgcctt cagcgatcca gaacacgctc   6240
cagaacgtcc tggcagctgc cacaaaaaga aattgcaatg tcacgcaaat gagagaattg   6300
cccgtattgg attcggcggc ctttaatgtg gaatgcttca agaaatatgc gtgtaataat   6360
gaatattggg aaacgtttaa agaaaacccc atcaggctta ctgaagaaaa cgtggtaaat   6420
tacattacca aattaaaagg accaaaagct gctgctcttt ttgcgaagac acataatttg   6480
aatatgttgc aggacatacc aatggacagg tttgtaatgg acttaaagag agacgtgaaa   6540
gtgactccag gaacaaaaca tactgaagaa cggcccaagg tacaggtgat ccaggctgcc   6600
gatccgctag caacagcgta tctgtgcgga atccaccgag agctggttag gagattaaat   6660
gcggtcctgc ttccgaacat tcatacactg tttgatatgt cggctgaaga ctttgacgct   6720
attatagccg agcacttcca gcctggggat tgtgttctgg aaactgacat cgcgtcgttt   6780
gataaaagtg aggacgacgc catggctctg accgcgttaa tgattctgga agacttaggt   6840
gtggacgcag agctgttgac gctgattgag gcggctttcg gcgaaatttc atcaatacat   6900
ttgcccacta aaactaaatt taaattcgga gccatgatga aatctggaat gttcctcaca   6960
ctgtttgtga acacagtcat taacattgta atcgcaagca gagtgttgag agaacggcta   7020
accggatcac catgtgcagc attcattgga gatgacaata tcgtgaaagg agtcaaatcg   7080
gacaaattaa tggcagacag gtgcgccacc tggttgaata tggaagtcaa gattatagat   7140
```

gctgtggtgg gcgagaaagc gccttatttc tgtggagggt ttattttgtg tgactccgtg 7200
accggcacag cgtgccgtgt ggcagacccc ctaaaaaggc tgtttaagct tggcaaacct 7260
ctggcagcag acgatgaaca tgatgatgac aggagaaggg cattgcatga agagtcaaca 7320
cgctggaacc gagtgggtat tctttcagag ctgtgcaagg cagtagaatc aaggtatgaa 7380
accgtaggaa cttccatcat agttatggcc atgactactc tagctagcag tgttaaatca 7440
ttcagctacc tgagaggggc ccctataact ctctacggct aa 7482

<210> SEQ ID NO 8
<211> LENGTH: 7482
<212> TYPE: DNA
<213> ORGANISM: Artificial Sequence
<220> FEATURE:
<223> OTHER INFORMATION: Synthetic construct, C08 nsP coding sequence DNA

<400> SEQUENCE: 8
atggaaaagg tgcacgtgga catcgaagag gacagcccat tcctgagagc cctgcagaga 60
agcttccctc agttcgaggt ggaagccaaa caagtgaccg acaacgatca cgccaacgcg 120
agggccttct ctcacctcgc aagcaagctg atcgagacag aggtggaccc cagcgacacc 180
atcctggata ttggatctgc ccctgccaga agaatgtatt ctaagcacaa gtatcattgt 240
atctgtccga tgagatgtgc ggaagatccg gacagattgt ataagtatgc aactaagctg 300
aagaaaaact gtaaggaaat aactgataag gaattggaca agaaaatgaa ggagctcgcc 360
gccgtcatga gcgaccctga cctggaaact gagactatgt gcctccacga cgacgagtcg 420
tgtcgctacg aagggcaagt cgctgtttac caggatgtat acgcggttga cggaccgaca 480
agtctctatc accaagccaa taagggagtt agagtcgcct actggatagg ctttgacacc 540 accccttta tgtttaagaa cttggctgga gcatatccat catactctac caactgggcc 600
gacgaaaccg tgttaacggc tcgtaacata ggcctatgca gctctgacgt tatggagcgg 660
tcacgtagag ggatgtccat tcttagaaag aagtatttga aaccatccaa caatgttcta 720
ttctctgttg gctcgaccat ctaccacgag aagagggact tactgaggag ctggcacctg 780
ccgtctgtat ttcacttacg tggcaagcaa aattacacat gtcggtgtga gactatagtt 840
agttgcgacg ggtacgtcgt taaaagaata gctatcagtc caggcctgta tgggaagcct 900
tcaggctatg ctgctacgat gcaccgcgag ggattcttgt gctgcaaagt gacagacaca 960
ttgaacgggg agagggtctc ttttcccgtg tgcacgtatg tgccagctac attgtgtgac 1020
caaatgactg gcatactggc aacagatgtc agtgcggacg acgcgcaaaa actgctggtt 1080
gggctcaacc agcgtatagt cgtcaacggt cgcacccaga gaaacaccaa taccatgaaa 1140
aattaccttt tgcccgtagt ggcccaggca tttgctaggt gggcaaagga atataaggaa 1200
gatcaagaag atgaaaggcc actaggacta cgagatagac agttagtcat ggggtgttgt 1260
tgggctttta gaaggcacaa gataacatct atttataagc gcccggatac ccaaaccatc 1320
atcaaagtga acagcgattt ccactcattc gtgctgccca ggataggcag taacacattg 1380
gagatcgggc tgagaacaag aatcaggaaa atgttagagg agcacaagga gccgtcacct 1440
ctcattaccg ccgaggacgt acaagaagct aagtgcgcag ccgatgaggc taaggaggtg 1500
cgtgaagccg aggagttgcg cgcagctcta ccacctttgg cagctgatgt tgaggagccc 1560
actctggaag ccgatgtcga cttgatgtta caagaggctg gggccggctc agtggagaca 1620
cctcgtggct tgataaaggt taccagctac gctggcgagg acaagatcgg ctcttacgct 1680

-continued gtgctttctc cgcaggctgt actcaagagt gaaaaattat cttgcatcca ccctctcgct 1740
gaacaagtca tagtgataac acactctggc cgaaaagggc gttatgccgt ggaaccatac 1800
catggtaaag tagtggtgcc agagggacat gcaatacccg tccaggactt tcaagctctg 1860
agtgaaagtg ccaccattgt gtacaacgaa cgtgagttcg taaacaggta cctgcaccat 1920
attgccacac atggaggagc gctgaacact gatgaagaat attacaaaac tgtcaagccc 1980
agcgagcacg acggcgaata cctgtacgac atcgacagga aacagtgcgt caagaaagaa 2040
ctagtcactg ggctagggct cacaggcgag ctggtggatc ctcccttcca tgaattcgcc 2100
tacgagagtc tgagaacacg accagccgct ccttaccaag taccaaccat aggggtgtat 2160
ggcgtgccag gatcaggcaa gtctggcatc attaaaagcg cagtcaccaa aaaagatcta 2220
gtggtgagcg ccaagaaaga aaactgtgca gaaattataa gggacgtcaa gaaaatgaaa 2280
gggctggacg tcaatgccag aactgtggac tcagtgctct tgaatggatg caaacacccc 2340
gtagagaccc tgtatattga cgaagctttt gcttgtcatg caggtactct cagagcgctc 2400
atagccatta taagacctaa aaaggcagtg ctctgcgggg atcccaaaca gtgcggtttt 2460
tttaacatga tgtgcctgaa agtgcatttt aaccacgaga tttgcacaca agtcttccac 2520
aaaagcatct ctcgccgttg cactaaatct gtgacttcgg tcgtctcaac cttgttttac 2580
gacaaaaaaa tgagaacgac gaatccgaaa gagactaaga ttgtgattga cactaccggc 2640
agtaccaaac ctaagcagga cgatctcatt ctcacttgtt tcagagggtg ggtgaagcag 2700
ttgcaaatag attacaaagg caacgaaata atgacggcag ctgcctctca agggctgacc 2760
cgtaaaggtg tgtatgccgt tcggtacaag gtgaatgaaa atcctctgta cgcacccacc 2820
tcagaacatg tgaacgtcct actgacccgc acggaggacc gcatcgtgtg gaaaacacta 2880
gccggcgacc catggataaa aacactgact gccaagtacc ctgggaattt cactgccacg 2940
atagaggagt ggcaagcaga gcatgatgcc atcatgaggc acatcttgga gagaccggac 3000
cctaccgacg tcttccagaa taaggcaaac gtgtgttggg ccaaggcttt agtgccggtg 3060
ctgaagaccg ctggcataga catgaccact gaacaatgga acactgtgga ttattttgaa 3120
acggacaaag ctcactcagc agagatagta ttgaaccaac tatgcgtgag gttctttgga 3180
ctcgatctgg actccggtct attttctgca cccactgttc cgttatccat taggaataat 3240
cactgggata actccccgtc gcctaacatg tacgggctga ataaagaagt ggtccgtcag 3300
ctctctcgca ggtacccaca actgcctcgg gcagttgcca ctggaagagt ctatgacatg 3360
aacactggta cactgcgcaa ttatgatccg cgcataaacc tagtacctgt aaacagaaga 3420
ctgcctcatg ctttagtcct ccaccataat gaacacccac agagtgactt ttcttcattc 3480
gtcagcaaat tgaagggcag aactgtcctg gtggtcgggg aaaagttgtc cgtcccaggc 3540
aaaatggttg actggttgtc agaccggcct gaggctacct tcagagctcg gctggattta 3600
ggcatcccag gtgatgtgcc caaatatgac ataatatttg ttaatgtgag gaccccatat 3660
aaataccatc actatcagca gtgtgaagac catgccatta agcttagcat gttgaccaag 3720
aaagcttgtc tgcatctgaa tcccggcgga acctgtgtca gcataggtta tggttacgct 3780
gacagggcca gcgaaagcat cattggtgct atagcgcggc agttcaagtt ttcccgggta 3840
tgcaaaccga aatcctcact tgaagagacg gaagttctgt ttgtattcat tgggtacgat 3900
cgcaaggccc gtacgcacaa tccttacaag ctttcatcaa ccttgaccaa catttataca 3960
ggttccagac tccacgaagc cggatgtgca ccctcatatc atgtggtgcg aggggatatt 4020
gccacggcca ccgaaggagt gattataaat gctgctaaca gcaaaggaca acctggcgga 4080

```
ggggtgtgcg gagcgctgta taagaaattc ccggaaagct tcgatttaca gccgatcgaa   4140
gtaggaaaag cgcgactggt caaaggtgca gctaaacata tcattcatgc cgtaggacca   4200
aacttcaaca aagtttcgga ggttgaaggt gacaaacagt tggcagaggc ttatgagtcc   4260
atcgctaaga ttgtcaacga taacaattac aagtcagtag cgattccact gttgtccacc   4320
ggcatctttt ccgggaacaa agatcgacta acccaatcat tgaaccattt gctgacagct   4380
ttagacacca ctgatgcaga tgtagccata tactgcaggg acaagaaatg ggaaatgact   4440
ctcaaggaag cagtggctag gagagaagca gtggaggaga tatgcatatc cgacgactct   4500
tcagtgacag aacctgatgc agagctggtg agggtgcatc cgaagagttc tttggctgga   4560
aggaagggct acagcacaag cgatggcaaa actttctcat atttggaagg gaccaagttt   4620
caccaggcgg ccaaggatat agcagaaatt aatgccatgt ggcccgttgc aacggaggcc   4680
aatgagcagg tatgcatgta tatcctcgga gaaagcatga gcagtattag gtcgaaatgc   4740
cccgtcgaag agtcggaagc ctccacacca cctagcacgc tgccttgctt gtgcatccat   4800
gccatgactc cagaaagagt acagcgccta aaagcctcac gtccagaaca aattactgtg   4860
tgctcatcct ttccattgcc gaagtataga atcactggtg tgcagaagat ccaatgctcc   4920
cagcctatat tgttctcacc gaaagtgcct gcgtatattc atccaaggaa gtatctcgtg   4980
gaaacaccac cggtagacga gactccggag ccatcggcag agaaccaatc cacagagggg   5040
acacctgaac aaccaccact tataaccgag gatgagacca ggactagaac gcctgagccg   5100
atcatcatcg aagaggaaga agaggatagc ataagtttgc tgtcagatgg cccgacccac   5160
caggtgctgc aagtcgaggc agacattcac gggccgccct ctgtatctag ctcatcctgg   5220
tccattcctc atgcatccga ctttgatgtg gacagtttat ccatacttga caccctggag   5280
ggagctagcg tgaccagcgg ggcaacgtca gccgagacta actcttactt cgcaaagagt   5340
atggagtttc tggcgcgacc ggtgcctgcg cctcgaacag tattcaggaa ccctccacat   5400
cccgctccgc gcacaagaac accgtcactt gcacccagca gggcctgctc gagaaccagc   5460
ctagtttcca ccccgccagg cgtgaatagg gtgatcacta gagaggagct cgaggcgctt   5520
accccgtcac gcactcctag caggtcggtc tcgagaacca gcctggtctc caacccgcca   5580
ggcgtaaata gggtgattac aagagaggag tttgaggcgt tcgtagcaca acaacaatga   5640
cggtttgatg cgggtgcata catcttttcc tccgacaccg gtcaagggca tttacaacaa   5700
aaatcagtaa ggcaaacggt gctatccgaa gtggtgttgg agaggaccga attggagatt   5760
tcgtatgccc cgcgcctcga ccaagaaaaa gaagaattac tacgcaagaa attacagtta   5820
aatcccacac ctgctaacag aagcagatac cagtccagga aggtggagaa catgaaagcc   5880
ataacagcta gacgtattct gcaaggccta gggcattatt tgaaggcaga aggaaaagtg   5940
gagtgctacc gaaccctgca tcctgttcct ttgtattcat ctagtgtgaa ccgtgccttt   6000
tcaagcccca aggtcgcagt ggaagcctgt aacgccatgt tgaaagagaa ctttccgact   6060
gtggcttctt actgtattat tccagagtac gatgcctatt tggacatggt tgacggagct   6120
tcatgctgct tagacactgc cagtttttgc cctgcaaagc tgcgcagctt tccaaagaaa   6180
cactcctatt tggaacccac aatacgatcg gcagtgcctt cagcgatcca gaacacgctc   6240
cagaacgtcc tggcagctgc cacaaaaaga aattgcaatg tcacgcaaat gagagaattg   6300
cccgtattgg attcggcggc ctttaatgtg gaatgcttca agaaatatgc gtgtaataat   6360
gaatattggg aaacgtttaa agaaaacccc atcaggctta ctgaagaaaa cgtggtaaat   6420
```

tacattacca aattaaaagg accaaaagct gctgctcttt ttgcgaagac acataatttg 6480
aatatgttgc aggacatacc aatggacagg tttgtaatgg acttaaagag agacgtgaaa 6540
gtgactccag gaacaaaaca tactgaagaa cggcccaagg tacaggtgat ccaggctgcc 6600
gatccgctag caacagcgta tctgtgcgga atccaccgag agctggttag gagattaaat 6660
gcggtcctgc ttccgaacat tcatacactg tttgatatgt cggctgaaga ctttgacgct 6720
attatagccg agcacttcca gcctggggat tgtgttctgg aaactgacat cgcgtcgttt 6780
gataaaagtg aggacgacgc catggctctg accgcgttaa tgattctgga agacttaggt 6840
gtggacgcag agctgttgac gctgattgag gcggctttcg gcgaaatttc atcaatacat 6900
ttgcccacta aaactaaatt taaattcgga gccatgatga aatctggaat gttcctcaca 6960
ctgtttgtga acacagtcat taacattgta atcgcaagca gagtgttgag agaacggcta 7020
accggatcac catgtgcagc attcattgga gatgacaata tcgtgaaagg agtcaaatcg 7080
gacaaattaa tggcagacag gtgcgccacc tggttgaata tggaagtcaa gattatagat 7140
gctgtggtgg gcgagaaagc gccttatttc tgtggagggt ttattttgtg tgactccgtg 7200
accggcacag cgtgccgtgt ggcagacccc ctaaaaaggc tgtttaagct tggcaaacct 7260
ctggcagcag acgatgaaca tgatgatgac aggagaaggg cattgcatga agagtcaaca 7320
cgctggaacc gagtgggtat tctttcagag ctgtgcaagg cagtagaatc aaggtatgaa 7380
accgtaggaa cttccatcat agttatggcc atgactactc tagctagcag tgttaaatca 7440
ttcagctacc tgagaggggc ccctataact ctctacggct aa 7482

<210> SEQ ID NO 9
<211> LENGTH: 7482
<212> TYPE: DNA
<213> ORGANISM: Artificial Sequence
<220> FEATURE:
<223> OTHER INFORMATION: Synthetic construct, C09 nsP coding sequence DNA

<400> SEQUENCE: 9
atggagaaag ttcacgttga catcgaggaa gacagcccat tcctcagagc tttgcagcgg 60
agcttcccgc agtttgaggt agaagccaag caggtcactg ataatgacca tgctaatgcc 120
agagcgtttt cgcatctggc ttcaaaactg atcgaaacgg aggtggaccc atccgacacg 180
atccttgaca ttggaagtgc gcccgcccgc agaatgtatt ctaagcacaa gtatcattgt 240
atctgtccga tgagatgtgc ggaagatccg gacagattgt ataagtatgc aactaagctg 300
aagaaaaact gtaaggaaat aactgataag gaattggaca agaaaatgaa ggagctcgcc 360
gccgtcatga gcgaccctga cctggaaact gagactatgt gcctccacga cgacgagtcg 420
tgtcgctacg aagggcaagt cgctgtttac caggatgtat acgcggttga cggaccgaca 480
agtctctatc accaagccaa taagggagtt agagtcgcct actggatagg ctttgacacc 540
acccctttta tgtttaagaa cttggctgga gcatatccat catactctac caactgggcc 600
gacgaaaccg tgttaacggc cagaaatatc ggcctgtgta gcagcgacgt gatggaaaga 660
tccagacggg gcatgagcat cctgcggaag aagtacctga agcctagcaa caacgtgctg 720
ttcagcgtgg gcagcaccat ctaccacgag aagagggacc tgctgcggag ctggcatctg 780
ccttccgtgt ttcacctgag aggcaagcag aactacacct gtagatgcga gacaatcgtg 840
tcctgcgacg gctacgtggt caagcggatc gccatttctc ctggcctgta cggcaagcct 900
tctggctatg ccgccaccat gcacagagaa ggctttctgt gttgcaaagt gaccgacaca 960

-continued

```
ctgaacggcg agcgggtgtc ctttcctgtg tgtacctatg tgcccgccac actgtgcgat   1020
cagatgacag gcattctggc caccgacgtg tcagccgacg atgcccagaa actgctcgtg   1080
ggcctgaacc agagaatcgt ggtcaacggc agaacccagc ggaacaccaa caccatgaag   1140
aactacctgc tgcctgtggt ggcccaggcc tttgccagat gggccaaaga gtacaaagag   1200
gatcaagagg acgagcggcc cctgggcctg agagatagac aactggtcat gggctgctgc   1260
tgggccttca gaaggcacaa gatcaccagc atctacaagc ggcccgacac acagaccatc   1320
atcaaagtga acagcgactt ccacagcttc gtgctgcctc ggatcggcag caacacactg   1380
gaaatcggcc tgcggacccg gatcagaaag atgctggaag aacacaaaga gccctctcca   1440
ctgatcaccg ccgaggatgt gcaagaggcc aaatgtgccg ccgacgaggc taaagaagtg   1500
cgcgaagccg aggaactgag agccgcactt cctcctctgg ccgccgatgt tgaagaaccc   1560
actctggaag ccgacgtcga cttgatgtta caagaggctg gggccggctc agtggagaca   1620
cctcgtggct tgataaaggt taccagctac gctggcgagg acaagatcgg ctcttacgct   1680
gtgctttctc cgcaggctgt actcaagagt gaaaaattat cttgcatcca ccctctcgct   1740
gaacaagtca tagtgataac acactctggc cgaaaagggc gttatgccgt ggaaccatac   1800
catggtaaag tagtggtgcc agagggacat gcaatacccg tccaggactt tcaagctctg   1860
agtgaaagtg ccaccattgt gtacaacgaa cgtgagttcg taaacaggta cctgcaccat   1920
attgccacac atggaggagc gctgaacact gatgaagaat attacaaaac tgtcaagccc   1980
agcgagcacg acggcgaata cctgtacgac atcgacagga aacagtgcgt caagaaagaa   2040
ctagtcactg ggctagggct cacaggcgag ctggtggatc ctcccttcca tgaattcgcc   2100
tacgagagtc tgagaacacg accagccgct ccttaccaag taccaaccat aggggtgtat   2160
ggcgtgccag gatcaggcaa gtctggcatc attaaaagcg cagtcaccaa aaaagatcta   2220
gtggtgagcg ccaagaaaga aaactgtgca gaaattataa gggacgtcaa gaaaatgaaa   2280
gggctggacg tcaatgccag aactgtggac tcagtgctct tgaatggatg caaacacccc   2340
gtagagaccc tgtatattga cgaagctttt gcttgtcatg caggtactct cagagcgctc   2400
atagccatta taagacctaa aaaggcagtg ctctgcgggg atcccaaaca gtgcggtttt   2460
tttaacatga tgtgcctgaa agtgcatttt aaccacgaga tttgcacaca agtcttccac   2520
aagagcatca gcagacggtg caccaagagc gtgaccagcg tggtgtctac cctgttctac   2580
gacaagaaga tgcggacgac aaaccccaaa gagacaaaga tcgtcatcga caccaccggc   2640
agcaccaagc ctaagcagga cgatctgatc ctgacctgct tcagaggctg ggtcaagcag   2700
ctgcagatcg actacaaggg caacgagatc atgaccgccg ctgcctctca gggcctgaca   2760
agaaaaggcg tgtacgccgt gcggtacaaa gtgaacgaga accctctgta cgcccctacc   2820
agcgagcatg tgaatgtgct gctgacccgg accgaggacc ggatcgtttg gaaaacactg   2880
gccggcgatc cctggatcaa gaccctgaca gccaagtatc ccggcaactt caccgccacc   2940
atcgaggaat ggcaggccga gcacgatgcc atcatgcggc acatcctgga aagacccgat   3000
cctaccgacg tgttccagaa caaggccaac gtgtgctggg ccaaagctct ggtgcctgtg   3060
ctgaaaaccg ccggcatcga tatgaccacc gagcagtgga acaccgtgga ctacttcgag   3120
acagacaagg cccacagcgc cgagatcgtg ctgaatcagc tgtgcgtgcg gttcttcggc   3180
ctggatctgg atagcggcct gttctctgct cctaccgtgc ctctgagcat ccggaacaac   3240
cactgggaca acagcccctc tcctaatatg tacggcctga acaaagaagt cgtgcggcag   3300
ctgagcagaa gatacccaca gctgcctaga gccgtggcca caggcagagt gtacgacatg   3360
```

-continued aataccggca cactgcggaa ctacgacccc agaatcaatc tggtgcccgt gaacagaagg 3420
ctgccccacg ctctggttct gcaccacaat gagcaccctc agagcgactt cagcagcttc 3480
gtgtccaagc tgaagggcag aaccgtgctg gttgtgggcg agaagctgtc tgtgcctggc 3540
aagatggtgg actggctgag cgatagaccc gaggccacct ttagagccag actggacctt 3600
ggaatccctg gcgacgtgcc caaatacgac atcatcttcg tgaacgtgcg gacgccctac 3660
aagtaccacc actaccagca gtgcgaggac cacgccatca agctgagcat gctgaccaag 3720
aaggcctgcc tgcacctgaa tcctggcggc acctgtgtgt ctatcggcta cggctatgcc 3780
gacagagcca gcgagtctat catcggcgcc attgccagac agttcaagtt cagcagagtg 3840
tgcaagccca agagcagcct ggaagagaca gaggtgctgt tcgtgttcat cggctatgac 3900
cggaaggccc gtacgcacaa tccttacaag ctttcatcaa ccttgaccaa catttataca 3960
ggttccagac tccacgaagc cggatgtgca ccctcatatc atgtggtgcg aggggatatt 4020
gccacggcca ccgaaggagt gattataaat gctgctaaca gcaaaggaca acctggcgga 4080
ggggtgtgcg gagcgctgta taagaaattc ccggaaagct tcgatttaca gccgatcgaa 4140
gtaggaaaag cgcgactggt caaaggtgca gctaaacata tcattcatgc cgtaggacca 4200
aacttcaaca aagtttcgga ggttgaaggt gacaaacagt tggcagaggc ttatgagtcc 4260
atcgctaaga ttgtcaacga taacaattac aagtcagtag cgattccact gttgtccacc 4320
ggcatctttt ccgggaacaa agatcgacta acccaatcat tgaaccattt gctgacagct 4380
ttagacacca ctgatgcaga tgtagccata tactgcaggg acaagaaatg ggaaatgact 4440
ctcaaggaag cagtggctag gagagaagca gtggaggaga tatgcatatc cgacgactct 4500
tcagtgacag aacctgatgc agagctggtg agggtgcatc cgaagagttc tttggctgga 4560
aggaagggct acagcacaag cgatggcaaa actttctcat atttggaagg gaccaagttt 4620
caccaggcgg ccaaggatat agcagaaatt aatgccatgt ggcccgttgc aacggaggcc 4680
aatgagcagg tatgcatgta tatcctcgga gaaagcatga gcagtattag gtcgaaatgc 4740
cccgtcgaag agtcggaagc ctccacacca cctagcacgc tgccttgctt gtgcatccat 4800
gccatgactc cagaaagagt acagcgccta aaagcctcac gtccagaaca aattactgtg 4860
tgctcatcct ttccattgcc gaagtataga atcactggtg tgcagaagat ccaatgctcc 4920
cagcctatat tgttctcacc gaaagtgcct gcgtatattc atccaaggaa gtatctcgtg 4980
gaaacaccac cggtagacga gactccggag ccatcggcag agaaccaatc cacagagggg 5040
acacctgaac aaccaccact tataaccgag gatgagacca ggactagaac gcctgagccg 5100
atcatcatcg aagaggaaga agaggatagc ataagtttgc tgtcagatgg cccgacccac 5160
caggtgctgc aagtcgaggc agacattcac gggccgccct ctgtatctag ctcatcctgg 5220
tccattcctc atgcatccga ctttgatgtg gacagtttat ccatacttga caccctggag 5280
ggagctagcg tgaccagcgg ggcaacgtca gccgagacta actcttactt cgcaaagagt 5340
atggagtttc tggcgcgacc ggtgcctgcg cctcgaacag tattcaggaa ccctccacat 5400
cccgctccgc gcacaagaac accgtcactt gcacccagca gggcctgctc gagaaccagc 5460
ctagtttcca ccccgccagg cgtgaatagg gtgatcacta gagaggagct cgaggcgctt 5520
accccgtcac gcactcctag caggtcggtc tcgagaacca gcctggtctc caacccgcca 5580
ggcgtaaata gggtgattac aagagaggag tttgaggcgt tcgtagcaca acaacaatga 5640
cggtttgatg cgggtgcata catcttttcc tccgacaccg gtcaagggca tttacaacaa 5700

```
aaatcagtaa ggcaaacggt gctatccgaa gtggtgttgg agaggaccga attggagatt   5760

tcgtatgccc cgcgcctcga ccaagaaaaa gaagaattac tacgcaagaa attacagtta   5820

aatcccacac ctgctaacag aagcagatac cagtccagga aggtggagaa catgaaagcc   5880

ataacagcta gacgtattct gcaaggccta gggcattatt tgaaggcaga aggaaaagtg   5940

gagtgctacc gaaccctgca tcctgttcct ttgtattcat ctagtgtgaa ccgtgccttt   6000

tcaagcccca aggtcgcagt ggaagcctgt aacgccatgt tgaaagagaa ctttccgact   6060

gtggcttctt actgtattat tccagagtac gatgcctatt tggacatggt tgacggagct   6120

tcatgctgct tagacactgc cagtttttgc cctgcaaagc tgcgcagctt tccaaagaaa   6180

cactcctatt tggaacccac aatacgatcg gcagtgcctt cagcgatcca gaacacgctc   6240

cagaacgtcc tggcagctgc cacaaaaaga aattgcaatg tcacgcaaat gagagaattg   6300

cccgtattgg attcggcggc ctttaatgtg gaatgcttca agaaatatgc gtgtaataat   6360

gaatattggg aaacgtttaa agaaaacccc atcaggctta ctgaagaaaa cgtggtaaat   6420

tacattacca aattaaaagg accaaaagct gctgctcttt ttgcgaagac acataatttg   6480

aatatgttgc aggacatacc aatggacagg tttgtaatgg acttaaagag agacgtgaaa   6540

gtgactccag gaacaaaaca tactgaagaa cggcccaagg tacaggtgat ccaggctgcc   6600

gatccgctag caacagcgta tctgtgcgga atccaccgag agctggttag gagattaaat   6660

gcggtcctgc ttccgaacat tcatacactg tttgatatgt cggctgaaga ctttgacgct   6720

attatagccg agcacttcca gcctggggat tgtgttctgg aaactgacat cgcgtcgttt   6780

gataaaagtg aggacgacgc catggctctg accgcgttaa tgattctgga agacttaggt   6840

gtggacgcag agctgttgac gctgattgag gcggctttcg gcgaaatttc atcaatacat   6900

ttgcccacta aaactaaatt taaattcgga gccatgatga aatctggaat gttcctcaca   6960

ctgtttgtga acacagtcat taacattgta atcgcaagca gagtgttgag agaacggcta   7020

accggatcac catgtgcagc attcattgga gatgacaata tcgtgaaagg agtcaaatcg   7080

gacaaattaa tggcagacag gtgcgccacc tggttgaata tggaagtcaa gattatagat   7140

gctgtggtgg gcgagaaagc gccttatttc tgtggagggt ttattttgtg tgactccgtg   7200

accggcacag cgtgccgtgt ggcagacccc ctaaaaaggc tgtttaagct tggcaaacct   7260

ctggcagcag acgatgaaca tgatgatgac aggagaaggg cattgcatga agagtcaaca   7320

cgctggaacc gagtgggtat tctttcagag ctgtgcaagg cagtagaatc aaggtatgaa   7380

accgtaggaa cttccatcat agttatggcc atgactactc tagctagcag tgttaaatca   7440

ttcagctacc tgagaggggc ccctataact ctctacggct aa                      7482
```

<210> SEQ ID NO 10
<211> LENGTH: 7482
<212> TYPE: DNA
<213> ORGANISM: Artificial Sequence
<220> FEATURE:
<223> OTHER INFORMATION: Synthetic construct, C10 nsP coding sequence DNA

<400> SEQUENCE: 10

```
atggagaaag ttcacgttga catcgaggaa gacagcccat tcctcagagc tttgcagcgg     60

agcttcccgc agtttgaggt agaagccaag caggtcactg ataatgacca tgctaatgcc    120

agagcgtttt cgcatctggc ttcaaaactg atcgaaacgg aggtggaccc atccgacacg    180

atccttgaca ttggaagtgc gcccgcccgc agaatgtatt ctaagcacaa gtatcattgt    240
```

-continued

```
atctgtccga tgagatgtgc ggaagatccg gacagattgt ataagtatgc aactaagctg    300
aagaaaaact gtaaggaaat aactgataag gaattggaca agaaaatgaa ggagctcgcc    360
gccgtcatga gcgaccctga cctggaaact gagactatgt gcctccacga cgacgagtcg    420
tgtcgctacg aagggcaagt cgctgtttac caggatgtat acgcggttga cggaccgaca    480
agtctctatc accaagccaa taagggagtt agagtcgcct actggatagg ctttgacacc    540
accccttta tgtttaagaa cttggctgga gcatatccat catactctac caactgggcc    600
gacgaaaccg tgttaacggc tcgtaacata ggcctatgca gctctgacgt tatggagcgg    660
tcacgtagag ggatgtccat tcttagaaag aagtatttga aaccatccaa caatgttcta    720
ttctctgttg gctcgaccat ctaccacgag aagagggact tactgaggag ctggcacctg    780
ccgtctgtat ttcacttacg tggcaagcaa aattacacat gtcggtgtga gactatagtt    840
agttgcgacg ggtacgtcgt taaaagaata gctatcagtc caggcctgta tgggaagcct    900
tcaggctatg ctgctacgat gcaccgcgag ggattcttgt gctgcaaagt gacagacaca    960
ttgaacgggg agagggtctc ttttcccgtg tgcacgtatg tgccagctac attgtgtgac   1020
caaatgactg gcatactggc aacagatgtc agtgcggacg acgcgcaaaa actgctggtt   1080
gggctcaacc agcgtatagt cgtcaacggt cgcacccaga gaaacaccaa taccatgaaa   1140
aattaccttt tgcccgtagt ggcccaggca tttgctaggt gggcaaagga atataaggaa   1200
gatcaagaag atgaaaggcc actaggacta cgagatagac agttagtcat ggggtgttgt   1260
tgggctttta gaaggcacaa gataacatct atttataagc gcccggatac ccaaaccatc   1320
atcaaagtga acagcgattt ccactcattc gtgctgccca ggataggcag taacacattg   1380
gagatcgggc tgagaacaag aatcaggaaa atgttagagg agcacaagga gccgtcacct   1440
ctcattaccg ccgaggacgt acaagaagct aagtgcgcag ccgatgaggc taaggaggtg   1500
cgtgaagccg aggagttgcg cgcagctcta ccacctttgg cagctgatgt tgaggagccc   1560
actctggaag ccgatgtcga cttgatgtta caagaggctg gggccggctc agtggagaca   1620
cctcgtggct tgataaaggt taccagctac gctggcgagg acaagatcgg ctcttacgct   1680
gtgctttctc cgcaggctgt actcaagagt gaaaaattat cttgcatcca ccctctcgct   1740
gaacaagtca tagtgataac acactctggc cgaaaagggc gttatgccgt ggaaccatac   1800
catggtaaag tagtggtgcc agagggacat gcaatacccg tccaggactt tcaagctctg   1860
agtgaaagtg ccaccattgt gtacaacgaa cgtgagttcg taaacaggta cctgcaccat   1920
attgccacac atggaggagc gctgaacact gatgaagaat attacaaaac tgtcaagccc   1980
agcgagcacg acggcgaata cctgtacgac atcgacagga aacagtgcgt caagaaagaa   2040
ctagtcactg ggctagggct cacaggcgag ctggtggatc ctcccttcca tgaattcgcc   2100
tacgagagtc tgagaacacg accagccgct ccttaccaag taccaaccat aggggtgtat   2160
ggcgtgccag gatcaggcaa gtctggcatc attaaaagcg cagtcaccaa aaaagatcta   2220
gtggtgagcg ccaagaaaga aaactgtgca gaaattataa gggacgtcaa gaaaatgaaa   2280
gggctggacg tcaatgccag aactgtggac tcagtgctct tgaatggatg caaacacccc   2340
gtagagaccc tgtatattga cgaagctttt gcttgtcatg caggtactct cagagcgctc   2400
atagccatta taagacctaa aaaggcagtg ctctgcgggg atcccaaaca gtgcggtttt   2460
tttaacatga tgtgcctgaa agtgcatttt aaccacgaga tttgcacaca agtcttccac   2520
aaaagcatct ctcgccgttg cactaaatct gtgacttcgg tcgtctcaac cttgttttac   2580
gacaaaaaaa tgagaacgac gaatccgaaa gagactaaga ttgtgattga cactaccggc   2640
```

-continued

```
agtaccaaac ctaagcagga cgatctcatt ctcacttgtt tcagagggtg ggtgaagcag   2700
ttgcaaatag attacaaagg caacgaaata atgacggcag ctgcctctca agggctgacc   2760
cgtaaaggtg tgtatgccgt tcggtacaag gtgaatgaaa atcctctgta cgcacccacc   2820
tcagaacatg tgaacgtcct actgacccgc acggaggacc gcatcgtgtg gaaaacacta   2880
gccggcgacc catggataaa aacactgact gccaagtacc ctgggaattt cactgccacg   2940
atagaggagt ggcaagcaga gcatgatgcc atcatgaggc acatcttgga gagaccggac   3000
cctaccgacg tcttccagaa taaggcaaac gtgtgttggg ccaaggcttt agtgccggtg   3060
ctgaagaccg ctggcataga catgaccact gaacaatgga acactgtgga ttattttgaa   3120
acggacaaag ctcactcagc agagatagta ttgaaccaac tatgcgtgag gttctttgga   3180
ctcgatctgg actccggtct attttctgca cccactgttc cgttatccat taggaataat   3240
cactgggata actccccgtc gcctaacatg tacgggctga ataaagaagt ggtccgtcag   3300
ctctctcgca ggtacccaca actgcctcgg gcagttgcca ctggaagagt ctatgacatg   3360
aacactggta cactgcgcaa ttatgatccg cgcataaacc tagtacctgt aaacagaaga   3420
ctgcctcatg ctttagtcct ccaccataat gaacacccac agagtgactt ttcttcattc   3480
gtcagcaaat tgaagggcag aactgtcctg gtggtcgggg aaaagttgtc cgtcccaggc   3540
aaaatggttg actggttgtc agaccggcct gaggctacct tcagagctcg gctggattta   3600
ggcatcccag gtgatgtgcc caaatatgac ataatatttg ttaatgtgag gaccccctac   3660
aagtaccacc actaccagca gtgcgaggac cacgccatca agctgagcat gctgaccaag   3720
aaggcctgcc tgcatctgaa tcccggcgga acctgtgtca gcataggtta tggttacgct   3780
gacagggcca gcgaaagcat cattggtgct atagcgcggc agttcaagtt ttcccgggta   3840
tgcaaaccga aatcctcact tgaagagacg gaagttctgt ttgtattcat cggctacgac   3900
agaaaggccc gtacgcacaa tccttacaag ctttcatcaa ccttgaccaa catttataca   3960
ggttccagac tccacgaagc cggatgtgca ccctcatatc atgtggtgcg aggggatatt   4020
gccacggcca ccgaaggagt gattataaat gctgctaaca gcaaaggaca acctggcgga   4080
ggggtgtgcg gagcgctgta taagaaattc ccggaaagct tcgatttaca gccgatcgaa   4140
gtaggaaaag cgcgactggt caaaggtgca gctaaacata tcattcatgc cgtaggacca   4200
aacttcaaca aagtttcgga ggttgaaggt gacaaacagt tggcagaggc ttatgagtcc   4260
atcgctaaga ttgtcaacga taacaattac aagtcagtag cgattccact gttgtccacc   4320
ggcatctttt ccgggaacaa agatcgacta acccaatcat tgaaccattt gctgacagct   4380
ttagacacca ctgatgcaga tgtagccata tactgcaggg acaagaaatg ggaaatgact   4440
ctcaaggaag cagtggctag gagagaagca gtggaggaga tatgcatatc cgacgactct   4500
tcagtgacag aacctgatgc agagctggtg agggtgcatc cgaagagttc tttggctgga   4560
aggaagggct acagcacaag cgatggcaaa actttctcat atttggaagg gaccaagttt   4620
caccaggcgg ccaaggatat agcagaaatt aatgccatgt ggcccgttgc aacggaggcc   4680
aatgagcagg tatgcatgta tatcctcgga gaaagcatga gcagtattag gtcgaaatgc   4740
cccgtcgaag agtcggaagc ctccacacca cctagcacgc tgccttgctt gtgcatccat   4800
gccatgactc cagaaagagt acagcgccta aaagcctcac gtccagaaca aattactgtg   4860
tgctcatcct ttccattgcc gaagtataga atcactggtg tgcagaagat ccaatgctcc   4920
cagcctatat tgttctcacc gaaagtgcct gcgtatattc atccaaggaa gtatctcgtg   4980
```

gaaacaccac cggtagacga gactccggag ccatcggcag agaaccaatc cacagagggg 5040
acacctgaac aaccaccact tataaccgag gatgagacca ggactagaac gcctgagccg 5100
atcatcatcg aagaggaaga agaggatagc ataagtttgc tgtcagatgg cccgacccac 5160
caggtgctgc aagtcgaggc agacattcac gggccgccct ctgtatctag ctcatcctgg 5220
tccattcctc atgcatccga ctttgatgtg gacagtttat ccatacttga caccctggag 5280
ggagctagcg tgaccagcgg ggcaacgtca gccgagacta actcttactt cgcaaagagt 5340
atggagtttc tggcgcgacc ggtgcctgcg cctcgaacag tattcaggaa ccctccacat 5400
cccgctccgc gcacaagaac accgtcactt gcacccagca gggcctgctc gagaaccagc 5460
ctagtttcca ccccgccagg cgtgaatagg gtgatcacta gagaggagct cgaggcgctt 5520
accccgtcac gcactcctag caggtcggtc tcgagaacca gcctggtctc caacccgcca 5580
ggcgtaaata gggtgattac aagagaggag tttgaggcgt tcgtagcaca acaacaatga 5640
cggtttgatg cgggtgcata catcttttcc tccgacaccg gtcaagggca tttacaacaa 5700
aaatcagtaa ggcaaacggt gctatccgaa gtggtgttgg agaggaccga attggagatt 5760
tcgtatgccc cgcgcctcga ccaagaaaaa gaagaattac tacgcaagaa attacagtta 5820
aatcccacac ctgctaacag aagcagatac cagtccagga aggtggagaa catgaaagcc 5880
ataacagcta gacgtattct gcaaggccta gggcattatt tgaaggcaga aggaaaagtg 5940
gagtgctacc gaaccctgca tcctgttcct ttgtattcat ctagtgtgaa ccgtgccttt 6000
tcaagcccca aggtcgcagt ggaagcctgt aacgccatgt tgaaagagaa ctttccgact 6060
gtggcttctt actgtattat tccagagtac gatgcctatt tggacatggt tgacggagct 6120
tcatgctgct tagacactgc cagtttttgc cctgcaaagc tgcgcagctt tccaaagaaa 6180
cactcctatt tggaacccac aatacgatcg gcagtgcctt cagcgatcca gaacacgctc 6240
cagaacgtcc tggcagctgc cacaaaaaga aattgcaatg tcacgcaaat gagagaattg 6300
cccgtattgg attcggcggc ctttaatgtg gaatgcttca agaagtacgc ctgcaacaac 6360
gagtactggg agacattcaa agagaacccc atccggctga ccgaggaaaa cgtggtcaac 6420
tacatcacca agctgaaggg ccccaaagcc gccgctctgt ttgccaagac acacaacctg 6480
aacatgctgc aggacatccc catggacaga ttcgtgatgg acctgaagcg ggacgtgaaa 6540
gtgacccctg gcaccaagca caccgaggaa cggcctaagg tgcaagtgat ccaggccgct 6600
gatcctctgg ccacagccta tctgtgtggc atccacagag aactcgtgcg gagactgaat 6660
gccgtgctgc ttccgaacat tcatacactg tttgatatgt cggctgaaga ctttgacgct 6720
attatagccg agcacttcca gcctggggat tgtgttctgg aaactgacat cgcgtcgttt 6780
gataaaagtg aggacgacgc catggctctg accgcgctga tgattctgga agatctcgga 6840
gtggacgccg agctgctgac actgattgaa gccgcctttg gcgagatcag cagcatccat 6900
ctgcctacca agaccaagtt caagttcggc gccatgatga aatctggaat gttcctcaca 6960
ctgtttgtga acacagtcat taacattgta atcgcaagca gagtgttgag agaacggcta 7020
acaggcagcc cttgtgcagc attcattgga gatgacaata tcgtgaaagg agtcaaatcg 7080
gacaaattaa tggcagacag gtgcgccacc tggttgaata tggaagtcaa gattatagat 7140
gctgtggtgg gcgagaaagc gccttatttc tgtggagggt ttattttgtg tgactccgtg 7200
accggcacag cgtgccgtgt ggcagacccc ctaaaaaggc tgtttaagct tggcaaacct 7260
ctggcagcag acgatgaaca tgatgatgac aggagaaggg cattgcatga agagtcaaca 7320
cgctggaacc gagtgggtat tctttcagag ctgtgcaagg cagtagaatc aaggtatgaa 7380
accgtaggaa cttccatcat agttatggcc atgactactc tagctagcag tgttaaatca 7440
ttcagctacc tgagaggggc ccctataact ctctacggct aa 7482

<210> SEQ ID NO 11
<211> LENGTH: 7482
<212> TYPE: DNA
<213> ORGANISM: Artificial Sequence
<220> FEATURE:
<223> OTHER INFORMATION: Synthetic construct, C11 nsP coding sequence DNA

<400> SEQUENCE: 11
atggagaaag ttcacgttga catcgaggaa gacagcccat tcctcagagc tttgcagcgg 60
agcttcccgc agtttgaggt agaagccaag caggtcactg ataatgacca tgctaatgcc 120
agagcgtttt cgcatctggc ttcaaaactg atcgaaacgg aggtggaccc atccgacacg 180
atccttgaca ttggaagtgc gcccgcccgc agaatgtatt ctaagcacaa gtatcattgt 240
atctgtccga tgagatgtgc ggaagatccg gacagattgt ataagtatgc aactaagctg 300
aagaaaaact gtaaggaaat aactgataag gaattggaca agaaaatgaa ggagctcgcc 360
gccgtcatga gcgaccctga cctggaaact gagactatgt gcctccacga cgacgagtcg 420
tgtcgctacg aagggcaagt cgctgtttac caggatgtat atgccgtgga tggccctaca 480
agcctgtacc accaggccaa caagggcgtc agagtggcct actggatcgg cttcgacacc 540
acacctttca tgttcaagaa cctggctggc gcttacccca gctacagcac aaactgggcc 600
gacgaaaccg tgttaacggc cagaaatatc ggcctgtgta gcagcgacgt gatggaaaga 660
tccagacggg gcatgagcat cctgcggaag aagtacctga agcctagcaa caacgtgctg 720
ttcagcgtgg gcagcaccat ctaccacgag aagagggacc tgctgcggag ctggcatctg 780
ccttccgtgt ttcacctgag aggcaagcag aactacacct gtagatgcga gacaatcgtg 840
tcctgcgacg gctacgtggt caagcggatc gccatttctc ctggcctgta cggcaagcct 900
tctggctatg ccgccaccat gcacagagaa ggctttctgt gttgcaaagt gaccgacaca 960
ctgaacggcg agcgggtgtc ctttcctgtg tgtacctatg tgcccgccac actgtgcgat 1020
cagatgacag gcattctggc caccgacgtg tcagccgacg atgcccagaa actgctcgtg 1080
ggcctgaacc agagaatcgt ggtcaacggc agaacccagc ggaacaccaa caccatgaag 1140
aactacctgc tgcctgtggt ggcccaggcc tttgccagat gggccaaaga gtacaaagag 1200
gatcaagagg acgagcggcc cctgggcctg agagatagac aactggtcat gggctgctgc 1260
tgggccttca gaaggcacaa gatcaccagc atctacaagc ggcccgacac acagaccatc 1320
atcaaagtga acagcgactt ccacagcttc gtgctgcctc ggatcggcag caacacactg 1380
gaaatcggcc tgcggacccg gatcagaaag atgctggaag aacacaaaga gccctctcca 1440
ctgatcaccg ccgaggatgt gcaagaggcc aaatgtgccg ccgacgaggc taaagaagtg 1500
cgcgaagccg aggaactgag agccgcactt cctcctctgg ccgccgatgt tgaagaaccc 1560
actctggaag ccgacgtcga cttgatgtta caagaggctg gggccggctc agtggagaca 1620
cctcgtggct tgataaaggt taccagctac gctggcgagg acaagatcgg ctcttacgct 1680
gtgctttctc cgcaggctgt actcaagagc gagaagctga gctgcattca ccctctggcc 1740
gagcaagtga tcgtgatcac acacagcggc cggaagggca gatatgccgt ggaaccttat 1800
cacggcaagg tggtggtgcc tgagggacac gctattccag tgcaggactt tcaggccctg 1860
agcgagtctg ccaccatcgt gtacaacgag cgcgagttcg tgaacagata cctgcaccac 1920

-continued

```
attgccacac acggcggagc cctgaacacc gacgaagagt actacaagac cgtgaagccc   1980
agcgagcacg acggcgaata cctgtacgac atcgacagga aacagtgcgt caagaaagaa   2040
ctagtcactg ggctagggct cacaggcgag ctggtggatc ctcccttcca tgaattcgcc   2100
tacgagagtc tgagaacacg accagccgct ccttaccaag taccaaccat aggggtgtat   2160
ggcgtgccag gatcaggcaa gtctggcatc attaaaagcg cagtcaccaa aaaagatcta   2220
gtggtgagcg ccaagaaaga aaactgtgca gaaattataa gggacgtcaa gaaaatgaaa   2280
gggctggacg tcaatgccag aactgtggat agcgtgctgc tgaacggctg caagcacccc   2340
gtagagaccc tgtatattga cgaagctttt gcttgtcatg caggtactct cagagcgctc   2400
atagccatta taagacctaa aaaggcagtg ctctgcgggg atcctaagca gtgcggcttc   2460
ttcaacatga tgtgcctgaa agtgcatttt aaccacgaga tttgcacaca agtcttccac   2520
aagagcatca gcagacggtg caccaagagc gtgaccagcg tggtgtctac cctgttctac   2580
gacaagaaga tgcggacgac aaaccccaaa gagacaaaga tcgtcatcga caccaccggc   2640
agcaccaagc ctaagcagga cgatctgatc ctgacctgct tcagaggctg ggtcaagcag   2700
ctgcagatcg actacaaggg caacgagatc atgaccgccg ctgcctctca gggcctgaca   2760
agaaaaggcg tgtacgccgt gcggtacaaa gtgaacgaga accctctgta cgcccctacc   2820
agcgagcatg tgaatgtgct gctgacccgg accgaggacc ggatcgtttg gaaaacactg   2880
gccggcgatc cctggatcaa gaccctgaca gccaagtatc ccggcaactt caccgccacc   2940
atcgaggaat ggcaggccga gcacgatgcc atcatgcggc acatcctgga aagacccgat   3000
cctaccgacg tgttccagaa caaggccaac gtgtgctggg ccaaagctct ggtgcctgtg   3060
ctgaaaaccg ccggcatcga tatgaccacc gagcagtgga acaccgtgga ctacttcgag   3120
acagacaagg cccacagcgc cgagatcgtg ctgaatcagc tgtgcgtgcg gttcttcggc   3180
ctggatctgg atagcggcct gttctctgct cctaccgtgc ctctgagcat ccggaacaac   3240
cactgggaca acagcccctc tcctaatatg tacggcctga acaaagaagt cgtgcggcag   3300
ctgagcagaa gatacccaca gctgcctaga gccgtggcca caggcagagt gtacgacatg   3360
aataccggca cactgcggaa ctacgacccc agaatcaatc tggtgcccgt gaacagaagg   3420
ctgccccacg ctctggttct gcaccacaat gagcaccctc agagcgactt cagcagcttc   3480
gtgtccaagc tgaagggcag aaccgtgctg gttgtgggcg agaagctgtc tgtgcctggc   3540
aagatggtgg actggctgag cgatagaccc gaggccacct ttagagccag actggacctt   3600
ggaatccctg gcgacgtgcc caaatacgac atcatcttcg tgaacgtgcg gacgccctac   3660
aagtaccacc actaccagca gtgcgaggac cacgccatca agctgagcat gctgaccaag   3720
aaggcctgcc tgcacctgaa tcctggcggc acctgtgtgt ctatcggcta cggctatgcc   3780
gacagagcca gcgagtctat catcggcgcc attgccagac agttcaagtt cagcagagtg   3840
tgcaagccca agagcagcct ggaagagaca gaggtgctgt tcgtgttcat cggctatgac   3900
cggaaggccc gtacgcacaa cccctacaag ctgagcagca ccctgaccaa catctacacc   3960
ggcagcagac tgcacgaagc cggatgtgca ccctcatatc atgtggtgcg aggggatatt   4020
gccacagcca cagaaggagt gattataaat gctgctaaca gcaaaggaca acctggcgga   4080
ggggtgtgcg gagcgctgta taagaaattc ccggaaagct tcgatttaca gccgatcgaa   4140
gtaggaaaag cgcgactggt caaaggtgca gctaaacata tcattcatgc cgtaggacca   4200
aacttcaaca aagtttcgga ggttgaaggt gacaaacagt tggcagaggc ttatgagtcc   4260
```

-continued

```
atcgctaaga ttgtcaacga taacaattac aagtcagtag cgattccact gttgtccacc   4320
ggcatctttt ccgggaacaa agatcgacta acccaatcat tgaaccattt gctgacagct   4380
ttagacacca ctgatgcaga tgtagccata tactgcaggg acaagaaatg ggaaatgact   4440
ctcaaggaag cagtggctag gagagaagca gtggaggaga tatgcatatc cgacgactct   4500
tcagtgacag aacctgatgc agagctggtg agggtgcatc cgaagagttc tttggctgga   4560
aggaagggct acagcacaag cgatggcaaa actttctcat atttggaagg gaccaagttt   4620
caccaggcgg ccaaggatat agcagaaatt aatgccatgt ggcccgttgc aacggaggcc   4680
aatgagcagg tatgcatgta tatcctcgga gaaagcatga gcagtattag gtcgaaatgc   4740
cccgtcgaag agtcggaagc ctccacacca cctagcacgc tgccttgctt gtgcatccat   4800
gccatgactc cagaaagagt acagcgccta aaagcctcac gtccagaaca aattactgtg   4860
tgctcatcct ttccattgcc gaagtataga atcactggtg tgcagaagat ccaatgctcc   4920
cagcctatat tgttctcacc gaaagtgcct gcgtatattc atccaaggaa gtatctcgtg   4980
gaaacaccac cggtagacga gactccggag ccatcggcag agaaccaatc cacagagggg   5040
acacctgaac aaccaccact tataaccgag gatgagacca ggactagaac gcctgagccg   5100
atcatcatcg aagaggaaga agaggatagc ataagtttgc tgtcagatgg cccgacccac   5160
caggtgctgc aagtcgaggc agacattcac gggccgccct ctgtatctag ctcatcctgg   5220
tccattcctc atgcatccga ctttgatgtg gacagtttat ccatacttga caccctggag   5280
ggagctagcg tgaccagcgg ggcaacgtca gccgagacta actcttactt cgcaaagagt   5340
atggagtttc tggcgcgacc ggtgcctgcg cctcgaacag tattcaggaa ccctccacat   5400
cccgctccgc gcacaagaac accgtcactt gcacccagca gggcctgctc gagaaccagc   5460
ctagtttcca ccccgccagg cgtgaatagg gtgatcacta gagaggagct cgaggcgctt   5520
accccgtcac gcactcctag caggtcggtc tcgagaacca gcctggtctc caacccgcca   5580
ggcgtaaata gggtgattac aagagaggag tttgaggcgt tcgtagcaca acaacaatga   5640
cggtttgatg cgggtgcata catcttttcc tccgacaccg gtcaagggca tttacaacaa   5700
aaatcagtaa ggcaaacggt gctatccgaa gtggtgttgg agaggaccga attggagatt   5760
tcgtatgccc cgcgcctcga ccaagaaaaa gaagaattac tacgcaagaa attacagtta   5820
aatcccacac ctgctaacag aagcagatac cagtccagga aggtggagaa catgaaagcc   5880
ataacagcta gacgtattct gcaaggccta gggcattatt tgaaggcaga aggaaaagtg   5940
gagtgctacc gaaccctgca tcctgttcct ttgtattcat ctagtgtgaa ccgtgccttt   6000
tcaagcccca aggtcgcagt ggaagcctgt aacgccatgt tgaaagagaa ctttccgact   6060
gtggcttctt actgtattat tccagagtac gatgcctatt tggacatggt tgacggagct   6120
tcatgctgct tagacactgc cagtttttgc cctgcaaagc tgcgcagctt tccaaagaaa   6180
cactcctatt tggaacccac aatacgatcg gcagtgcctt cagcgatcca gaacacgctc   6240
cagaacgtcc tggcagctgc cacaaaaaga aattgcaatg tcacgcaaat gagagaattg   6300
cccgtattgg attcggcggc ctttaatgtg gaatgcttca agaagtacgc ctgcaacaac   6360
gagtactggg agacattcaa agagaacccc atccggctga ccgaggaaaa cgtggtcaac   6420
tacatcacca agctgaaggg ccccaaagcc gccgctctgt ttgccaagac acacaacctg   6480
aacatgctgc aggacatccc catggacaga ttcgtgatgg acctgaagcg ggacgtgaaa   6540
gtgacccctg gcaccaagca caccgaggaa cggcctaagg tgcaagtgat ccaggccgct   6600
gatcctctgg ccacagccta tctgtgtggc atccacagag aactcgtgcg gagactgaat   6660
```

```
gccgtgctgc ttccgaacat tcatacactg tttgatatgt cggctgaaga ctttgacgct   6720

attatagccg agcacttcca gcctggggat tgtgttctgg aaactgacat cgcgtcgttt   6780

gataaaagtg aggacgacgc catggctctg accgcgctga tgattctgga agatctcgga   6840

gtggacgccg agctgctgac actgattgaa gccgcctttg gcgagatcag cagcatccat   6900

ctgcctacca agaccaagtt caagttcggc gccatgatga aatctggaat gttcctcaca   6960

ctgtttgtga acacagtcat taacattgta atcgcaagca gagtgttgag agaacggcta   7020

acaggcagcc cttgtgcagc attcattgga gatgacaata tcgtgaaagg agtcaaatcg   7080

gacaaattaa tggcagacag gtgcgccacc tggttgaata tggaagtcaa gattatagat   7140

gctgtggtgg gcgagaaagc gccttatttc tgtggagggt ttattttgtg tgactccgtg   7200

accggcacag cgtgccgtgt ggcagacccc ctaaaaaggc tgtttaagct tggcaaacct   7260

ctggcagcag acgatgaaca tgatgatgac aggagaaggg cattgcatga agagtcaaca   7320

cgctggaacc gagtgggtat tctttcagag ctgtgcaagg cagtagaatc aaggtatgaa   7380

accgtaggaa cttccatcat agttatggcc atgactactc tagctagcag tgttaaatca   7440

ttcagctacc tgagaggggc ccctataact ctctacggct aa                      7482
```

```
<210> SEQ ID NO 12
<211> LENGTH: 2513
<212> TYPE: PRT
<213> ORGANISM: Artificial Sequence
<220> FEATURE:
<223> OTHER INFORMATION: Synthetic construct, C16 nsP-2A protein amino
      acid
<220> FEATURE:
<221> NAME/KEY: misc_feature
<222> LOCATION: (1880)..(1880)
<223> OTHER INFORMATION: Xaa can be any naturally occurring amino acid

<400> SEQUENCE: 12

Met Glu Lys Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser
        35                  40                  45

Lys Leu Ile Glu Thr Glu Val Asp Pro Ser Asp Thr Ile Leu Asp Ile
    50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
    130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190
```

```
Pro Ser Tyr Ser Thr Asn Trp Ala Asp Glu Thr Val Leu Thr Ala Arg
        195                 200                 205

Asn Ile Gly Leu Cys Ser Ser Asp Val Met Glu Arg Ser Arg Arg Gly
    210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
    450                 455                 460

Arg Thr Arg Ile Arg Lys Met Leu Glu Glu His Lys Glu Pro Ser Pro
465                 470                 475                 480

Leu Ile Thr Ala Glu Asp Val Gln Glu Ala Lys Cys Ala Ala Asp Glu
                485                 490                 495

Ala Lys Glu Val Arg Glu Ala Glu Glu Leu Arg Ala Ala Leu Pro Pro
            500                 505                 510

Leu Ala Ala Asp Val Glu Glu Pro Thr Leu Glu Ala Asp Val Asp Leu
        515                 520                 525

Met Leu Gln Glu Ala Gly Ala Gly Ser Val Glu Thr Pro Arg Gly Leu
    530                 535                 540

Ile Lys Val Thr Ser Tyr Ala Gly Glu Asp Lys Ile Gly Ser Tyr Ala
545                 550                 555                 560

Val Leu Ser Pro Gln Ala Val Leu Lys Ser Glu Lys Leu Ser Cys Ile
                565                 570                 575

His Pro Leu Ala Glu Gln Val Ile Val Ile Thr His Ser Gly Arg Lys
            580                 585                 590

Gly Arg Tyr Ala Val Glu Pro Tyr His Gly Lys Val Val Val Pro Glu
        595                 600                 605
```

-continued

```
Gly His Ala Ile Pro Val Gln Asp Phe Gln Ala Leu Ser Glu Ser Ala
    610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
                645                 650                 655

Thr Val Lys Pro Ser Glu His Asp Gly Glu Tyr Leu Tyr Asp Ile Asp
            660                 665                 670

Arg Lys Gln Cys Val Lys Lys Glu Leu Val Thr Gly Leu Gly Leu Thr
        675                 680                 685

Gly Glu Leu Val Asp Pro Pro Phe His Glu Phe Ala Tyr Glu Ser Leu
    690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
                725                 730                 735

Lys Lys Asp Leu Val Val Ser Ala Lys Lys Glu Asn Cys Ala Glu Ile
            740                 745                 750

Ile Arg Asp Val Lys Lys Met Lys Gly Leu Asp Val Asn Ala Arg Thr
        755                 760                 765

Val Asp Ser Val Leu Leu Asn Gly Cys Lys His Pro Val Glu Thr Leu
    770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
                805                 810                 815

Gln Cys Gly Phe Phe Asn Met Met Cys Leu Lys Val His Phe Asn His
            820                 825                 830

Glu Ile Cys Thr Gln Val Phe His Lys Ser Ile Ser Arg Arg Cys Thr
        835                 840                 845

Lys Ser Val Thr Ser Val Val Ser Thr Leu Phe Tyr Asp Lys Lys Met
    850                 855                 860

Arg Thr Thr Asn Pro Lys Glu Thr Lys Ile Val Ile Asp Thr Thr Gly
865                 870                 875                 880

Ser Thr Lys Pro Lys Gln Asp Asp Leu Ile Leu Thr Cys Phe Arg Gly
                885                 890                 895

Trp Val Lys Gln Leu Gln Ile Asp Tyr Lys Gly Asn Glu Ile Met Thr
            900                 905                 910

Ala Ala Ala Ser Gln Gly Leu Thr Arg Lys Gly Val Tyr Ala Val Arg
        915                 920                 925

Tyr Lys Val Asn Glu Asn Pro Leu Tyr Ala Pro Thr Ser Glu His Val
    930                 935                 940

Asn Val Leu Leu Thr Arg Thr Glu Asp Arg Ile Val Trp Lys Thr Leu
945                 950                 955                 960

Ala Gly Asp Pro Trp Ile Lys Thr Leu Thr Ala Lys Tyr Pro Gly Asn
                965                 970                 975

Phe Thr Ala Thr Ile Glu Glu Trp Gln Ala Glu His Asp Ala Ile Met
            980                 985                 990

Arg His Ile Leu Glu Arg Pro Asp  Pro Thr Asp Val Phe  Gln Asn Lys
        995                 1000                1005

Ala Asn  Val Cys Trp Ala Lys  Ala Leu Val Pro Val  Leu Lys Thr
    1010                1015                1020

Ala Gly  Ile Asp Met Thr Thr  Glu Gln Trp Asn Thr  Val Asp Tyr
```

-continued

```
    1025                1030                1035

Phe Glu  Thr Asp Lys Ala His  Ser Ala Glu Ile Val  Leu Asn Gln
    1040                1045                1050

Leu Cys  Val Arg Phe Phe Gly  Leu Asp Leu Asp Ser  Gly Leu Phe
    1055                1060                1065

Ser Ala  Pro Thr Val Pro Leu  Ser Ile Arg Asn Asn  His Trp Asp
    1070                1075                1080

Asn Ser  Pro Ser Pro Asn Met  Tyr Gly Leu Asn Lys  Glu Val Val
    1085                1090                1095

Arg Gln  Leu Ser Arg Arg Tyr  Pro Gln Leu Pro Arg  Ala Val Ala
    1100                1105                1110

Thr Gly  Arg Val Tyr Asp Met  Asn Thr Gly Thr Leu  Arg Asn Tyr
    1115                1120                1125

Asp Pro  Arg Ile Asn Leu Val  Pro Val Asn Arg Arg  Leu Pro His
    1130                1135                1140

Ala Leu  Val Leu His His Asn  Glu His Pro Gln Ser  Asp Phe Ser
    1145                1150                1155

Ser Phe  Val Ser Lys Leu Lys  Gly Arg Thr Val Leu  Val Val Gly
    1160                1165                1170

Glu Lys  Leu Ser Val Pro Gly  Lys Met Val Asp Trp  Leu Ser Asp
    1175                1180                1185

Arg Pro  Glu Ala Thr Phe Arg  Ala Arg Leu Asp Leu  Gly Ile Pro
    1190                1195                1200

Gly Asp  Val Pro Lys Tyr Asp  Ile Ile Phe Val Asn  Val Arg Thr
    1205                1210                1215

Pro Tyr  Lys Tyr His His Tyr  Gln Gln Cys Glu Asp  His Ala Ile
    1220                1225                1230

Lys Leu  Ser Met Leu Thr Lys  Lys Ala Cys Leu His  Leu Asn Pro
    1235                1240                1245

Gly Gly  Thr Cys Val Ser Ile  Gly Tyr Gly Tyr Ala  Asp Arg Ala
    1250                1255                1260

Ser Glu  Ser Ile Ile Gly Ala  Ile Ala Arg Gln Phe  Lys Phe Ser
    1265                1270                1275

Arg Val  Cys Lys Pro Lys Ser  Ser Leu Glu Glu Thr  Glu Val Leu
    1280                1285                1290

Phe Val  Phe Ile Gly Tyr Asp  Arg Lys Ala Arg Thr  His Asn Pro
    1295                1300                1305

Tyr Lys  Leu Ser Ser Thr Leu  Thr Asn Ile Tyr Thr  Gly Ser Arg
    1310                1315                1320

Leu His  Glu Ala Gly Cys Ala  Pro Ser Tyr His Val  Val Arg Gly
    1325                1330                1335

Asp Ile  Ala Thr Ala Thr Glu  Gly Val Ile Ile Asn  Ala Ala Asn
    1340                1345                1350

Ser Lys  Gly Gln Pro Gly Gly  Gly Val Cys Gly Ala  Leu Tyr Lys
    1355                1360                1365

Lys Phe  Pro Glu Ser Phe Asp  Leu Gln Pro Ile Glu  Val Gly Lys
    1370                1375                1380

Ala Arg  Leu Val Lys Gly Ala  Ala Lys His Ile Ile  His Ala Val
    1385                1390                1395

Gly Pro  Asn Phe Asn Lys Val  Ser Glu Val Glu Gly  Asp Lys Gln
    1400                1405                1410

Leu Ala  Glu Ala Tyr Glu Ser  Ile Ala Lys Ile Val  Asn Asp Asn
    1415                1420                1425
```

-continued

```
Asn Tyr  Lys Ser Val Ala Ile  Pro Leu Leu Ser Thr  Gly Ile Phe
    1430                 1435                 1440

Ser Gly  Asn Lys Asp Arg Leu  Thr Gln Ser Leu Asn  His Leu Leu
    1445                 1450                 1455

Thr Ala  Leu Asp Thr Thr Asp  Ala Asp Val Ala Ile  Tyr Cys Arg
    1460                 1465                 1470

Asp Lys  Lys Trp Glu Met Thr  Leu Lys Glu Ala Val  Ala Arg Arg
    1475                 1480                 1485

Glu Ala  Val Glu Glu Ile Cys  Ile Ser Asp Asp Ser  Ser Val Thr
    1490                 1495                 1500

Glu Pro  Asp Ala Glu Leu Val  Arg Val His Pro Lys  Ser Ser Leu
    1505                 1510                 1515

Ala Gly  Arg Lys Gly Tyr Ser  Thr Ser Asp Gly Lys  Thr Phe Ser
    1520                 1525                 1530

Tyr Leu  Glu Gly Thr Lys Phe  His Gln Ala Ala Lys  Asp Ile Ala
    1535                 1540                 1545

Glu Ile  Asn Ala Met Trp Pro  Val Ala Thr Glu Ala  Asn Glu Gln
    1550                 1555                 1560

Val Cys  Met Tyr Ile Leu Gly  Glu Ser Met Ser Ser  Ile Arg Ser
    1565                 1570                 1575

Lys Cys  Pro Val Glu Glu Ser  Glu Ala Ser Thr Pro  Pro Ser Thr
    1580                 1585                 1590

Leu Pro  Cys Leu Cys Ile His  Ala Met Thr Pro Glu  Arg Val Gln
    1595                 1600                 1605

Arg Leu  Lys Ala Ser Arg Pro  Glu Gln Ile Thr Val  Cys Ser Ser
    1610                 1615                 1620

Phe Pro  Leu Pro Lys Tyr Arg  Ile Thr Gly Val Gln  Lys Ile Gln
    1625                 1630                 1635

Cys Ser  Gln Pro Ile Leu Phe  Ser Pro Lys Val Pro  Ala Tyr Ile
    1640                 1645                 1650

His Pro  Arg Lys Tyr Leu Val  Glu Thr Pro Pro Val  Asp Glu Thr
    1655                 1660                 1665

Pro Glu  Pro Ser Ala Glu Asn  Gln Ser Thr Glu Gly  Thr Pro Glu
    1670                 1675                 1680

Gln Pro  Pro Leu Ile Thr Glu  Asp Glu Thr Arg Thr  Arg Thr Pro
    1685                 1690                 1695

Glu Pro  Ile Ile Ile Glu Glu  Glu Glu Glu Asp Ser  Ile Ser Leu
    1700                 1705                 1710

Leu Ser  Asp Gly Pro Thr His  Gln Val Leu Gln Val  Glu Ala Asp
    1715                 1720                 1725

Ile His  Gly Pro Pro Ser Val  Ser Ser Ser Ser Trp  Ser Ile Pro
    1730                 1735                 1740

His Ala  Ser Asp Phe Asp Val  Asp Ser Leu Ser Ile  Leu Asp Thr
    1745                 1750                 1755

Leu Glu  Gly Ala Ser Val Thr  Ser Gly Ala Thr Ser  Ala Glu Thr
    1760                 1765                 1770

Asn Ser  Tyr Phe Ala Lys Ser  Met Glu Phe Leu Ala  Arg Pro Val
    1775                 1780                 1785

Pro Ala  Pro Arg Thr Val Phe  Arg Asn Pro Pro His  Pro Ala Pro
    1790                 1795                 1800

Arg Thr  Arg Thr Pro Ser Leu  Ala Pro Ser Arg Ala  Cys Ser Arg
    1805                 1810                 1815
```

```
Thr Ser  Leu Val Ser Thr Pro  Pro Gly Val Asn Arg  Val Ile Thr
    1820                 1825                 1830

Arg Glu  Glu Leu Glu Ala Leu  Thr Pro Ser Arg Thr  Pro Ser Arg
    1835                 1840                 1845

Ser Val  Ser Arg Thr Ser Leu  Val Ser Asn Pro Pro  Gly Val Asn
    1850                 1855                 1860

Arg Val  Ile Thr Arg Glu Glu  Phe Glu Ala Phe Val  Ala Gln Gln
    1865                 1870                 1875

Gln Xaa  Arg Phe Asp Ala Gly  Ala Tyr Ile Phe Ser  Ser Asp Thr
    1880                 1885                 1890

Gly Gln  Gly His Leu Gln Gln  Lys Ser Val Arg Gln  Thr Val Leu
    1895                 1900                 1905

Ser Glu  Val Val Leu Glu Arg  Thr Glu Leu Glu Ile  Ser Tyr Ala
    1910                 1915                 1920

Pro Arg  Leu Asp Gln Glu Lys  Glu Glu Leu Leu Arg  Lys Lys Leu
    1925                 1930                 1935

Gln Leu  Asn Pro Thr Pro Ala  Asn Arg Ser Arg Tyr  Gln Ser Arg
    1940                 1945                 1950

Lys Val  Glu Asn Met Lys Ala  Ile Thr Ala Arg Arg  Ile Leu Gln
    1955                 1960                 1965

Gly Leu  Gly His Tyr Leu Lys  Ala Glu Gly Lys Val  Glu Cys Tyr
    1970                 1975                 1980

Arg Thr  Leu His Pro Val Pro  Leu Tyr Ser Ser Ser  Val Asn Arg
    1985                 1990                 1995

Ala Phe  Ser Ser Pro Lys Val  Ala Val Glu Ala Cys  Asn Ala Met
    2000                 2005                 2010

Leu Lys  Glu Asn Phe Pro Thr  Val Ala Ser Tyr Cys  Ile Ile Pro
    2015                 2020                 2025

Glu Tyr  Asp Ala Tyr Leu Asp  Met Val Asp Gly Ala  Ser Cys Cys
    2030                 2035                 2040

Leu Asp  Thr Ala Ser Phe Cys  Pro Ala Lys Leu Arg  Ser Phe Pro
    2045                 2050                 2055

Lys Lys  His Ser Tyr Leu Glu  Pro Thr Ile Arg Ser  Ala Val Pro
    2060                 2065                 2070

Ser Ala  Ile Gln Asn Thr Leu  Gln Asn Val Leu Ala  Ala Ala Thr
    2075                 2080                 2085

Lys Arg  Asn Cys Asn Val Thr  Gln Met Arg Glu Leu  Pro Val Leu
    2090                 2095                 2100

Asp Ser  Ala Ala Phe Asn Val  Glu Cys Phe Lys Lys  Tyr Ala Cys
    2105                 2110                 2115

Asn Asn  Glu Tyr Trp Glu Thr  Phe Lys Glu Asn Pro  Ile Arg Leu
    2120                 2125                 2130

Thr Glu  Glu Asn Val Val Asn  Tyr Ile Thr Lys Leu  Lys Gly Pro
    2135                 2140                 2145

Lys Ala  Ala Ala Leu Phe Ala  Lys Thr His Asn Leu  Asn Met Leu
    2150                 2155                 2160

Gln Asp  Ile Pro Met Asp Arg  Phe Val Met Asp Leu  Lys Arg Asp
    2165                 2170                 2175

Val Lys  Val Thr Pro Gly Thr  Lys His Thr Glu Glu  Arg Pro Lys
    2180                 2185                 2190

Val Gln  Val Ile Gln Ala Ala  Asp Pro Leu Ala Thr  Ala Tyr Leu
    2195                 2200                 2205

Cys Gly  Ile His Arg Glu Leu  Val Arg Arg Leu Asn  Ala Val Leu
```

2210 2215 2220

Leu Pro Asn Ile His Thr Leu Phe Asp Met Ser Ala Glu Asp Phe
2225 2230 2235

Asp Ala Ile Ile Ala Glu His Phe Gln Pro Gly Asp Cys Val Leu
2240 2245 2250

Glu Thr Asp Ile Ala Ser Phe Asp Lys Ser Glu Asp Asp Ala Met
2255 2260 2265

Ala Leu Thr Ala Leu Met Ile Leu Glu Asp Leu Gly Val Asp Ala
2270 2275 2280

Glu Leu Leu Thr Leu Ile Glu Ala Ala Phe Gly Glu Ile Ser Ser
2285 2290 2295

Ile His Leu Pro Thr Lys Thr Lys Phe Lys Phe Gly Ala Met Met
2300 2305 2310

Lys Ser Gly Met Phe Leu Thr Leu Phe Val Asn Thr Val Ile Asn
2315 2320 2325

Ile Val Ile Ala Ser Arg Val Leu Arg Glu Arg Leu Thr Gly Ser
2330 2335 2340

Pro Cys Ala Ala Phe Ile Gly Asp Asp Asn Ile Val Lys Gly Val
2345 2350 2355

Lys Ser Asp Lys Leu Met Ala Asp Arg Cys Ala Thr Trp Leu Asn
2360 2365 2370

Met Glu Val Lys Ile Ile Asp Ala Val Val Gly Glu Lys Ala Pro
2375 2380 2385

Tyr Phe Cys Gly Gly Phe Ile Leu Cys Asp Ser Val Thr Gly Thr
2390 2395 2400

Ala Cys Arg Val Ala Asp Pro Leu Lys Arg Leu Phe Lys Leu Gly
2405 2410 2415

Lys Pro Leu Ala Ala Asp Asp Glu His Asp Asp Asp Arg Arg Arg
2420 2425 2430

Ala Leu His Glu Glu Ser Thr Arg Trp Asn Arg Val Gly Ile Leu
2435 2440 2445

Ser Glu Leu Cys Lys Ala Val Glu Ser Arg Tyr Glu Thr Val Gly
2450 2455 2460

Thr Ser Ile Ile Val Met Ala Met Thr Thr Leu Ala Ser Ser Val
2465 2470 2475

Lys Ser Phe Ser Tyr Leu Arg Gly Ala Pro Ile Thr Leu Tyr Gly
2480 2485 2490

Ser Gly Glu Gly Arg Gly Ser Leu Leu Thr Cys Gly Asp Val Glu
2495 2500 2505

Glu Asn Pro Gly Pro
2510

<210> SEQ ID NO 13
<211> LENGTH: 7539
<212> TYPE: DNA
<213> ORGANISM: Artificial Sequence
<220> FEATURE:
<223> OTHER INFORMATION: Synthetic construct, C16 nsP-2A coding sequence DNA

<400> SEQUENCE: 13
atggagaaag ttcacgttga catcgaggaa gacagcccat tcctcagagc tttgcagcgg 60
agcttcccgc agtttgaggt agaagccaag caggtcactg ataatgacca tgctaatgcc 120
agagcgtttt cgcatctggc ttcaaaactg atcgaaacgg aggtggaccc atccgacacg 180

-continued

```
atccttgaca ttggaagtgc gcccgcccgc agaatgtatt ctaagcacaa gtatcattgt    240
atctgtccga tgagatgtgc ggaagatccg gacagattgt ataagtatgc aactaagctg    300
aagaaaaact gtaaggaaat aactgataag gaattggaca agaaaatgaa ggagctcgcc    360
gccgtcatga gcgaccctga cctggaaact gagactatgt gcctccacga cgacgagtcg    420
tgtcgctacg aagggcaagt cgctgtttac caggatgtat acgcggttga cggaccgaca    480
agtctctatc accaagccaa taagggagtt agagtcgcct actggatagg ctttgacacc    540
accccttta tgtttaagaa cttggctgga gcatatccat catactctac caactgggcc    600
gacgaaaccg tgttaacggc tcgtaacata ggcctatgca gctctgacgt tatggagcgg    660
tcacgtagag ggatgtccat tcttagaaag aagtatttga aaccatccaa caatgttcta    720
ttctctgttg gctcgaccat ctaccacgag aagagggact tactgaggag ctggcacctg    780
ccgtctgtat ttcacttacg tggcaagcaa aattacacat gtcggtgtga gactatagtt    840
agttgcgacg ggtacgtcgt taaaagaata gctatcagtc caggcctgta tgggaagcct    900
tcaggctatg ctgctacgat gcaccgcgag ggattcttgt gctgcaaagt gacagacaca    960
ttgaacgggg agagggtctc ttttcccgtg tgcacgtatg tgccagctac attgtgtgac   1020
caaatgactg gcatactggc aacagatgtc agtgcggacg acgcgcaaaa actgctggtt   1080
gggctcaacc agcgtatagt cgtcaacggt cgcacccaga gaaacaccaa taccatgaaa   1140
aattaccttt tgcccgtagt ggcccaggca tttgctaggt gggcaaagga atataaggaa   1200
gatcaagaag atgaaaggcc actaggacta cgagatagac agttagtcat ggggtgttgt   1260
tgggctttta gaaggcacaa gataacatct atttataagc gcccggatac ccaaaccatc   1320
atcaaagtga acagcgattt ccactcattc gtgctgccca ggataggcag taacacattg   1380
gagatcgggc tgagaacaag aatcaggaaa atgttagagg agcacaagga gccgtcacct   1440
ctcattaccg ccgaggacgt acaagaagct aagtgcgcag ccgatgaggc taaggaggtg   1500
cgtgaagccg aggagttgcg cgcagctcta ccacctttgg cagctgatgt tgaggagccc   1560
actctggaag ccgatgtcga cttgatgtta caagaggctg gggccggctc agtggagaca   1620
cctcgtggct tgataaaggt taccagctac gctggcgagg acaagatcgg ctcttacgct   1680
gtgctttctc cgcaggctgt actcaagagt gaaaaattat cttgcatcca ccctctcgct   1740
gaacaagtca tagtgataac acactctggc cgaaaagggc gttatgccgt ggaaccatac   1800
catggtaaag tagtggtgcc agagggacat gcaatacccg tccaggactt tcaagctctg   1860
agtgaaagtg ccaccattgt gtacaacgaa cgtgagttcg taaacaggta cctgcaccat   1920
attgccacac atggaggagc gctgaacact gatgaagaat attacaaaac tgtcaagccc   1980
agcgagcacg acggcgaata cctgtacgac atcgacagga aacagtgcgt caagaaagaa   2040
ctagtcactg ggctagggct cacaggcgag ctggtggatc ctcccttcca tgaattcgcc   2100
tacgagagtc tgagaacacg accagccgct ccttaccaag taccaaccat aggggtgtat   2160
ggcgtgccag gatcaggcaa gtctggcatc attaaaagcg cagtcaccaa aaaagatcta   2220
gtggtgagcg ccaagaaaga aaactgtgca gaaattataa gggacgtcaa gaaaatgaaa   2280
gggctggacg tcaatgccag aactgtggac tcagtgctct tgaatggatg caaacacccc   2340
gtagagaccc tgtatattga cgaagctttt gcttgtcatg caggtactct cagagcgctc   2400
atagccatta taagacctaa aaaggcagtg ctctgcgggg atcccaaaca gtgcggtttt   2460
tttaacatga tgtgcctgaa agtgcatttt aaccacgaga tttgcacaca agtcttccac   2520
aaaagcatct ctcgccgttg cactaaatct gtgacttcgg tcgtctcaac cttgttttac   2580
```

gacaaaaaaa tgagaacgac gaatccgaaa gagactaaga ttgtgattga cactaccggc 2640
agtaccaaac ctaagcagga cgatctcatt ctcacttgtt tcagagggtg ggtgaagcag 2700
ttgcaaatag attacaaagg caacgaaata atgacggcag ctgcctctca agggctgacc 2760
cgtaaaggtg tgtatgccgt tcggtacaag gtgaatgaaa atcctctgta cgcacccacc 2820
tcagaacatg tgaacgtcct actgacccgc acggaggacc gcatcgtgtg gaaaacacta 2880
gccggcgacc catggataaa aacactgact gccaagtacc ctgggaattt cactgccacg 2940
atagaggagt ggcaagcaga gcatgatgcc atcatgaggc acatcttgga gagaccggac 3000
cctaccgacg tcttccagaa taaggcaaac gtgtgttggg ccaaggcttt agtgccggtg 3060
ctgaagaccg ctggcataga catgaccact gaacaatgga acactgtgga ttattttgaa 3120
acggacaaag ctcactcagc agagatagta ttgaaccaac tatgcgtgag gttctttgga 3180
ctcgatctgg actccggtct attttctgca cccactgttc cgttatccat taggaataat 3240
cactgggata actccccgtc gcctaacatg tacgggctga ataaagaagt ggtccgtcag 3300
ctctctcgca ggtacccaca actgcctcgg gcagttgcca ctggaagagt ctatgacatg 3360
aacactggta cactgcgcaa ttatgatccg cgcataaacc tagtacctgt aaacagaaga 3420
ctgcctcatg ctttagtcct ccaccataat gaacacccac agagtgactt ttcttcattc 3480
gtcagcaaat tgaagggcag aactgtcctg gtggtcgggg aaaagttgtc cgtcccaggc 3540
aaaatggttg actggttgtc agaccggcct gaggctacct tcagagctcg gctggattta 3600
ggcatcccag gtgatgtgcc caaatatgac ataatatttg ttaatgtgag gaccccatat 3660
aaataccatc actatcagca gtgtgaagac catgccatta agcttagcat gttgaccaag 3720
aaagcttgtc tgcatctgaa tcccggcgga acctgtgtca gcataggtta tggttacgct 3780
gacagggcca gcgaaagcat cattggtgct atagcgcggc agttcaagtt ttcccgggta 3840
tgcaaaccga aatcctcact tgaagagacg gaagttctgt ttgtattcat tgggtacgat 3900
cgcaaggccc gtacgcacaa tccttacaag ctttcatcaa ccttgaccaa catttataca 3960
ggttccagac tccacgaagc cggatgtgca ccctcatatc atgtggtgcg aggggatatt 4020
gccacggcca ccgaaggagt gattataaat gctgctaaca gcaaaggaca acctggcgga 4080
ggggtgtgcg gagcgctgta taagaaattc ccggaaagct tcgatttaca gccgatcgaa 4140
gtaggaaaag cgcgactggt caaaggtgca gctaaacata tcattcatgc cgtaggacca 4200
aacttcaaca aagtttcgga ggttgaaggt gacaaacagt tggcagaggc ttatgagtcc 4260
atcgctaaga ttgtcaacga taacaattac aagtcagtag cgattccact gttgtccacc 4320
ggcatctttt ccgggaacaa agatcgacta acccaatcat tgaaccattt gctgacagct 4380
ttagacacca ctgatgcaga tgtagccata tactgcaggg acaagaaatg ggaaatgact 4440
ctcaaggaag cagtggctag gagagaagca gtggaggaga tatgcatatc cgacgactct 4500
tcagtgacag aacctgatgc agagctggtg agggtgcatc cgaagagttc tttggctgga 4560
aggaagggct acagcacaag cgatggcaaa actttctcat atttggaagg gaccaagttt 4620
caccaggcgg ccaaggatat agcagaaatt aatgccatgt ggcccgttgc aacggaggcc 4680
aatgagcagg tatgcatgta tatcctcgga gaaagcatga gcagtattag gtcgaaatgc 4740
cccgtcgaag agtcggaagc ctccacacca cctagcacgc tgccttgctt gtgcatccat 4800
gccatgactc cagaaagagt acagcgccta aaagcctcac gtccagaaca aattactgtg 4860
tgctcatcct ttccattgcc gaagtataga atcactggtg tgcagaagat ccaatgctcc 4920

-continued

```
cagcctatat tgttctcacc gaaagtgcct gcgtatattc atccaaggaa gtatctcgtg   4980
gaaacaccac cggtagacga gactccggag ccatcggcag agaaccaatc cacagagggg   5040
acacctgaac aaccaccact tataaccgag gatgagacca ggactagaac gcctgagccg   5100
atcatcatcg aagaggaaga agaggatagc ataagtttgc tgtcagatgg cccgacccac   5160
caggtgctgc aagtcgaggc agacattcac gggccgccct ctgtatctag ctcatcctgg   5220
tccattcctc atgcatccga ctttgatgtg gacagtttat ccatacttga caccctggag   5280
ggagctagcg tgaccagcgg ggcaacgtca gccgagacta actcttactt cgcaaagagt   5340
atggagtttc tggcgcgacc ggtgcctgcg cctcgaacag tattcaggaa ccctccacat   5400
cccgctccgc gcacaagaac accgtcactt gcacccagca gggcctgctc gagaaccagc   5460
ctagtttcca ccccgccagg cgtgaatagg gtgatcacta gagaggagct cgaggcgctt   5520
accccgtcac gcactcctag caggtcggtc tcgagaacca gcctggtctc caacccgcca   5580
ggcgtaaata gggtgattac aagagaggag tttgaggcgt tcgtagcaca acaacaatga   5640
cggtttgatg cgggtgcata catcttttcc tccgacaccg gtcaagggca tttacaacaa   5700
aaatcagtaa ggcaaacggt gctatccgaa gtggtgttgg agaggaccga attggagatt   5760
tcgtatgccc cgcgcctcga ccaagaaaaa gaagaattac tacgcaagaa attacagtta   5820
aatcccacac ctgctaacag aagcagatac cagtccagga aggtggagaa catgaaagcc   5880
ataacagcta gacgtattct gcaaggccta gggcattatt tgaaggcaga aggaaaagtg   5940
gagtgctacc gaaccctgca tcctgttcct ttgtattcat ctagtgtgaa ccgtgccttt   6000
tcaagcccca aggtcgcagt ggaagcctgt aacgccatgt tgaaagagaa ctttccgact   6060
gtggcttctt actgtattat tccagagtac gatgcctatt tggacatggt tgacggagct   6120
tcatgctgct tagacactgc cagtttttgc cctgcaaagc tgcgcagctt tccaaagaaa   6180
cactcctatt tggaacccac aatacgatcg gcagtgcctt cagcgatcca gaacacgctc   6240
cagaacgtcc tggcagctgc cacaaaaaga aattgcaatg tcacgcaaat gagagaattg   6300
cccgtattgg attcggcggc ctttaatgtg gaatgcttca agaaatatgc gtgtaataat   6360
gaatattggg aaacgtttaa agaaaacccc atcaggctta ctgaagaaaa cgtggtaaat   6420
tacattacca aattaaaagg accaaaagct gctgctcttt ttgcgaagac acataatttg   6480
aatatgttgc aggacatacc aatggacagg tttgtaatgg acttaaagag agacgtgaaa   6540
gtgactccag gaacaaaaca tactgaagaa cggcccaagg tacaggtgat ccaggctgcc   6600
gatccgctag caacagcgta tctgtgcgga atccaccgag agctggttag gagattaaat   6660
gcggtcctgc ttccgaacat tcatacactg tttgatatgt cggctgaaga ctttgacgct   6720
attatagccg agcacttcca gcctggggat tgtgttctgg aaactgacat cgcgtcgttt   6780
gataaaagtg aggacgacgc catggctctg accgcgttaa tgattctgga agacttaggt   6840
gtggacgcag agctgttgac gctgattgag gcggctttcg gcgaaatttc atcaatacat   6900
ttgcccacta aaactaaatt taagttcggc gccatgatga agtccggcat gtttctgacc   6960
ctgttcgtga acaccgtgat caacatcgtg atcgccagcc gggtgctgag agagagactg   7020
acaggatctc cttgcgccgc cttcatcggc gacgacaata tcgtgaaggg cgtgaagtcc   7080
gacaagctga tggccgatag atgcgccacc tggctgaaca tggaagtgaa gatcatcgac   7140
gccgtcgtgg gcgagaaggc cccttatttt tgcggcggct tcatcctgtg cgacagcgtg   7200
acaggcacag cctgcagagt tgccgatcct ctgaagcggc tgttcaagct gggaaaacct   7260
ctggccgccg acgacgagca cgacgacgat agacgtagag ccctgcacga ggaatccacc   7320
```

```
agatggaaca gagtgggcat cctgagcgag ctgtgcaagg ccgtggaaag cagatacgag   7380

acagtgggca ccagcatcat tgtgatggca atgaccacac tggccagcag cgtgaaaagc   7440

ttcagctacc taaggggcgc ccctatcaca ctgtacggct ctggcgaagg cagaggcagc   7500

cttctgacat gtggcgacgt ggaagagaac cccggacct                          7539


<210> SEQ ID NO 14
<211> LENGTH: 128
<212> TYPE: DNA
<213> ORGANISM: Artificial Sequence
<220> FEATURE:
<223> OTHER INFORMATION: Synthetic construct, C16 subgenomic promoter
      DNA

<400> SEQUENCE: 14

acttccatca tagttatggc catgactact ctagctagca gtgttaaatc attcagctac     60

ctgagagggg cccctataac tctctacggc taacctgaat ggactacgac atagtctagt    120

ccgccaag                                                             128


<210> SEQ ID NO 15
<211> LENGTH: 2751
<212> TYPE: PRT
<213> ORGANISM: Artificial Sequence
<220> FEATURE:
<223> OTHER INFORMATION: Synthetic construct, C16 nsP-2A-eGFP protein
<220> FEATURE:
<221> NAME/KEY: misc_feature
<222> LOCATION: (1880)..(1880)
<223> OTHER INFORMATION: Xaa can be any naturally occurring amino acid

<400> SEQUENCE: 15

Met Glu Lys Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
            20                  25                  30

Thr Asp Asn Asp His Ala Asn Ala Arg Ala Phe Ser His Leu Ala Ser
        35                  40                  45

Lys Leu Ile Glu Thr Glu Val Asp Pro Ser Asp Thr Ile Leu Asp Ile
    50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
            100                 105                 110

Asp Lys Lys Met Lys Glu Leu Ala Ala Val Met Ser Asp Pro Asp Leu
        115                 120                 125

Glu Thr Glu Thr Met Cys Leu His Asp Asp Glu Ser Cys Arg Tyr Glu
    130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
            180                 185                 190

Pro Ser Tyr Ser Thr Asn Trp Ala Asp Glu Thr Val Leu Thr Ala Arg
        195                 200                 205
```

```
Asn Ile Gly Leu Cys Ser Ser Asp Val Met Glu Arg Ser Arg Arg Gly
    210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
        275                 280                 285

Arg Ile Ala Ile Ser Pro Gly Leu Tyr Gly Lys Pro Ser Gly Tyr Ala
    290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Asp Val Ser Ala
            340                 345                 350

Asp Asp Ala Gln Lys Leu Leu Val Gly Leu Asn Gln Arg Ile Val Val
        355                 360                 365

Asn Gly Arg Thr Gln Arg Asn Thr Asn Thr Met Lys Asn Tyr Leu Leu
    370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
        435                 440                 445

Ser Phe Val Leu Pro Arg Ile Gly Ser Asn Thr Leu Glu Ile Gly Leu
    450                 455                 460

Arg Thr Arg Ile Arg Lys Met Leu Glu Glu His Lys Glu Pro Ser Pro
465                 470                 475                 480

Leu Ile Thr Ala Glu Asp Val Gln Glu Ala Lys Cys Ala Ala Asp Glu
                485                 490                 495

Ala Lys Glu Val Arg Glu Ala Glu Glu Leu Arg Ala Ala Leu Pro Pro
            500                 505                 510

Leu Ala Ala Asp Val Glu Glu Pro Thr Leu Glu Ala Asp Val Asp Leu
        515                 520                 525

Met Leu Gln Glu Ala Gly Ala Gly Ser Val Glu Thr Pro Arg Gly Leu
    530                 535                 540

Ile Lys Val Thr Ser Tyr Ala Gly Glu Asp Lys Ile Gly Ser Tyr Ala
545                 550                 555                 560

Val Leu Ser Pro Gln Ala Val Leu Lys Ser Glu Lys Leu Ser Cys Ile
                565                 570                 575

His Pro Leu Ala Glu Gln Val Ile Val Ile Thr His Ser Gly Arg Lys
            580                 585                 590

Gly Arg Tyr Ala Val Glu Pro Tyr His Gly Lys Val Val Val Pro Glu
        595                 600                 605

Gly His Ala Ile Pro Val Gln Asp Phe Gln Ala Leu Ser Glu Ser Ala
    610                 615                 620

Thr Ile Val Tyr Asn Glu Arg Glu Phe Val Asn Arg Tyr Leu His His
```

-continued

```
625                 630                 635                 640

Ile Ala Thr His Gly Gly Ala Leu Asn Thr Asp Glu Glu Tyr Tyr Lys
                645                 650                 655

Thr Val Lys Pro Ser Glu His Asp Gly Glu Tyr Leu Tyr Asp Ile Asp
            660                 665                 670

Arg Lys Gln Cys Val Lys Lys Glu Leu Val Thr Gly Leu Gly Leu Thr
        675                 680                 685

Gly Glu Leu Val Asp Pro Pro Phe His Glu Phe Ala Tyr Glu Ser Leu
    690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
                725                 730                 735

Lys Lys Asp Leu Val Val Ser Ala Lys Lys Glu Asn Cys Ala Glu Ile
            740                 745                 750

Ile Arg Asp Val Lys Lys Met Lys Gly Leu Asp Val Asn Ala Arg Thr
        755                 760                 765

Val Asp Ser Val Leu Leu Asn Gly Cys Lys His Pro Val Glu Thr Leu
    770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
                805                 810                 815

Gln Cys Gly Phe Phe Asn Met Met Cys Leu Lys Val His Phe Asn His
            820                 825                 830

Glu Ile Cys Thr Gln Val Phe His Lys Ser Ile Ser Arg Arg Cys Thr
        835                 840                 845

Lys Ser Val Thr Ser Val Val Ser Thr Leu Phe Tyr Asp Lys Lys Met
    850                 855                 860

Arg Thr Thr Asn Pro Lys Glu Thr Lys Ile Val Ile Asp Thr Thr Gly
865                 870                 875                 880

Ser Thr Lys Pro Lys Gln Asp Asp Leu Ile Leu Thr Cys Phe Arg Gly
                885                 890                 895

Trp Val Lys Gln Leu Gln Ile Asp Tyr Lys Gly Asn Glu Ile Met Thr
            900                 905                 910

Ala Ala Ala Ser Gln Gly Leu Thr Arg Lys Gly Val Tyr Ala Val Arg
        915                 920                 925

Tyr Lys Val Asn Glu Asn Pro Leu Tyr Ala Pro Thr Ser Glu His Val
    930                 935                 940

Asn Val Leu Leu Thr Arg Thr Glu Asp Arg Ile Val Trp Lys Thr Leu
945                 950                 955                 960

Ala Gly Asp Pro Trp Ile Lys Thr Leu Thr Ala Lys Tyr Pro Gly Asn
                965                 970                 975

Phe Thr Ala Thr Ile Glu Glu Trp Gln Ala Glu His Asp Ala Ile Met
            980                 985                 990

Arg His Ile Leu Glu Arg Pro Asp  Pro Thr Asp Val Phe  Gln Asn Lys
        995                 1000                1005

Ala Asn  Val Cys Trp Ala Lys  Ala Leu Val Pro Val  Leu Lys Thr
    1010                1015                1020

Ala Gly  Ile Asp Met Thr Thr  Glu Gln Trp Asn Thr  Val Asp Tyr
    1025                1030                1035

Phe Glu  Thr Asp Lys Ala His  Ser Ala Glu Ile Val  Leu Asn Gln
    1040                1045                1050
```

Leu Cys Val Arg Phe Phe Gly Leu Asp Leu Asp Ser Gly Leu Phe
1055 1060 1065

Ser Ala Pro Thr Val Pro Leu Ser Ile Arg Asn Asn His Trp Asp
1070 1075 1080

Asn Ser Pro Ser Pro Asn Met Tyr Gly Leu Asn Lys Glu Val Val
1085 1090 1095

Arg Gln Leu Ser Arg Arg Tyr Pro Gln Leu Pro Arg Ala Val Ala
1100 1105 1110

Thr Gly Arg Val Tyr Asp Met Asn Thr Gly Thr Leu Arg Asn Tyr
1115 1120 1125

Asp Pro Arg Ile Asn Leu Val Pro Val Asn Arg Arg Leu Pro His
1130 1135 1140

Ala Leu Val Leu His His Asn Glu His Pro Gln Ser Asp Phe Ser
1145 1150 1155

Ser Phe Val Ser Lys Leu Lys Gly Arg Thr Val Leu Val Val Gly
1160 1165 1170

Glu Lys Leu Ser Val Pro Gly Lys Met Val Asp Trp Leu Ser Asp
1175 1180 1185

Arg Pro Glu Ala Thr Phe Arg Ala Arg Leu Asp Leu Gly Ile Pro
1190 1195 1200

Gly Asp Val Pro Lys Tyr Asp Ile Ile Phe Val Asn Val Arg Thr
1205 1210 1215

Pro Tyr Lys Tyr His His Tyr Gln Gln Cys Glu Asp His Ala Ile
1220 1225 1230

Lys Leu Ser Met Leu Thr Lys Lys Ala Cys Leu His Leu Asn Pro
1235 1240 1245

Gly Gly Thr Cys Val Ser Ile Gly Tyr Gly Tyr Ala Asp Arg Ala
1250 1255 1260

Ser Glu Ser Ile Ile Gly Ala Ile Ala Arg Gln Phe Lys Phe Ser
1265 1270 1275

Arg Val Cys Lys Pro Lys Ser Ser Leu Glu Glu Thr Glu Val Leu
1280 1285 1290

Phe Val Phe Ile Gly Tyr Asp Arg Lys Ala Arg Thr His Asn Pro
1295 1300 1305

Tyr Lys Leu Ser Ser Thr Leu Thr Asn Ile Tyr Thr Gly Ser Arg
1310 1315 1320

Leu His Glu Ala Gly Cys Ala Pro Ser Tyr His Val Val Arg Gly
1325 1330 1335

Asp Ile Ala Thr Ala Thr Glu Gly Val Ile Ile Asn Ala Ala Asn
1340 1345 1350

Ser Lys Gly Gln Pro Gly Gly Gly Val Cys Gly Ala Leu Tyr Lys
1355 1360 1365

Lys Phe Pro Glu Ser Phe Asp Leu Gln Pro Ile Glu Val Gly Lys
1370 1375 1380

Ala Arg Leu Val Lys Gly Ala Ala Lys His Ile Ile His Ala Val
1385 1390 1395

Gly Pro Asn Phe Asn Lys Val Ser Glu Val Glu Gly Asp Lys Gln
1400 1405 1410

Leu Ala Glu Ala Tyr Glu Ser Ile Ala Lys Ile Val Asn Asp Asn
1415 1420 1425

Asn Tyr Lys Ser Val Ala Ile Pro Leu Leu Ser Thr Gly Ile Phe
1430 1435 1440

-continued

```
Ser Gly  Asn Lys Asp Arg Leu  Thr Gln Ser Leu Asn  His Leu Leu
    1445                 1450                 1455

Thr Ala  Leu Asp Thr Thr Asp  Ala Asp Val Ala Ile  Tyr Cys Arg
    1460                 1465                 1470

Asp Lys  Lys Trp Glu Met Thr  Leu Lys Glu Ala Val  Ala Arg Arg
    1475                 1480                 1485

Glu Ala  Val Glu Glu Ile Cys  Ile Ser Asp Asp Ser  Ser Val Thr
    1490                 1495                 1500

Glu Pro  Asp Ala Glu Leu Val  Arg Val His Pro Lys  Ser Ser Leu
    1505                 1510                 1515

Ala Gly  Arg Lys Gly Tyr Ser  Thr Ser Asp Gly Lys  Thr Phe Ser
    1520                 1525                 1530

Tyr Leu  Glu Gly Thr Lys Phe  His Gln Ala Ala Lys  Asp Ile Ala
    1535                 1540                 1545

Glu Ile  Asn Ala Met Trp Pro  Val Ala Thr Glu Ala  Asn Glu Gln
    1550                 1555                 1560

Val Cys  Met Tyr Ile Leu Gly  Glu Ser Met Ser Ser  Ile Arg Ser
    1565                 1570                 1575

Lys Cys  Pro Val Glu Glu Ser  Glu Ala Ser Thr Pro  Pro Ser Thr
    1580                 1585                 1590

Leu Pro  Cys Leu Cys Ile His  Ala Met Thr Pro Glu  Arg Val Gln
    1595                 1600                 1605

Arg Leu  Lys Ala Ser Arg Pro  Glu Gln Ile Thr Val  Cys Ser Ser
    1610                 1615                 1620

Phe Pro  Leu Pro Lys Tyr Arg  Ile Thr Gly Val Gln  Lys Ile Gln
    1625                 1630                 1635

Cys Ser  Gln Pro Ile Leu Phe  Ser Pro Lys Val Pro  Ala Tyr Ile
    1640                 1645                 1650

His Pro  Arg Lys Tyr Leu Val  Glu Thr Pro Pro Val  Asp Glu Thr
    1655                 1660                 1665

Pro Glu  Pro Ser Ala Glu Asn  Gln Ser Thr Glu Gly  Thr Pro Glu
    1670                 1675                 1680

Gln Pro  Pro Leu Ile Thr Glu  Asp Glu Thr Arg Thr  Arg Thr Pro
    1685                 1690                 1695

Glu Pro  Ile Ile Ile Glu Glu  Glu Glu Glu Asp Ser  Ile Ser Leu
    1700                 1705                 1710

Leu Ser  Asp Gly Pro Thr His  Gln Val Leu Gln Val  Glu Ala Asp
    1715                 1720                 1725

Ile His  Gly Pro Pro Ser Val  Ser Ser Ser Ser Trp  Ser Ile Pro
    1730                 1735                 1740

His Ala  Ser Asp Phe Asp Val  Asp Ser Leu Ser Ile  Leu Asp Thr
    1745                 1750                 1755

Leu Glu  Gly Ala Ser Val Thr  Ser Gly Ala Thr Ser  Ala Glu Thr
    1760                 1765                 1770

Asn Ser  Tyr Phe Ala Lys Ser  Met Glu Phe Leu Ala  Arg Pro Val
    1775                 1780                 1785

Pro Ala  Pro Arg Thr Val Phe  Arg Asn Pro Pro His  Pro Ala Pro
    1790                 1795                 1800

Arg Thr  Arg Thr Pro Ser Leu  Ala Pro Ser Arg Ala  Cys Ser Arg
    1805                 1810                 1815

Thr Ser  Leu Val Ser Thr Pro  Pro Gly Val Asn Arg  Val Ile Thr
    1820                 1825                 1830

Arg Glu  Glu Leu Glu Ala Leu  Thr Pro Ser Arg Thr  Pro Ser Arg
```

```
    1835                1840                1845

Ser Val  Ser Arg Thr Ser Leu  Val Ser Asn Pro Pro  Gly Val Asn
    1850                1855                1860

Arg Val  Ile Thr Arg Glu Glu  Phe Glu Ala Phe Val  Ala Gln Gln
    1865                1870                1875

Gln Xaa  Arg Phe Asp Ala Gly  Ala Tyr Ile Phe Ser  Ser Asp Thr
    1880                1885                1890

Gly Gln  Gly His Leu Gln Gln  Lys Ser Val Arg Gln  Thr Val Leu
    1895                1900                1905

Ser Glu  Val Val Leu Glu Arg  Thr Glu Leu Glu Ile  Ser Tyr Ala
    1910                1915                1920

Pro Arg  Leu Asp Gln Glu Lys  Glu Glu Leu Leu Arg  Lys Lys Leu
    1925                1930                1935

Gln Leu  Asn Pro Thr Pro Ala  Asn Arg Ser Arg Tyr  Gln Ser Arg
    1940                1945                1950

Lys Val  Glu Asn Met Lys Ala  Ile Thr Ala Arg Arg  Ile Leu Gln
    1955                1960                1965

Gly Leu  Gly His Tyr Leu Lys  Ala Glu Gly Lys Val  Glu Cys Tyr
    1970                1975                1980

Arg Thr  Leu His Pro Val Pro  Leu Tyr Ser Ser Ser  Val Asn Arg
    1985                1990                1995

Ala Phe  Ser Ser Pro Lys Val  Ala Val Glu Ala Cys  Asn Ala Met
    2000                2005                2010

Leu Lys  Glu Asn Phe Pro Thr  Val Ala Ser Tyr Cys  Ile Ile Pro
    2015                2020                2025

Glu Tyr  Asp Ala Tyr Leu Asp  Met Val Asp Gly Ala  Ser Cys Cys
    2030                2035                2040

Leu Asp  Thr Ala Ser Phe Cys  Pro Ala Lys Leu Arg  Ser Phe Pro
    2045                2050                2055

Lys Lys  His Ser Tyr Leu Glu  Pro Thr Ile Arg Ser  Ala Val Pro
    2060                2065                2070

Ser Ala  Ile Gln Asn Thr Leu  Gln Asn Val Leu Ala  Ala Ala Thr
    2075                2080                2085

Lys Arg  Asn Cys Asn Val Thr  Gln Met Arg Glu Leu  Pro Val Leu
    2090                2095                2100

Asp Ser  Ala Ala Phe Asn Val  Glu Cys Phe Lys Lys  Tyr Ala Cys
    2105                2110                2115

Asn Asn  Glu Tyr Trp Glu Thr  Phe Lys Glu Asn Pro  Ile Arg Leu
    2120                2125                2130

Thr Glu  Glu Asn Val Val Asn  Tyr Ile Thr Lys Leu  Lys Gly Pro
    2135                2140                2145

Lys Ala  Ala Ala Leu Phe Ala  Lys Thr His Asn Leu  Asn Met Leu
    2150                2155                2160

Gln Asp  Ile Pro Met Asp Arg  Phe Val Met Asp Leu  Lys Arg Asp
    2165                2170                2175

Val Lys  Val Thr Pro Gly Thr  Lys His Thr Glu Glu  Arg Pro Lys
    2180                2185                2190

Val Gln  Val Ile Gln Ala Ala  Asp Pro Leu Ala Thr  Ala Tyr Leu
    2195                2200                2205

Cys Gly  Ile His Arg Glu Leu  Val Arg Arg Leu Asn  Ala Val Leu
    2210                2215                2220

Leu Pro  Asn Ile His Thr Leu  Phe Asp Met Ser Ala  Glu Asp Phe
    2225                2230                2235
```

-continued

```
Asp Ala  Ile Ile Ala Glu His  Phe Gln Pro Gly Asp  Cys Val Leu
    2240                 2245                 2250

Glu Thr  Asp Ile Ala Ser Phe  Asp Lys Ser Glu Asp  Asp Ala Met
    2255                 2260                 2265

Ala Leu  Thr Ala Leu Met Ile  Leu Glu Asp Leu Gly  Val Asp Ala
    2270                 2275                 2280

Glu Leu  Leu Thr Leu Ile Glu  Ala Ala Phe Gly Glu  Ile Ser Ser
    2285                 2290                 2295

Ile His  Leu Pro Thr Lys Thr  Lys Phe Lys Phe Gly  Ala Met Met
    2300                 2305                 2310

Lys Ser  Gly Met Phe Leu Thr  Leu Phe Val Asn Thr  Val Ile Asn
    2315                 2320                 2325

Ile Val  Ile Ala Ser Arg Val  Leu Arg Glu Arg Leu  Thr Gly Ser
    2330                 2335                 2340

Pro Cys  Ala Ala Phe Ile Gly  Asp Asp Asn Ile Val  Lys Gly Val
    2345                 2350                 2355

Lys Ser  Asp Lys Leu Met Ala  Asp Arg Cys Ala Thr  Trp Leu Asn
    2360                 2365                 2370

Met Glu  Val Lys Ile Ile Asp  Ala Val Val Gly Glu  Lys Ala Pro
    2375                 2380                 2385

Tyr Phe  Cys Gly Gly Phe Ile  Leu Cys Asp Ser Val  Thr Gly Thr
    2390                 2395                 2400

Ala Cys  Arg Val Ala Asp Pro  Leu Lys Arg Leu Phe  Lys Leu Gly
    2405                 2410                 2415

Lys Pro  Leu Ala Ala Asp Asp  Glu His Asp Asp Asp  Arg Arg Arg
    2420                 2425                 2430

Ala Leu  His Glu Glu Ser Thr  Arg Trp Asn Arg Val  Gly Ile Leu
    2435                 2440                 2445

Ser Glu  Leu Cys Lys Ala Val  Glu Ser Arg Tyr Glu  Thr Val Gly
    2450                 2455                 2460

Thr Ser  Ile Ile Val Met Ala  Met Thr Thr Leu Ala  Ser Ser Val
    2465                 2470                 2475

Lys Ser  Phe Ser Tyr Leu Arg  Gly Ala Pro Ile Thr  Leu Tyr Gly
    2480                 2485                 2490

Ser Gly  Glu Gly Arg Gly Ser  Leu Leu Thr Cys Gly  Asp Val Glu
    2495                 2500                 2505

Glu Asn  Pro Gly Pro Val Ser  Lys Gly Glu Glu Leu  Phe Thr Gly
    2510                 2515                 2520

Val Val  Pro Ile Leu Val Glu  Leu Asp Gly Asp Val  Asn Gly His
    2525                 2530                 2535

Lys Phe  Ser Val Ser Gly Glu  Gly Glu Gly Asp Ala  Thr Tyr Gly
    2540                 2545                 2550

Lys Leu  Thr Leu Lys Phe Ile  Cys Thr Thr Gly Lys  Leu Pro Val
    2555                 2560                 2565

Pro Trp  Pro Thr Leu Val Thr  Thr Leu Thr Tyr Gly  Val Gln Cys
    2570                 2575                 2580

Phe Ser  Arg Tyr Pro Asp His  Met Lys Gln His Asp  Phe Phe Lys
    2585                 2590                 2595

Ser Ala  Met Pro Glu Gly Tyr  Val Gln Glu Arg Thr  Ile Phe Phe
    2600                 2605                 2610

Lys Asp  Asp Gly Asn Tyr Lys  Thr Arg Ala Glu Val  Lys Phe Glu
    2615                 2620                 2625
```

```
Gly Asp  Thr Leu Val Asn Arg  Ile Glu Leu Lys Gly  Ile Asp Phe
    2630                 2635                 2640

Lys Glu  Asp Gly Asn Ile Leu  Gly His Lys Leu Glu  Tyr Asn Tyr
    2645                 2650                 2655

Asn Ser  His Asn Val Tyr Ile  Met Ala Asp Lys Gln  Lys Asn Gly
    2660                 2665                 2670

Ile Lys  Val Asn Phe Lys Ile  Arg His Asn Ile Glu  Asp Gly Ser
    2675                 2680                 2685

Val Gln  Leu Ala Asp His Tyr  Gln Gln Asn Thr Pro  Ile Gly Asp
    2690                 2695                 2700

Gly Pro  Val Leu Leu Pro Asp  Asn His Tyr Leu Ser  Thr Gln Ser
    2705                 2710                 2715

Lys Leu  Ser Lys Asp Pro Asn  Glu Lys Arg Asp His  Met Val Leu
    2720                 2725                 2730

Leu Glu  Phe Val Thr Ala Ala  Gly Ile Thr Leu Gly  Met Asp Glu
    2735                 2740                 2745

Leu Tyr  Lys
    2750


<210> SEQ ID NO 16
<211> LENGTH: 8256
<212> TYPE: DNA
<213> ORGANISM: Artificial Sequence
<220> FEATURE:
<223> OTHER INFORMATION: Synthetic construct, C16 nsP-2A-eGFP coding
      sequence DNA

<400> SEQUENCE: 16

atggagaaag ttcacgttga catcgaggaa gacagcccat tcctcagagc tttgcagcgg     60

agcttcccgc agtttgaggt agaagccaag caggtcactg ataatgacca tgctaatgcc    120

agagcgtttt cgcatctggc ttcaaaactg atcgaaacgg aggtggaccc atccgacacg    180

atccttgaca ttggaagtgc gcccgcccgc agaatgtatt ctaagcacaa gtatcattgt    240

atctgtccga tgagatgtgc ggaagatccg gacagattgt ataagtatgc aactaagctg    300

aagaaaaact gtaaggaaat aactgataag gaattggaca agaaaatgaa ggagctcgcc    360

gccgtcatga gcgaccctga cctggaaact gagactatgt gcctccacga cgacgagtcg    420

tgtcgctacg aagggcaagt cgctgtttac caggatgtat acgcggttga cggaccgaca    480

agtctctatc accaagccaa taagggagtt agagtcgcct actggatagg ctttgacacc    540

accccttta tgtttaagaa cttggctgga gcatatccat catactctac caactgggcc    600

gacgaaaccg tgttaacggc tcgtaacata ggcctatgca gctctgacgt tatggagcgg    660

tcacgtagag ggatgtccat tcttagaaag aagtatttga aaccatccaa caatgttcta    720

ttctctgttg gctcgaccat ctaccacgag aagagggact tactgaggag ctggcacctg    780

ccgtctgtat ttcacttacg tggcaagcaa aattacacat gtcggtgtga gactatagtt    840

agttgcgacg ggtacgtcgt taaaagaata gctatcagtc caggcctgta tgggaagcct    900

tcaggctatg ctgctacgat gcaccgcgag ggattcttgt gctgcaaagt gacagacaca    960

ttgaacgggg agagggtctc ttttcccgtg tgcacgtatg tgccagctac attgtgtgac   1020

caaatgactg gcatactggc aacagatgtc agtgcggacg acgcgcaaaa actgctggtt   1080

gggctcaacc agcgtatagt cgtcaacggt cgcacccaga gaaacaccaa taccatgaaa   1140

aattaccttt tgcccgtagt ggcccaggca tttgctaggt gggcaaagga atataaggaa   1200

gatcaagaag atgaaaggcc actaggacta cgagatagac agttagtcat ggggtgttgt   1260
```

tgggctttta gaaggcacaa gataacatct atttataagc gcccggatac ccaaaccatc 1320
atcaaagtga acagcgattt ccactcattc gtgctgccca ggataggcag taacacattg 1380
gagatcgggc tgagaacaag aatcaggaaa atgttagagg agcacaagga gccgtcacct 1440
ctcattaccg ccgaggacgt acaagaagct aagtgcgcag ccgatgaggc taaggaggtg 1500
cgtgaagccg aggagttgcg cgcagctcta ccacctttgg cagctgatgt tgaggagccc 1560
actctggaag ccgatgtcga cttgatgtta caagaggctg gggccggctc agtggagaca 1620
cctcgtggct tgataaaggt taccagctac gctggcgagg acaagatcgg ctcttacgct 1680
gtgctttctc cgcaggctgt actcaagagt gaaaaattat cttgcatcca ccctctcgct 1740
gaacaagtca tagtgataac acactctggc cgaaaagggc gttatgccgt ggaaccatac 1800
catggtaaag tagtggtgcc agagggacat gcaatacccg tccaggactt tcaagctctg 1860
agtgaaagtg ccaccattgt gtacaacgaa cgtgagttcg taaacaggta cctgcaccat 1920
attgccacac atggaggagc gctgaacact gatgaagaat attacaaaac tgtcaagccc 1980
agcgagcacg acggcgaata cctgtacgac atcgacagga aacagtgcgt caagaaagaa 2040
ctagtcactg ggctagggct cacaggcgag ctggtggatc ctcccttcca tgaattcgcc 2100
tacgagagtc tgagaacacg accagccgct ccttaccaag taccaaccat aggggtgtat 2160
ggcgtgccag gatcaggcaa gtctggcatc attaaaagcg cagtcaccaa aaaagatcta 2220
gtggtgagcg ccaagaaaga aaactgtgca gaaattataa gggacgtcaa gaaaatgaaa 2280
gggctggacg tcaatgccag aactgtggac tcagtgctct tgaatggatg caaacacccc 2340
gtagagaccc tgtatattga cgaagctttt gcttgtcatg caggtactct cagagcgctc 2400
atagccatta taagacctaa aaaggcagtg ctctgcgggg atcccaaaca gtgcggtttt 2460
tttaacatga tgtgcctgaa agtgcatttt aaccacgaga tttgcacaca agtcttccac 2520
aaaagcatct ctcgccgttg cactaaatct gtgacttcgg tcgtctcaac cttgttttac 2580
gacaaaaaaa tgagaacgac gaatccgaaa gagactaaga ttgtgattga cactaccggc 2640
agtaccaaac ctaagcagga cgatctcatt ctcacttgtt tcagagggtg ggtgaagcag 2700
ttgcaaatag attacaaagg caacgaaata atgacggcag ctgcctctca agggctgacc 2760
cgtaaaggtg tgtatgccgt tcggtacaag gtgaatgaaa atcctctgta cgcacccacc 2820
tcagaacatg tgaacgtcct actgacccgc acggaggacc gcatcgtgtg gaaaacacta 2880
gccggcgacc catggataaa aacactgact gccaagtacc ctgggaattt cactgccacg 2940
atagaggagt ggcaagcaga gcatgatgcc atcatgaggc acatcttgga gagaccggac 3000
cctaccgacg tcttccagaa taaggcaaac gtgtgttggg ccaaggcttt agtgccggtg 3060
ctgaagaccg ctggcataga catgaccact gaacaatgga acactgtgga ttattttgaa 3120
acggacaaag ctcactcagc agagatagta ttgaaccaac tatgcgtgag gttctttgga 3180
ctcgatctgg actccggtct attttctgca cccactgttc cgttatccat taggaataat 3240
cactgggata actccccgtc gcctaacatg tacgggctga ataaagaagt ggtccgtcag 3300
ctctctcgca ggtacccaca actgcctcgg gcagttgcca ctggaagagt ctatgacatg 3360
aacactggta cactgcgcaa ttatgatccg cgcataaacc tagtacctgt aaacagaaga 3420
ctgcctcatg ctttagtcct ccaccataat gaacacccac agagtgactt ttcttcattc 3480
gtcagcaaat tgaagggcag aactgtcctg gtggtcgggg aaaagttgtc cgtcccaggc 3540
aaaatggttg actggttgtc agaccggcct gaggctacct tcagagctcg gctggattta 3600

-continued

```
ggcatcccag gtgatgtgcc caaatatgac ataatatttg ttaatgtgag gaccccatat   3660
aaataccatc actatcagca gtgtgaagac catgccatta agcttagcat gttgaccaag   3720
aaagcttgtc tgcatctgaa tcccggcgga acctgtgtca gcataggtta tggttacgct   3780
gacagggcca gcgaaagcat cattggtgct atagcgcggc agttcaagtt ttcccgggta   3840
tgcaaaccga aatcctcact tgaagagacg gaagttctgt ttgtattcat tgggtacgat   3900
cgcaaggccc gtacgcacaa tccttacaag ctttcatcaa ccttgaccaa catttataca   3960
ggttccagac tccacgaagc cggatgtgca ccctcatatc atgtggtgcg aggggatatt   4020
gccacggcca ccgaaggagt gattataaat gctgctaaca gcaaaggaca acctggcgga   4080
ggggtgtgcg gagcgctgta taagaaattc ccggaaagct tcgatttaca gccgatcgaa   4140
gtaggaaaag cgcgactggt caaaggtgca gctaaacata tcattcatgc cgtaggacca   4200
aacttcaaca aagtttcgga ggttgaaggt gacaaacagt tggcagaggc ttatgagtcc   4260
atcgctaaga ttgtcaacga taacaattac aagtcagtag cgattccact gttgtccacc   4320
ggcatctttt ccgggaacaa agatcgacta acccaatcat tgaaccattt gctgacagct   4380
ttagacacca ctgatgcaga tgtagccata tactgcaggg acaagaaatg ggaaatgact   4440
ctcaaggaag cagtggctag gagagaagca gtggaggaga tatgcatatc cgacgactct   4500
tcagtgacag aacctgatgc agagctggtg agggtgcatc cgaagagttc tttggctgga   4560
aggaagggct acagcacaag cgatggcaaa actttctcat atttggaagg gaccaagttt   4620
caccaggcgg ccaaggatat agcagaaatt aatgccatgt ggcccgttgc aacggaggcc   4680
aatgagcagg tatgcatgta tatcctcgga gaaagcatga gcagtattag gtcgaaatgc   4740
cccgtcgaag agtcggaagc ctccacacca cctagcacgc tgccttgctt gtgcatccat   4800
gccatgactc cagaaagagt acagcgccta aaagcctcac gtccagaaca aattactgtg   4860
tgctcatcct ttccattgcc gaagtataga atcactggtg tgcagaagat ccaatgctcc   4920
cagcctatat tgttctcacc gaaagtgcct gcgtatattc atccaaggaa gtatctcgtg   4980
gaaacaccac cggtagacga gactccggag ccatcggcag agaaccaatc cacagagggg   5040
acacctgaac aaccaccact tataaccgag gatgagacca ggactagaac gcctgagccg   5100
atcatcatcg aagaggaaga agaggatagc ataagtttgc tgtcagatgg cccgacccac   5160
caggtgctgc aagtcgaggc agacattcac gggccgccct ctgtatctag ctcatcctgg   5220
tccattcctc atgcatccga ctttgatgtg gacagtttat ccatacttga caccctggag   5280
ggagctagcg tgaccagcgg ggcaacgtca gccgagacta actcttactt cgcaaagagt   5340
atggagtttc tggcgcgacc ggtgcctgcg cctcgaacag tattcaggaa ccctccacat   5400
cccgctccgc gcacaagaac accgtcactt gcacccagca gggcctgctc gagaaccagc   5460
ctagtttcca ccccgccagg cgtgaatagg gtgatcacta gagaggagct cgaggcgctt   5520
accccgtcac gcactcctag caggtcggtc tcgagaacca gcctggtctc caacccgcca   5580
ggcgtaaata gggtgattac aagagaggag tttgaggcgt tcgtagcaca acaacaatga   5640
cggtttgatg cgggtgcata catcttttcc tccgacaccg gtcaagggca tttacaacaa   5700
aaatcagtaa ggcaaacggt gctatccgaa gtggtgttgg agaggaccga attggagatt   5760
tcgtatgccc cgcgcctcga ccaagaaaaa gaagaattac tacgcaagaa attacagtta   5820
aatcccacac ctgctaacag aagcagatac cagtccagga aggtggagaa catgaaagcc   5880
ataacagcta gacgtattct gcaaggccta gggcattatt tgaaggcaga aggaaaagtg   5940
gagtgctacc gaaccctgca tcctgttcct ttgtattcat ctagtgtgaa ccgtgccttt   6000
```

tcaagcccca aggtcgcagt ggaagcctgt aacgccatgt tgaaagagaa ctttccgact 6060
gtggcttctt actgtattat tccagagtac gatgcctatt tggacatggt tgacggagct 6120
tcatgctgct tagacactgc cagtttttgc cctgcaaagc tgcgcagctt tccaaagaaa 6180
cactcctatt tggaacccac aatacgatcg gcagtgcctt cagcgatcca gaacacgctc 6240
cagaacgtcc tggcagctgc cacaaaaaga aattgcaatg tcacgcaaat gagagaattg 6300
cccgtattgg attcggcggc ctttaatgtg gaatgcttca agaaatatgc gtgtaataat 6360
gaatattggg aaacgtttaa agaaaacccc atcaggctta ctgaagaaaa cgtggtaaat 6420
tacattacca aattaaaagg accaaaagct gctgctcttt ttgcgaagac acataatttg 6480
aatatgttgc aggacatacc aatggacagg tttgtaatgg acttaaagag agacgtgaaa 6540
gtgactccag gaacaaaaca tactgaagaa cggcccaagg tacaggtgat ccaggctgcc 6600
gatccgctag caacagcgta tctgtgcgga atccaccgag agctggttag gagattaaat 6660
gcggtcctgc ttccgaacat tcatacactg tttgatatgt cggctgaaga ctttgacgct 6720
attatagccg agcacttcca gcctggggat tgtgttctgg aaactgacat cgcgtcgttt 6780
gataaaagtg aggacgacgc catggctctg accgcgttaa tgattctgga agacttaggt 6840
gtggacgcag agctgttgac gctgattgag gcggctttcg gcgaaatttc atcaatacat 6900
ttgcccacta aaactaaatt taagttcggc gccatgatga agtccggcat gtttctgacc 6960
ctgttcgtga acaccgtgat caacatcgtg atcgccagcc gggtgctgag agagagactg 7020
acaggatctc cttgcgccgc cttcatcggc gacgacaata tcgtgaaggg cgtgaagtcc 7080
gacaagctga tggccgatag atgcgccacc tggctgaaca tggaagtgaa gatcatcgac 7140
gccgtcgtgg gcgagaaggc cccttatttt tgcggcggct tcatcctgtg cgacagcgtg 7200
acaggcacag cctgcagagt tgccgatcct ctgaagcggc tgttcaagct gggaaaacct 7260
ctggccgccg acgacgagca cgacgacgat agacgtagag ccctgcacga ggaatccacc 7320
agatggaaca gagtgggcat cctgagcgag ctgtgcaagg ccgtggaaag cagatacgag 7380
acagtgggca ccagcatcat tgtgatggca atgaccacac tggccagcag cgtgaaaagc 7440
ttcagctacc taaggggcgc ccctatcaca ctgtacggct ctggcgaagg cagaggcagc 7500
cttctgacat gtggcgacgt ggaagagaac cccggacctg tgtctaaggg cgaagaactg 7560
tttaccggcg tggtgcccat cctggtggaa ctggatgggg atgtgaacgg ccacaagttc 7620
agcgttagcg gagaaggcga aggcgacgcc acatacggaa agctgaccct gaagttcatc 7680
tgcaccaccg gcaagctgcc tgtgccatgg cctacactgg tcaccacact gacatacggc 7740
gtgcagtgct tcagcagata ccccgaccat atgaagcagc acgacttctt caagagcgcc 7800
atgcctgagg gctacgtgca agagcggacc atcttcttta aggacgacgg caactacaag 7860
accagggccg aagtgaagtt cgagggcgac accctggtca accggatcga gctgaagggc 7920
atcgacttca aagaggacgg caatatcctg ggccacaagc tcgagtacaa ctacaacagc 7980
cacaacgtgt acatcatggc cgacaagcag aaaaacggca tcaaagtgaa cttcaagatc 8040
cggcacaaca tcgaggacgg ctctgtgcag ctggccgatc actaccagca gaacacaccc 8100
atcggagatg gccctgtgct gctgcccgat aaccactacc tgagcaccca gagcaagctg 8160
agcaaggacc ccaacgagaa gcgggaccac atggtgctgc tggaatttgt gacagccgcc 8220
ggaatcaccc tcggcatgga tgagctgtac aagtga 8256

<210> SEQ ID NO 17

<211> LENGTH: 11447
<212> TYPE: DNA
<213> ORGANISM: Venezuelan equine encephalitis virus
<220> FEATURE:
<221> NAME/KEY: misc_feature
<222> LOCATION: (1)..(11447)
<223> OTHER INFORMATION: VEEV genome L01442.2

<400> SEQUENCE: 17

```
atgggcggcg catgagagaa gcccagacca attacctacc caaaatggag aaagttcacg     60
ttgacatcga ggaagacagc ccattcctca gagctttgca gcggagcttc ccgcagtttg    120
aggtagaagc caagcaggtc actgataatg accatgctaa tgccagagcg ttttcgcatc    180
tggcttcaaa actgatcgaa acggaggtgg acccatccga cacgatcctt gacattggaa    240
gtgcgcccgc ccgcagaatg tattctaagc acaagtatca ttgtatctgt ccgatgagat    300
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020
tctcttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tcgacttgat gttacaagag gctggggccg gctcagtgga gacacctcgt ggcttgataa   1680
aggttaccag ctacgctggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
```

ggctcacagg cgagctggtg gatcctccct tccatgaatt cgcctacgag agtctgagaa 2160
cacgaccagc cgctccttac caagtaccaa ccataggggt gtatggcgtg ccaggatcag 2220
gcaagtctgg catcattaaa agcgcagtca ccaaaaaaga tctagtggtg agcgccaaga 2280
aagaaaactg tgcagaaatt ataagggacg tcaagaaaat gaaagggctg gacgtcaatg 2340
ccagaactgt ggactcagtg ctcttgaatg gatgcaaaca ccccgtagag accctgtata 2400
ttgacgaagc ttttgcttgt catgcaggta ctctcagagc gctcatagcc attataagac 2460
ctaaaaaggc agtgctctgc ggggatccca aacagtgcgg tttttttaac atgatgtgcc 2520
tgaaagtgca ttttaaccac gagatttgca cacaagtctt ccacaaaagc atctctcgcc 2580
gttgcactaa atctgtgact tcggtcgtct caaccttgtt ttacgacaaa aaaatgagaa 2640
cgacgaatcc gaaagagact aagattgtga ttgacactac cggcagtacc aaacctaagc 2700
aggacgatct cattctcact tgtttcagag ggtgggtgaa gcagttgcaa atagattaca 2760
aaggcaacga aataatgacg gcagctgcct ctcaagggct gacccgtaaa ggtgtgtatg 2820
ccgttcggta caaggtgaat gaaaatcctc tgtacgcacc cacctcagaa catgtgaacg 2880
tcctactgac ccgcacggag gaccgcatcg tgtggaaaac actagccggc gacccatgga 2940
taaaaacact gactgccaag taccctggga atttcactgc cacgatagag gagtggcaag 3000
cagagcatga tgccatcatg aggcacatct tggagagacc ggaccctacc gacgtcttcc 3060
agaataaggc aaacgtgtgt tgggccaagg ctttagtgcc ggtgctgaag accgctggca 3120
tagacatgac cactgaacaa tggaacactg tggattattt tgaaacggac aaagctcact 3180
cagcagagat agtattgaac caactatgcg tgaggttctt tggactcgat ctggactccg 3240
gtctattttc tgcacccact gttccgttat ccattaggaa taatcactgg gataactccc 3300
cgtcgcctaa catgtacggg ctgaataaag aagtggtccg tcagctctct cgcaggtacc 3360
cacaactgcc tcgggcagtt gccactggaa gagtctatga catgaacact ggtacactgc 3420
gcaattatga tccgcgcata aacctagtac ctgtaaacag aagactgcct catgctttag 3480
tcctccacca taatgaacac ccacagagtg actttttcttc attcgtcagc aaattgaagg 3540
gcagaactgt cctggtggtc ggggaaaagt tgtccgtccc aggcaaaatg gttgactggt 3600
tgtcagaccg gcctgaggct accttcagag ctcggctgga tttaggcatc ccaggtgatg 3660
tgcccaaata tgacataata tttgttaatg tgaggacccc atataaatac catcactatc 3720
agcagtgtga agaccatgcc attaagctta gcatgttgac caagaaagct tgtctgcatc 3780
tgaatcccgg cggaacctgt gtcagcatag gttatggtta cgctgacagg gccagcgaaa 3840
gcatcattgg tgctatagcg cggcagttca agttttcccg ggtatgcaaa ccgaaatcct 3900
cacttgaaga gacggaagtt ctgtttgtat tcattgggta cgatcgcaag gcccgtacgc 3960
acaatcctta caagctttca tcaaccttga ccaacattta tacaggttcc agactccacg 4020
aagccggatg tgcaccctca tatcatgtgg tgcgaggggga tattgccacg gccaccgaag 4080
gagtgattat aaatgctgct aacagcaaag gacaacctgg cggagggggtg tgcggagcgc 4140
tgtataagaa attcccggaa agcttcgatt tacagccgat cgaagtagga aaagcgcgac 4200
tggtcaaagg tgcagctaaa catatcattc atgccgtagg accaaacttc aacaaagttt 4260
cggaggttga aggtgacaaa cagttggcag aggcttatga gtccatcgct aagattgtca 4320
acgataacaa ttacaagtca gtagcgattc cactgttgtc caccggcatc ttttccggga 4380
acaaagatcg actaacccaa tcattgaacc atttgctgac agctttagac accactgatg 4440

-continued

```
cagatgtagc catatactgc agggacaaga aatgggaaat gactctcaag gaagcagtgg   4500
ctaggagaga agcagtggag gagatatgca tatccgacga ctcttcagtg acagaacctg   4560
atgcagagct ggtgagggtg catccgaaga gttctttggc tggaaggaag ggctacagca   4620
caagcgatgg caaaactttc tcatatttgg aagggaccaa gtttcaccag gcggccaagg   4680
atatagcaga aattaatgcc atgtggcccg ttgcaacgga ggccaatgag caggtatgca   4740
tgtatatcct cggagaaagc atgagcagta ttaggtcgaa atgccccgtc gaagagtcgg   4800
aagcctccac accacctagc acgctgcctt gcttgtgcat ccatgccatg actccagaaa   4860
gagtacagcg cctaaaagcc tcacgtccag aacaaattac tgtgtgctca tcctttccat   4920
tgccgaagta tagaatcact ggtgtgcaga agatccaatg ctcccagcct atattgttct   4980
caccgaaagt gcctgcgtat attcatccaa ggaagtatct cgtggaaaca ccaccggtag   5040
acgagactcc ggagccatcg gcagagaacc aatccacaga ggggacacct gaacaaccac   5100
cacttataac cgaggatgag accaggacta gaacgcctga gccgatcatc atcgaagagg   5160
aagaagagga tagcataagt ttgctgtcag atggcccgac ccaccaggtg ctgcaagtcg   5220
aggcagacat tcacgggccg ccctctgtat ctagctcatc ctggtccatt cctcatgcat   5280
ccgactttga tgtggacagt ttatccatac ttgacaccct ggagggagct agcgtgacca   5340
gcggggcaac gtcagccgag actaactctt acttcgcaaa gagtatggag tttctggcgc   5400
gaccggtgcc tgcgcctcga acagtattca ggaaccctcc acatcccgct ccgcgcacaa   5460
gaacaccgtc acttgcaccc agcagggcct gctcgagaac cagcctagtt tccaccccgc   5520
caggcgtgaa tagggtgatc actagagagg agctcgaggc gcttaccccg tcacgcactc   5580
ctagcaggtc ggtctcgaga accagcctgg tctccaaccc gccaggcgta aatagggtga   5640
ttacaagaga ggagtttgag gcgttcgtag cacaacaaca atgacggttt gatgcgggtg   5700
catacatctt ttcctccgac accggtcaag ggcatttaca acaaaaatca gtaaggcaaa   5760
cggtgctatc cgaagtggtg ttggagagga ccgaattgga gatttcgtat gccccgcgcc   5820
tcgaccaaga aaaagaagaa ttactacgca agaaattaca gttaaatccc acacctgcta   5880
acagaagcag ataccagtcc aggaaggtgg agaacatgaa agccataaca gctagacgta   5940
ttctgcaagg cctagggcat tatttgaagg cagaaggaaa agtggagtgc taccgaaccc   6000
tgcatcctgt tcctttgtat tcatctagtg tgaaccgtgc cttttcaagc cccaaggtcg   6060
cagtggaagc ctgtaacgcc atgttgaaag agaactttcc gactgtggct tcttactgta   6120
ttattccaga gtacgatgcc tatttggaca tggttgacgg agcttcatgc tgcttagaca   6180
ctgccagttt ttgccctgca aagctgcgca gctttccaaa gaaacactcc tatttggaac   6240
ccacaatacg atcggcagtg ccttcagcga tccagaacac gctccagaac gtcctggcag   6300
ctgccacaaa aagaaattgc aatgtcacgc aaatgagaga attgcccgta ttggattcgg   6360
cggcctttaa tgtggaatgc ttcaagaaat atgcgtgtaa taatgaatat tgggaaacgt   6420
ttaaagaaaa ccccatcagg cttactgaag aaaacgtggt aaattacatt accaaattaa   6480
aaggaccaaa agctgctgct ctttttgcga agacacataa tttgaatatg ttgcaggaca   6540
taccaatgga caggtttgta atggacttaa agagagacgt gaaagtgact ccaggaacaa   6600
aacatactga agaacggccc aaggtacagg tgatccaggc tgccgatccg ctagcaacag   6660
cgtatctgtg cggaatccac cgagagctgg ttaggagatt aaatgcggtc ctgcttccga   6720
acattcatac actgtttgat atgtcggctg aagactttga cgctattata gccgagcact   6780
tccagcctgg ggattgtgtt ctggaaactg acatcgcgtc gtttgataaa agtgaggacg   6840
```

```
acgccatggc tctgaccgcg ttaatgattc tggaagactt aggtgtggac gcagagctgt   6900
tgacgctgat tgaggcggct ttcggcgaaa tttcatcaat acatttgccc actaaaacta   6960
aatttaaatt cggagccatg atgaaatctg gaatgttcct cacactgttt gtgaacacag   7020
tcattaacat tgtaatcgca agcagagtgt tgagagaacg gctaaccgga tcaccatgtg   7080
cagcattcat tggagatgac aatatcgtga aaggagtcaa atcggacaaa ttaatggcag   7140
acaggtgcgc cacctggttg aatatggaag tcaagattat agatgctgtg gtgggcgaga   7200
aagcgcctta tttctgtgga gggtttattt tgtgtgactc cgtgaccggc acagcgtgcc   7260
gtgtggcaga cccccctaaaa aggctgttta agcttggcaa acctctggca gcagacgatg   7320
aacatgatga tgacaggaga agggcattgc atgaagagtc aacacgctgg aaccgagtgg   7380
gtattctttc agagctgtgc aaggcagtag aatcaaggta tgaaaccgta ggaacttcca   7440
tcatagttat ggccatgact actctagcta gcagtgttaa atcattcagc tacctgagag   7500
gggcccctat aactctctac ggctaacctg aatggactac gacatagtct agtccgccaa   7560
gatgttcccg ttccagccaa tgtatccgat gcagccaatg ccctatcgca acccgttcgc   7620
ggccccgcgc aggccctggt tccccagaac cgaccctttt ctggcgatgc aggtgcagga   7680
attaacccgc tcgatggcta acctgacgtt caagcaacgc cgggacgcgc cacctgaggg   7740
gccatccgct aagaaaccga agaaggaggc ctcgcaaaaa cagaaagggg gaggccaagg   7800
gaagaagaag aagaaccaag ggaagaagaa ggctaagaca gggccgccta atccgaaggc   7860
acagaatgga aacaagaaga agaccaacaa gaaaccaggc aagagacagc gcatggtcat   7920
gaaattggaa tctgacaaga cgttcccaat catgttggaa gggaagataa acggctacgc   7980
ttgtgtggtc ggagggaagt tattcaggcc gatgcatgtg gaaggcaaga tcgacaacga   8040
cgttctggcc gcgcttaaga cgaagaaagc atccaaatac gatcttgagt atgcagatgt   8100
gccacagaac atgcgggccg atacattcaa atacacccat gagaaacccc aaggctatta   8160
cagctggcat catggagcag tccaatatga aaatgggcgt ttcacggtgc cgaaaggagt   8220
tggggccaag ggagacagcg gacgacccat tctggataac cagggacggg tggtcgctat   8280
tgtgctggga ggtgtgaatg aaggatctag gacagccctt tcagtcgtca tgtggaacga   8340
gaagggagtt accgtgaagt atactccgga gaactgcgag caatggtcac tagtgaccac   8400
catgtgtctg ctcgccaatg tgacgttccc atgtgctcaa ccaccaattt gctacgacag   8460
aaaaccagca gagactttgg ccatgctcag cgttaacgtt gacaacccgg gctacgatga   8520
gctgctggaa gcagctgtta agtgccccgg aaggaaaagg agatccaccg aggagctgtt   8580
taaggagtat aagctaacgc gcccttacat ggccagatgc atcagatgtg cagttgggag   8640
ctgccatagt ccaatagcaa tcgaggcagt aaaagagcgac gggcacgacg gttatgttag   8700
acttcagact tcctcgcagt atggcctgga ttcctccggc aacttaaagg gcaggaccat   8760
gcggtatgac atgcacggga ccattaaaga gataccacta catcaagtgt cactccatac   8820
atctcgcccg tgtcacattg tggatgggca cggttatttc ctgcttgcca ggtgcccggc   8880
aggggactcc atcaccatgg aatttaagaa agattccgtc acacactcct gctcggtgcc   8940
gtatgaagtg aaatttaatc ctgtaggcag agaactctat actcatcccc cagaacacgg   9000
agtagagcaa gcgtgccaag tctacgcaca tgatgcacag aacagaggag cttatgtcga   9060
gatgcacctc ccgggctcag aagtggacag cagtttggtt tccttgagcg gcagttcagt   9120
caccgtgaca cctcctgttg ggactagcgc cctggtggaa tgcgagtgtg gcggcacaaa   9180
```

-continued

```
gatctccgag accatcaaca agacaaaaca gttcagccag tgcacaaaga aggagcagtg   9240
cagagcatat cggctgcaga acgataagtg ggtgtataat tctgacaaac tgcccaaagc   9300
agcgggagcc accttaaaag gaaaactgca tgtcccattc ttgctggcag acggcaaatg   9360
caccgtgcct ctagcaccag aacctatgat aacctttggt ttcagatcag tgtcactgaa   9420
actgcaccct aagaatccca catatctaac cacccgccaa cttgctgatg agcctcacta   9480
cacgcacgag ctcatatctg aaccagctgt taggaatttt accgtcaccg aaaaagggtg   9540
ggagtttgta tggggaaacc acccgccgaa aaggttttgg gcacaggaaa cagcacccgg   9600
aaatccacat gggctaccgc acgaggtgat aactcattat taccacagat accctatgtc   9660
caccatcctg ggtttgtcaa tttgtgccgc cattgcaacc gtttccgttg cagcgtctac   9720
ctggctgttt tgcagatcta gagttgcgtg cctaactcct taccggctaa cacctaacgc   9780
taggatacca ttttgtctgg ctgtgctttg ctgcgcccgc actgcccggg ccgagaccac   9840
ctgggagtcc ttggatcacc tatggaacaa taaccaacag atgttctgga ttcaattgct   9900
gatccctctg gccgccttga tcgtagtgac tcgcctgctc aggtgcgtgt gctgtgtcgt   9960
gccttttta gtcatggccg gcgccgcagg cgccggcgcc tacgagcacg cgaccacgat  10020
gccgagccaa gcgggaatct cgtataacac tatagtcaac agagcaggct acgcaccact  10080
ccctatcagc ataacaccaa caaagatcaa gctgatacct acagtgaact tggagtacgt  10140
cacctgccac tacaaaacag gaatggattc accagccatc aaatgctgcg gatctcagga  10200
atgcactcca acttacaggc ctgatgaaca gtgcaaagtc ttcacagggg tttacccgtt  10260
catgtggggt ggtgcatatt gcttttgcga cactgagaac acccaagtca gcaaggccta  10320
cgtaatgaaa tctgacgact gccttgcgga tcatgctgaa gcatataaag cgcacacagc  10380
ctcagtgcag gcgttcctca acatcacagt gggagaacac tctattgtga ctaccgtgta  10440
tgtgaatgga gaaactcctg tgaatttcaa tggggtcaaa ttaactgcag gtccgctttc  10500
cacagcttgg acaccctttg atcgcaaaat cgtgcagtat gccggggaga tctataatta  10560
tgattttcct gagtatgggg caggacaacc aggagcattt ggagatatac aatccagaac  10620
agtctcaagc tcagatctgt atgccaatac caacctagtg ctgcagagac ccaaagcagg  10680
agcgatccac gtgccataca ctcaggcacc ttcgggtttt gagcaatgga agaaagataa  10740
agctccatca ttgaaattta ccgccccttt cggatgcgaa atatatacaa accccattcg  10800
cgccgaaaac tgtgctgtag ggtcaattcc attagccttt gacattcccg acgccttgtt  10860
caccagggtg tcagaaacac cgacactttc agcggccgaa tgcactctta acgagtgcgt  10920
gtattcttcc gactttggtg ggatcgccac ggtcaagtac tcggccagca agtcaggcaa  10980
gtgcgcagtc catgtgccat cagggactgc taccctaaaa gaagcagcag tcgagctaac  11040
cgagcaaggg tcggcgacta tccatttctc gaccgcaaat atccacccgg agttcaggct  11100
ccaaatatgc acatcatatg ttacgtgcaa aggtgattgt caccccccga aagaccatat  11160
tgtgacacac cctcagtatc acgcccaaac atttacagcc gcggtgtcaa aaaccgcgtg  11220
gacgtggtta acatccctgc tgggaggatc agccgtaatt attataattg gcttggtgct  11280
ggctactatt gtggccatgt acgtgctgac caaccagaaa cataattgaa tacagcagca  11340
attggcaagc tgcttacata gaactcgcgg cgattggcat gccgccttaa aatttttatt  11400
ttattttttc ttttcttttc cgaatcggat tttgttttta atatttc                11447
```

<210> SEQ ID NO 18
<211> LENGTH: 558

<212> TYPE: RNA
<213> ORGANISM: Artificial Sequence
<220> FEATURE:
<223> OTHER INFORMATION: Synthetic construct, VEEV rep RNA nt 6966-7523
with silent mutations

<400> SEQUENCE: 18
aaguucggcg ccaugaugaa guccggcaug uuucugaccc uguucgugaa caccgugauc 60
aacaucguga ucgccagccg ggugcugaga gagagacuga caggaucucc uugcgccgcc 120
uucaucggcg acgacaauau cgugaagggc gugaaguccg acaagcugau ggccgauaga 180
ugcgccaccu ggcugaacau ggaagugaag aucaucgacg ccgucguggg cgagaaggcc 240
ccuuauuuuu gcggcggcuu cauccugugc gacagcguga caggcacagc cugcagaguu 300
gccgauccuc ugaagcggcu guucaagcug ggaaaaccuc uggccgccga cgacgagcac 360
gacgacgaua gacguagagc ccugcacgag gaauccacca gauggaacag agugggcauc 420
cugagcgagc ugugcaaggc cguggaaagc agauacgaga cagugggcac cagcaucauu 480
gugauggcaa ugaccacacu ggccagcagc gugaaaagcu ucagcuaccu aaggggcgcc 540
ccuaucacac uguacggc 558

<210> SEQ ID NO 19
<211> LENGTH: 1821
<212> TYPE: RNA
<213> ORGANISM: Artificial Sequence
<220> FEATURE:
<223> OTHER INFORMATION: Synthetic construct, RNA nsP4 engineered RNA
+silent mutations

<400> SEQUENCE: 19
uacaucuuuu ccuccgacac cggucaaggg cauuuacaac aaaaaucagu aaggcaaacg 60
gugcuauccg aaguggugug ggagaggacc gaauuggaga uuucguaugc cccgcgccuc 120
gaccaagaaa aagaagaauu acuacgcaag aaauuacagu uaaaucccac accugcuaac 180
agaagcagau accaguccag gaagguggag aacaugaaag ccauaacagc uagacguauu 240
cugcaaggcc uagggcauua uuugaaggca gaaggaaaag uggagugcua ccgaacccug 300
cauccuguuc cuuuguauuc aucuagugug aaccgugccu uuucaagccc caaggucgca 360
guggaagccu guaacgccau guugaaagag aacuuuccga cuguggcuuc uuacuguauu 420
auuccagagu acgaugccua uuuggacaug guugacggag cuucaugcug cuuagacacu 480
gccaguuuuu gcccugcaaa gcugcgcagc uuuccaaaga aacacuccua uuuggaaccc 540
acaauacgau cggcagugcc uucagcgauc cagaacacgc uccagaacgu ccuggcagcu 600
gccacaaaaa gaaauugcaa ugucacgcaa augagagaau ugcccguauu ggauucggcg 660
gccuuuaaug uggaaugcuu caagaaauau gcguguaaua augaauauug ggaaacguuu 720
aaagaaaacc ccaucaggcu uacugaagaa aacgugguaa auuacauuac caaauuaaaa 780
ggaccaaaag cugcugcucu uuuugcgaag acacauaauu ugaauauguu gcaggacaua 840
ccaauggaca gguuuguaau ggacuuaaag agagacguga aagugacucc aggaacaaaa 900
cauacugaag aacggcccaa gguacaggug auccaggcug ccgauccgcu agcaacagcg 960
uaucugugcg gaauccaccg agagcugguu aggagauuaa augcgguccu gcuuccgaac 1020
auucauacac uguuugauau gucggcugaa gacuuugacg cuauuauagc cgagcacuuc 1080
cagccugggg auuguguucu ggaaacugac aucgcgucgu uugauaaaag ugaggacgac 1140
gccauggcuc ugaccgcguu aaugauucug gaagacuuag guguggacgc agagcuguug 1200
acgcugauug aggcggcuuu cggcgaaauu ucaucaauac auuugcccac uaaaacuaaa 1260
uuuaaguucg gcgccaugau gaaguccggc auguuucuga cccuguucgu gaacaccgug 1320
aucaacaucg ugaucgccag ccgggugcug agagagagac ugacaggauc uccuugcgcc 1380
gccuucaucg gcgacgacaa uaucgugaag ggcgugaagu ccgacaagcu gauggccgau 1440
agaugcgcca ccuggcugaa cauggaagug aagaucaucg acgccgucgu gggcgagaag 1500
gccccuuauu uuugcggcgg cuucauccug ugcgacagcg ugacaggcac agccugcaga 1560
guugccgauc cucugaagcg gcuguucaag cugggaaaac cucuggccgc cgacgacgag 1620
cacgacgacg auagacguag agcccugcac gaggaaucca ccagauggaa cagagugggc 1680
auccugagcg agcugugcaa ggccguggaa agcagauacg agacaguggg caccagcauc 1740
auugugaugg caaugaccac acuggccagc agcgugaaaa gcuucagcua ccuaaggggc 1800
gccccuauca cacuguacgg c 1821

<210> SEQ ID NO 20
<211> LENGTH: 7561
<212> TYPE: RNA
<213> ORGANISM: Artificial Sequence
<220> FEATURE:
<223> OTHER INFORMATION: Synthetic construct, C01 nsP1-4 ORF and SGP RNA
<400> SEQUENCE: 20
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440

-continued

```
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgcuggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggugugUaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggucg ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccuggugguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcaguguga agaccaugcc auuaagcuua gcauguugac caagaaagcu ugucugcauc   3780
```

ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggaggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauagggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaagu acgccugcaa caacgaguac ugggagacau 6420
ucaaagagaa ccccauccgg cugaccgagg aaaacguggu caacuacauc accaagcuga 6480
agggccccaa agccgccgcu cuguuugcca agacacacaa ccugaacaug cugcaggaca 6540
uccccaugga cagauucgug auggaccuga agcgggacgu gaaagugacc ccuggcacca 6600
agcacaccga ggaacggccu aaggugcaag ugauccaggc cgcugauccu cuggccacag 6660
ccuaucugug uggcauccac agagaacucg ugcggagacu gaaugccgug cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg cugaugauuc uggaagaucu cggaguggac gccgagcugc 6900
ugacacugau ugaagccgcc uuuggcgaga ucagcagcau ccaucugccu accaagacca 6960
aguucaaguu cggcgccaug augaaaucug gaauguuccu cacacuguuu gugaacacag 7020
ucauuaacau uguaaucgca agcagagugu ugagagaacg gcuaacaggc agcccuugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 21
<211> LENGTH: 7561
<212> TYPE: RNA
<213> ORGANISM: Artificial Sequence
<220> FEATURE:
<223> OTHER INFORMATION: Synthetic construct, C02 nsP1-4 ORF and SGP RNA

<400> SEQUENCE: 21
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauaugccg uggauggccc uacaagccug uaccaccagg 540
ccaacaaggg cgucagagug gccuacugga ucggcuucga caccacaccu uucauguuca 600

```
agaaccuggc uggcgcuuac cccagcuaca gcacaaacug ggccgacgaa accguguuaa    660
cggcucguaa cauaggccua ugcagcucug acguuaugga gcggucacgu agagggaugu    720
ccauucuuag aaagaaguau uugaaaccau ccaacaaugu ucuauucucu guuggcucga    780
ccaucuacca cgagaagagg gacuuacuga ggagcuggca ccugccgucu guauuucacu    840
uacguggcaa gcaaaauuac acaugucggu gugagacuau aguuaguugc gacggguacg    900
ucguuaaaag aauagcuauc aguccaggcc uguaugggaa gccuucaggc uaugcugcua    960
cgaugcaccg cgagggauuc uugugcugca aagugacaga cacauugaac ggggagaggg   1020
ucucuuuucc cgugugcacg uaugugccag cuacauugug ugaccaaaug acuggcauac   1080
uggcaacaga ugucagugcg gacgacgcgc aaaaacugcu gguugggcuc aaccagcgua   1140
uagucgucaa cggucgcacc cagagaaaca ccaauaccau gaaaaauuac cuuuugcccg   1200
uaguggccca ggcauuugcu aggugggcaa aggaauauaa ggaagaucaa gaagaugaaa   1260
ggccacuagg acuacgagau agacaguuag ucauggggug uuguugggcu uuuagaaggc   1320
acaagauaac aucuauuuau aagcgcccgg auacccaaac caucaucaaa gugaacagcg   1380
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgcuggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa gguguguaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
```

-continued

```
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggucccg ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccuggugguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcaguguga agaccaugcc auuaagcuua gcauguugac caagaaagcu ugucugcauc   3780
ugaaucccgg cggaaccugu gucagcauag guuaugguua cgcugacagg gccagcgaaa   3840
gcaucauugg ugcuauagcg cggcaguuca aguuuucccg gguaugcaaa ccgaaauccu   3900
cacuugaaga gacggaaguu cuguuuguau ucauugggua cgaucgcaag gcccguacgc   3960
acaauccuua caagcuuuca ucaaccuuga ccaacauuua uacagguucc agacuccacg   4020
aagccggaug ugcacccuca uaucaugugg ugcgagggga uauugccacg gccaccgaag   4080
gagugauuau aaaugcugcu aacagcaaag gacaaccugg cggagggggug ugcggagcgc   4140
uguauaagaa auucccggaa agcuucgauu uacagccgau cgaaguagga aaagcgcgac   4200
uggucaaagg ugcagcuaaa cauaucauuc augccguagg accaaacuuc aacaaaguuu   4260
cggagguuga aggugacaaa caguuggcag aggcuuauga guccaucgcu aagauuguca   4320
acgauaacaa uuacaaguca guagcgauuc cacuguuguc caccggcauc uuuuccggga   4380
acaaagaucg acuaacccaa ucauugaacc auuugcugac agcuuuagac accacugaug   4440
cagauguagc cauauacugc agggacaaga aaugggaaau gacucucaag gaagcagugg   4500
cuaggagaga agcaguggag gagauaugca uauccgacga cucuucagug acagaaccug   4560
augcagagcu ggugagggug cauccgaaga guucuuuggc uggaaggaag ggcuacagca   4620
caagcgaugg caaaacuuuc ucauauuugg aagggaccaa guuucaccag gcggccaagg   4680
auauagcaga aauuaaugcc auguggcccg uugcaacgga ggccaaugag cagguaugca   4740
uguauauccu cggagaaagc augagcagua uuaggucgaa augccccguc gaagagucgg   4800
aagccuccac accaccuagc acgcugccuu gcuugugcau ccaugccaug acuccagaaa   4860
gaguacagcg ccuaaaagcc ucacguccag aacaaauuac ugugugcuca uccuuuccau   4920
ugccgaagua uagaaucacu ggugugcaga agauccaaug cucccagccu auauuguucu   4980
caccgaaagu gccugcguau auucauccaa ggaaguaucu cguggaaaca ccaccgguag   5040
acgagacucc ggagccaucg gcagagaacc aauccacaga ggggacaccu gaacaaccac   5100
cacuuauaac cgaggaugag accaggacua gaacgccuga gccgaucauc aucgaagagg   5160
aagaagagga uagcauaagu uugcugucag auggcccgac ccaccaggug cugcaagucg   5220
aggcagacau ucacgggccg cccucuguau cuagcucauc cugguccauu ccucaugcau   5280
ccgacuuuga uguggacagu uuauccauac uugacacccu ggagggagcu agcgugacca   5340
```

gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu agguguggac gcagagcugu 6900
ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 22
<211> LENGTH: 7561

```
<212> TYPE: RNA
<213> ORGANISM: Artificial Sequence
<220> FEATURE:
<223> OTHER INFORMATION: Synthetic construct, C03 nsP1-4 ORF and SGP RNA

<400> SEQUENCE: 22

augggcggcg caugagagaa gcccagacca auuaccuacc caaaauggag aaaguucacg     60

uugacaucga ggaagacagc ccauuccuca gagcuuugca gcggagcuuc ccgcaguuug    120

agguagaagc caagcagguc acugauaaug accaugcuaa ugccagagcg uuuucgcauc    180

uggcuucaaa acugaucgaa acggaggugg acccauccga cacgauccuu gacauuggaa    240

gugcgcccgc ccgcagaaug uauucuaagc acaaguauca uuguaucugu ccgaugagau    300

gugcggaaga uccggacaga uuguauaagu augcaacuaa gcugaagaaa aacuguaagg    360

aaauaacuga uaaggaauug gacaagaaaa ugaaggagcu cgccgccguc augagcgacc    420

cugaccugga aacugagacu augugccucc acgacgacga gucgugucgc uacgaagggc    480

aagucgcugu uuaccaggau guauacgcgg uugacggacc gacaagucuc uaucaccaag    540

ccaauaaggg aguuagaguc gccuacugga uaggcuuuga caccaccccu uuuauguuua    600

agaacuuggc uggagcauau ccaucauacu cuaccaacug ggccgacgaa accguguuaa    660

cggcucguaa cauaggccua ugcagcucug acguuaugga gcggucacgu agagggaugu    720

ccauucuuag aaagaaguau uugaaaccau ccaacaaugu ucuauucucu guuggcucga    780

ccaucuacca cgagaagagg gacuuacuga ggagcuggca ccugccgucu guauuucacu    840

uacguggcaa gcaaaauuac acaugucggu gugagacuau aguuaguugc gacggguacg    900

ucguuaaaag aauagcuauc aguccaggcc uguaugggaa gccuucaggc uaugcugcua    960

cgaugcaccg cgagggauuc uugugcugca aagugacaga cacauugaac ggggagaggg   1020

ucucuuuucc cgugugcacg uaugugccag cuacauugug ugaccaaaug acuggcauac   1080

uggcaacaga ugucagugcg gacgacgcgc aaaaacugcu gguugggcuc aaccagcgua   1140

uagucgucaa cggucgcacc cagagaaaca ccaauaccau gaaaaauuac cuuuugcccg   1200

uaguggccca ggcauuugcu aggugggcaa aggaauauaa ggaagaucaa gaagaugaaa   1260

ggccacuagg acuacgagau agacaguuag ucauggggug uuguugggcu uuuagaaggc   1320

acaagauaac aucuauuuau aagcgcccgg auacccaaac caucaucaaa gugaacagcg   1380

auuuccacuc auucgugcug cccaggauag gcaguaacac auuggagauc gggcugagaa   1440

caagaaucag gaaaauguua gaggagcaca aggagccguc accucucauu accgccgagg   1500

acguacaaga agcuaagugc gcagccgaug aggcuaagga ggugcgugaa gccgaggagu   1560

ugcgcgcagc ucuaccaccu uuggcagcug auguugagga gcccacucug gaagccgaug   1620

ucgacuugau guuacaagag gcuggggccg gcucagugga gacaccucgu ggcuugauaa   1680

agguuaccag cuacgcuggc gaggacaaga ucggcucuua cgcugugcuu ucuccgcagg   1740

cuguacucaa gagugaaaaa uuaucuugca uccacccucu cgcugaacaa gucauaguga   1800

uaacacacuc uggccgaaaa gggcguuaug ccguggaacc auaccauggu aaaguagugg   1860

ugccagaggg acaugcaaua cccguccagg acuuucaagc ucugagugaa agugccacca   1920

uuguguacaa cgaacgugag uucguaaaca gguaccugca ccauauugcc acacauggag   1980

gagcgcugaa cacugaugaa gaauauuaca aaacugucaa gcccagcgag cacgacggcg   2040

aauaccugua cgacaucgac aggaaacagu gcgucaagaa agaacuaguc acugggcuag   2100

ggcucacagg cgagcuggug gauccucccu uccaugaauu cgccuacgag agucugagaa   2160
```

-continued

```
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa gguguguaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggucog ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccuggugguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc cuacaaguac caccacuacc   3720
agcagugcga ggaccacgcc aucaagcuga gcaugcugac caagaaggcc ugccugcauc   3780
ugaaucccgg cggaaccugu gucagcauag guuaugguua cgcugacagg gccagcgaaa   3840
gcaucauugg ugcuauagcg cggcaguuca aguuucccg gguaugcaaa ccgaaauccu   3900
cacuugaaga gacggaaguu cuguuuguau ucaucggcua cgacagaaag gcccguacgc   3960
acaauccuua caagcuuuca ucaaccuuga ccaacauuua uacagguucc agacuccacg   4020
aagccggaug ugcacccuca uaucaugugg ugcgaggga uauugccacg gccaccgaag   4080
gagugauuau aaaugcugcu aacagcaaag gacaaccugg cggagggug ugcggagcgc   4140
uguauaagaa auucccggaa agcuucgauu uacagccgau cgaaguagga aaagcgcgac   4200
uggucaaagg ugcagcuaaa cauaucauuc augccguagg accaaacuuc aacaaaguuu   4260
cggagguuga aggugacaaa caguuggcag aggcuuauga guccaucgcu aagauuguca   4320
acgauaacaa uuacaaguca guagcgauuc cacuguuguc caccggcauc uuuuccggga   4380
acaaagaucg acuaacccaa ucauugaacc auuugcugac agcuuuagac accacugaug   4440
cagauguagc cauauacugc agggacaaga aaugggaaau gacucucaag gaagcagugg   4500
cuaggagaga agcaguggag gagauaugca uauccgacga cucuucagug acagaaccug   4560
```

-continued augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu agguguggac gcagagcugu 6900

-continued ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 23
<211> LENGTH: 7561
<212> TYPE: RNA
<213> ORGANISM: Artificial Sequence
<220> FEATURE:
<223> OTHER INFORMATION: Synthetic construct, C04 nsP1-4 ORF and SGP RNA

<400> SEQUENCE: 23
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucauggggug uuguugggcu uuuagaaggc 1320
acaagauaac aucuauuuau aagcgcccgg auacccaaac caucaucaaa gugaacagcg 1380

-continued

```
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgcuggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggguguguaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggucccg ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccugguggu ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
```

-continued agcaguguga agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaaccccua caagcugagc agcacccuga ccaacaucua caccggcagc agacugcacg 4020
aagccggaug ugcacccuca uaucaugugg ugcgagggga uauugccaca gccacagaag 4080
gagugauuau aaaugcugcu aacagcaaag gacaaccugg cggagggggug ugcggagcgc 4140 uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauagggguga 5640 uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu aggugguggac gcagagcugu 6900 ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 24
<211> LENGTH: 7561
<212> TYPE: RNA
<213> ORGANISM: Artificial Sequence
<220> FEATURE:
<223> OTHER INFORMATION: Synthetic construct, C05 nsP1-4 ORF and SGP RNA

<400> SEQUENCE: 24
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440
caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaagccgaug 1620
ucgacuugau guuacaagag gcuggggccg gcucagugga gacaccucgu ggcuugauaa 1680
agguuaccag cuacgcuggc gaggacaaga ucggcucuua cgcugugcuu ucuccgcagg 1740
cuguacucaa gagcgagaag cugagcugca uucacccucu ggccgagcaa gugaucguga 1800
ucacacacag cggccggaag ggcagauaug ccguggaacc uuaucacggc aagguggugg 1860
ugccugaggg acacgcuauu ccagugcagg acuuucaggc ccugagcgag ucugccacca 1920
ucguguacaa cgagcgcgag uucgugaaca gauaccugca ccacauugcc acacacggcg 1980
gagcccugaa caccgacgaa gaguacuaca agaccgugaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggauagcgug cugcugaacg gcugcaagca ccccguagag acccuguaua 2400
uugacgaagc uuuugcuugu caugcaggua cucucagagc gcucauagcc auuauaagac 2460
cuaaaaaggc agugcucugc ggggauccua agcagugcgg cuucuucaac augaugugcc 2520
ugaaggugca cuucaaccac gagaucugca cccaggugu ccacaaaagc aucucucgcc 2580
guugcacuaa aucugugacu ucggucgucu caaccuuguu uuacgacaaa aaaaugagaa 2640
cgacgaaucc gaaagagacu aagauuguga uugacacuac cggcaguacc aaaccuaagc 2700
aggacgaucu cauucucacu uguuucagag ggugggugaa gcaguugcaa auagauuaca 2760
aaggcaacga aauaaugacg gcagcugccu cucaagggcu gacccguaaa ggguguguaug 2820 ccguucggua caaggugaau gaaaauccuc uguacgcacc caccucagaa caugugaacg 2880
uccuacugac ccgcacggag gaccgcaucg uguggaaaac acuagccggc gacccaugga 2940

```
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggucccg ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccugguggguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcaguguga agaccaugcc auuaagcuua gcauguugac caagaaagcu ugucugcauc   3780
ugaaucccgg cggaaccugu gucagcauag guuaugguua cgcugacagg gccagcgaaa   3840
gcaucauugg ugcuauagcg cggcaguuca aguuucccg gguaugcaaa ccgaaauccu   3900
cacuugaaga gacggaaguu cuguuuguau ucauugggua cgaucgcaag gcccguacgc   3960
acaauccuua caagcuuuca ucaaccuuga ccaacauuua uacagguucc agacuccacg   4020
aagccggaug ugcacccuca uaucaugugg ugcgagggga uauugccacg gccaccgaag   4080
gagugauuau aaaugcugcu aacagcaaag gacaaccugg cggagggggug ugcggagcgc   4140
uguauaagaa auucccggaa agcuucgauu uacagccgau cgaaguagga aaagcgcgac   4200
uggucaaagg ugcagcuaaa cauaucauuc augccguagg accaaacuuc aacaaaguuu   4260
cggagguuga aggugacaaa caguuggcag aggcuuauga guccaucgcu aagauuguca   4320
acgauaacaa uuacaaguca guagcgauuc cacuguuguc caccggcauc uuuuccggga   4380
acaaagaucg acuaacccaa ucauugaacc auuugcugac agcuuuagac accacugaug   4440
cagauguagc cauauacugc agggacaaga aaugggaaau gacucucaag gaagcagugg   4500
cuaggagaga agcaguggag gagauaugca uauccgacga cucuucagug acagaaccug   4560
augcagagcu ggugagggug cauccgaaga guucuuuggc uggaaggaag ggcuacagca   4620
caagcgaugg caaaacuuuc ucauauuugg aagggaccaa guuucaccag gcggccaagg   4680
auauagcaga aauuaaugcc auguggcccg uugcaacgga ggccaaugag cagguaugca   4740
uguauauccu cggagaaagc augagcagua uuaggucgaa augccccguc gaagagucgg   4800
aagccuccac accaccuagc acgcugccuu gcuugugcau ccaugccaug acuccagaaa   4860
gaguacagcg ccuaaaagcc ucacguccag aacaaauuac ugugugcuca uccuuuccau   4920
ugccgaagua uagaaucacu ggugugcaga agauccaaug cucccagccu auauuguucu   4980
caccgaaagu gccugcguau auucauccaa ggaaguaucu cguggaaaca ccaccgguag   5040
acgagacucc ggagccaucg gcagagaacc aauccacaga ggggacaccu gaacaaccac   5100
cacuuauaac cgaggaugag accaggacua gaacgccuga gccgaucauc aucgaagagg   5160
aagaagagga uagcauaagu uugcugucag auggcccgac ccaccaggug cugcaagucg   5220
aggcagacau ucacgggccg cccucuguau cuagcucauc cugguccauu ccucaugcau   5280
```

ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uucccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu aggugugggac gcagagcugu 6900
ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 25
<211> LENGTH: 7561
<212> TYPE: RNA
<213> ORGANISM: Artificial Sequence
<220> FEATURE:
<223> OTHER INFORMATION: Synthetic construct, C06 nsP1-4 ORF and SGP RNA

<400> SEQUENCE: 25
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggccagaaa uaucggccug uguagcagcg acgugaugga aagauccaga cggggcauga 720
gcauccugcg gaagaaguac cugaagccua gcaacaacgu gcuguucagc gugggcagca 780
ccaucuacca cgagaagagg gaccugcugc ggagcuggca ucugccuucc guguuucacc 840
ugagaggcaa gcagaacuac accuguagau gcgagacaau cguguccugc gacggcuacg 900
uggucaagcg gaucgccauu ucuccuggcc uguacggcaa gccuucuggc uaugccgcca 960
ccaugcacag agaaggcuuu cuguguugca aagugaccga cacacugaac ggcgagcggg 1020
uguccuuucc uguguguacc uaugugcccg ccacacugug cgaucagaug acaggcauuc 1080
uggccaccga cgugucagcc gacgaugccc agaaacugcu cgugggccug aaccagagaa 1140
ucguggucaa cggcagaacc cagcggaaca ccaacaccau gaagaacuac cugcugccug 1200
ugguggccca ggccuuugcc agaugggcca aagaguacaa agaggaucaa gaggacgagc 1260
ggccccuggg ccugagagau agacaacugg ucaugggcug cugcugggcc uucagaaggc 1320
acaagaucac cagcaucuac aagcggcccg acacacagac caucaucaaa gugaacagcg 1380
acuuccacag cuucgugcug ccucggaucg gcagcaacac acuggaaauc ggccugcgga 1440
cccggaucag aaagaugcug gaagaacaca aagagcccuc uccacugauc accgccgagg 1500
augugcaaga ggccaaaugu gccgccgacg aggcuaaaga agugcgcgaa gccgaggaac 1560
ugagagccgc acuuccuccu cuggccgccg auguugaaga acccacucug gaagccgacg 1620
ucgacuugau guuacaagag gcuggggccg gcucagugga gacaccucgu ggcuugauaa 1680
agguuaccag cuacgcuggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040
aauaccugua cgacaucgac aggaaacagu gcgucaagaa agaacuaguc acugggcuag 2100

-continued ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaaaagc aucucucgcc 2580
guugcacuaa aucugugacu ucggucgucu caaccuuguu uuacgacaaa aaaaugagaa 2640
cgacgaaucc gaaagagacu aagauuguga uugacacuac cggcaguacc aaaccuaagc 2700
aggacgaucu cauucucacu uguuucagag ggugggugaa gcaguugcaa auagauuaca 2760
aaggcaacga aauaaugacg gcagcugccu cucaagggcu gacccguaaa ggguguguaug 2820 ccguucggua caaggugaau gaaaauccuc uguacgcacc caccucagaa caugugaacg 2880
uccuacugac ccgcacggag gaccgcaucg uguggaaaac acuagccggc gacccaugga 2940
uaaaaacacu gacugccaag uacccuggga auuucacugc cacgauagag gaguggcaag 3000
cagagcauga ugccaucaug aggcacaucu uggagagacc ggacccuacc gacgucuucc 3060
agaauaaggc aaacgugugu ugggccaagg cuuuagugcc ggugcugaag accgcuggca 3120
uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggucg ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480 ucccuccacca uaaugaacac ccacagagug acuuuucuuc auucgucagc aaauugaagg 3540
gcagaacugu ccugguggguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720
agcaguguga agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggaggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauagggUga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu agguguggac gcagagcugu 6900
ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 26
<211> LENGTH: 7561
<212> TYPE: RNA
<213> ORGANISM: Artificial Sequence
<220> FEATURE:
<223> OTHER INFORMATION: Synthetic construct, C07 nsP1-4 ORF and SGP RNA

<400> SEQUENCE: 26
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440
caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaagccgaug 1620
ucgacuugau guuacaagag gcuggggccg gcucagugga gacaccucgu ggcuugauaa 1680
agguuaccag cuacgcuggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaagagc aucagcagac 2580
ggugcaccaa gagcgugacc agcguggugu cuacccuguu cuacgacaag aagaugcgga 2640
cgacaaaccc caaagagaca aagaucguca ucgacaccac cggcagcacc aagccuaagc 2700
aggacgaucu gauccugacc ugcuucagag gcugggucaa gcagcugcag aucgacuaca 2760
agggcaacga gaucaugacc gccgcugccu cucagggccu gacaagaaaa ggcguguacg 2820
ccgugcggua caaagugaac gagaacccuc uguacgcccc uaccagcgag caugugaaug 2880
ugcugcugac ccggaccgag gaccggaucg uuuggaaaac acuggccggc gaucccugga 2940
ucaagacccu gacagccaag uaucccggca acuucaccgc caccaucgag gaauggcagg 3000
ccgagcacga ugccaucaug cggcacaucc uggaaagacc cgauccuacc gacguguucc 3060
agaacaaggc caacgugugc ugggccaaag cucuggugcc ugugcugaaa accgccggca 3120
ucgauaugac caccgagcag uggaacaccg uggacuacuu cgagacagac aaggcccaca 3180
gcgccgagau cgugcugaau cagcugugcg ugcgguucuu cggccuggau cuggauagcg 3240
gccuguucuc ugcuccuacc gugccucuga gcauccggaa caaccacugg gacaacagcc 3300
ccucuccuaa uauguacggc cugaacaaag aagucgugcg gcagcugagc agaagauacc 3360
cacagcugcc uagagccgug gccacaggca gaguguacga caugaauacc ggcacacugc 3420
ggaacuacga ccccagaauc aaucuggugc ccgugaacag aaggcugccc cacgcucugg 3480
uucugcacca caaugagcac ccucagagcg acuucagcag cuucguguccc aagcugaagg 3540
gcagaaccgu gcugguugug ggcgagaagc ugucugugcc uggcaagaug guggacuggc 3600
ugagcgauag acccgaggcc accuuuagag ccagacugga ccuuggaauc ccuggcgacg 3660

-continued ugcccaaaua cgacaucauc uucgugaacg ugcggacgcc cuacaaguac caccacuacc 3720
agcagugcga ggaccacgcc aucaagcuga gcaugcugac caagaaggcc ugccugcacc 3780
ugaauccugg cggcaccugu gugucuaucg gcuacggcua ugccgacaga gccagcgagu 3840
cuaucaucgg cgccauugcc agacaguuca aguucagcag agugugcaag cccaagagca 3900
gccuggaaga gacagaggug cuguucgugu ucaucggcua ugaccggaag gcccguacgc 3960
acaauccuua caagcuuuca ucaaccuuga ccaacauuua uacagguucc agacuccacg 4020
aagccggaug ugcacccuca uaucaugugg ugcgaggga uauugccacg gccaccgaag 4080
gagugauuau aaaugcugcu aacagcaaag gacaaccugg cggagggggug ugcggagcgc 4140 uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauagggguga 5640 uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu agguguggac gcagagcugu 6900
ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 27
<211> LENGTH: 7561
<212> TYPE: RNA
<213> ORGANISM: Artificial Sequence
<220> FEATURE:
<223> OTHER INFORMATION: Synthetic construct, C08 nsP1-4 ORF and SGP RNA

<400> SEQUENCE: 27
augggcggcg caugagagaa gcccagacca auuaccuacc caaaauggaa aaggugcacg 60
uggacaucga agaggacagc ccauuccuga gagcccugca gagaagcuuc ccucaguucg 120
agguggaagc caaacaagug accgacaacg aucacgccaa cgcgagggcc uucucucacc 180
ucgcaagcaa gcugaucgag acagaggugg accccagcga caccauccug gauauuggau 240
cugccccugc cagaagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480

-continued aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuccc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440
caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaagccgaug 1620
ucgacuugau guuacaagag gcuggggccg gcucagugga gacaccucgu ggcuugauaa 1680
agguuaccag cuacgcuggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaaaagc aucucucgcc 2580
guugcacuaa aucugugacu ucggucgucu caaccuuguu uuacgacaaa aaaaugagaa 2640
cgacgaaucc gaaagagacu aagauuguga uugacacuac cggcaguacc aaaccuaagc 2700
aggacgaucu cauucucacu uguuucagag ggugggugaa gcaguugcaa auagauuaca 2760
aaggcaacga aauaaugacg gcagcugccu cucaagggcu gacccguaaa ggguguuaug 2820
ccguucggua caaggugaau gaaaauccuc uguacgcacc caccucagaa caugugaacg 2880
uccuacugac ccgcacggag gaccgcaucg uguggaaaac acuagccggc gacccaugga 2940
uaaaaacacu gacugccaag uacccuggga auuucacugc cacgauagag gaguggcaag 3000
cagagcauga ugccaucaug aggcacaucu uggagagacc ggacccuacc gacgucuucc 3060
agaauaaggc aaacgugugu ugggccaagg cuuuagugcc ggugcugaag accgcuggca 3120
uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggccg ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccuggugguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720
agcaguguga agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020
aagccggaug ugcacccuca uaucaugugg ugcgaggga uauugccacg gccaccgaag 4080
gagugauuau aaaugcugcu aacagcaaag gacaaccugg cggaggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220

-continued aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccacccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauagggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu agguguggac gcagagcugu 6900
ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 28
<211> LENGTH: 7561
<212> TYPE: RNA
<213> ORGANISM: Artificial Sequence
<220> FEATURE:
<223> OTHER INFORMATION: Synthetic construct, C09 nsP1-4 ORF and SGP RNA

<400> SEQUENCE: 28
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggccagaaa uaucggccug uguagcagcg acgugaugga aagauccaga cggggcauga 720
gcauccugcg gaagaaguac cugaagccua gcaacaacgu gcuguucagc gugggcagca 780
ccaucuacca cgagaagagg gaccugcugc ggagcuggca ucugccuucc guguuucacc 840
ugagaggcaa gcagaacuac accuguagau gcgagacaau cguguccugc gacggcuacg 900
uggucaagcg gaucgccauu ucuccuggcc uguacggcaa gccuucuggc uaugccgcca 960
ccaugcacag agaaggcuuu cuguguugca aagugaccga cacacugaac ggcgagcggg 1020
uguccuuucc ugugugtacc uaugugcccg ccacacugug cgaucagaug acaggcauuc 1080
uggccaccga cgugucagcc gacgaugccc agaaacugcu cgugggccug aaccagagaa 1140 ucgugguc aa cggcagaacc cagcggaaca ccaacaccau gaagaacuac cugcugccug 1200
ugguggccca ggccuuugcc agaugggcca aagaguacaa agaggaucaa gaggacgagc 1260
ggccccuggg ccugagagau agacaacugg ucaugggcug cugcugggcc uucagaaggc 1320
acaagaucac cagcaucuac aagcggcccg acacacagac caucaucaaa gugaacagcg 1380
acuuccacag cuucgugcug ccucggaucg gcagcaacac acuggaaauc ggccugcgga 1440
cccggaucag aaagaugcug gaagaacaca aagagcccuc uccacugauc accgccgagg 1500
augugcaaga ggccaaaugu gccgccgacg aggcuaaaga agugcgcgaa gccgaggaac 1560
ugagagccgc acuuccuccu cuggccgccg auguugaaga acccacucug gaagccgacg 1620
ucgacuugau guuacaagag gcuggggccg gcucagugga gacaccucgu ggcuugauaa 1680
agguuaccag cuacgcuggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040

-continued aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaagagc aucagcagac 2580
ggugcaccaa gagcgugacc agcguggugu cuacccuguu cuacgacaag aagaugcgga 2640
cgacaaaccc caaagagaca aagaucguca ucgacaccac cggcagcacc aagccuaagc 2700
aggacgaucu gauccugacc ugcuucagag gcugggucaa gcagcugcag aucgacuaca 2760
agggcaacga gaucaugacc gccgcugccu cucagggccu gacaagaaaa ggcguguacg 2820
ccgugcggua caaagugaac gagaacccuc uguacgcccc uaccagcgag caugugaaug 2880
ugcugcugac ccggaccgag gaccggaucg uuuggaaaac acuggccggc gaucccugga 2940
ucaagacccu gacagccaag uaucccggca acuucaccgc caccaucgag gaauggcagg 3000
ccgagcacga ugccaucaug cggcacaucc uggaaagacc cgauccuacc gacguguucc 3060
agaacaaggc caacgugugc ugggccaaag cucuggugcc ugugcugaaa accgccggca 3120
ucgauaugac caccgagcag uggaacaccg uggacuacuu cgagacagac aaggcccaca 3180
gcgccgagau cgugcugaau cagcugugcg ugcgguucuu cggccuggau cuggauagcg 3240
gccuguucuc ugcuccuacc gugccucuga gcauccggaa caaccacugg gacaacagcc 3300
ccucuccuaa uauguacggc cugaacaaag aagucgugcg gcagcugagc agaagauacc 3360
cacagcugcc uagagccgug gccacaggca gaguguacga caugaauacc ggcacacugc 3420
ggaacuacga ccccagaauc aaucuggugc ccgugaacag aaggcugccc cacgcucugg 3480
uucugcacca caaugagcac ccucagagcg acuucagcag cuucgugucc aagcugaagg 3540
gcagaaccgu gcugguugug ggcgagaagc ugucugugcc uggcaagaug guggacuggc 3600
ugagcgauag acccgaggcc accuuuagag ccagacugga ccuuggaauc ccuggcgacg 3660
ugcccaaaua cgacaucauc uucgugaacg ugcggacgcc cuacaaguac caccacuacc 3720
agcagugcga ggaccacgcc aucaagcuga gcaugcugac caagaaggcc ugccugcacc 3780
ugaauccugg cggcaccugu gugucuaucg gcuacggcua ugccgacaga gccagcgagu 3840
cuaucaucgg cgccauugcc agacaguuca aguucagcag agugugcaag cccaagagca 3900
gccuggaaga gacagaggug cuguucgugu ucaucggcua ugaccggaag gcccguacgc 3960
acaauccuua caagcuuuca ucaaccuuga ccaacauuua uacagguucc agacuccacg 4020
aagccggaug ugcacccuca uaucaugugg ugcgaggggga uauugccacg gccaccgaag 4080
gagugauuau aaaugcugcu aacagcaaag gacaaccugg cggagggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440

```
cagauguagc cauauacugc agggacaaga aaugggaaau gacucucaag gaagcagugg   4500
cuaggagaga agcaguggag gagauaugca uauccgacga cucuucagug acagaaccug   4560
augcagagcu ggugagggug cauccgaaga guucuuuggc uggaaggaag ggcuacagca   4620
caagcgaugg caaaacuuuc ucauauuugg aagggaccaa guuucaccag gcggccaagg   4680
auauagcaga aauuaaugcc auguggcccg uugcaacgga ggccaaugag cagguaugca   4740
uguauauccu cggagaaagc augagcagua uuaggucgaa augccccguc gaagagucgg   4800
aagccuccac accaccuagc acgcugccuu gcuugugcau ccaugccaug acuccagaaa   4860
gaguacagcg ccuaaaagcc ucacguccag aacaaauuac ugugugcuca uccuuuccau   4920
ugccgaagua uagaaucacu ggugugcaga agauccaaug cucccagccu auauuguucu   4980
caccgaaagu gccugcguau auucauccaa ggaaguaucu cguggaaaca ccaccgguag   5040
acgagacucc ggagccaucg gcagagaacc aauccacaga ggggacaccu gaacaaccac   5100
cacuuauaac cgaggaugag accaggacua gaacgccuga gccgaucauc aucgaagagg   5160
aagaagagga uagcauaagu uugcugucag auggcccgac ccaccaggug cugcaagucg   5220
aggcagacau ucacgggccg cccucuguau cuagcucauc cugguccauu ccucaugcau   5280
ccgacuuuga uguggacagu uuauccauac uugacacccu ggagggagcu agcgugacca   5340
gcggggcaac gucagccgag acuaacucuu acuucgcaaa gaguauggag uuucuggcgc   5400
gaccggugcc ugcgccucga acaguauuca ggaacccucc acaucccgcu ccgcgcacaa   5460
gaacaccguc acuugcaccc agcagggccu gcucgagaac cagccuaguu uccaccccgc   5520
caggcgugaa uagggugauc acuagagagg agcucgaggc gcuuaccccg ucacgcacuc   5580
cuagcagguc ggucucgaga accagccugg ucuccaaccc gccaggcgua aauaggguga   5640
uuacaagaga ggaguuugag gcguucguag cacaacaaca augacgguuu gaugcgggug   5700
cauacaucuu uuccuccgac accggucaag ggcauuuaca acaaaaauca guaaggcaaa   5760
cggugcuauc cgaaguggug uuggagagga ccgaauugga gauuucguau gccccgcgcc   5820
ucgaccaaga aaaagaagaa uuacuacgca agaaauuaca guuaaauccc acaccugcua   5880
acagaagcag auaccagucc aggaaggugg agaacaugaa agccauaaca gcuagacgua   5940
uucugcaagg ccuagggcau uauuugaagg cagaaggaaa aguggagugc uaccgaaccc   6000
ugcauccugu uccuuuguau ucaucuagug ugaaccgugc cuuuucaagc cccaaggucg   6060
caguggaagc cuguaacgcc auguugaaag agaacuuucc gacuguggcu ucuuacugua   6120
uuauuccaga guacgaugcc uauuuggaca ugguugacgg agcuucaugc ugcuuagaca   6180
cugccaguuu uugcccugca aagcugcgca gcuuuccaaa gaaacacucc uauuuggaac   6240
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420
uuaaagaaaa ccccaucagg cuuacugaag aaaacguggu aaauuacauu accaaauuaa   6480
aaggaccaaa agcugcugcu cuuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
cguaucugug cggaauccac cgagagcugg uuaggagauu aaaugcgguc cugcuuccga   6720
acauucauac acuguuugau augucggcug aagacuuuga cgcuauuaua gccgagcacu   6780
```

uccagccugg ggauuguguu cuggaaacug acaucgcguc guuugauaaa agugaggacg 6840
acgccauggc ucugaccgcg uuaaugauuc uggaagacuu aggugugac gcagagcugu 6900 ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 29
<211> LENGTH: 7561
<212> TYPE: RNA
<213> ORGANISM: Artificial Sequence
<220> FEATURE:
<223> OTHER INFORMATION: Synthetic construct, C10 nsP1-4 ORF and SGP RNA

<400> SEQUENCE: 29
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440
caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaagccgaug 1620
ucgacuugau guuacaagag gcuggggccg gcucagugga gacaccucgu ggcuugauaa 1680
agguuaccag cuacgcuggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980
gagcgcugaa cacugaugaa gaauauuaca aaacugucaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuaguggug agcgccaaga 2280
aagaaaacug ugcagaaauu auaagggacg ucaagaaaau gaaagggcug gacgucaaug 2340
ccagaacugu ggacucagug cucuugaaug gaugcaaaca ccccguagag acccuguaua 2400
uugacgaagc uuuugcuugu caugcaggua cucucagagc gcucauagcc auuauaagac 2460
cuaaaaaggc agugcucugc ggggauccca aacagugcgg uuuuuuuaac augaugugcc 2520
ugaaagugca uuuuaaccac gagauuugca cacaagucuu ccacaaaagc aucucucgcc 2580
guugcacuaa aucugugacu ucggucgucu caaccuuguu uuacgacaaa aaaaugagaa 2640
cgacgaaucc gaaagagacu aagauuguga uugacacuac cggcaguacc aaaccuaagc 2700
aggacgaucu cauucucacu uguuucagag ggugggugaa gcaguugcaa auagauuaca 2760
aaggcaacga aauaaugacg gcagcugccu cucaagggcu gacccguaaa ggguguguaug 2820
ccguucggua caaggugaau gaaaauccuc uguacgcacc caccucagaa caugugaacg 2880
uccuacugac ccgcacggag gaccgcaucg uguggaaaac acuagccggc gacccaugga 2940
uaaaaacacu gacugccaag uacccuggga auuucacugc cacgauagag gaguggcaag 3000
cagagcauga ugccaucaug aggcacaucu uggagagacc ggacccuacc gacgucuucc 3060
agaauaaggc aaacgugugu ugggccaagg cuuuagugcc ggugcugaag accgcuggca 3120
uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggucg ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccuggugguc ggggaaaagu uguccguccc aggcaaaaug guugacuggu 3600

-continued ugucagaccg gccugaggcu accuucagag cucggcugga uuuaggcauc ccaggugaug 3660
ugcccaaaua ugacauaaua uuuguuaaug ugaggacccc cuacaaguac caccacuacc 3720
agcagugcga ggaccacgcc aucaagcuga gcaugcugac caagaaggcc ugccugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucaucggcua cgacagaaag gcccguacgc 3960
acaauccuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggagggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauagggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaagugguug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaagu acgccugcaa caacgaguac ugggagacau 6420
ucaaagagaa ccccauccgg cugaccgagg aaaacguggu caacuacauc accaagcuga 6480
agggccccaa agccgccgcu cuguuugcca agacacacaa ccugaacaug cugcaggaca 6540
uccccaugga cagauucgug auggaccuga agcgggacgu gaaagugacc ccuggcacca 6600
agcacaccga ggaacggccu aaggugcaag ugauccaggc cgcugauccu cuggccacag 6660
ccuaucugug uggcauccac agagaacucg ugcggagacu gaaugccgug cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg cugaugauuc uggaagaucu cggaguggac gccgagcugc 6900
ugacacugau ugaagccgcc uuuggcgaga ucagcagcau ccaucugccu accaagacca 6960
aguucaaguu cggcgccaug augaaaucug gaauguuccu cacacuguuu gugaacacag 7020
ucauuaacau uguaaucgca agcagagugu ugagagaacg gcuaacaggc agcccuugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 30
<211> LENGTH: 7561
<212> TYPE: RNA
<213> ORGANISM: Artificial Sequence
<220> FEATURE:
<223> OTHER INFORMATION: Synthetic construct, C11 nsP1-4 ORF and SGP RNA
<400> SEQUENCE: 30
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauaugccg uggauggccc uacaagccug uaccaccagg 540
ccaacaaggg cgucagagug gccuacugga ucggcuucga caccacaccu uucauguuca 600
agaaccuggc uggcgcuuac cccagcuaca gcacaaacug ggccgacgaa accguguuaa 660
cggccagaaa uaucggccug uguagcagcg acgugaugga aagauccaga cggggcauga 720
gcauccugcg gaagaaguac cugaagccua gcaacaacgu gcuguucagc gugggcagca 780
ccaucuacca cgagaagagg gaccugcugc ggagcuggca ucugccuucc guguuucacc 840
ugagaggcaa gcagaacuac accuguagau gcgagacaau cguguccugc gacggcuacg 900
uggucaagcg gaucgccauu ucuccuggcc uguacggcaa gccuucuggc uaugccgcca 960
ccaugcacag agaaggcuuu cuguguugca aagugaccga cacacugaac ggcgagcggg 1020
uguccuuucc ugugugugacc uaugugcccg ccacacugug cgaucagaug acaggcauuc 1080
uggccaccga cgugucagcc gacgaugccc agaaacugcu cgugggccug aaccagagaa 1140
ucgugguucaa cggcagaacc cagcggaaca ccaacaccau gaagaacuac cugcugccug 1200
uggugggccca ggccuuugcc agaugggcca aagaguacaa agaggaucaa gaggacgagc 1260
ggccccuggg ccugagagau agacaacugg ucaugggcug cugcugggcc uucagaaggc 1320
acaagaucac cagcaucuac aagcggcccg acacacagac caucaucaaa gugaacagcg 1380
acuuccacag cuucgugcug ccucggaucg gcagcaacac acuggaaauc ggccugcgga 1440
cccggaucag aaagaugcug gaagaacaca aagagcccuc uccacugauc accgccgagg 1500
augugcaaga ggccaaaugu gccgccgacg aggcuaaaga agugcgcgaa gccgaggaac 1560
ugagagccgc acuuccuccu cuggccgccg auguugaaga acccacucug gaagccgacg 1620
ucgacuugau guuacaagag gcugggggccg gcucagugga gacaccucgu ggcuugauaa 1680
agguuaccag cuacgcuggc gaggacaaga ucggcucuua cgcugugcuu ucuccgcagg 1740
cuguacucaa gagcgagaag cugagcugca uucacccucu ggccgagcaa gugaucguga 1800
ucacacacag cggccggaag ggcagauaug ccguggaacc uuaucacggc aagguggugg 1860
ugccugaggg acacgcuauu ccagugcagg acuuucaggc ccugagcgag ucugccacca 1920
ucguguacaa cgagcgcgag uucgugaaca gauaccugca ccacauugcc acacacggcg 1980
gagcccugaa caccgacgaa gaguacuaca agaccgugaa gcccagcgag cacgacggcg 2040
aauaccugua cgacaucgac aggaaacagu gcgucaagaa agaacuaguc acugggcuag 2100
ggcucacagg cgagcuggug gauccucccu uccaugaauu cgccuacgag agucugagaa 2160
cacgaccagc cgcuccuuac caaguaccaa ccauaggggu guauggcgug ccaggaucag 2220
gcaagucugg caucauuaaa agcgcaguca ccaaaaaaga ucuagugggug agcgccaaga 2280
aagaaaacug ugcagaaauu auaagggacg ucaagaaaau gaaagggcug gacgucaaug 2340
ccagaacugu ggauagcgug cugcugaacg gcugcaagca ccccguagag acccuguaua 2400
uugacgaagc uuuugcuugu caugcaggua cucucagagc gcucauagcc auuauaagac 2460
cuaaaaaggc agugcucugc ggggauccua agcagugcgg cuucuucaac augaugugcc 2520
ugaaagugca uuuuaaccac gagauuugca cacaagucuu ccacaagagc aucagcagac 2580
ggugcaccaa gagcgugacc agcguggugu cuacccuguu cuacgacaag aagaugcgga 2640
cgacaaaccc caaagagaca aagaucguca ucgacaccac cggcagcacc aagccuaagc 2700
aggacgaucu gauccugacc ugcuucagag gcugggucaa gcagcugcag aucgacuaca 2760
agggcaacga gaucaugacc gccgcugccu cucagggccu gacaagaaaa ggcguguacg 2820
ccgugcggua caaagugaac gagaacccuc uguacgcccc uaccagcgag caugugaaug 2880
ugcugcugac ccggaccgag gaccggaucg uuuggaaaac acuggccggc gaucccugga 2940
ucaagacccu gacagccaag uaucccggca acuucaccgc caccaucgag gaauggcagg 3000
ccgagcacga ugccaucaug cggcacaucc uggaaagacc cgauccuacc gacguguucc 3060
agaacaaggc caacgugugc ugggccaaag cucuggugcc ugugcugaaa accgccggca 3120
ucgauaugac caccgagcag uggaacaccg uggacuacuu cgagacagac aaggcccaca 3180
gcgccgagau cgugcugaau cagcugugcg ugcgguucuu cggccuggau cuggauagcg 3240
gccuguucuc ugcuccuacc gugccucuga gcauccggaa caaccacugg gacaacagcc 3300
ccucuccuaa uauguacggc cugaacaaag aagucgugcg gcagcugagc agaagauacc 3360
cacagcugcc uagagccgug gccacaggca gaguguacga caugaauacc ggcacacugc 3420
ggaacuacga ccccagaauc aaucuggugc ccgugaacag aaggcugccc cacgcucugg 3480
uucugcacca caaugagcac ccucagagcg acuucagcag cuucgugucc aagcugaagg 3540
gcagaaccgu gcugguugug ggcgagaagc ugucugugcc uggcaagaug guggacuggc 3600
ugagcgauag acccgaggcc accuuuagag ccagacugga ccuuggaauc ccuggcgacg 3660
ugcccaaaua cgacaucauc uucgugaacg ugcggacgcc cuacaaguac caccacuacc 3720
agcagugcga ggaccacgcc aucaagcuga gcaugcugac caagaaggcc ugccugcacc 3780
ugaauccugg cggcaccugu gugucuaucg gcuacggcua ugccgacaga gccagcgagu 3840
cuaucaucgg cgccauugcc agacaguuca aguucagcag agugugcaag cccaagagca 3900
gccuggaaga gacagaggug cuguucgugu ucaucggcua ugaccggaag gcccguacgc 3960
acaaccccua caagcugagc agcacccuga ccaacaucua caccggcagc agacugcacg 4020
aagccggaug ugcacccuca uaucaugugg ugcgaggga uauugccaca gccacagaag 4080
gagugauuau aaaugcugcu aacagcaaag gacaaccugg cggaggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160

-continued aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaagu acgccugcaa caacgaguac ugggagacau 6420
ucaaagagaa ccccauccgg cugaccgagg aaaacguggu caacuacauc accaagcuga 6480
agggccccaa agccgccgcu cuguuugcca agacacacaa ccugaacaug cugcaggaca 6540
uccccaugga cagauucgug auggaccuga agcgggacgu gaaagugacc ccuggcacca 6600
agcacaccga ggaacggccu aaggugcaag ugauccaggc cgcugauccu cuggccacag 6660
ccuaucugug uggcauccac agagaacucg ugcggagacu gaaugccgug cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg cugaugauuc uggaagaucu cggaguggac gccgagcugc 6900
ugacacugau ugaagccgcc uuuggcgaga ucagcagcau ccaucugccu accaagacca 6960
aguucaaguu cggcgccaug augaaaucug gaauguuccu cacacuguuu gugaacacag 7020
ucauuaacau uguaaucgca agcagagugu ugagagaacg gcuaacaggc agcccuugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 31
<211> LENGTH: 8428
<212> TYPE: RNA
<213> ORGANISM: Artificial Sequence
<220> FEATURE:
<223> OTHER INFORMATION: Synthetic construct, C13 nsP1-4_GFP ORF and SGP RNA

<400> SEQUENCE: 31
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720
ccauucuuag aaagaaguau uugaaaccau ccaacaaugu ucuauucucu guuggcucga 780
ccaucuacca cgagaagagg gacuuacuga ggagcuggca ccugccgucu guauuucacu 840
uacguggcaa gcaaaauuac acaugucggu gugagacuau aguuaguugc gacggguacg 900
ucguuaaaag aauagcuauc aguccaggcc uguaugggaa gccuucaggc uaugcugcua 960
cgaugcaccg cgagggauuc uugugcugca aagugacaga cacauugaac ggggagaggg 1020
ucucuuuucc cgugugcacg uaugugccag cuacauugug ugaccaaaug acuggcauac 1080
uggcaacaga ugucagugcg gacgacgcgc aaaaacugcu gguugggcuc aaccagcgua 1140
uagucgucaa cggucgcacc cagagaaaca ccaauaccau gaaaaauuac cuuuugcccg 1200
uaguggccca ggcauuugcu aggugggcaa aggaauauaa ggaagaucaa gaagaugaaa 1260
ggccacuagg acuacgagau agacaguuag ucaugggggug uuguugggcu uuuagaaggc 1320
acaagauaac aucuauuuau aagcgcccgg auacccaaac caucaucaaa gugaacagcg 1380
auuuccacuc auucgugcug cccaggauag gcaguaacac auuggagauc gggcugagaa 1440
caagaaucag gaaaauguua gaggagcaca aggagccguc accucucauu accgccgagg 1500
acguacaaga agcuaagugc gcagccgaug aggcuaagga ggugcgugaa gccgaggagu 1560
ugcgcgcagc ucuaccaccu uuggcagcug auguugagga gcccacucug gaagccgaug 1620
ucgacuugau guuacaagag gcuggggccg gcucagugga gacaccucgu ggcuugauaa 1680
agguuaccag cuacgcuggc gaggacaaga ucggcucuua cgcugugcuu ucuccgcagg 1740
cuguacucaa gagugaaaaa uuaucuugca uccacccucu cgcugaacaa gucauaguga 1800
uaacacacuc uggccgaaaa gggcguuaug ccguggaacc auaccauggu aaaguagugg 1860
ugccagaggg acaugcaaua cccguccagg acuuucaagc ucugagugaa agugccacca 1920
uuguguacaa cgaacgugag uucguaaaca gguaccugca ccauauugcc acacauggag 1980

```
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggugugguaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacguguguu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggucccg ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
ucccuccacca uaaugaacac ccacagagug acuuuucuuc auucgucagc aaauugaagg   3540
gcagaacugu ccugguggguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcagugua agaccaugcc auuaagcuua gcauguugac caagaaagcu ugucugcauc   3780
ugaaucccgg cggaaccugu gucagcauag guuaugguua cgcugacagg gccagcgaaa   3840
gcaucauugg ugcuauagcg cggcaguuca aguuuucccg gguaugcaaa ccgaaauccu   3900
cacuugaaga gacggaaguu cuguuuguau ucauugggua cgaucgcaag gcccguacgc   3960
acaauccuua caagcuuuca ucaaccuuga ccaacauuua uacagguucc agacuccacg   4020
aagccggaug ugcacccuca uaucaugugg ugcgaggggga uauugccacg gccaccgaag   4080
gagugauuau aaaugcugcu aacagcaaag gacaaccugg cggagggggug ugcggagcgc   4140
uguauaagaa auucccggaa agcuucgauu uacagccgau cgaaguagga aaagcgcgac   4200
uggucaaagg ugcagcuaaa cauaucauuc augccguagg accaaacuuc aacaaaguuu   4260
cggagguuga aggugacaaa caguuggcag aggcuuauga guccaucgcu aagauuguca   4320
```

-continued acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauaggguga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaagguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu aggugugggac gcagagcugu 6900 ugacgcugau ugaggcggcu uucggcgaaa uuucaucaau acauuugccc acuaaaacua 6960
aauuuaaguu cggcgccaug augaaguccg gcauguuucu gacccuguuc gugaacaccg 7020
ugaucaacau cgugaucgcc agccgggugc ugagagagag acugacagga ucuccuugcg 7080
ccgccuucau cggcgacgac aauaucguga agggcgugaa guccgacaag cugauggccg 7140
auagaugcgc caccuggcug aacauggaag ugaagaucau cgacgccguc gugggcgaga 7200
aggccccuua uuuuugcggc ggcuucaucc ugugcgacag cgugacaggc acagccugca 7260
gaguugccga uccucugaag cggcuguuca agcugggaaa accucuggcc gccgacgacg 7320
agcacgacga cgauagacgu agagcccugc acgaggaauc caccagaugg aacagagugg 7380
gcauccugag cgagcugugc aaggccgugg aaagcagaua cgagacagug ggcaccagca 7440
ucauugugau ggcaaugacc acacuggcca gcagcgugaa aagcuucagc uaccuaaggg 7500
gcgccccuau cacacuguac ggcucuggcg aaggcagagg cagccuucug acauguggcg 7560
acguggaaga gaaccccgga ccugugucua agggcgaaga acuguuuacc ggcgugguggc 7620 ccauccuggu ggaacuggau ggggauguga acggccacaa guucagcguu agcggagaag 7680
gcgaaggcga cgccacauac ggaaagcuga cccugaaguu caucugcacc accggcaagc 7740
ugccugugcc auggccuaca cuggucacca cacugacaua cggcgugcag ugcuucagca 7800
gauaccccga ccauaugaag cagcacgacu ucuucaagag cgccaugccu gagggcuacg 7860
ugcaagagcg gaccaucuuc uuuaaggacg acggcaacua caagaccagg gccgaaguga 7920
aguucgaggg cgacacccug gucaaccgga ucgagcugaa gggcaucgac uucaaagagg 7980
acggcaauau ccugggccac aagcucgagu acaacuacaa cagccacaac guguacauca 8040
uggccgacaa gcagaaaaac ggcaucaaag ugaacuucaa gauccggcac aacaucgagg 8100
acggcucugu gcagcuggcc gaucacuacc agcagaacac acccaucgga gauggcccug 8160
ugcugcugcc cgauaaccac uaccugagca cccagagcaa gcugagcaag gaccccaacg 8220
agaagcggga ccacauggug cugcuggaau uugugacagc cgccggaauc acccucggca 8280
uggaugagcu guacaaguga acuuccauca uaguuauggc caugacuacu cuagcuagca 8340
guguuaaauc auucagcuac cugagagggg ccccuauaac ucucuacggc uaaccugaau 8400
ggacuacgac auagucuagu ccgccaag 8428

<210> SEQ ID NO 32
<211> LENGTH: 8353
<212> TYPE: RNA
<213> ORGANISM: Artificial Sequence
<220> FEATURE:
<223> OTHER INFORMATION: Synthetic construct, nsP1-4_3Cpro and SGP_VEEVrep-nsP4[3C]

<400> SEQUENCE: 32
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300

-continued

```
gugcggaaga uccggacaga uuguauaagu augcaacuaa gcugaagaaa aacuguaagg    360
aaauaacuga uaaggaauug gacaagaaaa ugaaggagcu cgccgccguc augagcgacc    420
cugaccugga aacugagacu augugccucc acgacgacga gucgugucgc uacgaagggc    480
aagucgcugu uuaccaggau guauacgcgg uugacggacc gacaagucuc uaucaccaag    540
ccaauaaggg aguuagaguc gccuacugga uaggcuuuga caccaccccu uuuauguuua    600
agaacuuggc uggagcauau ccaucauacu cuaccaacug ggccgacgaa accguguuaa    660
cggcucguaa cauaggccua ugcagcucug acguuaugga gcggucacgu agagggaugu    720
ccauucuuag aaagaaguau uugaaaccau ccaacaaugu ucuauucucu guuggcucga    780
ccaucuacca cgagaagagg gacuuacuga ggagcuggca ccugccgucu guauuucacu    840
uacguggcaa gcaaaauuac acaugucggu gugagacuau aguuaguugc gacggguacg    900
ucguuaaaag aauagcuauc aguccaggcc uguaugggaa gccuucaggc uaugcugcua    960
cgaugcaccg cgagggauuc uugugcugca aagugacaga cacauugaac ggggagaggg   1020
ucucuuuucc cgugugcacg uaugugccag cuacauugug ugaccaaaug acuggcauac   1080
uggcaacaga ugucagugcg gacgacgcgc aaaaacugcu gguugggcuc aaccagcgua   1140
uagucgucaa cggucgcacc cagagaaaca ccaauaccau gaaaaauuac cuuuugcccg   1200
uaguggccca ggcauuugcu agguggggcaa aggaauauaa ggaagaucaa gaagaugaaa   1260
ggccacuagg acuacgagau agacaguuag ucauggggug uuguugggcu uuuagaaggc   1320
acaagauaac aucuauuuau aagcgcccgg auacccaaac caucaucaaa gugaacagcg   1380
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgcuggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuagugggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
```

-continued

```
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa gguguguaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggucug ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccugguggcuc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcaguguga agaccaugcc auuaagcuua gcauguugac caagaaagcu ugucugcauc   3780
ugaaucccgg cggaaccugu gucagcauag guuaugguua cgcugacagg gccagcgaaa   3840
gcaucauugg ugcuauagcg cggcaguuca aguuuucccg gguaugcaaa ccgaaauccu   3900
cacuugaaga gacggaaguu cuguuuguau ucauugggua cgaucgcaag gcccguacgc   3960
acaauccuua caagcuuuca ucaaccuuga ccaacauuua uacagguucc agacuccacg   4020
aagccggaug ugcacccuca uaucaugugg ugcgaggga uauugccacg gccaccgaag   4080
gagugauuau aaaugcugcu aacagcaaag gacaaccugg cggagggug ugcggagcgc   4140
uguauaagaa auucccggaa agcuucgauu uacagccgau cgaaguagga aaagcgcgac   4200
uggucaaagg ugcagcuaaa cauaucauuc augccguagg accaaacuuc aacaaaguuu   4260
cggagguuga aggugacaaa caguuggcag aggcuuauga guccaucgcu aagauuguca   4320
acgauaacaa uuacaaguca guagcgauuc cacuguuguc caccggcauc uuuuccggga   4380
acaaagaucg acuaacccaa ucauugaacc auuugcugac agcuuuagac accacugaug   4440
cagauguagc cauauacugc agggacaaga aaugggaaau gacucucaag gaagcagugg   4500
cuaggagaga agcaguggag gagauaugca uauccgacga cucuucagug acagaaccug   4560
augcagagcu ggugagggug cauccgaaga guucuuuggc uggaaggaag ggcuacagca   4620
caagcgaugg caaaacuuuc ucauauuugg aagggaccaa guuucaccag gcggccaagg   4680
auauagcaga aauuaaugcc auguggcccg uugcaacgga ggccaaugag cagguaugca   4740
uguauauccu cggagaaagc augagcagua uuaggucgaa augccccguc gaagagucgg   4800
aagccuccac accaccuagc acgcugccuu gcuugugcau ccaugccaug acuccagaaa   4860
gaguacagcg ccuaaaagcc ucacguccag aacaaauuac ugugugcuca uccuuuccau   4920
ugccgaagua uagaaucacu ggugugcaga agauccaaug cucccagccu auauuguucu   4980
caccgaaagu gccugcguau auucauccaa ggaaguaucu cguggaaaca ccaccgguag   5040
```

```
acgagacucc ggagccaucg gcagagaacc aauccacaga ggggacaccu gaacaaccac   5100
cacuuauaac cgaggaugag accaggacua gaacgccuga gccgaucauc aucgaagagg   5160
aagaagagga uagcauaagu uugcugucag auggcccgac ccaccaggug cugcaagucg   5220
aggcagacau ucacgggccg cccucuguau cuagcucauc cugguccauu ccucaugcau   5280
ccgacuuuga uguggacagu uuauccauac uugacacccu ggagggagcu agcgugacca   5340
gcggggcaac gucagccgag acuaacucuu acuucgcaaa gaguauggag uuucuggcgc   5400
gaccggugcc ugcgccucga acaguauuca ggaacccucc acaucccgcu ccgcgcacaa   5460
gaacaccguc acuugcaccc agcagggccu gcucgagaac cagccuaguu uccaccccgc   5520
caggcgugaa uagggugauc acuagagagg agcucgaggc gcuuaccccg ucacgcacuc   5580
cuagcagguc ggucucgaga accagccugg ucuccaaccc gccaggcgua aauagggaga   5640
uuacaagaga ggaguuugag gcguucguag cacaacaaca augacgguuu gaugcgggug   5700
cauacaucuu uuccuccgac accggucaag ggcauuuaca acaaaaauca guaaggcaaa   5760
cggugcuauc cgaaguggug uuggagagga ccgaauugga gauuucguau gccccgcgcc   5820
ucgaccaaga aaaagaagaa uuacuacgca agaaauuaca guuaaauccc acaccugcua   5880
acagaagcag auaccagucc aggaaggugg agaacaugaa agccauaaca gcuagacgua   5940
uucugcaagg ccuagggcau uauuugaagg cagaaggaaa aguggagugc uaccgaaccc   6000
ugcauccugu uccuuuguau ucaucuagug ugaaccgugc cuuuucaagc cccaaggucg   6060
caguggaagc cuguaacgcc auguugaaag agaacuuucc gacuguggcu ucuuacugua   6120
uuauuccaga guacgaugcc uauuuggaca ugguugacgg agcuucaugc ugcuuagaca   6180
cugccaguuu uugcccugca aagcugcgca gcuuuccaaa gaaacacucc uauuuggaac   6240
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420
uuaaagaaaa ccccaucagg cuuacugaag aaaacguggu aaauuacauu accaaauuaa   6480
aaggaccaaa agcugcugcu cuuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
cguaucugug cggaauccac cgagagcugg uuaggagauu aaaugcgguc cugcuuccga   6720
acauucauac acuguuugau augucggcug aagacuuuga cgcuauuaua gccgagcacu   6780
uccagccugg ggauuguguu cuggaaacug acaucgcguc guuugauaaa agugaggacg   6840
acgccauggc ucugaccgcg uuaaugauuc uggaagacuu agguguggac gcagagcugu   6900
ugacgcugau ugaggcggcu uucggcgaaa uuucaucaau acauuugccc acuaaaacua   6960
aauuuaaguu cggcgccaug augaaguccg gcauguuucu gacccuguuc gugaacaccg   7020
ugaucaacau cgugaucgcc agccgggugc ugagagagag acugacagga ucuccuugcg   7080
ccgccuucau cggcgacgac aauaucguga agggcgugaa guccgacaag cugauggccg   7140
auagaugcgc caccuggcug aacauggaag ugaagaucau cgacgccguc gugggcgaga   7200
aggccccuua uuuuugcggc ggcuucaucc ugugcgacag cgugacaggc acagccugca   7260
gaguugccga uccucugaag cggcuguuca agcugggaaa accucuggcc gccgacgacg   7320
agcacgacga cgauagacgu agagcccugc acgaggaauc caccagaugg aacagagugg   7380
```

```
gcauccugag cgagcugugc aaggccgugg aaagcagaua cgagacagug ggcaccagca   7440

ucauugugau ggcaaugacc acacuggcca gcagcgugaa aagcuucagc uaccuaaggg   7500

gcgccccuau cacacuguac ggcucuggcg aaggcagagg cagccuucug acauguggcg   7560

acguggaaga gaaccccgga ccuaguggug ccccaccgac cgacuugcaa aagaugguca   7620

ugggcaacac aaagccuguu gagcucaucc uugacgggaa gacaguagcc aucuguugug   7680

cuacuggagu guuuggcacu gcuuaccucg ugccucguca ucuuuucgca gagaaguaug   7740

acaagaucau gcuggauggc agagccauga cagacaguga cuacagagug uuugaguuug   7800

agauuaaagu aaaaggacag gacaugcucu cagacgcugc gcucauggug cuccaccgug   7860

ggaaccgcgu gagagauauc acgaaacacu uucgugauac agcaagaaug aagaaaggca   7920

cccccgucgu cggugugguc aacaacgccg acguugggag acugauuuuc ucuggugagg   7980

cccucaccua caaggauauu guagugugca uggacggaga caccaugccu agccucuuug   8040

ccuacaaagc cgccaccaag gcaggcuacu guggaggagc cguucucgcc aaggacgggg   8100

ccgacacuuu caucgucggc acucacuccg caggaggcaa uggaguugga uacugcucau   8160

gcguuuccaa guccaugcuu cucagaauga aggcacacgu ugacccugaa ccacaacacg   8220

aguagacuuc caucauaguu auggccauga cuacucuagc uagcaguguu aaaucauuca   8280

gcuaccugag aggggccccu auaacucucu acggcuaacc ugaauggacu acgacauagu   8340

cuaguccgcc aag                                                      8353
```

```
<210> SEQ ID NO 33
<211> LENGTH: 2322
<212> TYPE: RNA
<213> ORGANISM: Artificial Sequence
<220> FEATURE:
<223> OTHER INFORMATION: Synthetic construct, 01 Manisa P1 pr _ RNA
      coding sequence (SG ORF)

<400> SEQUENCE: 33

augggagcug gacagagcuc cccugcuacc ggcagccaga aucaguccgg caacaccggc     60

uccaucauca acaacuacua caugcagcag uaccagaaca gcauggacac ccagcugggc    120

gacaacgcua ccagcggcgg cuccaacgag ggaagcaccg acaccaccuc cacccacacc    180

accaacaccc agaacaacga cugguucucc aagcuggcca gcagcgccuu cagcggccug    240

uucggagccc ugcuggccga caagaagacc gaggagacaa cccugcugga ggaccggauc    300

cugaccacca gaaacggaca cacuaccucc accacccaga gcuccguggg agugaccuac    360

ggauacgcua ccgcugagga cuucgugucc ggaccaaaca ccuccggccu ggagacaagg    420

guggcucagg cugagagauu cuucaagacc caccuguucg acugggugac cagcgaccca    480

uucggaagau gccaccugcu ggagcugccc accgaccaca agggcgugua cggcagccug    540

accgacuccu acgccuacau gagaaacgga ugggacgugg aggugaccgc ugugggaaac    600

caguucaacg gcggaugccu gcugguggcu auggugcccg agcugugcuc cauccagaag    660

agggagcugu accagcugac ccuguucccc caccaguuca ucaaccccag aaccaacaug    720

accgcucaca ucaccgugcc cuucguggga gugaaccggu acgaccagua caaggugcac    780

aagcccugga cccugguggu caugguggug gccccacuga ccgugaacag cgagggagcc    840

ccacagauca agguguacgc caacaucgcu ccaaccaacg ugcacguggc uggagaguuc    900

cccuccaaag agggcaucuu cccuguggcu ugcagcgacg gauacggcgg ccuggugacc    960

accgacccaa agaccgcuga cccagccuac ggcaaggugu ucaacccacc ccggaacaug   1020
```

cugccuggac gcuucaccaa cuuccuggac guggcugagg ccugcccaac cuuccugcac 1080
uucgagggcg acgugcccua cgugaccacc aagaccgacu ccgacagagu gcuggcccag 1140
uucgaccugu cccuggccgc caagcacaug agcaacaccu uccuggccgg ccuggcccag 1200
uacuacaccc aguacagcgg caccaucaac cugcacuuca uguucaccgg accaaccgac 1260
gcuaaggcua gguacaugau cgcuuacgcc ccacccggaa uggagccccc aaagaccccu 1320
gaggcugcug cucacugcau ccacgccgag ugggacaccg gccugaacag caaguucacc 1380
uucuccaucc ccuaccugag cgcugcugac uacgcuuaca ccgccuccga caccgcugag 1440
acaaccaacg ugcagggcug ggugugccug uuccagauca cccacggcaa ggcugacggc 1500
gacgcucugg uggugcuggc cagcgccggc aaggacuucg agcugaggcu gcccguggac 1560
gcuagaaccc agaccaccag cgcuggagag uccgcugacc cagugaccgc caccguggag 1620
aacuacggcg gcgagacaca ggugcagcgg aggcagcaca ccgacguguc cuucauccug 1680
gacagauucg ugaaggugac ccccaaggac cagaucaacg ugcuggaccu gaugcagacc 1740
ccugcucaca cccugguggg agcccugcug cggaccgcca ccuacuacuu cgccgaccug 1800
gagguggccg ugaagcacga gggcaaccug accugggugc ccaacggagc uccugaggcu 1860
gcccuggaca acaccaccaa ccccaccgcu uaccauaagg ccccacugac ccggcuggcc 1920
cugcccuaca ccgccccaca ccgcgugcug gccaccgugu acaacggcaa cugcaaguac 1980
ggcgacggca ccguggccaa cgugcggggc gaccugcagg ugcuggccca gaaggcugcu 2040
agagcccugc ccaccagcuu caacuacggc gccaucaagg ccaccagagu gaccgagcug 2100
cuguacagga ugaagagagc cgagacauac ugccccaggc cccugcuggc cauccaccca 2160
gaccaggcca gacacaagca gaagaucgug gcccccguga agcagcugcu gaacuucgac 2220
cugcugaagc uggccggcga cguggagucc aacccuggac ccuucuucuu cagcgacgug 2280
cgcagcaacu ucuccaagcu gguggagaca aucaaccagu ga 2322

<210> SEQ ID NO 34
<211> LENGTH: 8848
<212> TYPE: RNA
<213> ORGANISM: Artificial Sequence
<220> FEATURE:
<223> OTHER INFORMATION: Synthetic construct, nsP1-4-STING pr ORF, and SGP_VEEVrep-nsP4[STING]

<400> SEQUENCE: 34
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240
gugcgcccgc ccgcagaaug uauucuaagc acaaguauca uuguaucugu ccgaugagau 300
gugcggaaga uccggacaga uuguauaagu augcaacuaa gcugaagaaa aacuguaagg 360
aaauaacuga uaaggaauug gacaagaaaa ugaaggagcu cgccgccguc augagcgacc 420
cugaccugga aacugagacu augugccucc acgacgacga gucgugucgc uacgaagggc 480
aagucgcugu uuaccaggau guauacgcgg uugacggacc gacaagucuc uaucaccaag 540
ccaauaaggg aguuagaguc gccuacugga uaggcuuuga caccaccccu uuuauguuua 600
agaacuuggc uggagcauau ccaucauacu cuaccaacug ggccgacgaa accguguuaa 660
cggcucguaa cauaggccua ugcagcucug acguuaugga gcggucacgu agagggaugu 720

```
ccauucuuag aaagaaguau uugaaaccau ccaacaaugu ucuauucucu guuggcucga    780
ccaucuacca cgagaagagg gacuuacuga ggagcuggca ccugccgucu guauuucacu    840
uacguggcaa gcaaaauuac acaugucggu gugagacuau aguuaguugc gacggguacg    900
ucguuaaaag aauagcuauc aguccaggcc uguaugggaa gccuucaggc uaugcugcua    960
cgaugcaccg cgagggauuc uugugcugca aagugacaga cacauugaac ggggagaggg   1020
ucucuuuucc cgugugcacg uaugugccag cuacauugug ugaccaaaug acuggcauac   1080
uggcaacaga ugucagugcg gacgacgcgc aaaaacugcu gguugggcuc aaccagcgua   1140
uagucgucaa cggucgcacc cagagaaaca ccaauaccau gaaaaauuac cuuuugcccg   1200
uaguggccca ggcauuugcu aggugggcaa aggaauauaa ggaagaucaa gaagaugaaa   1260
ggccacuagg acuacgagau agacaguuag ucauggggug uuguugggcu uuuagaaggc   1320
acaagauaac aucuauuuau aagcgcccgg auacccaaac caucaucaaa gugaacagcg   1380
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgcuggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa ggguguguaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
```

uagacaugac cacugaacaa uggaacacug uggauuauuu ugaaacggac aaagcucacu 3180
cagcagagau aguauugaac caacuaugcg ugagguucuu uggacucgau cuggacuccg 3240
gucuauuuuc ugcacccacu guuccguuau ccauuaggaa uaaucacugg gauaacuccc 3300
cgucgccuaa cauguacggg cugaauaaag aaguggucog ucagcucucu cgcagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccuggugguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720
agcaguguga agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggagggggug ugcggagcgc 4140 uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc auguggcccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460

-continued

```
gaacaccguc acuugcaccc agcagggccu gcucgagaac cagccuaguu uccaccccgc   5520
caggcgugaa uagggugauc acuagagagg agcucgaggc gcuuaccccg ucacgcacuc   5580
cuagcagguc ggucucgaga accagccugg ucuccaaccc gccaggcgua aauaggguga   5640
uuacaagaga ggaguuugag gcguucguag cacaacaaca augacgguuu gaugcgggug   5700
cauacaucuu uuccuccgac accggucaag ggcauuuaca acaaaaauca guaaggcaaa   5760
cggugcuauc cgaaguggug uuggagagga ccgaauugga gauuucguau gccccgcgcc   5820
ucgaccaaga aaaagaagaa uuacuacgca agaaauuaca guuaaauccc acaccugcua   5880
acagaagcag auaccagucc aggaaggugg agaacaugaa agccauaaca gcuagacgua   5940
uucugcaagg ccuagggcau uauuugaagg cagaaggaaa aguggagugc uaccgaaccc   6000
ugcauccugu uccuuuguau ucaucuagug ugaaccgugc cuuuucaagc cccaaggucg   6060
caguggaagc cuguaacgcc auguugaaag agaacuuucc gacuguggcu ucuuacugua   6120
uuauuccaga guacgaugcc uauuuggaca ugguugacgg agcuucaugc ugcuuagaca   6180
cugccaguuu uugcccugca aagcugcgca gcuuuccaaa gaaacacucc uauuuggaac   6240
ccacaauacg aucggcagug ccuucagcga uccagaacac gcuccagaac guccuggcag   6300
cugccacaaa aagaaauugc aaugucacgc aaaugagaga auugcccgua uuggauucgg   6360
cggccuuuaa uguggaaugc uucaagaaau augcguguaa uaaugaauau ugggaaacgu   6420
uuaaagaaaa ccccaucagg cuuacugaag aaaacguggu aaauuacauu accaaauuaa   6480
aaggaccaaa agcugcugcu cuuuuugcga agacacauaa uuugaauaug uugcaggaca   6540
uaccaaugga cagguuugua auggacuuaa agagagacgu gaaagugacu ccaggaacaa   6600
aacauacuga agaacggccc aagguacagg ugauccaggc ugccgauccg cuagcaacag   6660
cguaucugug cggaauccac cgagagcugg uuaggagauu aaaugcgguc cugcuuccga   6720
acauucauac acuguuugau augucggcug aagacuuuga cgcuauuaua gccgagcacu   6780
uccagccugg ggauuguguu cuggaaacug acaucgcguc guuugauaaa agugaggacg   6840
acgccauggc ucugaccgcg uuaaugauuc uggaagacuu aggugugggac gcagagcugu   6900
ugacgcugau ugaggcggcu uucggcgaaa uuucaucaau acauuugccc acuaaaacua   6960
aauuuaaguu cggcgccaug augaaguccg gcauguuucu gacccuguuc gugaacaccg   7020
ugaucaacau cgugaucgcc agccgggugc ugagagagag acugacagga ucuccuugcg   7080
ccgccuucau cggcgacgac aauaucguga agggcgugaa guccgacaag cugauggccg   7140
auagaugcgc caccuggcug aacauggaag ugaagaucau cgacgccguc gugggcgaga   7200
aggccccuua uuuuugcggc ggcuucaucc ugugcgacag cgugacaggc acagccugca   7260
gaguugccga uccucugaag cggcuguuca agcugggaaa accucuggcc gccgacgacg   7320
agcacgacga cgauagacgu agagcccugc acgaggaauc caccagaugg aacagagugg   7380
gcauccugag cgagcugugc aaggccgugg aaagcagaua cgagacagug ggcaccagca   7440
ucauugugau ggcaaugacc acacuggcca gcagcgugaa aagcuucagc uaccuaaggg   7500
gcgccccuau cacacuguac ggcucuggcg aaggcagagg cagccuucug acauguggcg   7560
acguggaaga gaaccccgga ccuccucaca gcucucugca cccuagcauc ccuuguccua   7620
gaggacacgg cgcccagaaa gcugcucugg uucugcuguc ugccugccug guuacacugu   7680
ggggacuggg agagccuccu gagcacacac ugagauaccu ggugcugcac cuggcuucuc   7740
ugcagcuggg acugcugcug aacggcgugu guucucuggc cgaggaacug agacacaucc   7800
acagcagaua caggggcagc uacuggcgga cagucagagc uugucugggc ugcccucuua   7860
```

```
gaagaggcgc ucugcugcug cuguccaucu acuucuacua cagccugccu aacgcugugg   7920

gccccuccuuu cacauggaug cuggcucugc ugggccuguc ucaggcucug aauauccugc   7980

uggggcugaa aggccuggcu ccugcugaaa ucucugccgu gugcgagaag ggcaacuucu   8040

cuguggcuca cggccuggcc ugguccuacu acaucggaua ccugagacug auccugccug   8100

agcugcaggc cagaaucaga accuacaacc agcacuacaa caaccugcug agaggcgcug   8160

ugucccagag acuguacauc cugcugccuc uggacugugg cgugccagac aaccugucua   8220

uggccgaucc uaacauccgg uuucuggaca agcugccuca gcagacaggc gaucacgccg   8280

gcaucaagga cagaguguac agcaacagca ucuacgagcu gcuggaaaac ggccagcgag   8340

ccggaacaug cgugcuggaa uaugccacac cucugcagac ccuguucgcc augagccagu   8400

acucucaggc cggcuucagc cgcgaggaua ugcuggaaca ggccaagcug uucugcagga   8460

cccucgagga cauccuggcu gaugcuccag agagccagaa caacugcaga cugaucgccu   8520

accaagagcc ugccgacgac agcagcuuua gccugagcca agaggugcug agacaccuga   8580

gacaagaaga gaaagaggaa gucaccgucg gcagccugaa aaccagcgcc gugccuagca   8640

ccagcaccau gucucaagaa cccgaacugc ugaucuccgg cauggaaaag ccccugccuc   8700

ugagaaccga cuucagcuga acuuccauca uaguuauggc caugacuacu cuagcuagca   8760

guguuaaauc auucagcuac cugagagggg ccccuauaac ucucuacggc uaaccugaau   8820

ggacuacgac auagucuagu ccgccaag                                      8848
```

```
<210> SEQ ID NO 35
<211> LENGTH: 7561
<212> TYPE: RNA
<213> ORGANISM: Artificial Sequence
<220> FEATURE:
<223> OTHER INFORMATION: Synthetic construct, C12_nsP1-4 ORF, and SGP

<400> SEQUENCE: 35
```

```
augggcggcg caugagagaa gcccagacca auuaccuacc caaaauggag aaaguucacg     60

uugacaucga ggaagacagc ccauuccuca gagcuuugca gcggagcuuc ccgcaguuug    120

agguagaagc caagcagguc acugauaaug accaugcuaa ugccagagcg uuuucgcauc    180

uggcuucaaa acugaucgaa acggaggugg acccauccga cacgauccuu gacauuggaa    240

gugcgcccgc ccgcagaaug uauucuaagc acaaguauca uuguaucugu ccgaugagau    300

gugcggaaga uccggacaga uuguauaagu augcaacuaa gcugaagaaa aacuguaagg    360

aaauaacuga uaaggaauug gacaagaaaa ugaaggagcu cgccgccguc augagcgacc    420

cugaccugga aacugagacu augugccucc acgacgacga gucgugucgc uacgaagggc    480

aagucgcugu uuaccaggau guauacgcgg uugacggacc gacaagucuc uaucaccaag    540

ccaauaaggg aguuagaguc gccuacugga uaggcuuuga caccaccccu uuuauguuua    600

agaacuuggc uggagcauau ccaucauacu cuaccaacug ggccgacgaa accguguuaa    660

cggccagaaa caucggccug ugcagcagcg acgugaugga acggucuaga cggggcauga    720

gcauccugcg gaagaaguac cugaagccua gcaacaacgu gcuguucagc gugggcagca    780

ccaucuacca cgagaagagg gaccugcugc ggagcuggca ucugccuucc guguuucacc    840

ugagaggcaa gcagaacuac accuguagau gcgagacaau cguguccugc gacggcuacg    900

uggucaagcg gaucgccauu ucuccuggcc uguacggcaa gccuucuggc uaugccgcca    960

ccaugcacag agaaggcuuu cuguguugca aagugaccga cacacugaac ggcgagcggg   1020
```

uguccuuucc uguguguacc uaugugcccg ccacacugug cgaucagaug acaggcauuc 1080
uggccaccga cgugucagcc gacgaugccc agaaacugcu cgugggccug aaccagagaa 1140
ucguggucaa cggcagaacc cagcggaaca ccaacaccau gaagaacuac cugcugccug 1200
ugguggccca ggccuuugcc agaugggcca aagaguacaa agaggaucaa gaggacgagc 1260
ggccccuggg ccugagagau agacaacugg ucaugggcug cugcugggcc uucagaaggc 1320
acaagaucac cagcaucuac aagcggcccg acacacagac caucaucaaa gugaacagcg 1380
acuuccacag cuucgugcug ccucggaucg gcagcaacac acuggaaauc ggccugcgga 1440
cccggaucag aaagaugcug gaagaacaca aagagcccuc uccacugauc accgccgagg 1500
augugcaaga ggccaaaugu gccgccgacg aggcuaaaga agugcgcgaa gccgaggaac 1560
ugagagccgc acuuccuccu cuggccgccg auguugaaga acccacucug gaagccgacg 1620
uggaccugau gcuucaagaa gccggcgcug gcagcgugga aacaccuaga ggacugauca 1680
aagucaccag cuacgccggc gaggacaaga ucggaucuua ugccgugcug agcccucagg 1740
cugugcugaa gucugagaag cugagcugca uucacccacu ggccgagcaa gugaucguga 1800
ucacacacag cggccggaag ggcagauaug ccguggaacc uuaucacggc aagguggugg 1860
ugccugaggg acacgcuauu ccagugcagg acuuucaggc ccugagcgag ucugccacca 1920
ucguguacaa cgagcgcgag uucgugaaca gauaccugca ccacauugcc acacacggcg 1980
gagcccugaa uaccgacgaa gaguacuaca agaccgugaa gcccagcgag cacgacggcg 2040
aguaccugua cgacaucgac agaaagcagu gcgugaagaa agagcugguc accggcuugg 2100
gacugacagg cgaacuggug gauccuccau uccacgaguu ugccuacgag agccugagaa 2160
ccagaccugc cgcuccuuac caggugccaa caaucggagu guauggcgug ccaggcucug 2220
gcaagagcgg caucauuaag agcgccguga ccaaaaagga ccugguggug uccgccaaga 2280
aagagaacug cgccgagauc auccgggacg ugaagaagau gaagggccuc gacgugaacg 2340
ccagaaccgu ggauagcgug cugcugaacg gaugcaagca ccccguggaa acccuguaca 2400
ucgaugaggc cuucgccugc caugccggaa cacugagagc acugaucgcc aucaucagac 2460
ccaagaaagc cgugcugugc ggcgacccua agcagugugg cuucuucaau augaugugcc 2520
ugaaggugca cuucaaccac gagaucugca cccagguguu ccacaagagc aucagcagac 2580
ggugcaccaa gagcgugacc agcguggugu cuacccuguu cuacgacaag aagaugcgga 2640
cgacaaaccc caaagagacu aagaucguca ucgacaccac cggcuccacc aagccuaagc 2700
aggacgaucu gauccugacc ugcuucagag gcugggucaa gcagcugcag aucgacuaca 2760
agggcaacga gaucaugacc gcugccgcuu cucagggacu gaccagaaaa ggcguguacg 2820
ccgugcggua caaagugaau gagaacccuc uguacgcccc uaccuccgag caugugaaug 2880
uccugcugac caggaccgag gaccggaucg uguggaaaac acuggcuggc gaccccugga 2940
ucaagacccu gacagccaag uaucccggca acuucaccgc cacaaucgag gaauggcagg 3000
ccgagcacga ugccauuaug cggcacaucc uggaacggcc cgauccuacc gauguguucc 3060
agaacaaggc caacgugugc ugggcuaaag cccuggugcc agugcugaaa accgccggca 3120
ucgauaugac caccgagcag uggaauaccg uggacuacuu cgagacagac aaggcccacu 3180
cugccgagau cgugcugaau cagcugugcg ugcgguucuu cggccuggau cuggauagcg 3240
gccuguuuag cgcuccuacc gugccucuga gcauccggaa caaccacugg gacaacagcc 3300
ccucuccuaa uauguacggc cugaacaaag aaguugugcg gcagcugagc agaagguacc 3360
cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccuggugguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720
agcaguguga agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020
aagccggaug ugcacccuca uaucaugugg ugcgagggga uauugccacg gccaccgaag 4080
gagugauuau aaaugcugcu aacagcaaag gacaaccugg cggagggggug ugcggagcgc 4140
uguauaagaa auucccggaa agcuucgauu uacagccgau cgaaguagga aaagcgcgac 4200
uggucaaagg ugcagcuaaa cauaucauuc augccguagg accaaacuuc aacaaaguuu 4260
cggagguuga aggugacaaa caguuggcag aggcuuauga guccaucgcu aagauuguca 4320
acgauaacaa uuacaaguca guagcgauuc cacuguuguc caccggcauc uuuuccggga 4380
acaaagaucg acuaacccaa ucauugaacc auuugcugac agcuuuagac accacugaug 4440
cagauguagc cauauacugc agggacaaga aaugggaaau gacucucaag gaagcagugg 4500
cuaggagaga agcaguggag gagauaugca uauccgacga cucuucagug acagaaccug 4560
augcagagcu ggugagggug cauccgaaga guucuuuggc uggaaggaag ggcuacagca 4620
caagcgaugg caaaacuuuc ucauauuugg aagggaccaa guuucaccag gcggccaagg 4680
auauagcaga aauuaaugcc augugggccg uugcaacgga ggccaaugag cagguaugca 4740
uguauauccu cggagaaagc augagcagua uuaggucgaa augccccguc gaagagucgg 4800
aagccuccac accaccuagc acgcugccuu gcuugugcau ccaugccaug acuccagaaa 4860
gaguacagcg ccuaaaagcc ucacguccag aacaaauuac ugugugcuca uccuuuccau 4920
ugccgaagua uagaaucacu ggugugcaga agauccaaug cucccagccu auauuguucu 4980
caccgaaagu gccugcguau auucauccaa ggaaguaucu cguggaaaca ccaccgguag 5040
acgagacucc ggagccaucg gcagagaacc aauccacaga ggggacaccu gaacaaccac 5100
cacuuauaac cgaggaugag accaggacua gaacgccuga gccgaucauc aucgaagagg 5160
aagaagagga uagcauaagu uugcugucag auggcccgac ccaccaggug cugcaagucg 5220
aggcagacau ucacgggccg cccucuguau cuagcucauc cugguccauu ccucaugcau 5280
ccgacuuuga uguggacagu uuauccauac uugacacccu ggagggagcu agcgugacca 5340
gcggggcaac gucagccgag acuaacucuu acuucgcaaa gaguauggag uuucuggcgc 5400
gaccggugcc ugcgccucga acaguauuca ggaacccucc acaucccgcu ccgcgcacaa 5460
gaacaccguc acuugcaccc agcagggccu gcucgagaac cagccuaguu uccaccccgc 5520
caggcgugaa uagggugauc acuagagagg agcucgaggc gcuuaccccg ucacgcacuc 5580
cuagcagguc ggucucgaga accagccugg ucuccaaccc gccaggcgua aauagggnga 5640
uuacaagaga ggaguuugag gcguucguag cacaacaaca augacgguuu gaugcgggug 5700
cauacaucuu uuccuccgac accggucaag ggcauuuaca acaaaaauca guaaggcaaa 5760
cggugcuauc cgaaguggug uuggagagga ccgaauugga gauuucguau gccccgcgcc 5820
ucgaccaaga aaaagaagaa uuacuacgca agaaauuaca guuaaauccc acaccugcua 5880
acagaagcag auaccagucc aggaaggugg agaacaugaa agccauaaca gcuagacgua 5940
uucugcaagg ccuagggcau uauuugaagg cagaaggaaa aguggagugc uaccgaaccc 6000
ugcauccugu uccuuuguau ucaucuagug ugaaccgugc cuuuucaagc cccaaggucg 6060
caguggaagc cuguaacgcc auguugaaag agaacuuucc gacuguggcu ucuuacugua 6120
uuauuccaga guacgaugcc uauuuggaca ugguugacgg agcuucaugc ugcuuagaca 6180
cugccaguuu uugcccugca aagcugcgca gcuuuccaaa gaaacacucc uauuuggaac 6240
ccacaauacg aucggcagug ccuucagcga uccagaacac gcuccagaac guccuggcag 6300
cugccacaaa aagaaauugc aaugucacgc aaaugagaga auugcccgua uuggauucgg 6360
cggccuuuaa uguggaaugc uucaagaaau augcguguaa uaaugaauau ugggaaacgu 6420
uuaaagaaaa ccccaucagg cuuacugaag aaaacguggu aaauuacauu accaaauuaa 6480
aaggaccaaa agcugcugcu cuuuuugcga agacacauaa uuugaauaug uugcaggaca 6540
uaccaaugga cagguuugua auggacuuaa agagagacgu gaaagugacu ccaggaacaa 6600
aacauacuga agaacggccc aagguacagg ugauccaggc ugccgauccg cuagcaacag 6660
cguaucugug cggaauccac cgagagcugg uuaggagauu aaaugcgguc cugcuuccga 6720
acauucauac acuguuugau augucggcug aagacuuuga cgcuauuaua gccgagcacu 6780
uccagccugg ggauuguguu cuggaaacug acaucgcguc guuugauaaa agugaggacg 6840
acgccauggc ucugaccgcg uuaaugauuc uggaagacuu agguguggac gcagagcugu 6900
ugacgcugau ugaggcggcu uucggcgaaa uuucaucaau acauuugccc acuaaaacua 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 36
<211> LENGTH: 7561
<212> TYPE: RNA
<213> ORGANISM: Artificial Sequence
<220> FEATURE:
<223> OTHER INFORMATION: Synthetic construct, C13_nsP1-4 ORF, and SGP

<400> SEQUENCE: 36
augggcggcg caugagagaa gcccagacca auuaccuacc caaaauggag aaaguucacg 60
uugacaucga ggaagacagc ccauuccuca gagcuuugca gcggagcuuc ccgcaguuug 120
agguagaagc caagcagguc acugauaaug accaugcuaa ugccagagcg uuuucgcauc 180
uggcuucaaa acugaucgaa acggaggugg acccauccga cacgauccuu gacauuggaa 240

```
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug gacaagaaaa ugaaggagcu cgccgccguc augagcgacc    420
cugaccugga aacugagacu augugccucc acgacgacga gucgugucgc uacgaagggc    480
aagucgcugu uuaccaggau guauacgcgg uugacggacc gacaagucuc uaucaccaag    540
ccaauaaggg aguuagaguc gccuacugga uaggcuuuga caccaccccu uuuauguuua    600
agaacuuggc uggagcauau ccaucauacu cuaccaacug ggccgacgaa accguguuaa    660
cggccagaaa caucggccug ugcagcagcg acgugaugga acggagcaga cggggcauga    720
gcauccugcg gaagaaguac cugaagccca gcaacaacgu gcuguucagc gugggcagca    780
ccaucuacca cgagaagagg gaccugcugc ggagcuggca ccugcccagc guguuccacc    840
ugagaggcaa gcagaacuac accugcagau gcgagacaau cgugagcugc gacggcuacg    900
uggucaagcg gaucgccaua agccccggcc uguacggcaa gcccagcggc uacgccgcca    960
ccaugcacag agaaggcuuc cugugcugca aagugaccga cacacugaac ggcgagcggg   1020
ugagcuuccc cgugugcacc uacgugcccg ccacacugug cgaccagaug acaggcauac   1080
uggccaccga cgugagcgcc gacgacgccc agaaacugcu cgugggccug aaccagagaa   1140
ucgugguc aa cggcagaacc cagcggaaca ccaacaccau gaagaacuac cugcugccag   1200
ugguggccca ggccuucgcc agaugggcca aagaguacaa agaggaccaa gaggacgagc   1260
ggccccuggg ccugagagac agacaacugg ucaugggcug cugcugggcc uucagaaggc   1320
acaagaucac cagcaucuac aagcggcccg acacacagac caucaucaaa gugaacagcg   1380
acuuccacag cuucgugcug ccacggaucg gcagcaacac acuggaaauc ggccugcgga   1440
cccggaucag aaagaugcug gaagaacaca aagagcccag cccacugauc accgccgagg   1500
acgugcaaga ggccaaaugc gccgccgacg aggcaaaaga agugcgcgaa gccgaggaac   1560
ugagagccgc acuccccccca cuggccgccg acguagaaga acccacccug gaagccgacg   1620
uggaccugau gcuccaagaa gccggcgcag gcagcgugga aacaccgaga ggacugauca   1680
aagucaccag cuacgccggc gaggacaaga ucggaagcua cgccgugcug agcccccagg   1740
ccgugcugaa aagcgagaag cugagcugca uccacccacu ggccgagcaa gugaucguga   1800
ucacacacag cggccggaag ggcagauacg ccguggaacc cuaccacggc aagguggugg   1860
ugccagaggg acacgcaauc ccagugcagg acuuccaggc ccugagcgag agcgccacca   1920
ucguguacaa cgagcgcgag uucgugaaca gauaccugca ccacauagcc acacacggcg   1980
gagcccugaa caccgacgaa gaguacuaca agaccgugaa gcccagcgag cacgacggcg   2040
aguaccugua cgacaucgac agaaagcagu gcgugaagaa agagcugguc accggccuag   2100
gacugacagg cgaacuggug gacccacccu uccacgaguu cgccuacgag agccugagaa   2160
ccagaccagc cgcacccuac cagguggcaa caaucggagu guacggcgug ccaggcagcg   2220
gcaagagcgg caucauaaag agcgccguga ccaaaaagga ccugguggug agcgccaaga   2280
aagagaacug cgccgagauc auccgggacg ugaagaagau gaagggccuc gacgugaacg   2340
ccagaaccgu ggacagcgug cugcugaacg gaugcaagca ccccguggaa acccuguaca   2400
ucgacgaggc cuucgccugc cacgccggaa cacugagagc acugaucgcc aucaucagac   2460
ccaagaaagc cgugcugugc ggcgaccccca agcagugcgg cuucuucaac augaugugcc   2520
ugaaggugca cuucaaccac gagaucugca cccaggugu u ccacaagagc aucagcagac   2580
```

-continued

```
ggugcaccaa gagcgugacc agcgugguga gcacccuguu cuacgacaag aagaugcgga   2640
cgacaaaccc caaagagacc aagaucguca ucgacaccac cggcagcacc aagccaaagc   2700
aggacgaccu gauccugacc ugcuucagag gcugggucaa gcagcugcag aucgacuaca   2760
agggcaacga gaucaugacc gccgccgcaa gccagggacu gaccagaaaa ggcguguacg   2820
ccgugcggua caaagugaac gagaacccac uguacgcccc caccagcgag cacgugaacg   2880
uccugcugac caggaccgag gaccggaucg uguggaaaac acuggccggc gaccccugga   2940
ucaagacccu gacagccaag uaccccggca acuucaccgc cacaaucgag gaauggcagg   3000
ccgagcacga cgccauaaug cggcacaucc uggaacggcc cgacccaacc gacguguucc   3060
agaacaaggc caacgugugc ugggcaaaag cccuggugcc agugcugaaa accgccggca   3120
ucgacaugac caccgagcag uggaacaccg uggacuacuu cgagacagac aaggcccaca   3180
gcgccgagau cgugcugaac cagcugugcg ugcgguucuu cggccuggac cuggacagcg   3240
gccuguucag cgcacccacc gugccccuga gcauccggaa caaccacugg gacaacagcc   3300
ccagcccaaa cauguacggc cugaacaaag aagucgugcg gcagcugagc agaagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccuggugguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcaguguga agaccaugcc auuaagcuua gcauguugac caagaaagcu ugucugcauc   3780
ugaaucccgg cggaaccugu gucagcauag guuaugguua cgcugacagg gccagcgaaa   3840
gcaucauugg ugcuauagcg cggcaguuca aguuuucccg gguaugcaaa ccgaaauccu   3900
cacuugaaga gacggaaguu cuguuuguau ucauugggua cgaucgcaag gcccguacgc   3960
acaauccuua caagcuuuca ucaaccuuga ccaacauuua uacagguucc agacuccacg   4020
aagccggaug ugcacccuca uaucaugugg ugcgagggga uauugccacg gccaccgaag   4080
gagugauuau aaaugcugcu aacagcaaag gacaaccugg cggagggggug ugcggagcgc   4140
uguauaagaa auucccggaa agcuucgauu uacagccgau cgaaguagga aaagcgcgac   4200
uggucaaagg ugcagcuaaa cauaucauuc augccguagg accaaacuuc aacaaaguuu   4260
cggagguuga aggugacaaa caguuggcag aggcuuauga guccaucgcu aagauuguca   4320
acgauaacaa uuacaaguca guagcgauuc cacuguuguc caccggcauc uuuuccggga   4380
acaaagaucg acuaacccaa ucauugaacc auuugcugac agcuuuagac accacugaug   4440
cagauguagc cauauacugc agggacaaga aaugggaaau gacucucaag gaagcagugg   4500
cuaggagaga agcaguggag gagauaugca uauccgacga cucuucagug acagaaccug   4560
augcagagcu ggugagggug cauccgaaga guucuuuggc uggaaggaag ggcuacagca   4620
caagcgaugg caaaacuuuc ucauauuugg aagggaccaa guuucaccag gcggccaagg   4680
auauagcaga aauuaaugcc auguggcccg uugcaacgga ggccaaugag cagguaugca   4740
uguauauccu cggagaaagc augagcagua uuaggucgaa augccccguc gaagagucgg   4800
aagccuccac accaccuagc acgcugccuu gcuugugcau ccaugccaug acuccagaaa   4860
gaguacagcg ccuaaaagcc ucacguccag aacaaauuac ugugugcuca uccuuuccau   4920
ugccgaagua uagaaucacu ggugugcaga agauccaaug cucccagccu auauuguucu   4980
```

```
caccgaaagu gccugcguau auucauccaa ggaaguaucu cguggaaaca ccaccgguag   5040

acgagacucc ggagccaucg gcagagaacc aauccacaga ggggacaccu gaacaaccac   5100

cacuuauaac cgaggaugag accaggacua gaacgccuga gccgaucauc aucgaagagg   5160

aagaagagga uagcauaagu uugcugucag auggcccgac ccaccaggug cugcaagucg   5220

aggcagacau ucacgggccg cccucuguau cuagcucauc cugguccauu ccucaugcau   5280

ccgacuuuga uguggacagu uuauccauac uugacacccu ggagggagcu agcgugacca   5340

gcggggcaac gucagccgag acuaacucuu acuucgcaaa gaguauggag uuucuggcgc   5400

gaccggugcc ugcgccucga acaguauuca ggaacccucc acaucccgcu ccgcgcacaa   5460

gaacaccguc acuugcaccc agcagggccu gcucgagaac cagccuaguu uccaccccgc   5520

caggcgugaa uagggugauc acuagagagg agcucgaggc gcuuaccccg ucacgcacuc   5580

cuagcagguc ggucucgaga accagccugg ucuccaaccc gccaggcgua aauaggguga   5640

uuacaagaga ggaguuugag gcguucguag cacaacaaca augacgguuu gaugcgggug   5700

cauacaucuu uuccuccgac accggucaag ggcauuuaca acaaaaauca guaaggcaaa   5760

cggugcuauc cgaaguggug uuggagagga ccgaauugga gauuucguau gccccgcgcc   5820

ucgaccaaga aaaagaagaa uuacuacgca agaaauuaca guuaaauccc acaccugcua   5880

acagaagcag auaccagucc aggaaggugg agaacaugaa agccauaaca gcuagacgua   5940

uucugcaagg ccuagggcau uauuugaagg cagaaggaaa aguggagugc uaccgaaccc   6000

ugcauccugu uccuuuguau ucaucuagug ugaaccgugc cuuuucaagc cccaaggucg   6060

caguggaagc cuguaacgcc auguugaaag agaacuuucc gacuguggcu ucuuacugua   6120

uuauuccaga guacgaugcc uauuuggaca ugguugacgg agcuucaugc ugcuuagaca   6180

cugccaguuu uugcccugca aagcugcgca gcuuuccaaa gaaacacucc uauuuggaac   6240

ccacaauacg aucggcagug ccuucagcga uccagaacac gcuccagaac guccuggcag   6300

cugccacaaa aagaaauugc aaugucacgc aaaugagaga auugcccgua uuggauucgg   6360

cggccuuuaa uguggaaugc uucaagaaau augcguguaa uaaugaauau ugggaaacgu   6420

uuaaagaaaa ccccaucagg cuuacugaag aaaacguggu aaauuacauu accaaauuaa   6480

aaggaccaaa agcugcugcu cuuuuugcga agacacauaa uuugaauaug uugcaggaca   6540

uaccaaugga cagguuugua auggacuuaa agagagacgu gaaagugacu ccaggaacaa   6600

aacauacuga agaacggccc aagguacagg ugauccaggc ugccgauccg cuagcaacag   6660

cguaucugug cggaauccac cgagagcugg uuaggagauu aaaugcgguc cugcuuccga   6720

acauucauac acuguuugau augucggcug aagacuuuga cgcuauuaua gccgagcacu   6780

uccagccugg ggauuguguu cuggaaacug acaucgcguc guuugauaaa agugaggacg   6840

acgccauggc ucugaccgcg uuaaugauuc uggaagacuu aggugugggac gcagagcugu   6900

ugacgcugau ugaggcggcu uucggcgaaa uuucaucaau acauuugccc acuaaaacua   6960

aauuuaaauu cggagccaug augaaaucug gaauguuccu cacacuguuu gugaacacag   7020

ucauuaacau uguaaucgca agcagagugu ugagagaacg gcuaaccgga ucaccaugug   7080

cagcauucau uggagaugac aauaucguga aaggagucaa aucggacaaa uuaauggcag   7140

acaggugcgc caccugguug aauauggaag ucaagauuau agaugcugug gugggcgaga   7200

aagcgccuua uuucugugga ggguuuauuu ugugugacuc cgugaccggc acagcgugcc   7260

guguggcaga cccccuaaaa aggcuguuua agcuuggcaa accucuggca gcagacgaug   7320
```

```
aacaugauga ugacaggaga agggcauugc augaagaguc aacacgcugg aaccgagugg   7380
guauucuuuc agagcugugc aaggcaguag aaucaaggua ugaaaccgua ggaacuucca   7440
ucauaguuau ggccaugacu acucuagcua gcaguguuaa aucauucagc uaccugagag   7500
gggccccuau aacucucuac ggcuaaccug aauggacuac gacauagucu aguccgccaa   7560
g                                                                   7561
```

```
<210> SEQ ID NO 37
<211> LENGTH: 7561
<212> TYPE: RNA
<213> ORGANISM: Artificial Sequence
<220> FEATURE:
<223> OTHER INFORMATION: Synthetic construct, C14_nsP1-4 ORF, and SGP

<400> SEQUENCE: 37
```

```
augggcggcg caugagagaa gcccagacca auuaccuacc caaaauggag aaaguucacg     60
uugacaucga ggaagacagc ccauuccuca gagcuuugca gcggagcuuc ccgcaguuug    120
agguagaagc caagcagguc acugauaaug accaugcuaa ugccagagcg uuuucgcauc    180
uggcuucaaa acugaucgaa acggaggugg acccauccga cacgauccuu gacauuggaa    240
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug gacaagaaaa ugaaggagcu cgccgccguc augagcgacc    420
cugaccugga aacugagacu augugccucc acgacgacga gucgugucgc uacgaagggc    480
aagucgcugu uuaccaggau guauacgcgg uugacggacc gacaagucuc uaucaccaag    540
ccaauaaggg aguuagaguc gccuacugga uaggcuuuga caccaccccu uuuauguuua    600
agaacuuggc uggagcauau ccaucauacu cuaccaacug ggccgacgaa accguguuaa    660
cggcucguaa cauaggccua ugcagcucug acguuaugga gcggucacgu agagggaugu    720
ccauucuuag aaagaaguau uugaaaccau ccaacaaugu ucuauucucu guuggcucga    780
ccaucuacca cgagaagagg gacuuacuga ggagcuggca ccugccgucu guauuucacu    840
uacguggcaa gcaaaauuac acaugucggu gugagacuau aguuaguugc gacggguacg    900
ucguuaaaag aauagcuauc aguccaggcc uguaugggaa gccuucaggc uaugcugcua    960
cgaugcaccg cgagggauuc uugugcugca aagugacaga cacauugaac ggggagaggg   1020
ucucuuuucc cgugugcacg uaugugccag cuacauugug ugaccaaaug acuggcauac   1080
uggcaacaga ugucagugcg gacgacgcgc aaaaacugcu gguugggcuc aaccagcgua   1140
uagucgucaa cggucgcacc cagagaaaca ccaauaccau gaaaaauuac cuuuugcccg   1200
uaguggccca ggcauuugcu aggugggcaa aggaauauaa ggaagaucaa gaagaugaaa   1260
ggccacuagg acuacgagau agacaguuag ucauggggug uuguugggcu uuuagaaggc   1320
acaagauaac aucuauuuau aagcgcccgg auacccaaac caucaucaaa gugaacagcg   1380
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgcuggc gaggacaaga ucggcucuua cgcugugcuu ucuccgcagg   1740
cuguacucaa gagugaaaaa uuaucuugca uccacccucu cgcugaacaa gucauaguga   1800
```

```
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa gguguguaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggucog ucagcucucu cgcagguacc   3360
cacaacugcc ucgggcaguu gccacuggaa gagucuauga caugaacacu gguacacugc   3420
gcaauuauga uccgcgcaua aaccuaguac cuguaaacag aagacugccu caugcuuuag   3480
uccuccacca uaaugaacac ccacagagug acuuuucuuc auucgucagc aaauugaagg   3540
gcagaacugu ccuggugguc ggggaaaagu uguccguccc aggcaaaaug guugacuggu   3600
ugucagaccg gccugaggcu accuucagag cucggcugga uuuaggcauc ccaggugaug   3660
ugcccaaaua ugacauaaua uuuguuaaug ugaggacccc auauaaauac caucacuauc   3720
agcaguguga agaccaugcc auuaagcuua gcauguugac caagaaagcu ugucugcauc   3780
ugaaucccgg cggaaccugu gucagcauag guuaugguua cgcugacagg gccagcgaaa   3840
gcaucauugg ugcuauagcg cggcaguuca aguuuucccg gguaugcaaa ccgaaauccu   3900
cacuugaaga gacggaaguu cuguuuguau ucauugggua cgaucgcaag gcccguacgc   3960
acaauccuua caagcuuuca ucaaccuuga ccaacauuua uacagguucc agacuccacg   4020
aagccggaug ugcacccuca uaucaugugg ugcgagggga uauugccacg gccaccgaag   4080
gagugauuau aaaugcugcu aacagcaaag gacaaccugg cggagggguu ugcggagccc   4140
```

-continued uguacaagaa guuccccgag agcuucgacc ugcagccuau cgaagugggc aaagccagac 4200
ugguuaaggg cgcugccaag cacaucaucc augccguggg acccaacuuc aacaaggugu 4260
ccgaggugga aggcgacaag cagcuggccg aggccuauga gucuaucgcc aagaucguga 4320
acgacaacaa cuacaagagc guggccauuc cucugcugag caccggcauc uucagcggca 4380
acaaggacag acugacccag agccugaacc aucugcugac agcccuggau accaccgaug 4440
ccgauguggc caucuacugc cgggacaaga aaugggagau gacccugaaa gaagccgugg 4500
ccagacgcga ggccguggaa gagaucugua ucagcgacga cagcagcgug accgagccug 4560
augccgaacu cguuagagug caccccaagu cuagccuggc cggcagaaag ggcuacagca 4620
ccucugaugg caagaccuuc agcuaccugg aaggcaccaa guuccaccag gccgccaagg 4680
auaucgccga gaucaacgcu auguggcccg uggccaccga ggccaaugaa caagugugca 4740
uguacauccu gggcgagagc augagcagca uccgcagcaa guguccugug gaagaguccg 4800
aggccagcac accuccuagc acacugccuu gccugugcau ccacgccaug acaccugaga 4860
gagugcagcg gcugaaggcc ucuagaccug agcagaucac cgugugcagc agcuucccac 4920
ugccuaagua cagaaucacc ggcgugcaga aaauccagug cagccagccu auccuguuca 4980
gcccuaaggu gcccgccuac auucacccca gaaaguaucu gguggaaacc ccaccugugg 5040
acgagacacc ugaaccuagc gccgagaauc agagcaccga gggaacacca gaacagccuc 5100
cacugaucac cgaggacgaa accaggacca gaacacccga gccuaucauc aucgaggaag 5160
aagaagagga cagcaucagc cugcugagcg acggaccuac acaccaggug cugcaagugg 5220
aagccgacau ccauggaccu ccaagcgugu ccagcagcag cuggucuauu ccucacgcca 5280
gcgacuucga cguggacagc cugagcaucc uggacacacu ggaaggcgcc ucugugacau 5340
cuggcgccac auccgccgag acaaacagcu acuucgccaa gagcauggaa uuucuggcca 5400
ggccugugcc ugcuccucgg accguguuua gaaacccucc ucauccugcu ccuagaacca 5460
ggacaccuuc ucuggcccu agcagagccu guagcagaac cagccuggug ucuacaccuc 5520
cuggcgugaa cagagugauc accagagagg aacuggaagc ccugacaccu agcaggaccc 5580
caagcagauc cgugucuaga acaucccugg uguccaaucc uccaggcguc aaccggguca 5640
ucacccggga agaguuugag gccuuugugg cucagcagca gugaagauuc gacgcaggcg 5700
ccuacaucuu cuccagcgau acaggccagg gccaucugca gcagaaaagc gucagacaga 5760
ccgugcuguc cgaaguggug cuggaaagaa ccgagcugga aaucagcuac gccccucggc 5820
uggaccaaga gaaagaagaa cugcugcgga agaaacugca gcugaacccc acaccagcca 5880
acagaagcag auaccagagc cggaaggugg aaaacaugaa ggccaucacc gccagacgga 5940
uccugcaagg ccugggccau uaucugaagg ccgagggcaa aguggaaugc uacagaacac 6000
ugcaccccgu gccucuguac agcagcuccg ugaauagggc cuuuagcagc ccaaaggugg 6060
ccgucgaagc cugcaacgcc augcugaaag aaaacuuccc uaccguggcc uccuacugca 6120
ucauccccga guacgacgcc uaccuggaca ugguggaugg cgcuagcugu ugucuggaua 6180
ccgccagcuu cugccccgcc aagcugagaa gcuuccccaa gaagcacagc uaucuggaac 6240
ccaccaucag auccgccgug ccuuccgcca uucagaauac ccugcagaac gugcuggccg 6300
cugccaccaa gaggaauugc aacgugaccc agaugcgcga gcugcccguu cuggauagcg 6360
ccgccuucaa cguggaaugu uucaagaagu acgccugcaa caacgaguac ugggagacau 6420
ucaaagagaa ccccauccgg cugaccgagg aaaacguggu caacuacauc accaagcuga 6480
agggccccaa agccgccgcu cuguuugcca agacacacaa ccugaacaug cugcaggaca 6540

```
uccccaugga cagauucgug auggaccuga agcgggacgu gaaagugacc ccuggcacca   6600
agcacaccga ggaacggccu aaagugcaag ugauccaggc cgcugauccu cuggccacag   6660
ccuaucugug uggcauccac agagaacucg ugcggagacu gaaugccgug cugcugccca   6720
acauccacac acuguucgac augagcgccg aggacuucga ugccaucauu gccgagcacu   6780
uccagccugg cgauugcgug cucgagacag auaucgccuc cuucgacaag agcgaggacg   6840
acgccauggc ucugacugcc cugaugaucc uggaagaucu gggcguugac gccgagcugc   6900
ugacacugau ugaagccgcc uuuggcgaga ucagcuccau ccaucugccu accaagacca   6960
aauuuaaauu cggagccaug augaaaucug gaauguuccu cacacuguuu gugaacacag   7020
ucauuaacau uguaaucgca agcagagugu ugagagaacg gcuaaccgga ucaccaugug   7080
cagcauucau uggagaugac aauaucguga aaggagucaa aucggacaaa uuaauggcag   7140
acaggugcgc caccugguug aauauggaag ucaagauuau agaugcugug gugggcgaga   7200
aagcgccuua uuucugugga ggguuuauuu ugugugacuc cgugaccggc acagcgugcc   7260
guguggcaga cccccuaaaa aggcuguuua agcuuggcaa accucuggca gcagacgaug   7320
aacaugauga ugacaggaga agggcauugc augaagaguc aacacgcugg aaccgagugg   7380
guauucuuuc agagcugugc aaggcaguag aaucaaggua ugaaaccgua ggaacuucca   7440
ucauaguuau ggccaugacu acucuagcua gcaguguuaa aucauucagc uaccugagag   7500
gggccccuau aacucucuac ggcuaaccug aauggacuac gacauagucu aguccgccaa   7560
g                                                                   7561
```

<210> SEQ ID NO 38
<211> LENGTH: 7561
<212> TYPE: RNA
<213> ORGANISM: Artificial Sequence
<220> FEATURE:
<223> OTHER INFORMATION: Synthetic construct, C15_nsP1-4 ORF, and SGP

<400> SEQUENCE: 38

```
augggcggcg caugagagaa gcccagacca auuaccuacc caaaauggag aaaguucacg     60
uugacaucga ggaagacagc ccauuccuca gagcuuugca gcggagcuuc ccgcaguuug    120
agguagaagc caagcagguc acugauaaug accaugcuaa ugccagagcg uuuucgcauc    180
uggcuucaaa acugaucgaa acggaggugg acccauccga cacgauccuu gacauuggaa    240
gugcgcccgc ccgcagaaug uauucuaagc acaaguauca uuguaucugu ccgaugagau    300
gugcggaaga uccggacaga uuguauaagu augcaacuaa gcugaagaaa aacuguaagg    360
aaauaacuga uaaggaauug gacaagaaaa ugaaggagcu cgccgccguc augagcgacc    420
cugaccugga aacugagacu augugccucc acgacgacga gucgugucgc uacgaagggc    480
aagucgcugu uuaccaggau guauacgcgg uugacggacc gacaagucuc uaucaccaag    540
ccaauaaggg aguuagaguc gccuacugga uaggcuuuga caccaccccu uuuauguuua    600
agaacuuggc uggagcauau ccaucauacu cuaccaacug ggccgacgaa accguguuaa    660
cggcucguaa cauaggccua ugcagcucug acguuaugga gcggucacgu agagggaugu    720
ccauucuuag aaagaaguau uugaaaccau ccaacaaugu ucuauucucu guuggcucga    780
ccaucuacca cgagaagagg gacuuacuga ggagcuggca ccugccgucu guauuucacu    840
uacguggcaa gcaaaauuac acaugucggu gugagacuau aguuaguugc gacggguacg    900
ucguuaaaag aauagcuauc aguccaggcc uguaugggaa gccuucaggc uaugcugcua    960
```

-continued

```
cgaugcaccg cgagggauuc uugugcugca aagugacaga cacauugaac ggggagaggg   1020
ucucuuuucc cgugugcacg uaugugccag cuacauugug ugaccaaaug acuggcauac   1080
uggcaacaga ugucagugcg gacgacgcgc aaaaacugcu gguugggcuc aaccagcgua   1140
uagucgucaa cggucgcacc cagagaaaca ccaauaccau gaaaaauuac cuuuugcccg   1200
uaguggccca ggcauuugcu aggugggcaa aggaauauaa ggaagaucaa gaagaugaaa   1260
ggccacuagg acuacgagau agacaguuag ucauggggug uuguugggcu uuuagaaggc   1320
acaagauaac aucuauuuau aagcgcccgg auacccaaac caucaucaaa gugaacagcg   1380
auuuccacuc auucgugcug cccaggauag gcaguaacac auuggagauc gggcugagaa   1440
caagaaucag gaaaauguua gaggagcaca aggagccguc accucucauu accgccgagg   1500
acguacaaga agcuaagugc gcagccgaug aggcuaagga ggugcgugaa gccgaggagu   1560
ugcgcgcagc ucuaccaccu uuggcagcug auguugagga gcccacucug gaagccgaug   1620
ucgacuugau guuacaagag gcuggggccg gcucagugga gacaccucgu ggcuugauaa   1680
agguuaccag cuacgcuggc gaggacaaga ucggcucuua cgcugugcuu ucuccgcagg   1740
cuguacucaa gagugaaaaa uuaucuugca uccacccucu cgcugaacaa gucauaguga   1800
uaacacacuc uggccgaaaa gggcguuaug ccguggaacc auaccauggu aaaguagugg   1860
ugccagaggg acaugcaaua cccguccagg acuuucaagc ucugagugaa agugccacca   1920
uuguguacaa cgaacgugag uucguaaaca gguaccugca ccauauugcc acacauggag   1980
gagcgcugaa cacugaugaa gaauauuaca aaacugucaa gcccagcgag cacgacggcg   2040
aauaccugua cgacaucgac aggaaacagu gcgucaagaa agaacuaguc acugggcuag   2100
ggcucacagg cgagcuggug gauccucccu uccaugaauu cgccuacgag agucugagaa   2160
cacgaccagc cgcuccuuac caaguaccaa ccauaggggu guauggcgug ccaggaucag   2220
gcaagucugg caucauuaaa agcgcaguca ccaaaaaaga ucuaguggug agcgccaaga   2280
aagaaaacug ugcagaaauu auaagggacg ucaagaaaau gaaagggcug gacgucaaug   2340
ccagaacugu ggacucagug cucuugaaug gaugcaaaca ccccguagag acccuguaua   2400
uugacgaagc uuuugcuugu caugcaggua cucucagagc gcucauagcc auuauaagac   2460
cuaaaaaggc agugcucugc ggggauccca aacagugcgg uuuuuuuaac augaugugcc   2520
ugaaagugca uuuuaaccac gagauuugca cacaagucuu ccacaaaagc aucucucgcc   2580
guugcacuaa aucugugacu ucggucgucu caaccuuguu uuacgacaaa aaaaugagaa   2640
cgacgaaucc gaaagagacu aagauuguga uugacacuac cggcaguacc aaaccuaagc   2700
aggacgaucu cauucucacu uguuucagag ggugggugaa gcaguugcaa auagauuaca   2760
aaggcaacga aauaaugacg gcagcugccu cucaagggcu gacccguaaa gguguguaug   2820
ccguucggua caaggugaau gaaaauccuc uguacgcacc caccucagaa caugugaacg   2880
uccuacugac ccgcacggag gaccgcaucg uguggaaaac acuagccggc gacccaugga   2940
uaaaaacacu gacugccaag uacccuggga auuucacugc cacgauagag gaguggcaag   3000
cagagcauga ugccaucaug aggcacaucu uggagagacc ggacccuacc gacgucuucc   3060
agaauaaggc aaacgugugu ugggccaagg cuuuagugcc ggugcugaag accgcuggca   3120
uagacaugac cacugaacaa uggaacacug uggauuauuu ugaaacggac aaagcucacu   3180
cagcagagau aguauugaac caacuaugcg ugagguucuu uggacucgau cuggacuccg   3240
gucuauuuuc ugcacccacu guuccguuau ccauuaggaa uaaucacugg gauaacuccc   3300
cgucgccuaa cauguacggg cugaauaaag aaguggaccg ucagcucucu cgcagguacc   3360
```

cacaacugcc ucgggcaguu gccacuggaa gagucuauga caugaacacu gguacacugc 3420
gcaauuauga uccgcgcaua aaccuaguac cuguaaacag aagacugccu caugcuuuag 3480
uccuccacca uaaugaacac ccacagagug acuuuucuuc auucgucagc aaauugaagg 3540
gcagaacugu ccuggugguc ggggaaaagu uguccguccc aggcaaaaug guugacuggu 3600
ugucagaccg gccugaggcu accuucagag cucggcugga uuuaggcauc ccaggugaug 3660
ugcccaaaua ugacauaaua uuuguuaaug ugaggacccc auauaaauac caucacuauc 3720
agcaguguga agaccaugcc auuaagcuua gcauguugac caagaaagcu ugucugcauc 3780
ugaaucccgg cggaaccugu gucagcauag guuaugguua cgcugacagg gccagcgaaa 3840
gcaucauugg ugcuauagcg cggcaguuca aguuuucccg gguaugcaaa ccgaaauccu 3900
cacuugaaga gacggaaguu cuguuuguau ucauugggua cgaucgcaag gcccguacgc 3960
acaauccuua caagcuuuca ucaaccuuga ccaacauuua uacagguucc agacuccacg 4020
aagccggaug ugcacccuca uaucauguggugcgaggggauauugccacggccaccgaag 4080
gagugauuau aaaugcugcu aacagcaaag gacaaccugg cggaggggug ugcggagccc 4140
uguacaagaa guuccccgag agcuucgacc ugcagccaau cgaagugggc aaagccagac 4200
uggucaaggg cgcagccaag cacaucaucc acgccguggg acccaacuuc aacaagguga 4260
gcgaggugga aggcgacaag cagcuggccg aggccuacga gagcaucgcc aagaucguga 4320
acgacaacaa cuacaagagc guggccauac cccugcugag caccggcauc uucagcggca 4380
acaaggacag acugacccag agccugaacc accugcugac agcccuggac accaccgacg 4440
ccgacguggc caucuacugc cgggacaaga aaugggagau gacccugaaa gaagccgugg 4500
ccagacgcga ggccguggaa gagaucugca ucagcgacga cagcagcgug accgagccag 4560
acgccgaacu cgucagagug caccccaaga gcagccuggc cggcagaaag ggcuacagca 4620
ccagcgacgg caagaccuuc agcuaccugg aaggcaccaa guuccaccag gccgccaagg 4680
acaucgccga gaucaacgca auguggcccg uggccaccga ggccaacgaa caagugugca 4740
uguacauccu gggcgagagc augagcagca uccgcagcaa gugccccgug gaagagagcg 4800
aggccagcac accacccagc acacugcccu gccugugcau ccacgccaug acaccagaga 4860
gagugcagcg gcugaaggcc agcagacccg agcagaucac cgugugcagc agcuucccac 4920
ugcccaagua cagaaucacc ggcgugcaga aaauccagug cagccagcca auccuguuca 4980
gccccaaggu gcccgccuac auacacccca gaaaguaccu gguggaaacc ccacccgugg 5040
acgagacacc cgaaccaagc gccgagaacc agagcaccga gggaacacca gaacagcccc 5100
cacugaucac cgaggacgaa accaggacca gaacacccga gccaaucauc aucgaggaag 5160
aagaagagga cagcaucagc cugcugagcg acggacccac acaccaggug cugcaagugg 5220
aagccgacau ccacggaccc ccaagcguga gcagcagcag cuggagcauc ccccacgcca 5280
gcgacuucga cguggacagc cugagcaucc uggacacacu ggaaggcgcc agcgugacaa 5340
gcggcgccac aagcgccgag acaaacagcu acuucgccaa gagcauggaa uuccuggcca 5400
ggcccgugcc agcaccccgg accguguuca gaaacccccc ucacccagcc cccagaacca 5460
ggacacccag ccuggcccca agcagagccu gcagcagaac cagccuggug agcacacccc 5520
ccggcgugaa cagagugauc accagagagg aacuggaagc ccugacaccc agcaggaccc 5580
caagcagaag cgugagcaga acaagccugg ugagcaaccc accaggcguc aaccggguca 5640
ucacccggga agaguucgag gccuucgugg cacagcagca gugaagauuc gacgcaggcg 5700
ccuacaucuu cagcagcgac acaggccagg gccaccugca gcagaaaagc gucagacaga 5760
ccgugcugag cgaagguggug cuggaaagaa ccgagcugga aaucagcuac gcccccggc 5820 uggaccaaga gaaagaagaa cugcugcgga agaaacugca gcugaacccc acaccagcca 5880
acagaagcag auaccagagc cggaaggugg aaaacaugaa ggccaucacc gccagacgga 5940
uccugcaagg ccugggccac uaccugaagg ccgagggcaa aguggaaugc uacagaacac 6000
ugcaccccgu gccacuguac agcagcagcg ugaacagggc cuucagcagc ccaaaggugg 6060
ccgucgaagc cugcaacgcc augcugaaag aaaacuuccc caccguggcc agcuacugca 6120
ucauccccga guacgacgcc uaccuggaca ugguggacgg cgcaagcugc ugccuggaca 6180
ccgccagcuu cugccccgcc aagcugagaa gcuuccccaa gaagcacagc uaccuggaac 6240
ccaccaucag aagcgccgug ccaagcgcca uucagaacac ccugcagaac gugcuggccg 6300
cagccaccaa gaggaacugc aacgugaccc agaugcgcga gcugcccguc cuggacagcg 6360
ccgccuucaa cguggaaugc uucaagaagu acgccugcaa caacgaguac ugggagacau 6420
ucaaagagaa ccccauccgg cugaccgagg aaaacguggu caacuacauc accaagcuga 6480
agggccccaa agccgcagcc cuguucgcca agacacacaa ccugaacaug cugcaggaca 6540
uccccaugga cagauucgug auggaccuga agcgggacgu gaaagugacc ccaggcacca 6600
agcacaccga ggaacggccc aaagugcaag ugauccaggc cgcagacccc cuggccacag 6660
ccuaccugug cggcauccac agagaacucg ugcggagacu gaacgccgug cugcugccca 6720
acauccacac acuguucgac augagcgccg aggacuucga cgccaucaua gccgagcacu 6780
uccagccagg cgacugcgug cucgagacag acaucgccag cuucgacaag agcgaggacg 6840
acgccauggc acugaccgcc cugaugaucc uggaagaccu gggcguggac gccgagcugc 6900
ugacacugau agaagccgcc uucggcgaga ucagcagcau ccaccugccc accaagacca 6960
aauuuaaauu cggagccaug augaaaucug gaauguuccu cacacuguuu gugaacacag 7020
ucauuaacau uguaaucgca agcagagugu ugagagaacg gcuaaccgga ucaccaugug 7080
cagcauucau uggagaugac aauaucguga aaggagucaa aucggacaaa uuaauggcag 7140
acaggugcgc caccugguug aauauggaag ucaagauuau agaugcugug gugggcgaga 7200
aagcgccuua uuucugugga ggguuuauuu ugugugacuc cgugaccggc acagcgugcc 7260
guguggcaga cccccuaaaa aggcuguuua agcuuggcaa accucuggca gcagacgaug 7320
aacaugauga ugacaggaga agggcauugc augaagaguc aacacgcugg aaccgagugg 7380
guauucuuuc agagcugugc aaggcaguag aaucaaggua ugaaaccgua ggaacuucca 7440
ucauaguuau ggccaugacu acucuagcua gcaguguuaa aucauucagc uaccugagag 7500
gggccccuau aacucucuac ggcuaaccug aauggacuac gacauagucu aguccgccaa 7560
g 7561

<210> SEQ ID NO 39
<211> LENGTH: 627
<212> TYPE: PRT
<213> ORGANISM: Artificial Sequence
<220> FEATURE:
<223> OTHER INFORMATION: Synthetic construct, VEEV nsP4-2A polyprotein

<400> SEQUENCE: 39

Tyr Ile Phe Ser Ser Asp Thr Gly Gln Gly His Leu Gln Gln Lys Ser
1 5 10 15

Val Arg Gln Thr Val Leu Ser Glu Val Val Leu Glu Arg Thr Glu Leu
20 25 30

```
Glu Ile Ser Tyr Ala Pro Arg Leu Asp Gln Glu Lys Glu Glu Leu Leu
        35                  40                  45

Arg Lys Lys Leu Gln Leu Asn Pro Thr Pro Ala Asn Arg Ser Arg Tyr
    50                  55                  60

Gln Ser Arg Lys Val Glu Asn Met Lys Ala Ile Thr Ala Arg Arg Ile
65                  70                  75                  80

Leu Gln Gly Leu Gly His Tyr Leu Lys Ala Glu Gly Lys Val Glu Cys
                85                  90                  95

Tyr Arg Thr Leu His Pro Val Pro Leu Tyr Ser Ser Ser Val Asn Arg
            100                 105                 110

Ala Phe Ser Ser Pro Lys Val Ala Val Glu Ala Cys Asn Ala Met Leu
        115                 120                 125

Lys Glu Asn Phe Pro Thr Val Ala Ser Tyr Cys Ile Ile Pro Glu Tyr
    130                 135                 140

Asp Ala Tyr Leu Asp Met Val Asp Gly Ala Ser Cys Cys Leu Asp Thr
145                 150                 155                 160

Ala Ser Phe Cys Pro Ala Lys Leu Arg Ser Phe Pro Lys Lys His Ser
                165                 170                 175

Tyr Leu Glu Pro Thr Ile Arg Ser Ala Val Pro Ser Ala Ile Gln Asn
            180                 185                 190

Thr Leu Gln Asn Val Leu Ala Ala Ala Thr Lys Arg Asn Cys Asn Val
        195                 200                 205

Thr Gln Met Arg Glu Leu Pro Val Leu Asp Ser Ala Ala Phe Asn Val
    210                 215                 220

Glu Cys Phe Lys Lys Tyr Ala Cys Asn Asn Glu Tyr Trp Glu Thr Phe
225                 230                 235                 240

Lys Glu Asn Pro Ile Arg Leu Thr Glu Glu Asn Val Val Asn Tyr Ile
                245                 250                 255

Thr Lys Leu Lys Gly Pro Lys Ala Ala Ala Leu Phe Ala Lys Thr His
            260                 265                 270

Asn Leu Asn Met Leu Gln Asp Ile Pro Met Asp Arg Phe Val Met Asp
        275                 280                 285

Leu Lys Arg Asp Val Lys Val Thr Pro Gly Thr Lys His Thr Glu Glu
    290                 295                 300

Arg Pro Lys Val Gln Val Ile Gln Ala Ala Asp Pro Leu Ala Thr Ala
305                 310                 315                 320

Tyr Leu Cys Gly Ile His Arg Glu Leu Val Arg Arg Leu Asn Ala Val
                325                 330                 335

Leu Leu Pro Asn Ile His Thr Leu Phe Asp Met Ser Ala Glu Asp Phe
            340                 345                 350

Asp Ala Ile Ile Ala Glu His Phe Gln Pro Gly Asp Cys Val Leu Glu
        355                 360                 365

Thr Asp Ile Ala Ser Phe Asp Lys Ser Glu Asp Asp Ala Met Ala Leu
    370                 375                 380

Thr Ala Leu Met Ile Leu Glu Asp Leu Gly Val Asp Ala Glu Leu Leu
385                 390                 395                 400

Thr Leu Ile Glu Ala Ala Phe Gly Glu Ile Ser Ser Ile His Leu Pro
                405                 410                 415

Thr Lys Thr Lys Phe Lys Phe Gly Ala Met Met Lys Ser Gly Met Phe
            420                 425                 430

Leu Thr Leu Phe Val Asn Thr Val Ile Asn Ile Val Ile Ala Ser Arg
        435                 440                 445
```

```
Val Leu Arg Glu Arg Leu Thr Gly Ser Pro Cys Ala Ala Phe Ile Gly
    450                 455                 460

Asp Asp Asn Ile Val Lys Gly Val Lys Ser Asp Lys Leu Met Ala Asp
465                 470                 475                 480

Arg Cys Ala Thr Trp Leu Asn Met Glu Val Lys Ile Ile Asp Ala Val
                485                 490                 495

Val Gly Glu Lys Ala Pro Tyr Phe Cys Gly Gly Phe Ile Leu Cys Asp
            500                 505                 510

Ser Val Thr Gly Thr Ala Cys Arg Val Ala Asp Pro Leu Lys Arg Leu
        515                 520                 525

Phe Lys Leu Gly Lys Pro Leu Ala Ala Asp Asp Glu His Asp Asp Asp
    530                 535                 540

Arg Arg Arg Ala Leu His Glu Glu Ser Thr Arg Trp Asn Arg Val Gly
545                 550                 555                 560

Ile Leu Ser Glu Leu Cys Lys Ala Val Glu Ser Arg Tyr Glu Thr Val
                565                 570                 575

Gly Thr Ser Ile Ile Val Met Ala Met Thr Thr Leu Ala Ser Ser Val
            580                 585                 590

Lys Ser Phe Ser Tyr Leu Arg Gly Ala Pro Ile Thr Leu Tyr Gly Ser
        595                 600                 605

Gly Glu Gly Arg Gly Ser Leu Leu Thr Cys Gly Asp Val Glu Glu Asn
    610                 615                 620

Pro Gly Pro
625


<210> SEQ ID NO 40
<211> LENGTH: 840
<212> TYPE: PRT
<213> ORGANISM: Artificial Sequence
<220> FEATURE:
<223> OTHER INFORMATION: Synthetic construct, VEEV nsP4-2A-3Cpro

<400> SEQUENCE: 40

Tyr Ile Phe Ser Ser Asp Thr Gly Gln Gly His Leu Gln Gln Lys Ser
1               5                   10                  15

Val Arg Gln Thr Val Leu Ser Glu Val Val Leu Glu Arg Thr Glu Leu
            20                  25                  30

Glu Ile Ser Tyr Ala Pro Arg Leu Asp Gln Glu Lys Glu Glu Leu Leu
        35                  40                  45

Arg Lys Lys Leu Gln Leu Asn Pro Thr Pro Ala Asn Arg Ser Arg Tyr
    50                  55                  60

Gln Ser Arg Lys Val Glu Asn Met Lys Ala Ile Thr Ala Arg Arg Ile
65                  70                  75                  80

Leu Gln Gly Leu Gly His Tyr Leu Lys Ala Glu Gly Lys Val Glu Cys
                85                  90                  95

Tyr Arg Thr Leu His Pro Val Pro Leu Tyr Ser Ser Ser Val Asn Arg
            100                 105                 110

Ala Phe Ser Ser Pro Lys Val Ala Val Glu Ala Cys Asn Ala Met Leu
        115                 120                 125

Lys Glu Asn Phe Pro Thr Val Ala Ser Tyr Cys Ile Ile Pro Glu Tyr
    130                 135                 140

Asp Ala Tyr Leu Asp Met Val Asp Gly Ala Ser Cys Cys Leu Asp Thr
145                 150                 155                 160

Ala Ser Phe Cys Pro Ala Lys Leu Arg Ser Phe Pro Lys Lys His Ser
                165                 170                 175
```

-continued

```
Tyr Leu Glu Pro Thr Ile Arg Ser Ala Val Pro Ser Ala Ile Gln Asn
            180                 185                 190

Thr Leu Gln Asn Val Leu Ala Ala Ala Thr Lys Arg Asn Cys Asn Val
        195                 200                 205

Thr Gln Met Arg Glu Leu Pro Val Leu Asp Ser Ala Ala Phe Asn Val
    210                 215                 220

Glu Cys Phe Lys Lys Tyr Ala Cys Asn Asn Glu Tyr Trp Glu Thr Phe
225                 230                 235                 240

Lys Glu Asn Pro Ile Arg Leu Thr Glu Glu Asn Val Val Asn Tyr Ile
                245                 250                 255

Thr Lys Leu Lys Gly Pro Lys Ala Ala Ala Leu Phe Ala Lys Thr His
            260                 265                 270

Asn Leu Asn Met Leu Gln Asp Ile Pro Met Asp Arg Phe Val Met Asp
        275                 280                 285

Leu Lys Arg Asp Val Lys Val Thr Pro Gly Thr Lys His Thr Glu Glu
    290                 295                 300

Arg Pro Lys Val Gln Val Ile Gln Ala Ala Asp Pro Leu Ala Thr Ala
305                 310                 315                 320

Tyr Leu Cys Gly Ile His Arg Glu Leu Val Arg Arg Leu Asn Ala Val
                325                 330                 335

Leu Leu Pro Asn Ile His Thr Leu Phe Asp Met Ser Ala Glu Asp Phe
            340                 345                 350

Asp Ala Ile Ile Ala Glu His Phe Gln Pro Gly Asp Cys Val Leu Glu
        355                 360                 365

Thr Asp Ile Ala Ser Phe Asp Lys Ser Glu Asp Asp Ala Met Ala Leu
    370                 375                 380

Thr Ala Leu Met Ile Leu Glu Asp Leu Gly Val Asp Ala Glu Leu Leu
385                 390                 395                 400

Thr Leu Ile Glu Ala Ala Phe Gly Glu Ile Ser Ser Ile His Leu Pro
                405                 410                 415

Thr Lys Thr Lys Phe Lys Phe Gly Ala Met Met Lys Ser Gly Met Phe
            420                 425                 430

Leu Thr Leu Phe Val Asn Thr Val Ile Asn Ile Val Ile Ala Ser Arg
        435                 440                 445

Val Leu Arg Glu Arg Leu Thr Gly Ser Pro Cys Ala Ala Phe Ile Gly
    450                 455                 460

Asp Asp Asn Ile Val Lys Gly Val Lys Ser Asp Lys Leu Met Ala Asp
465                 470                 475                 480

Arg Cys Ala Thr Trp Leu Asn Met Glu Val Lys Ile Ile Asp Ala Val
                485                 490                 495

Val Gly Glu Lys Ala Pro Tyr Phe Cys Gly Gly Phe Ile Leu Cys Asp
            500                 505                 510

Ser Val Thr Gly Thr Ala Cys Arg Val Ala Asp Pro Leu Lys Arg Leu
        515                 520                 525

Phe Lys Leu Gly Lys Pro Leu Ala Ala Asp Asp Glu His Asp Asp Asp
    530                 535                 540

Arg Arg Arg Ala Leu His Glu Glu Ser Thr Arg Trp Asn Arg Val Gly
545                 550                 555                 560

Ile Leu Ser Glu Leu Cys Lys Ala Val Glu Ser Arg Tyr Glu Thr Val
                565                 570                 575

Gly Thr Ser Ile Ile Val Met Ala Met Thr Thr Leu Ala Ser Ser Val
            580                 585                 590

Lys Ser Phe Ser Tyr Leu Arg Gly Ala Pro Ile Thr Leu Tyr Gly Ser
```

```
        595                 600                 605

Gly Glu Gly Arg Gly Ser Leu Leu Thr Cys Gly Asp Val Glu Glu Asn
    610                 615                 620

Pro Gly Pro Ser Gly Ala Pro Pro Thr Asp Leu Gln Lys Met Val Met
625                 630                 635                 640

Gly Asn Thr Lys Pro Val Glu Leu Ile Leu Asp Gly Lys Thr Val Ala
                645                 650                 655

Ile Cys Cys Ala Thr Gly Val Phe Gly Thr Ala Tyr Leu Val Pro Arg
            660                 665                 670

His Leu Phe Ala Glu Lys Tyr Asp Lys Ile Met Leu Asp Gly Arg Ala
        675                 680                 685

Met Thr Asp Ser Asp Tyr Arg Val Phe Glu Phe Glu Ile Lys Val Lys
    690                 695                 700

Gly Gln Asp Met Leu Ser Asp Ala Ala Leu Met Val Leu His Arg Gly
705                 710                 715                 720

Asn Arg Val Arg Asp Ile Thr Lys His Phe Arg Asp Thr Ala Arg Met
                725                 730                 735

Lys Lys Gly Thr Pro Val Val Gly Val Val Asn Asn Ala Asp Val Gly
            740                 745                 750

Arg Leu Ile Phe Ser Gly Glu Ala Leu Thr Tyr Lys Asp Ile Val Val
        755                 760                 765

Cys Met Asp Gly Asp Thr Met Pro Ser Leu Phe Ala Tyr Lys Ala Ala
    770                 775                 780

Thr Lys Ala Gly Tyr Cys Gly Gly Ala Val Leu Ala Lys Asp Gly Ala
785                 790                 795                 800

Asp Thr Phe Ile Val Gly Thr His Ser Ala Gly Gly Asn Gly Val Gly
                805                 810                 815

Tyr Cys Ser Cys Val Ser Lys Ser Met Leu Leu Arg Met Lys Ala His
            820                 825                 830

Val Asp Pro Glu Pro Gln His Glu
        835                 840


<210> SEQ ID NO 41
<211> LENGTH: 865
<212> TYPE: PRT
<213> ORGANISM: Artificial Sequence
<220> FEATURE:
<223> OTHER INFORMATION: Synthetic construct, VEEV nsP4-2A-GFP

<400> SEQUENCE: 41

Tyr Ile Phe Ser Ser Asp Thr Gly Gln Gly His Leu Gln Gln Lys Ser
1               5                   10                  15

Val Arg Gln Thr Val Leu Ser Glu Val Val Leu Glu Arg Thr Glu Leu
            20                  25                  30

Glu Ile Ser Tyr Ala Pro Arg Leu Asp Gln Glu Lys Glu Glu Leu Leu
        35                  40                  45

Arg Lys Lys Leu Gln Leu Asn Pro Thr Pro Ala Asn Arg Ser Arg Tyr
    50                  55                  60

Gln Ser Arg Lys Val Glu Asn Met Lys Ala Ile Thr Ala Arg Arg Ile
65                  70                  75                  80

Leu Gln Gly Leu Gly His Tyr Leu Lys Ala Glu Gly Lys Val Glu Cys
                85                  90                  95

Tyr Arg Thr Leu His Pro Val Pro Leu Tyr Ser Ser Ser Val Asn Arg
            100                 105                 110

Ala Phe Ser Ser Pro Lys Val Ala Val Glu Ala Cys Asn Ala Met Leu
```

-continued

```
        115                 120                 125

Lys Glu Asn Phe Pro Thr Val Ala Ser Tyr Cys Ile Ile Pro Glu Tyr
    130                 135                 140

Asp Ala Tyr Leu Asp Met Val Asp Gly Ala Ser Cys Cys Leu Asp Thr
145                 150                 155                 160

Ala Ser Phe Cys Pro Ala Lys Leu Arg Ser Phe Pro Lys Lys His Ser
                165                 170                 175

Tyr Leu Glu Pro Thr Ile Arg Ser Ala Val Pro Ser Ala Ile Gln Asn
            180                 185                 190

Thr Leu Gln Asn Val Leu Ala Ala Ala Thr Lys Arg Asn Cys Asn Val
        195                 200                 205

Thr Gln Met Arg Glu Leu Pro Val Leu Asp Ser Ala Ala Phe Asn Val
    210                 215                 220

Glu Cys Phe Lys Lys Tyr Ala Cys Asn Asn Glu Tyr Trp Glu Thr Phe
225                 230                 235                 240

Lys Glu Asn Pro Ile Arg Leu Thr Glu Glu Asn Val Val Asn Tyr Ile
                245                 250                 255

Thr Lys Leu Lys Gly Pro Lys Ala Ala Ala Leu Phe Ala Lys Thr His
            260                 265                 270

Asn Leu Asn Met Leu Gln Asp Ile Pro Met Asp Arg Phe Val Met Asp
        275                 280                 285

Leu Lys Arg Asp Val Lys Val Thr Pro Gly Thr Lys His Thr Glu Glu
    290                 295                 300

Arg Pro Lys Val Gln Val Ile Gln Ala Ala Asp Pro Leu Ala Thr Ala
305                 310                 315                 320

Tyr Leu Cys Gly Ile His Arg Glu Leu Val Arg Arg Leu Asn Ala Val
                325                 330                 335

Leu Leu Pro Asn Ile His Thr Leu Phe Asp Met Ser Ala Glu Asp Phe
            340                 345                 350

Asp Ala Ile Ile Ala Glu His Phe Gln Pro Gly Asp Cys Val Leu Glu
        355                 360                 365

Thr Asp Ile Ala Ser Phe Asp Lys Ser Glu Asp Asp Ala Met Ala Leu
    370                 375                 380

Thr Ala Leu Met Ile Leu Glu Asp Leu Gly Val Asp Ala Glu Leu Leu
385                 390                 395                 400

Thr Leu Ile Glu Ala Ala Phe Gly Glu Ile Ser Ser Ile His Leu Pro
                405                 410                 415

Thr Lys Thr Lys Phe Lys Phe Gly Ala Met Met Lys Ser Gly Met Phe
            420                 425                 430

Leu Thr Leu Phe Val Asn Thr Val Ile Asn Ile Val Ile Ala Ser Arg
        435                 440                 445

Val Leu Arg Glu Arg Leu Thr Gly Ser Pro Cys Ala Ala Phe Ile Gly
    450                 455                 460

Asp Asp Asn Ile Val Lys Gly Val Lys Ser Asp Lys Leu Met Ala Asp
465                 470                 475                 480

Arg Cys Ala Thr Trp Leu Asn Met Glu Val Lys Ile Ile Asp Ala Val
                485                 490                 495

Val Gly Glu Lys Ala Pro Tyr Phe Cys Gly Gly Phe Ile Leu Cys Asp
            500                 505                 510

Ser Val Thr Gly Thr Ala Cys Arg Val Ala Asp Pro Leu Lys Arg Leu
        515                 520                 525

Phe Lys Leu Gly Lys Pro Leu Ala Ala Asp Asp Glu His Asp Asp Asp
    530                 535                 540
```

```
Arg Arg Arg Ala Leu His Glu Glu Ser Thr Arg Trp Asn Arg Val Gly
545                 550                 555                 560

Ile Leu Ser Glu Leu Cys Lys Ala Val Glu Ser Arg Tyr Glu Thr Val
                565                 570                 575

Gly Thr Ser Ile Ile Val Met Ala Met Thr Thr Leu Ala Ser Ser Val
            580                 585                 590

Lys Ser Phe Ser Tyr Leu Arg Gly Ala Pro Ile Thr Leu Tyr Gly Ser
        595                 600                 605

Gly Glu Gly Arg Gly Ser Leu Leu Thr Cys Gly Asp Val Glu Glu Asn
    610                 615                 620

Pro Gly Pro Val Ser Lys Gly Glu Glu Leu Phe Thr Gly Val Val Pro
625                 630                 635                 640

Ile Leu Val Glu Leu Asp Gly Asp Val Asn Gly His Lys Phe Ser Val
                645                 650                 655

Ser Gly Glu Gly Glu Gly Asp Ala Thr Tyr Gly Lys Leu Thr Leu Lys
            660                 665                 670

Phe Ile Cys Thr Thr Gly Lys Leu Pro Val Pro Trp Pro Thr Leu Val
        675                 680                 685

Thr Thr Leu Thr Tyr Gly Val Gln Cys Phe Ser Arg Tyr Pro Asp His
    690                 695                 700

Met Lys Gln His Asp Phe Phe Lys Ser Ala Met Pro Glu Gly Tyr Val
705                 710                 715                 720

Gln Glu Arg Thr Ile Phe Phe Lys Asp Asp Gly Asn Tyr Lys Thr Arg
                725                 730                 735

Ala Glu Val Lys Phe Glu Gly Asp Thr Leu Val Asn Arg Ile Glu Leu
            740                 745                 750

Lys Gly Ile Asp Phe Lys Glu Asp Gly Asn Ile Leu Gly His Lys Leu
        755                 760                 765

Glu Tyr Asn Tyr Asn Ser His Asn Val Tyr Ile Met Ala Asp Lys Gln
    770                 775                 780

Lys Asn Gly Ile Lys Val Asn Phe Lys Ile Arg His Asn Ile Glu Asp
785                 790                 795                 800

Gly Ser Val Gln Leu Ala Asp His Tyr Gln Gln Asn Thr Pro Ile Gly
                805                 810                 815

Asp Gly Pro Val Leu Leu Pro Asp Asn His Tyr Leu Ser Thr Gln Ser
            820                 825                 830

Lys Leu Ser Lys Asp Pro Asn Glu Lys Arg Asp His Met Val Leu Leu
        835                 840                 845

Glu Phe Val Thr Ala Ala Gly Ile Thr Leu Gly Met Asp Glu Leu Tyr
    850                 855                 860

Lys
865
```

<210> SEQ ID NO 42
<211> LENGTH: 1005
<212> TYPE: PRT
<213> ORGANISM: Artificial Sequence
<220> FEATURE:
<223> OTHER INFORMATION: Synthetic construct, VEEV nsP4-2A-STING

<400> SEQUENCE: 42

```
Tyr Ile Phe Ser Ser Asp Thr Gly Gln Gly His Leu Gln Gln Lys Ser
1               5                   10                  15

Val Arg Gln Thr Val Leu Ser Glu Val Val Leu Glu Arg Thr Glu Leu
            20                  25                  30
```

```
Glu Ile Ser Tyr Ala Pro Arg Leu Asp Gln Glu Lys Glu Glu Leu Leu
        35                  40                  45

Arg Lys Lys Leu Gln Leu Asn Pro Thr Pro Ala Asn Arg Ser Arg Tyr
    50                  55                  60

Gln Ser Arg Lys Val Glu Asn Met Lys Ala Ile Thr Ala Arg Arg Ile
65                  70                  75                  80

Leu Gln Gly Leu Gly His Tyr Leu Lys Ala Glu Gly Lys Val Glu Cys
                85                  90                  95

Tyr Arg Thr Leu His Pro Val Pro Leu Tyr Ser Ser Ser Val Asn Arg
            100                 105                 110

Ala Phe Ser Ser Pro Lys Val Ala Val Glu Ala Cys Asn Ala Met Leu
        115                 120                 125

Lys Glu Asn Phe Pro Thr Val Ala Ser Tyr Cys Ile Ile Pro Glu Tyr
    130                 135                 140

Asp Ala Tyr Leu Asp Met Val Asp Gly Ala Ser Cys Cys Leu Asp Thr
145                 150                 155                 160

Ala Ser Phe Cys Pro Ala Lys Leu Arg Ser Phe Pro Lys Lys His Ser
                165                 170                 175

Tyr Leu Glu Pro Thr Ile Arg Ser Ala Val Pro Ser Ala Ile Gln Asn
            180                 185                 190

Thr Leu Gln Asn Val Leu Ala Ala Ala Thr Lys Arg Asn Cys Asn Val
        195                 200                 205

Thr Gln Met Arg Glu Leu Pro Val Leu Asp Ser Ala Ala Phe Asn Val
    210                 215                 220

Glu Cys Phe Lys Lys Tyr Ala Cys Asn Asn Glu Tyr Trp Glu Thr Phe
225                 230                 235                 240

Lys Glu Asn Pro Ile Arg Leu Thr Glu Glu Asn Val Val Asn Tyr Ile
                245                 250                 255

Thr Lys Leu Lys Gly Pro Lys Ala Ala Ala Leu Phe Ala Lys Thr His
            260                 265                 270

Asn Leu Asn Met Leu Gln Asp Ile Pro Met Asp Arg Phe Val Met Asp
        275                 280                 285

Leu Lys Arg Asp Val Lys Val Thr Pro Gly Thr Lys His Thr Glu Glu
    290                 295                 300

Arg Pro Lys Val Gln Val Ile Gln Ala Ala Asp Pro Leu Ala Thr Ala
305                 310                 315                 320

Tyr Leu Cys Gly Ile His Arg Glu Leu Val Arg Arg Leu Asn Ala Val
                325                 330                 335

Leu Leu Pro Asn Ile His Thr Leu Phe Asp Met Ser Ala Glu Asp Phe
            340                 345                 350

Asp Ala Ile Ile Ala Glu His Phe Gln Pro Gly Asp Cys Val Leu Glu
        355                 360                 365

Thr Asp Ile Ala Ser Phe Asp Lys Ser Glu Asp Asp Ala Met Ala Leu
    370                 375                 380

Thr Ala Leu Met Ile Leu Glu Asp Leu Gly Val Asp Ala Glu Leu Leu
385                 390                 395                 400

Thr Leu Ile Glu Ala Ala Phe Gly Glu Ile Ser Ser Ile His Leu Pro
                405                 410                 415

Thr Lys Thr Lys Phe Lys Phe Gly Ala Met Met Lys Ser Gly Met Phe
            420                 425                 430

Leu Thr Leu Phe Val Asn Thr Val Ile Asn Ile Val Ile Ala Ser Arg
        435                 440                 445
```

-continued

```
Val Leu Arg Glu Arg Leu Thr Gly Ser Pro Cys Ala Ala Phe Ile Gly
    450                 455                 460

Asp Asp Asn Ile Val Lys Gly Val Lys Ser Asp Lys Leu Met Ala Asp
465                 470                 475                 480

Arg Cys Ala Thr Trp Leu Asn Met Glu Val Lys Ile Ile Asp Ala Val
                485                 490                 495

Val Gly Glu Lys Ala Pro Tyr Phe Cys Gly Gly Phe Ile Leu Cys Asp
            500                 505                 510

Ser Val Thr Gly Thr Ala Cys Arg Val Ala Asp Pro Leu Lys Arg Leu
        515                 520                 525

Phe Lys Leu Gly Lys Pro Leu Ala Ala Asp Asp Glu His Asp Asp Asp
    530                 535                 540

Arg Arg Arg Ala Leu His Glu Glu Ser Thr Arg Trp Asn Arg Val Gly
545                 550                 555                 560

Ile Leu Ser Glu Leu Cys Lys Ala Val Glu Ser Arg Tyr Glu Thr Val
                565                 570                 575

Gly Thr Ser Ile Ile Val Met Ala Met Thr Thr Leu Ala Ser Ser Val
            580                 585                 590

Lys Ser Phe Ser Tyr Leu Arg Gly Ala Pro Ile Thr Leu Tyr Gly Ser
        595                 600                 605

Gly Glu Gly Arg Gly Ser Leu Leu Thr Cys Gly Asp Val Glu Glu Asn
    610                 615                 620

Pro Gly Pro Pro His Ser Ser Leu His Pro Ser Ile Pro Cys Pro Arg
625                 630                 635                 640

Gly His Gly Ala Gln Lys Ala Ala Leu Val Leu Leu Ser Ala Cys Leu
                645                 650                 655

Val Thr Leu Trp Gly Leu Gly Glu Pro Pro Glu His Thr Leu Arg Tyr
            660                 665                 670

Leu Val Leu His Leu Ala Ser Leu Gln Leu Gly Leu Leu Leu Asn Gly
        675                 680                 685

Val Cys Ser Leu Ala Glu Glu Leu Arg His Ile His Ser Arg Tyr Arg
    690                 695                 700

Gly Ser Tyr Trp Arg Thr Val Arg Ala Cys Leu Gly Cys Pro Leu Arg
705                 710                 715                 720

Arg Gly Ala Leu Leu Leu Leu Ser Ile Tyr Phe Tyr Tyr Ser Leu Pro
                725                 730                 735

Asn Ala Val Gly Pro Pro Phe Thr Trp Met Leu Ala Leu Leu Gly Leu
            740                 745                 750

Ser Gln Ala Leu Asn Ile Leu Leu Gly Leu Lys Gly Leu Ala Pro Ala
        755                 760                 765

Glu Ile Ser Ala Val Cys Glu Lys Gly Asn Phe Ser Val Ala His Gly
    770                 775                 780

Leu Ala Trp Ser Tyr Tyr Ile Gly Tyr Leu Arg Leu Ile Leu Pro Glu
785                 790                 795                 800

Leu Gln Ala Arg Ile Arg Thr Tyr Asn Gln His Tyr Asn Asn Leu Leu
                805                 810                 815

Arg Gly Ala Val Ser Gln Arg Leu Tyr Ile Leu Leu Pro Leu Asp Cys
            820                 825                 830

Gly Val Pro Asp Asn Leu Ser Met Ala Asp Pro Asn Ile Arg Phe Leu
        835                 840                 845

Asp Lys Leu Pro Gln Gln Thr Gly Asp His Ala Gly Ile Lys Asp Arg
    850                 855                 860

Val Tyr Ser Asn Ser Ile Tyr Glu Leu Leu Glu Asn Gly Gln Arg Ala
```

```
865                 870                 875                 880

Gly Thr Cys Val Leu Glu Tyr Ala Thr Pro Leu Gln Thr Leu Phe Ala
                885                 890                 895

Met Ser Gln Tyr Ser Gln Ala Gly Phe Ser Arg Glu Asp Met Leu Glu
            900                 905                 910

Gln Ala Lys Leu Phe Cys Arg Thr Leu Glu Asp Ile Leu Ala Asp Ala
        915                 920                 925

Pro Glu Ser Gln Asn Asn Cys Arg Leu Ile Ala Tyr Gln Glu Pro Ala
    930                 935                 940

Asp Asp Ser Ser Phe Ser Leu Ser Gln Glu Val Leu Arg His Leu Arg
945                 950                 955                 960

Gln Glu Glu Lys Glu Glu Val Thr Val Gly Ser Leu Lys Thr Ser Ala
                965                 970                 975

Val Pro Ser Thr Ser Thr Met Ser Gln Glu Pro Glu Leu Leu Ile Ser
            980                 985                 990

Gly Met Glu Lys Pro Leu Pro Leu  Arg Thr Asp Phe Ser
        995                 1000                 1005
```

<210> SEQ ID NO 43
<211> LENGTH: 18
<212> TYPE: PRT
<213> ORGANISM: Artificial Sequence
<220> FEATURE:
<223> OTHER INFORMATION: Synthetic construct, thosea asigna virus 2A protein

<400> SEQUENCE: 43

```
Glu Gly Arg Gly Ser Leu Leu Thr Cys Gly Asp Val Glu Glu Asn Pro
1               5                   10                  15

Gly Pro
```

<210> SEQ ID NO 44
<211> LENGTH: 19
<212> TYPE: PRT
<213> ORGANISM: Artificial Sequence
<220> FEATURE:
<223> OTHER INFORMATION: Synthetic construct, porcine teschovirus -1_2A protein

<400> SEQUENCE: 44

```
Ala Thr Asn Phe Ser Leu Leu Lys Gln Ala Gly Asp Val Glu Glu Asn
1               5                   10                  15

Pro Gly Pro
```

<210> SEQ ID NO 45
<211> LENGTH: 22
<212> TYPE: PRT
<213> ORGANISM: Foot-and-mouth disease virus
<220> FEATURE:
<221> NAME/KEY: MISC_FEATURE
<222> LOCATION: (1)..(22)
<223> OTHER INFORMATION: FMDV 2A protein

<400> SEQUENCE: 45

```
Val Lys Gln Thr Leu Asn Phe Asp Leu Leu Lys Leu Ala Gly Asp Val
1               5                   10                  15

Glu Ser Asn Pro Gly Pro
            20
```

<210> SEQ ID NO 46
<211> LENGTH: 20

-continued

```
<212> TYPE: PRT
<213> ORGANISM: Artificial Sequence
<220> FEATURE:
<223> OTHER INFORMATION: Syntehtic construct, equine rhinitis A virus 2A
      protein

<400> SEQUENCE: 46

Gln Cys Thr Asn Tyr Ala Leu Leu Lys Leu Ala Gly Asp Val Glu Ser
1               5                   10                  15

Asn Pro Gly Pro
            20
```